United States Patent
Cai et al.

(10) Patent No.: US 11,345,711 B2
(45) Date of Patent: May 31, 2022

(54) 8,9-DIHYDROIMIDAZO[1,2-A]PYRIMIDO[5,4-E]PYRIMIDIN-5(6H)-ONES

(71) Applicant: IMPACT THERAPEUTICS (SHANGHAI), INC, Shanghai (CN)

(72) Inventors: Sui Xiong Cai, Shanghai (CN); Ye Edward Tian, Shanghai (CN)

(73) Assignee: IMPACT THERAPEUTICS (SHANGHAI), INC, Shanghai (CN)

( * ) Notice: Subject to any disclaimer, the term of this patent is extended or adjusted under 35 U.S.C. 154(b) by 0 days.

(21) Appl. No.: 16/883,397

(22) Filed: May 26, 2020

(65) Prior Publication Data

US 2020/0385394 A1 Dec. 10, 2020

Related U.S. Application Data

(63) Continuation of application No. 16/461,512, filed as application No. PCT/CN2017/111230 on Nov. 16, 2017, now Pat. No. 10,703,759.

(30) Foreign Application Priority Data

Nov. 16, 2016 (CN) .......................... 201611009827.4
Jun. 12, 2017 (CN) .......................... 201710440456.3

(51) Int. Cl.
| | | |
|---|---|---|
| A61K 31/519 | (2006.01) | |
| A61P 35/00 | (2006.01) | |
| C07D 487/14 | (2006.01) | |
| C07D 519/00 | (2006.01) | |
| C07D 471/14 | (2006.01) | |
| A61P 35/02 | (2006.01) | |
| A61K 45/06 | (2006.01) | |

(52) U.S. Cl.
CPC .......... *C07D 487/14* (2013.01); *A61K 31/519* (2013.01); *A61P 35/00* (2018.01); *A61P 35/02* (2018.01); *C07D 471/14* (2013.01); *C07D 519/00* (2013.01); *A61K 45/06* (2013.01)

(58) Field of Classification Search
CPC ...... A61K 31/519; A61P 35/00; C07D 487/14
See application file for complete search history.

(56) References Cited

FOREIGN PATENT DOCUMENTS

| WO | WO 2005/021551 A1 | 3/2005 |
| WO | WO 2012/161812 A1 | 11/2012 |
| WO | WO 2015/092431 A1 | 6/2015 |

OTHER PUBLICATIONS

English Translation of International Search Report and Written Opinion for International Application No. PCT/CN2017/111230, State Intellectual Property Office of the P.R. China, China, dated Feb. 22, 2018.

Leijen, S., et al., "Phase II Study of WEE1 Inhibitor AZD1775 Plus Carboplatin in Patients With TP53-Mutated Ovarian Cancer Refractory or Resistant to First-Line Therapy Within 3 Months," *J. Clin. Oncol.* 34:4354-4361, American Society of Clinical Oncology, United States (2016).

Spigel, D.R., et al., "Phase II studies of AZD 1775, a WEE1 kinase inhibitor, and chemotherapy in non-small-cell lung cancer (NSCLC): Lead-in cohort results," *Annals of Oncology 27 (Supplement 6)*:vi114-vi135, European Society for Medical Oncology, United Kingdom (2016).

Blagden, S.P. and Nicum, S., "A source of hope for platinum-resistant ovarian cancer?," *The Lancet* 397:254-256, Oxford University Press, United Kingdom (2021).

Carrassa, L. and Damia, G., "DNA damage response inhibitors: Mechanisms and potential applications in cancer therapy," *Cancer Treatment Reviews* 60:139-151, Elsevier Ltd., United Kingdom (2017).

Do, K. et al., "Phase I Study of Single-Agent AZD1775 (MK-1775), a Wee1 Kinase Inhibitor, in Patients With Refractory Solid Tumors," *J. Clin. Oncol.* 33:3409-3415, American Society of Clinical Oncology, United States (2015).

Fu, S. et al., "Strategic development of AZD1775, a Wee1 kinase inhibitor, for cancer therapy," *Expert Opinion on Investigational Drugs*, 27:9, 741-751, DOI: 10.1080/13543784.2018.1511700, Informa UK Limited, United Kingdom (2018).

Karnak, D. et al., "Combined Inhibition of Wee1 and PARP1/2 for Radiosensitization in Pancreatic Cancer," *Clin. Cancer Res.* 20:5085-5096, American Association for Cancer Research, United States (2014).

Kong, A. and Mehanna, H., "WEE1 Inhibitor: Clinical Development," *Current Oncology Reports 23*:107, 8 pages, Springer, United States (2021).

Leijen, S. et al., "Phase I Study Evaluation WEE1 Inhibitor AZD1775 as Monotherapy and in Combination With Gemcitabine, Cisplatin, or Carboplatin in Patients With Advanced Solid Tumors," *J. Clin. Oncol.* 34:4371-4380, American Society of Clinical Oncology, United States (2016).

Lindqvist, A. et al., "The decision to enter mitosis: feedback and redundancy in the mitotic entry network," *J. Cell. Biol.* 785:193-202, The Rockefeller University Press, United States (2009).

(Continued)

*Primary Examiner* — Brenda L Coleman

(74) *Attorney, Agent, or Firm* — Sterne, Kessler, Goldstein & Fox P.L.L.C.

(57) ABSTRACT

Disclosed are 8,9-dihydroimidazo[1,2-a]pyrimido[5,4-e]pyrimidin-5(6H)-one compounds, specifically represented by the Formula I:

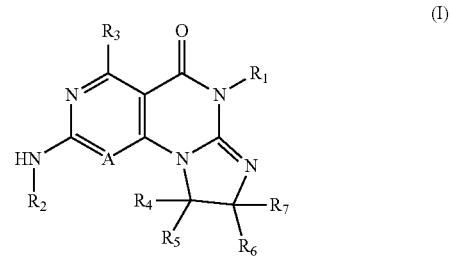

or a pharmaceutically acceptable salt or prodrug thereof, wherein A and $R_1$-$R_7$ are defined herein. Compounds having Formula I are Wee1 kinase inhibitors. Therefore, compounds of the disclosure may be used to treat diseases caused by abnormal Wee1 activity.

13 Claims, No Drawings

(56) References Cited

OTHER PUBLICATIONS

Magnussen, G.I. et al., "Combined inhibition of the cell cycle related proteins Wee1 and Chk1/2 induces synergistic anti-cancer effect in melanoma," *BMC Cancer* 15:1-11, BioMedCentral, United Kingdom (2015).

Matheson, C.J et al., "Targeting WEE1 Kinase in Cancer," *Trends in Pharmacological Sciences*, No. 1350, 10 pages, Elsevier Ltd., United Kingdom (2016).

McGowan, C.H. and Russell, P., "Human Wee1 kinase inhibits cell division by phosphorylating p34c$^{cdc2}$ exclusively on Tyr15," *The EMBO Journal* 12:75-85, Oxford University Press, United Kingdom (1993).

Nurse, P., "Universal control mechanism regulating onset of M-phase," *Nature* 344:503-508, Macmillan Magazines Ltd., United Kingdom (1990).

O'Connell, M.J. et al., "Chk1 is a wee1 kinase in the $G_2$ DNA damage checkpoint inhibiting cdc2 by Y15 phosphorylation," *EMBO Journal* 16:545-554, Oxford University Press, United Kingdom (1997).

Parker, L. et al., "Inactivation of the P34$^{cdc2}$-Cyclin B Complex by the Human WEE1 Tyrosine Kinase," *Science* 257:1955-1957, American Association for the Advancement of Science, United States (1992).

Ronco, C. et al., "ATM, ATR, CHK1, CHK2 and WEE1 inhibitors in cancer and cancer stem cells," *Med. Chem. Commun.*, DOI: 10.1039/C6MD00439C, 36 pages, Royal Society of Chemistry, United Kingdom (2016).

Sancar, A. et al., "Molecular Mechanisms of Mammalian DNA Repair and the DNA Damage Checkpoints," *Annu. Rev. Biochem.* 73:39-85, Annual Reviews, United States (2004).

Stumpff, J. et al., "*Drosophila* Wee1 Kinase Regulates Cdk1 and Mitotic Entry during Embryogenesis," *Current Biology* 74:2143-2148, Elsevier Ltd., United States (2004).

Wang, Y. et al., "Knockdown of Chk1, Wee1 and Myt1 by RNA Interference Abrogates $G_2$ Checkpoint and Induces Apoptosis," *Cancer Biology & Therapy* 3:305-313, Landes Bioscience, United States (2004).

8,9-DIHYDROIMIDAZO[1,2-A]PYRIMIDO [5,4-E]PYRIMIDIN-5(6H)-ONES

FIELD OF THE DISCLOSURE

This disclosure is in the field of medicinal chemistry. In particular, the disclosure relates to 8,9-dihydroimidazo[1,2-a]pyrimido[5,4-e]pyrimidin-5(6H)-ones, and the use of these compounds as Wee1 kinase inhibitors and anti-cancer drugs.

BACKGROUND OF THE INVENTION

The process of growth and proliferation of eukaryotic cell includes that the parent cell produces two identical daughter cells through the mitosis of the cell chromosome by accurately replicating its genome containing genetic information. This process of cell proliferation and division is called the cell cycle, and it involves the process of a cell going from one division to the next. The cell cycle consists of four growth stages: the G1 phase of massive synthesis of proteins and RNA after mitosis, the S phase of DNA synthesis and replication, the G2 phase of preparation before mitosis, and the M phase of mitosis. Cells divide and proliferate through the cell cycle, or stop, depending on the state and needs of the cell. It is necessary to keep genetic information complete and correct during cell proliferation and division. Whether or not to enter the next phase of cell cycle until the completion of the whole cell cycle is ensured and completed through the checkpoints in the cell cycle process.

During the whole process of cell cycle, there are many cell cycle checkpoints. Each cell cycle checkpoint consists of a very complex system and is composed of multiple factors. In the G1 phase, the checkpoint determines whether to enter the cell cycle by examining the state inside and outside the cell, so as to determine whether the cell enters the S phase of DNA synthesis. The G1 checkpoint is a complex system that includes the famous CDK4/CDK6. Another important checkpoint is the so-called G2-M checkpoint, where the cell completes DNA replication (S phase) and enters the cell growth phase (G2 phase). This checkpoint examines whether there is any DNA damage or defect after the cells have synthesized DNA, which determines whether the cells undergo mitosis (M-phase) with the separation of the following chromosomes. Cell cycle checkpoints at this stage include complex kinase Cdk1 complexes including Cyclin-B-cdc2 (Nurse, P., 1990, Nature 344, 503-508). Activation of Cdk1 leads to initiation of mitosis, and subsequent inactivation is accompanied by the completion of mitosis. The activity of Cdk1 is regulated by cdc2 binding to Cyclin-A or Cyclin-B and its phosphorylation. For example, the activation of the cyclin B-Cdk1 complex causes mitosis (Lindqvist, A., et al, 2009, The Journal of cell biology 185, 193-202). Cdc2 is kept inactive by phosphorylation before mitosis. Its phosphorylation state is achieved by tyrosine kinase Wee1, etc. In addition, there are M-phase cell cycle checkpoints.

Tyrosine 15 (Y15) on Cdk1 is phosphorylated by Wee1, thus inhibiting the activity of Cdk1 (McGowan, C. H., et al, 1993, The EMBO journal 12, 75-85; Parker, L. L., et al, 1992, Science 257, 1955-1957). Therefore, Wee1 is a key inhibitory regulator of Cdk1 activity and plays an important role in G2-M phase checkpoints to ensure the entry into mitosis without DNA damage after DNA replication (O'Connell, et al, 1997, The EMBO journal 16, 545-554). Loss or inactivation of Wee1 may result in premature entry into mitosis, leading to mitotic failure and cell death (Stumpff, J., et al, 2004, Curr Biol 14, 2143-2148). Some tumor cells have functional deficiency in G1 cell cycle checkpoint and rely on G2-M cell cycle checkpoints to ensure the progress of cell cycle (Sancar, A., et al, 2004, Annual review of biochemistry 73, 39-85). Due to the loss of p53 protein function, in these cancer cells, the loss of Wee1 expression or the inhibition of Wee1 activity will result in the loss of G2-M phase checkpoints, making tumor cells very sensitive to DNA damage, and this sensitivity is especially prominent in tumor cells that lose the ability of G1 phase checkpoint (Wang, Y., et al, 2004, Cancer biology & therapy 3, 305-313).

In summary, inhibition of Wee1 activity can selectively promote the death of cancer cells with defective cell cycle checkpoints; at the same time, has little effect on normal cells with normal cell cycle checkpoints. Therefore, Wee1 inhibitors may be used as targeted drugs for the treatment of cancer and other cell proliferation disorders.

In addition, because the inhibition of Wee1 activity increases the sensitivity of cells to DNA damage, Wee1 inhibitors can be used in combination with anticancer drugs that cause DNA damage or inhibit DNA repair mechanism, including PARP inhibitors, e.g. Olaparib, Niraparib, Rucaparib and Talazoparib; HDAC inhibitors, e.g. vorinotat, lomidacin, pabista, and belistatin; and the like, for treating cancer or other cell proliferation disorders. Wee1 inhibitors may also be used in combination with other anticancer drugs related to cell cycle checkpoints of cell division, including Chk1/2 inhibitors, CDK4/6 inhibitors such as Paboxini, ATM/ATR inhibitors etc. for the treatment of cancer and other diseases.

The study of Karnak et al. (Clin Cancer Res, 2014, 20(9): 5085-5096) shows that the combination of Wee1 inhibitor AZD1775 and PARP inhibitor olaparib can enhance the sensitivity of pancreatic cancer after radiotherapy. The results confirmed that the combination of Wee1 inhibitor and PARP inhibitor could enhance the radiosensitivity of pancreatic cancer, and supported the hypothesis that Wee1 inhibition could sensitize the cell to PARP inhibitor, i.e., sensitize the cell to radiotherapy by inhibiting the function of DNA repair and G2 checkpoint. It can eventually lead to the accumulation of unrepaired damaged DNA until the cell dies.

In addition, it was reported (BMC Cancer, 2015, 15: 462) that Wee1 inhibitor MK1775 and Chk1/2 inhibitor AZD7762 were used together in malignant melanoma cell and xenograft models. The results showed that the combined use of Wee1 and Chk1/2 inhibitors could synergize the inhibitory effect of single drug, thus reducing the proliferation capacity of tumor cells and activating the apoptosis mechanism. The combination of both inhibitors can inhibit tumor growth better in the xenograft model.

AZD1775 is the first Wee1 kinase inhibitor with single antitumor activity in a preclinical model. Phase I clinical studies showed the single drug efficacy of AZD1775 in patients with solid tumors with BRCA mutations, and the inhibition mechanism of Wee1 kinase was confirmed by paired tumor biopsy finding changes related to targeting and DNA damage response (J Clin Oncol, 2015, 33: 3409-3415). In a clinical phase I trial of AZD1775, which enrolled in more than 200 patients, the efficacy of AZD1775 alone or in combination with gemcitabine, cisplatin or carboplatin in the treatment of patients with advanced solid tumors was studied, showing that AZD1775 alone or in combination with chemotherapy was safe and tolerable at a certain dose. Of 176 evaluable patients, 94 (53%) had stable disease as the best response, and 17 (10%) had partial response. Importantly, the response rate of AZD1775 in patients with TP53 mutation (n=19) was 21%, while that in TP53 wild-type patients (n=33) was 12%, showing great potential for patients with TP53 mutation (J Clin Oncol, 2016 Sep. 6, pii: JC0675991).

WO2012161812 disclosed the following tricyclic compounds as Wee1 kinase inhibitors, wherein, X is N or $CR^1$; Y is N or $CR^2$; Z is O, S or NH; $R^1$ and $R^2$ are H or $C_{1-6}$ alkyl; $R^3$ is $C_{1-8}$ alkyl, $C_{2-8}$ alkenyl, $C_{3-8}$ cycloalkyl, aryl, or heteroaryl etc; $R^4$ is phenyl, naphthyl, tetrahydronaphthyl, indenyl or indanyl, or 5-16 member monocyclic, bicyclic or tricyclic heterocyclic groups, etc.

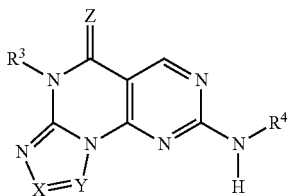

WO2005021551 disclosed the following tetracyclic pyrimidine or pyridine compounds as protein kinase inhibitors, wherein, X is N or CH; Y is NH, N(CN), O or S; L is a 4-atom chain made up of C and N atoms; $R^a$ is H, $C_{1-8}$ alkyl, CN, phenyl or benzyl; $R^1$ and $R^2$ are independently substituted saturated or unsaturated 5-, 6-, or 7-member monocyclic group, or 6-, 7-, 8-, 9-, 10- or 11-member bicyclic group (including 0, 1, 2, 3 or 4 atoms selected from N, O and S, of which O and S atoms do not exist at the same time, and the C atoms in the ring are substituted by 0, 1 or 2 oxygen groups) etc.

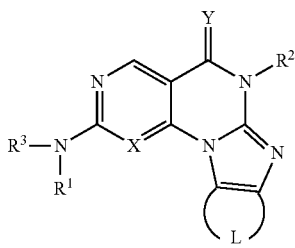

SUMMARY OF THE DISCLOSURE

The disclosure provides novel 8,9-dihydroimidazo[1,2-a]pyrimido[5,4-e]pyrimidin-5(6H)-ones, as represented in Formulae I, II and III as kinase inhibitors, especially Wee1 kinase inhibitors.

The present disclosure also provides pharmaceutical compositions comprising a compound of Formula I, II or III in an effective amount for the treatment of cancer.

In a concrete embodiment, the pharmaceutical composition useful for the treatment of cancer may also contain one or more pharmaceutically acceptable carriers or diluents.

In a concrete embodiment, the pharmaceutical composition useful for the treatment of cancer may also contain at least one known anticancer drugs or its pharmaceutically acceptable salts.

The disclosure is also directed to methods for the preparation of novel compounds of Formulae I, II and III.

DETAILED DESCRIPTION OF THE DISCLOSURE

The disclosure finds novel 8,9-dihydroimidazo[1,2-a]pyrimido[5,4-e]pyrimidin-5(6H)-ones as kinase inhibitors, especially Wee1 kinase inhibitors, as represented in Formulae I, II and III.

It should be understood that the characteristics of the embodiments described herein can be arbitrarily combined to form the technical solution of this disclosure; The definitions of each group herein shall apply to any of the embodiments described herein. For example, the definitions of substituents for alkyl groups herein shall apply to any of the embodiments described herein unless the substituents for alkyl groups are clearly defined in the embodiment.

Specifically, compounds of the present disclosure are represented by Formula I:

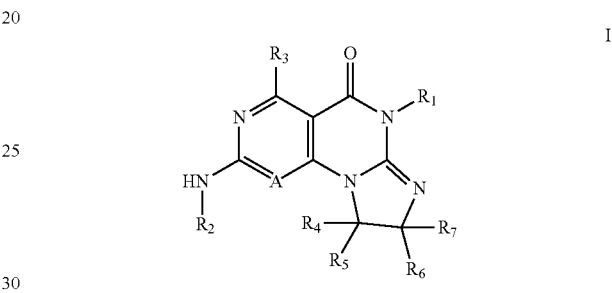

or pharmaceutically acceptable salts or prodrugs thereof, wherein:

A is N or $CR_{15}$;

$R_1$ is H, optionally substituted $C_1$-$C_8$ alkyl, optionally substituted $C_2$-$C_8$ alkenyl, optionally substituted $C_3$-$C_5$ cycloalkyl, optionally substituted aryl, an optionally substituted heterocyclic group or optionally substituted heteroaryl;

$R_2$ is an optionally substituted carbocyclic group, an optionally substituted heterocyclic group, optionally substituted aryl, or optionally substituted heteroaryl;

$R_3$-$R_7$ and $R_{15}$ are independently H, halo, optionally substituted amino, optionally substituted alkoxy, optionally substituted $C_{1-10}$ alkyl, haloalkyl, alkenyl, alkynyl, hydroxyalkyl, aminoalkyl, carboxyalkyl, nitro, cyano, acylamido, hydroxy, thiol, acyloxy, azido, carboxy, ethylenedioxo, hydroxyacylamido or optionally substituted alkylthiol.

In one or more embodiment, A is N.

In one or more of the foregoing embodiments, $R_1$ and $R_2$ are optionally substituted aryl.

In one or more of the foregoing embodiments, $R_3$-$R_7$ are each independently H, halo, or $C_1$-$C_6$ alkyl.

In one or more of the foregoing embodiments, $R_{15}$ is H or $C_1$-$C_6$ alkyl.

In one or more of the foregoing embodiments, the substituted groups on $R_1$ are selected from any one, two or three of the following groups: halo, $C_1$-$C_6$ alkyl, $C_1$-$C_6$ alkoxy, and halo $C_1$-$C_6$ alkyl.

In one or more of the foregoing embodiments, $R_1$ is selected from: H, $C_1$-$C_8$ alkyl, $C_2$-$C_8$ alkenyl, $C_3$-$C_8$ cycloalkyl, heteroaryl, and aryl which is optionally substituted by 1-4 groups selected from $C_1$-$C_6$ alkyl, $C_1$-$C_6$ alkoxy, and halo $C_1$-$C_6$ alkyl.

In one or more of the foregoing embodiments, $R_1$ is selected from phenyl which is optionally substituted by 1-4 groups selected from halo, $C_1$-$C_6$ alkyl, $C_1$-$C_6$ alkoxy, and halo $C_1$-$C_6$ alkyl; in some embodiments, the number of substituents is 2; in some embodiments, at least one substituent is in the ortho position; in some embodiments, at least one substituent is halo; in some embodiments, the number of substituents on the phenyl is 2, both are located adjacent to each other, and wherein at least one is halo.

In one or more of the foregoing embodiments, $R_1$ is selected from optionally substituted pyridyl, pyrimidyl, thiophenyl, furanyl, pyrrolyl and imidazolyl.

In one or more of the foregoing embodiments, $R_1$ is selected from H, optionally substituted $C_1$-$C_8$ alkyl, $C_3$-$C_5$ cycloalkyl, and $C_2$-$C_8$ alkenyl.

In one or more of the foregoing embodiments, the substituted groups on $R_2$ are selected from any one, two, three or four of the following groups: optionally substituted $C_1$-$C_6$ alkyl, optionally substituted $C_1$-$C_6$ acyl, optionally substituted heterocyclic group, halo, optionally substituted oxy group, nitro, and optionally substituted $C_1$-$C_6$ alkylamino; Preferably, the substituents on these substituted group may be 1-4 groups selected from the following groups: $C_1$-$C_6$ alkyl, $C_1$-$C_6$ acyl, a heterocyclic group optionally substituted by 1-4 of $C_1$-$C_6$ alkyl, H, —$NR_aR_b$ and hydroxy, wherein $R_a$ and $R_b$ are independently H and $C_1$-$C_6$ alkyl; Preferably, the heterocyclic group is selected from piperazinyl, piperidinyl, morpholinyl, and 1,4-diazepan-1-yl.

In one or more of the foregoing embodiments, the substituted groups on $R_2$ are selected from any one, two, three or four of the following groups: optionally substituted piperazinyl, optionally substituted piperazinyl-$C_1$-$C_4$ alkyl, optionally substituted piperidinyl, imidazolyl, optionally substituted 1,4-diazepan-1-yl, $C_1$-$C_6$ alkyl, $C_1$-$C_6$ acyl, optionally substituted morpholinyl, morpholinyl-$C_1$-$C_4$ alkyl, halo, halo $C_1$-$C_6$ alkyl, optionally substituted $C_1$-$C_6$ alkoxy, optionally substituted hydroxy $C_1$-$C_6$ alkyl, optionally substituted amino $C_1$-$C_6$ alkyl, optionally substituted piperidinylamino, optionally substituted $C_1$-$C_6$ alkyl amino, optionally substituted heterocyclic alkyl-O— and nitro; Preferably, the substituents on the optionally substituted group may be 1-4 groups selected from the following groups: $C_1$-$C_6$ alkyl, $C_1$-$C_6$ acyl, halo, —$NR_aR_b$ and $C_1$-$C_6$ alkyl substituted by hydroxy, wherein $R_a$ and $R_b$ are independently H and $C_1$-$C_6$ alkyl.

In one or more of the foregoing embodiments, the optionally substituted piperazinyl is the piperazinlyl which can be substituted by 1, 2 or 3 groups selected from: $C_1$-$C_6$ alkyl, hydroxy $C_1$-$C_6$ alkyl, and $C_1$-$C_6$ acyl.

In one or more of the foregoing embodiments, the piperazine group has at least one substituent at the para-position, and optionally, one or two substituents at the meta-position.

In one or more of the foregoing embodiments, the optionally substituted piperidinyl is the piperidinyl which can be substituted by 1 group selected from $C_1$-$C_6$ alkyl and $C_1$-$C_6$ alkyl amino.

In one or more of the foregoing embodiments, the optionally substituted morpholinyl is the morpholinyl which can be substituted by 1 or 2 groups selected from $C_1$-$C_6$ alkyl.

In one or more of the foregoing embodiments, $R_2$ is selected from optionally substituted phenyl, pyridyl, piperazinyl, tetrahydroisoquinolinyl, 2',3'-dihydro-1'H-spiro[cyclopropane-1,4'-isoquinolin]-7'-yl and 4,5,6,7-tetrahydropyrazolo[1,5-a]pyrazin-2-yl.

In one or more of the foregoing embodiments, $R_2$ is selected from phenyl substituted by piperazinyl which can be optionally substituted, phenyl substituted by pyridinyl which can be optionally substituted, and tetrahydroisoquinolinyl optionally substituted by 1-3 $C_1$-$C_6$ alkyl or halo.

In one or more of the foregoing embodiments, the piperazinyl is optionally substituted by 1-3 groups selected from $C_1$-$C_6$ alkyl, hydroxy $C_1$-$C_6$ alkyl and $C_1$-$C_6$ acyl.

In one or more of the foregoing embodiments, the piperidinyl is optionally substituted by 1 group selected from $C_1$-$C_6$ alkyl and $C_1$-$C_6$ alkyl amino.

In one or more of the foregoing embodiments, $R_4$ and $R_5$ are independently H, $C_1$-$C_6$ alkyl and halo, preferably, both H.

In one or more of the foregoing embodiments, $R_6$ and $R_7$ are independently H, $C_1$-$C_6$ alkyl and halo, preferably, both H.

One group of preferred compounds of the present disclosure are represented by Formula II:

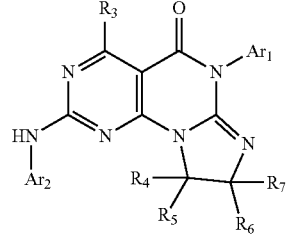

II or pharmaceutically acceptable salts or prodrugs thereof, wherein:

$R_3$-$R_7$ are defined as in Formula I;

$Ar_1$ is H, optionally substituted $C_1$-$C_8$ alkyl, optionally substituted $C_2$-$C_8$ alkenyl, optionally substituted $C_3$-$C_5$ cycloalkyl, optionally substituted aryl, optionally substituted heterocyclic group or optionally substituted heteroaryl; and $Ar_2$ is an optionally substituted carbocyclic group, optionally substituted heterocyclic group, optionally substituted aryl, or optionally substituted heteraryl;

In one or more of the foregoing embodiments, $R_3$-$R_7$ are H.

In one or more of the foregoing embodiments, $Ar_1$ and $Ar_2$ are optionally substituted aryl, more preferably optionally substituted phenyl.

In one or more of the foregoing embodiments, the substituents on $Ar_1$ is selected from any one, two or three groups from the following groups: halo, $C_1$-$C_6$ alkyl, $C_1$-$C_6$ alkoxy and halo $C_1$-$C_6$ alkyl; in some embodiments, the number of substituents is 2; in some embodiments, at least one substituent is in the ortho-position; in some embodiments, at least one substituent is halo; in some embodiments, the number of substituents on the phenyl is 2, both are located adjacent to each other, and wherein at least one is halo.

In one or more of the foregoing embodiments, $Ar_1$ is selected from optionally substituted heteraryl, and aryl optionally substituted by 1-4 substituents selected from halo, $C_1$-$C_6$ alkyl, $C_1$-$C_6$ alkoxy and halo $C_1$-$C_6$ alkyl.

In one or more of the foregoing embodiments, $Ar_1$ is selected from phenyl that is optionally substituted by 1-4 substituents selected from halo, $C_1$-$C_6$ alkyl, $C_1$-$C_6$ alkoxy and halo $C_1$-$C_6$ alkyl. Preferably, in these embodiments, the number of substituents is 2; more preferably, at least one substituent is in the ortho-position; more preferably, at least one substituent is halo.

In one or more of the foregoing embodiments, $Ar_1$ is selected from optionally substituted pyridyl, pyrimidyl, thiophenyl, furanyl, pyrrolyl and imidazolyl.

In one or more of the foregoing embodiments, the substituents on $Ar_2$ is selected from any one, two or three groups from the following groups: optionally substituted $C_1$-$C_6$ alkyl, optionally substituted $C_1$-$C_6$ acyl, optionally substituted heterocyclic group, halo, optionally substituted oxy group, nitro and optionally substituted $C_1$-$C_6$ alkyl amino; preferably, the substituents on the groups which can be optionally substituted may be 1-4 groups selected from the following groups: $C_1$-$C_6$ alkyl, $C_1$-$C_6$ acyl, a heterocyclic group optionally substituted by 1-4 $C_1$-$C_6$ alkyl, halo, —$NR_aR_b$ and hydroxy, wherein $R_a$ and $R_b$ are each independently H and $C_1$-$C_6$ alkyl; preferably, the heterocyclic group is selected from piperazinyl, piperidinyl, morpholinyl, and 1,4-diazepan-1-yl.

In one or more of the foregoing embodiments, the substituents on $Ar_2$ is selected from any one, two, three or four groups from the following groups: optionally substituted piperazinyl, optionally substituted piperazinyl-$C_1$-$C_4$ alkyl, optionally substituted piperidinyl, imidazolyl, optionally substituted 1,4-diazepan-1-yl, $C_1$-$C_6$ alkyl, $C_1$-$C_6$ acyl, optionally substituted morpholinyl, morpholinyl-$C_1$-$C_4$ alkyl, halo, halo $C_1$-$C_6$ alkyl, optionally substituted $C_1$-$C_6$ alkoxy, optionally substituted hydroxy $C_1$-$C_6$ alkyl, optionally substituted amino $C_1$-$C_6$ alkyl, optionally substituted piperidinylamino, optionally substituted $C_1$-$C_6$ alkyl amino, optionally substituted heterocyclic alkyl-O— and nitro; preferably, the substituents on the optionally substituted group may be 1-4 groups selected from the following groups: $C_1$-$C_6$ alkyl, $C_1$-$C_6$ acyl, halo, —$NR_aR_b$ and $C_1$-$C_6$ alkyl substituted by hydroxy, wherein $R_a$ and $R_b$ are each independently H and $C_1$-$C_6$ alkyl.

In one or more of the foregoing embodiments, the optionally substituted piperazinyl is the piperazinlyl which can be substituted by 1, 2 or 3 groups selected from: $C_1$-$C_6$ alkyl, hydroxy $C_1$-$C_6$ alkyl, and $C_1$-$C_6$ acyl.

In one or more of the foregoing embodiments, the piperazinyl has at least one substituent at the para-position, and optionally, one or two substituents at the meta-position.

In one or more of the foregoing embodiments, the optionally substituted piperidinyl is the piperidinyl which can be substituted by 1 group selected from $C_1$-$C_6$ alkyl and $C_1$-$C_6$ alkyl amino.

In one or more of the foregoing embodiments, the optionally substituted morpholinyl is the morpholinyl which can be substituted by 1 or 2 groups selected from $C_1$-$C_6$ alkyl.

In one or more of the foregoing embodiments, $Ar_2$ is selected from optionally substituted phenyl, pyridyl, piperazinyl, tetrahydroisoquinolinyl, 2',3'-dihydro-1'H-spiro[cyclopropane-1,4'-isoquinolin]-7'-yl and 4,5,6,7-tetrahydropyrazolo[1,5-a]pyrazin-2-yl.

In one or more of the foregoing embodiments, $Ar_2$ is selected from phenyl substituted by piperazinyl which can be optionally substituted, phenyl substituted by pyridinyl which can be optionally substituted, and tetrahydroisoquinolinyl optionally substituted by 1-3 $C_1$-$C_6$ alkyl or halo.

In one or more of the foregoing embodiments, the piperazinyl is optionally substituted by 1-3 groups selected from $C_1$-$C_6$ alkyl, hydroxy $C_1$-$C_6$ alkyl and $C_1$-$C_6$ acyl.

In one or more of the foregoing embodiments, the piperidinyl is optionally substituted by 1 group selected from $C_1$-$C_6$ alkyl and $C_1$-$C_6$ alkyl amino.

In one or more of the foregoing embodiments, $R_4$ and $R_5$ are each independently H, $C_1$-$C_6$ alkyl and halo, preferably, both H.

In one or more of the foregoing embodiments, $R_6$ and $R_7$ are each independently H, $C_1$-$C_6$ alkyl and halo, preferably, both H.

In one or more of the foregoing embodiments, $R_1$ or $Ar_1$ is selected from H, $C_1$-$C_6$ alkyl, $C_2$-$C_6$ alkenyl, $C_3$-$C_8$ cycloalkyl, thiazolyl, furyl, pyrrolyl, imidazolyl, pyrimidyl, pyridyl; and phenyl optionally substituted by 1 or 2 groups selected from halo, $C_1$-$C_4$ alkyl, halo $C_1$-$C_4$ alkyl, and $C_1$-$C_4$ alkoxy.

In one or more of the foregoing embodiments, $R_1$ or $Ar_1$ is selected from

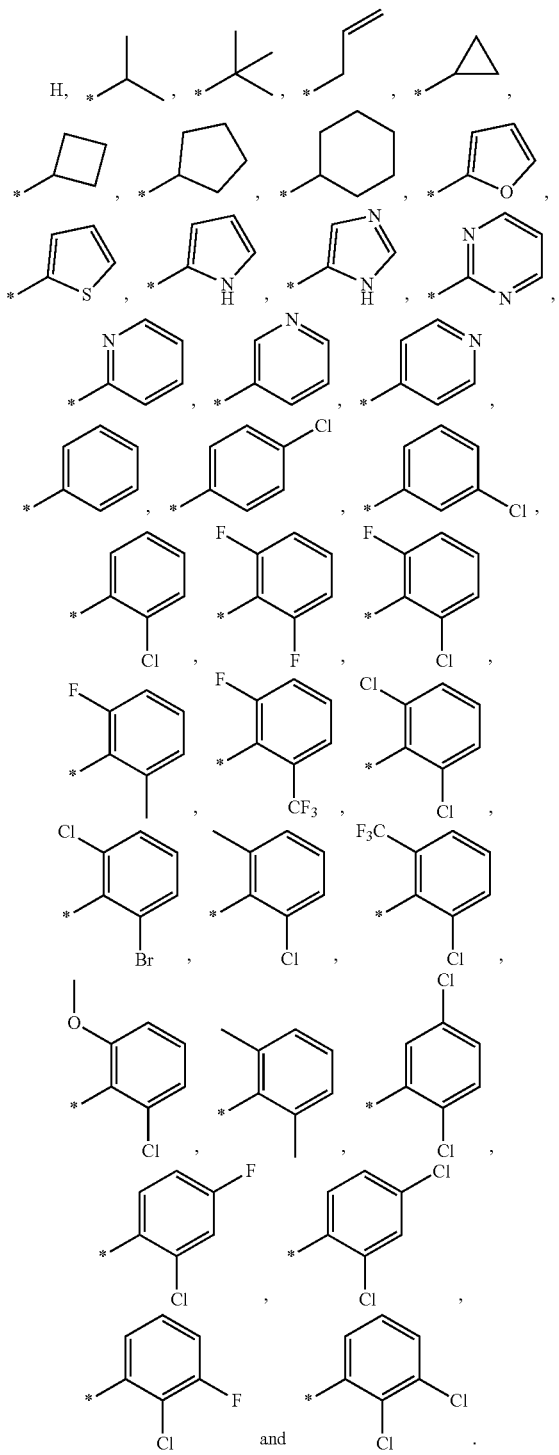

In one or more of the foregoing embodiments, $R_2$ or $Ar_2$ is selected from
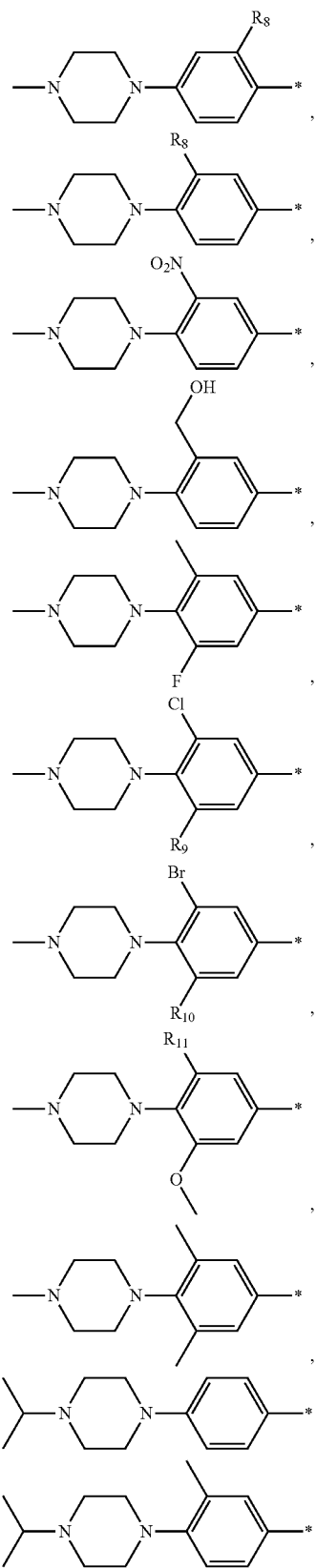
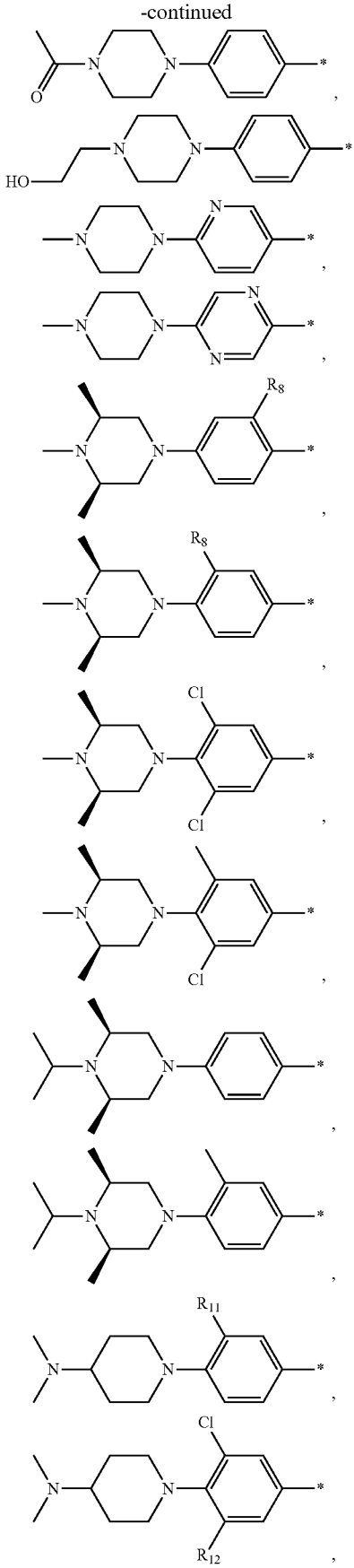

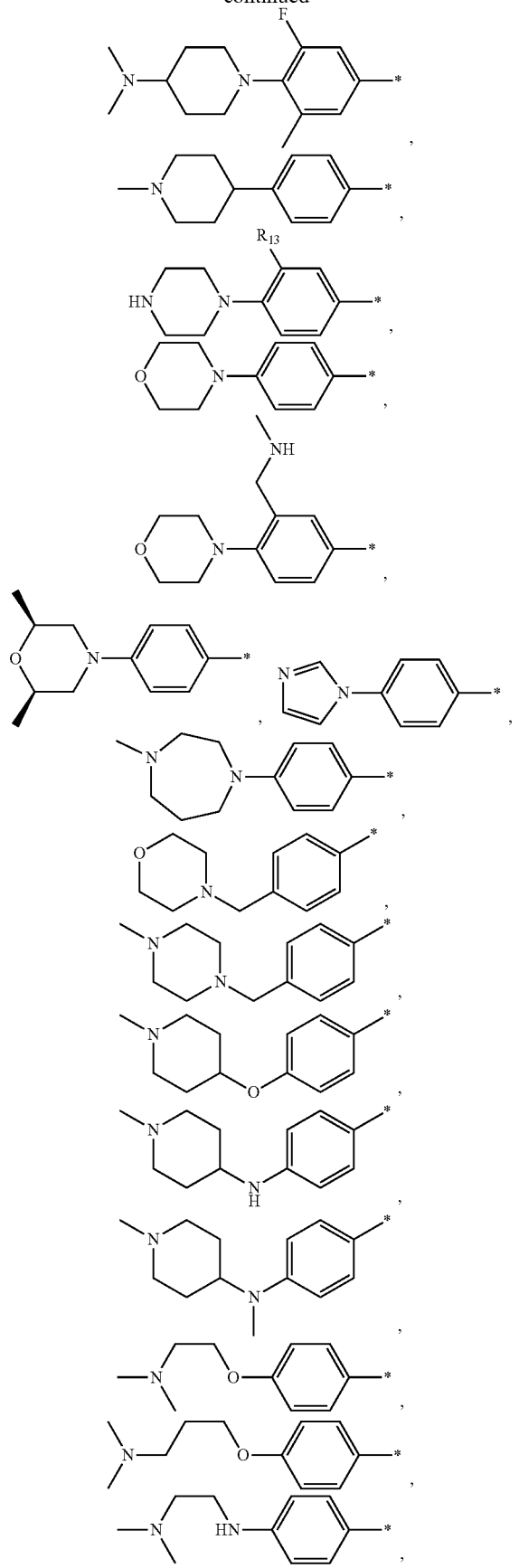

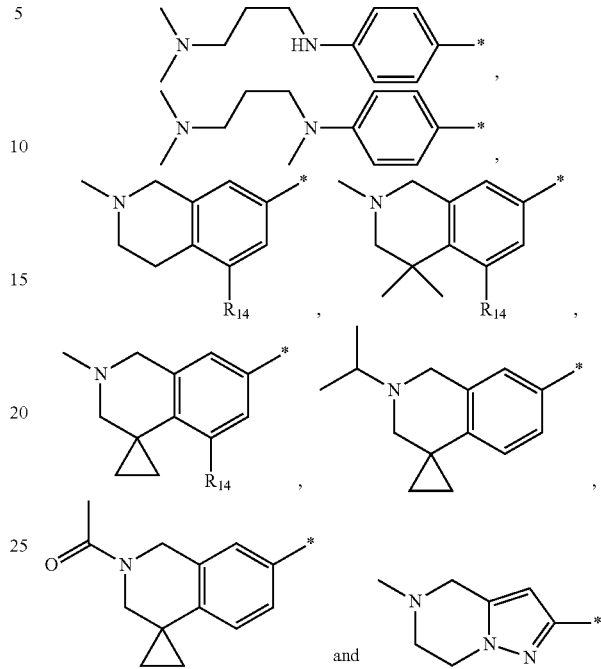

wherein $R_8$ is independently H, halo, $C_1$-$C_4$ alkyl and halo $C_1$-$C_4$ alkyl, preferably H, fluoro, chloro, bromo, methyl and trifluoromethyl; $R_9$ is independently halo, $C_1$-$C_4$ alkyl and halo $C_1$-$C_4$ alkyl, preferably fluoro, chloro, methyl and trifluoromethyl; $R_{10}$ is independently H, halo, $C_1$-$C_4$ alkyl and $C_1$-$C_4$ alkxoy, preferably H, fluoro, chloro, methyl and methoxy; $R_1$ is independently H, halo, and $C_1$-$C_4$ alkyl, preferably H, fluoro, chloro, bromo, and methyl; $R_{12}$ is independently halo and $C_1$-$C_4$ alkoxy, preferably chloro and methoxy; $R_{13}$ is independently H, halo, $C_1$-$C_4$ alkyl, $C_1$-$C_4$ alkxoy, and $C_1$-$C_4$ alkyl substituted by hydroxy, preferably H, chloro, methyl, methoxy and hydroxymethyl; $R_{14}$ is independently H, halo, and $C_1$-$C_4$ alkyl, preferably H, chloro and methyl.

In one or more of the foregoing embodiments, compounds of Formula II have the structures represented by Formula III: wherein,

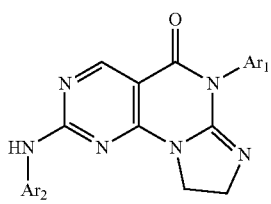

Ar₁ is selected from phenyl substituted by 1 or 2 substituents selected from halo, halo $C_1$-$C_6$ alkyl, $C_1$-$C_6$ alkoxy and $C_1$-$C_6$ alkyl; and Ar₂ is selected from substituted phenyl, of which the substituents are selected from: halo; nitro; $C_1$-$C_6$ alkyl, which is optionally substituted by one piperazinyl or one morpholinyl, 1-3 hydroxy, 1-5 halo, or —NR$_a$R$_b$, and the piperazinyl is optionally substituted by 1-3 substituents selected from C$_1$-C$_4$ alkyl; an oxy group, which is optionally substituted by C$_1$-C$_6$ alkyl or piperidinyl, and the piperidinyl is optionally substituted by 1-3 substituents selected from C$_1$-C$_4$ alkyl; amino, of which one hydrogen is replaced by piperidinyl, and the other hydrogen is not replaced or substituted by C$_1$-C$_4$ alkyl, or 1 or 2 hydrogens are substituted by C$_1$-C$_6$ alkyl, and the piperidinyl is optionally substituted by 1-3 substituents selected from C$_1$-C$_4$ alkyl, the C$_1$-C$_6$ alkyl is optionally substituted by —NR$_a$R$_b$; piperazinyl optionally substituted by 1-3 substituents selected from C$_1$-C$_6$ alkyl, hydroxy C$_1$-C$_6$ alkyl and C$_1$-C$_6$ acyl; piperidinyl optionally substituted by one substituent selected from —NR$_a$R$_b$; 1,4-diazepan-1-yl optionally substituted by 1-3 substituents selected from C$_1$-C$_6$ alkyl; imidazolyl; and morpholinyl optionally substituted by 1-3 C$_1$-C$_6$ alkyl;

tetrahydroisoquinolinyl optionally substituted by 1-3 substituents selected from C$_1$-C$_6$ alkyl and halo;

2',3'-dihydro-1'H-spiro[cyclopropane-1,4'-isoquinolin]-7'-yl optionally substituted by 1-3 substituents selected from C$_1$-C$_6$ alkyl, C$_1$-C$_6$ acyl and halo;

pyridyl optionally substituted by one piperazinyl which is optionally substituted by 1-3 C$_1$-C$_6$ alkyl;

pyrazinyl optionally substituted by one piperazinyl which is optionally substituted by 1-3 C$_1$-C$_6$ alkyl; and 4,5,6,7-tetrahydropyrazolo[1,5-a]pyrazin-2-yl optionally substituted by 1-3 C$_1$-C$_6$ alkyl;

wherein R$_a$ and R$_b$ are each independently H and C$_1$-C$_6$ alkyl.

In one or more of the foregoing embodiments, in Formula III,

Ar$_1$ is selected from phenyl substituted by 2 substituents selected from halo, and C$_1$-C$_6$ alkyl; and Ar$_2$ is selected from substituted phenyl, of which the substituents are selected from: halo, halo C$_1$-C$_6$ alkyl, C$_1$-C$_6$ alkyl, C$_1$-C$_6$ alkoxy, hydroxyl C$_1$-C$_6$ alkyl, NR$_a$R$_b$—C$_1$-C$_6$ alkyl, C$_1$-C$_4$ alkyl substituted by piperazinyl which is optionally substituted by 1-3 C$_1$-C$_4$ alkyl, piperidinyl —O— optionally substituted by 1-3 C$_1$-C$_4$ alkyl, NR$_a$R$_b$—C$_1$-C$_6$ alkoxy, NR$_a$R$_b$—C$_1$-C$_6$ alkyl —NR$_a$—, piperazinyl substituted by 1-3 substituents selected from C$_1$-C$_6$ alkyl, hydroxy C$_1$-C$_6$ alkyl and C$_1$-C$_6$ acyl, piperidinyl substituted by 1 substituent selected from C$_1$-C$_6$ alkyl and —NR$_a$R$_b$, 1,4-diazepan-1-yl optionally substituted by 1-3 C$_1$-C$_6$ alkyl and morpholinyl optionally substituted by 1-3 C$_1$-C$_6$ alkyl; tetrahydroisoquinolinyl substituted by 1-3 substituents selected from C$_1$-C$_6$ alkyl and halo; 2',3'-dihydro-1'H-spiro[cyclopropane-1,4'-isoquinolin]-7'-yl substituted by 1-3 substituents selected from C$_1$-C$_6$ alkyl, C$_1$-C$_4$ acyl and halo; 4,5,6,7-tetrahydropyrazolo[1,5-a]pyrazin-2-yl substituted by 1-3 C$_1$-C$_6$ alkyl; wherein R$_a$ and R$_b$ are independently H and C$_1$-C$_4$ alkyl.

In one or more of the foregoing embodiments, in Formula III, Ar$_1$ is disubstituted phenyl substituted by substituents selected from halo, C$_1$-C$_3$ alkyl, halo C$_1$-C$_3$ alkyl and C$_1$-C$_3$ alkoxy at two meta-positions, preferably, at least one of the two substituents is halo; Ar$_2$ is phenyl substituted by 1, 2 or 3 substituents, and the substituents are selected from halo, halo C$_1$-C$_6$ alkyl, C$_1$-C$_6$ alkyl, C$_1$-C$_6$ alkoxy, hydroxy C$_1$-C$_6$ alkyl, NR$_a$R$_b$—C$_1$-C$_6$ alkyl, C$_1$-C$_4$ alkyl substituted by piperazinyl optionally substituted by 1-3 C$_1$-C$_4$ alkyl, piperidinyl —O— optionally substituted by 1-3 C$_1$-C$_4$ alkyl, NR$_a$R$_b$—C$_1$-C$_6$ alkoxy, NR$_a$R$_b$—C$_1$-C$_6$ alkyl —NR$_a$—, piperazinyl optionally substituted by 1-3 substituents selected from C$_1$-C$_6$ alkyl and hydroxy C$_1$-C$_6$ alkyl, piperidinyl substituted by 1 substituent selected from C$_1$-C$_6$ alkyl and —NR$_a$R$_b$, 1,4-diazepan-1-yl optionally substituted by 1-3 C$_1$-C$_6$ alkyl and morpholinyl optionally substituted by 1-3 C$_1$-C$_6$ alkyl; tetrahydroisoquinolinyl substituted by 1-3 substituents selected from C$_1$-C$_6$ alkyl and halo; and 2',3'-dihydro-1'H-spiro[cyclopropane-1,4'-isoquinolin]-7'-yl substituted by 1-3 substituents selected from C$_1$-C$_6$ alkyl, C$_1$-C$_4$ acyl and halo; wherein R$_a$ and R$_b$ are independently H and C$_1$-C$_4$ alkyl.

In one or more of the foregoing embodiments, in Formula III, preferably, Ar$_1$ is

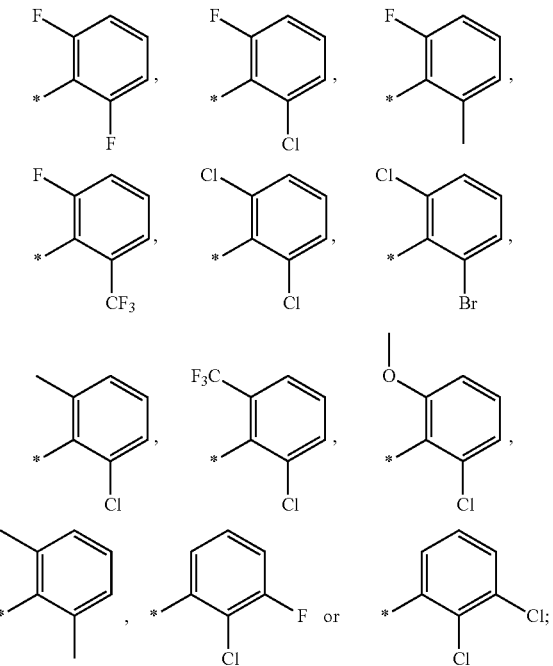

more preferably, Ar$_1$ is

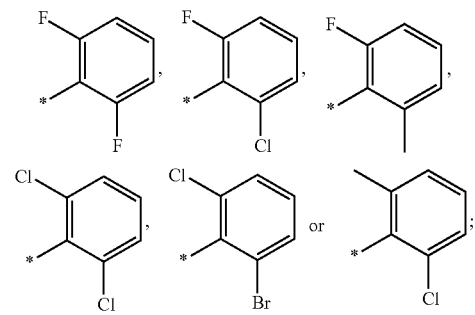

preferably, Ar$_2$ is

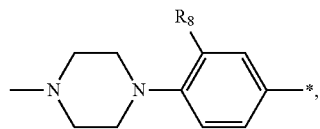

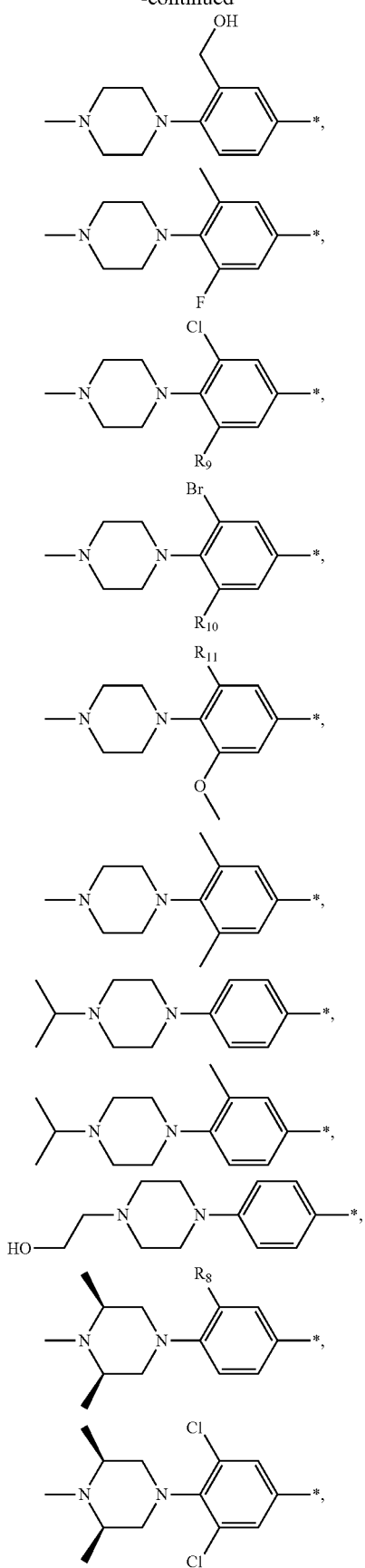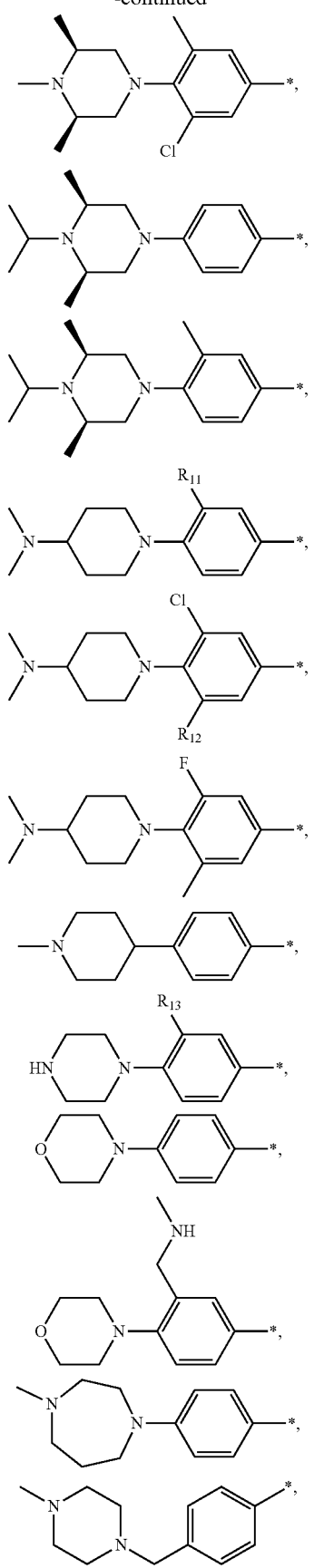

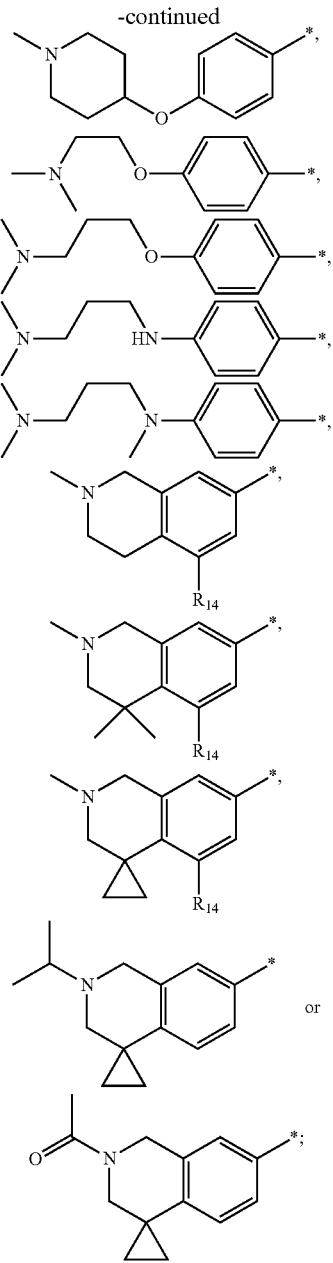

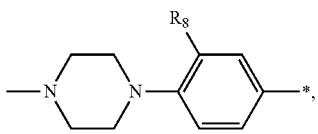

wherein $R_8$ is independently H, fluoro, chloro, bromo, methyl and trifluoromethyl; $R_9$ is independently H, fluoro, chloro, bromo, methyl and trifluoromethyl; $R_{10}$ is independently H, fluoro, chloro, bromo, methyl and methoxy; $R_{11}$ is independently H, fluoro, chloro, bromo, methyl and trifluoromethyl; $R_{12}$ is independently chloro, fluoro, bromo, methyl and methoxy; $R_{13}$ is independently H, chloro, methyl, methoxy and hydroxymethyl; $R_{14}$ is independently H, chloro, bromo and methyl;

more preferably, $Ar_2$ is

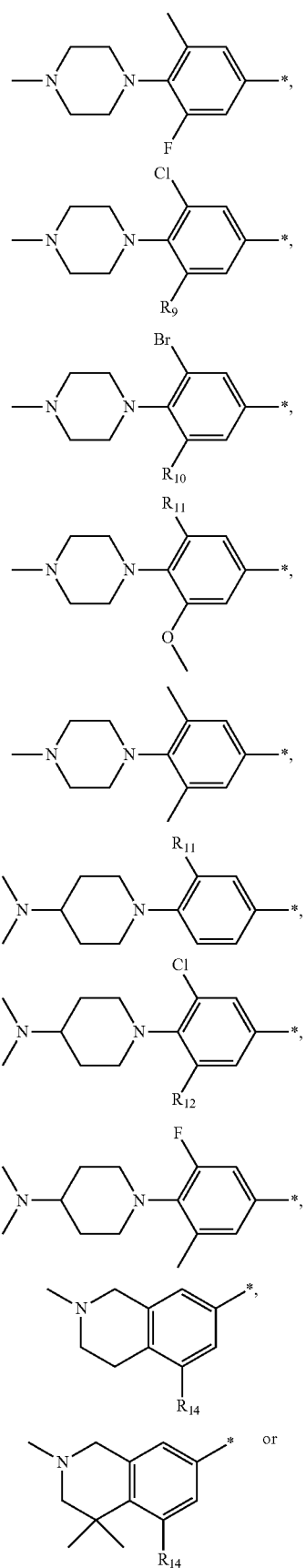

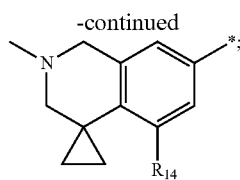

wherein R$_8$ is independently H, fluoro, chloro, bromo and methyl; R$_9$ is independently H, chloro and methyl; R$_{10}$ is independently H, chloro, methyl and methoxy; R$_{11}$ is independently H, fluoro, chloro, bromo and methyl; R$_{12}$ is independently H, chloro, methyl and methoxy; R$_{14}$ is independently H, chloro and methyl.

In one or more of the foregoing embodiments, the compounds do not include the compound of Example 83; in some embodiments, the compounds of Formula I do not include compounds of which R$_1$ is phenyl substituted by two methyl or two alkyl at ortho-position, R$_2$ is phenyl monosubstituted by piperazinyl that is substituted by methyl or alkyl, R$_3$-R$_7$ are H.

In one or more of the foregoing embodiments, preferred compounds of Formula I include, without limitation:

6-(2-Chlorophenyl)-2-((4-(4-methylpiperazin-1-yl)phenyl)amino)-8,9-dihydroimidazo[1,2-a]pyrimido[5,4-e]pyrimidin-5(6H)-one (Example 1);

6-(2-Chloro-6-fluorophenyl)-2-((4-(4-methylpiperazin-1-yl)phenyl)amino)-8,9-dihydroimidazo[1,2-a]pyrimido[5,4-e]pyrimidin-5(6H)-one (Example 2);

4-(2-Chlorophenyl)-8-((4-(4-methylpiperazin-1-yl)phenyl)amino)-2,4-dihydroimidazo[1,2-a]pyrido[3,4-e]pyrimidin-5(1H)-one (Example 3);

6-(2,6-Dichlorophenyl)-2-((4-(4-methylpiperazin-1-yl)phenyl)amino)-8,9-dihydroimidazo[1,2-a]pyrimido[5,4-e]pyrimidin-5(6H)-one (Example 4);

6-(2-Chloro-6-methylphenyl)-2-((4-(4-methylpiperazin-1-yl)phenyl)amino)-8,9-dihydroimidazo[1,2-a]pyrimido[5,4-e]pyrimidin-5(6H)-one (Example 5);

6-(2-Chloro-6-fluorophenyl)-2-((4-(4-isopropylpiperazin-1-yl)phenyl)amino)-8,9-dihydroimidazo[1,2-a]pyrimido[5,4-e]pyrimidin-5(6H)-one (Example 6);

2-((4-(4-Acetylpiperazin-1-yl)phenyl)amino)-6-(2-chloro-6-fluorophenyl)-8,9-dihydroimidazo[1,2-a]pyrimido[5,4-e]pyrimidin-5(6H)-one (Example 7);

6-(2-Chloro-6-fluorophenyl)-2-((2-methyl-1,2,3,4-tetrahydroisoquinolin-7-yl)amino)-8,9-dihydroimidazo[1,2-a]pyrimido[5,4-e]pyrimidin-5(6H)-one (Example 8);

6-(2-Chloro-6-fluorophenyl)-2-((2,4,4-trimethyl-1,2,3,4-tetrahydroisoquinolin-7-yl)amino)-8,9-dihydroimidazo[1,2-a]pyrimido[5,4-e]pyrimidin-5(6H)-one (Example 9);

6-(2-Chloro-6-fluorophenyl)-2-((2'-methyl-2',3'-dihydro-1'H-spiro[cyclopropane-1,4'-isoquinolin]-7'-yl)amino)-8,9-dihydroimidazo[1,2-a]pyrimido[5,4-e]pyrimidin-5(6H)-one (Example 10);

6-(2-Chloro-6-fluorophenyl)-2-((2'-acetyl-2',3'-dihydro-1'H-spiro[cyclopropane-1,4'-isoquinolin]-7'-yl)amino)-8,9-dihydroimidazo[1,2-a]pyrimido[5,4-e]pyrimidin-5(6H)-one (Example 11);

6-(2,6-Dichlorophenyl)-2-((2-methyl-1,2,3,4-tetrahydroisoquinolin-7-yl)amino)-8,9-dihydroimidazo[1,2-a]pyrimido[5,4-e]pyrimidin-5(6H)-one (Example 12);

6-(2,6-Dichlorophenyl)-2-((2,4,4-trimethyl-1,2,3,4-tetrahydroisoquinolin-7-yl)amino)-8,9-dihydroimidazo[1,2-a]pyrimido[5,4-e]pyrimidin-5(6H)-one (Example 13);

6-(2,6-Dichlorophenyl)-2-((2'-methyl-2',3'-dihydro-1'H-spiro[cyclopropane-1,4'-isoquinolin]-7'-yl)amino)-8,9-dihydroimidazo[1,2-a]pyrimido[5,4-e]pyrimidin-5(6H)-one (Example 14);

6-(2,6-Dimethylphenyl)-2-((2-methyl-1,2,3,4-tetrahydroisoquinolin-7-yl)amino)-8,9-dihydroimidazo[1,2-a]pyrimido[5,4-e]pyrimidin-5(6H)-one (Example 15);

6-(2,6-Dimethylphenyl)-2-((2,4,4-trimethyl-1,2,3,4-tetrahydroisoquinolin-7-yl)amino)-8,9-dihydroimidazo[1,2-a]pyrimido[5,4-e]pyrimidin-5(6H)-one (Example 16);

6-(2,6-Dimethylphenyl)-2-((2'-methyl-2',3'-dihydro-1'H-spiro[cyclopropane-1,4'-isoquinolin]-7'-yl)amino)-8,9-dihydroimidazo[1,2-a]pyrimido[5,4-e]pyrimidin-5(6H)-one (Example 17);

6-Isopropyl-2-((4-(4-methylpiperazin-1-yl)phenyl)amino)-8,9-dihydroimidazo[1,2-a]pyrimido[5,4-e]pyrimidin-5(6H)-one (Example 18);

6-(Tert-butyl)-2-((4-(4-methylpiperazin-1-yl)phenyl)amino)-8,9-dihydroimidazo[1,2-a]pyrimido[5,4-e]pyrimidin-5(6H)-one (Example 19);

6-Cyclopropyl-2-((4-(4-methylpiperazin-1-yl)phenyl)amino)-8,9-dihydroimidazo[1,2-a]pyrimido[5,4-e]pyrimidin-5(6H)-one (Example 20);

6-Cyclohexyl-2-((4-(4-methylpiperazin-1-yl)phenyl)amino)-8,9-dihydroimidazo[1,2-a]pyrimido[5,4-e]pyrimidin-5(6H)-one (Example 21);

6-Allyl-2-((4-(4-methylpiperazin-1-yl)phenyl)amino)-8,9-dihydroimidazo[1,2-a]pyrimido[5,4-e]pyrimidin-5(6H)-one (Example 22);

2-((4-(4-Methylpiperazin-1-yl)phenyl)amino)-6-(thiophen-2-yl)-8,9-dihydroimidazo[1,2-a]pyrimido[5,4-e]pyrimidin-5(6H)-one (Example 23);

6-(Furan-2-yl)-2-((4-(4-methylpiperazin-1-yl)phenyl)amino)-8,9-dihydroimidazo[1,2-a]pyrimido[5,4-e]pyrimidin-5(6H)-one (Example 24);

2-((4-(4-Methylpiperazin-1-yl)phenyl)amino)-6-(1H-pyrrol-2-yl)-8,9-dihydroimidazo[1,2-a]pyrimido[5,4-e]pyrimidin-5(6H)-one (Example 25);

6-(1H-Imidazol-5-yl)-2-((4-(4-methylpiperazin-1-yl)phenyl)amino)-8,9-dihydroimidazo[1,2-a]pyrimido[5,4-e]pyrimidin-5(6H)-one (Example 26);

6-(2-Chloro-6-fluorophenyl)-8,8-dimethyl-2-((4-(4-methylpiperazin-1-yl)phenyl)amino)-8,9-dihydroimidazo[1,2-a]pyrimido[5,4-e]pyrimidin-5(6H)-one (Example 27);

6-(2-Chloro-6-fluorophenyl)-8,8-dimethyl-2-((4-(4-methylpiperazin-1-yl)phenyl)amino)-8,9-dihydroimidazo[1,2-a]pyrimido[5,4-e]pyrimidin-5(6H)-one (Example 28);

6-(2-Chloro-6-fluorophenyl)-2-((4-((2S,6R)-2,6-dimethylmorpholino)phenyl)amino)-8,9-dihydroimidazo[1,2-a]pyrimido[5,4-e]pyrimidin-5(6H)-one (Example 32);

6-(2-Chloro-6-fluorophenyl)-2-((4-(morpholinomethyl)phenyl)amino)-8,9-dihydroimidazo[1,2-a]pyrimido[5,4-e]pyrimidin-5(6H)-one (Example 33);

6-(2-Chloro-6-fluorophenyl)-2-((4-((3S,5R)-3,4,5-trimethylpiperazin-1-yl)phenyl)amino)-8,9-dihydroimidazo[1,2-a]pyrimido[5,4-e]pyrimidin-5(6H)-one (Example 34);

6-(2-Chloro-6-fluorophenyl)-2-((4-((3S,5R)-4-isopropyl-3,5-dimethylpiperazin-1-yl)phenyl)amino)-8,9-dihydroimidazo[1,2-a]pyrimido[5,4-e]pyrimidin-5(6H)-one (Example 35);

6-(2-Chloro-6-fluorophenyl)-2-((2-fluoro-4-(4-methylpiperazin-1-yl)phenyl)amino)-8,9-dihydroimidazo[1,2-a]pyrimido[5,4-e]pyrimidin-5(6H)-one (Example 36);

6-(2-Chloro-6-fluorophenyl)-2-((2-fluoro-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 37);

6-(2-Chloro-6-fluorophenyl)-2-((2-chloro-4-(4-methylpiperazin-1-yl)phenyl)amino)-8,9-dihydroimidazo[1,2-a]pyrimido[5,4-e]pyrimidin-5(6H)-one (Example 38);

6-(2-Chloro-6-fluorophenyl)-2-((2-chloro-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 39);

6-(2-Chloro-6-fluorophenyl)-2-((4-(4-methylpiperazin-1-yl)-2-(trifluoromethyl)phenyl)amino)-8,9-dihydroimidazo[1,2-a]pyrimido[5,4-e]pyrimidin-5(6H)-one (Example 40);

6-(2-Chloro-6-fluorophenyl)-2-((2-trifluoromethyl-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 41);

6-(2-Chloro-6-fluorophenyl)-2-((2-methyl-4-(4-methylpiperazin-1-yl)phenyl)amino)-8,9-dihydroimidazo[1,2-a]pyrimido[5,4-e]pyrimidin-5(6H)-one (Example 42);

6-(2-Chloro-6-fluorophenyl)-2-((2-methyl-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 43);

6-(2-Chloro-6-fluorophenyl)-2-((3-fluoro-4-(4-methylpiperazin-1-yl)phenyl)amino)-8,9-dihydroimidazo[1,2-a]pyrimido[5,4-e]pyrimidin-5(6H)-one (Example 44);

6-(2-Chloro-6-fluorophenyl)-2-((3-fluoro-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 45);

6-(2-Chloro-6-fluorophenyl)-2-((3-chloro-4-(4-methylpiperazin-1-yl)phenyl)amino)-8,9-dihydroimidazo[1,2-a]pyrimido[5,4-e]pyrimidin-5(6H)-one (Example 46);

2-((3-Chloro-4-((3S,5R)-3,4,5-trimethylpiperazin-1-yl)phenyl)amino)-6-(2-chloro-6-fluorophenyl)-8,9-dihydroimidazo[1,2-a]pyrimido[5,4-e]pyrimidin-5(6H)-one (Example 47);

6-(2-Chloro-6-fluorophenyl)-2-((4-(4-methylpiperazin-1-yl)-3-(trifluoromethyl)phenyl)amino)-8,9-dihydroimidazo[1,2-a]pyrimido[5,4-e]pyrimidin-5(6H)-one (Example 48);

6-(2-Chloro-6-fluorophenyl)-2-((3-trifluoromethyl-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 49);

6-(2-Chloro-6-fluorophenyl)-2-((3-methyl-4-(4-methylpiperazin-1-yl)phenyl)amino)-8,9-dihydroimidazo[1,2-a]pyrimido[5,4-e]pyrimidin-5(6H)-one (Example 50);

6-(2-Chloro-6-fluorophenyl)-2-((3-methyl-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 51);

6-(2-Chloro-6-fluorophenyl)-2-((4-(4-isopropylpiperazin-1-yl)-3-methylphenyl)amino)-8,9-dihydroimidazo[1,2-a]pyrimido[5,4-e]pyrimidin-5(6H)-one (Example 52);

6-(2-Chloro-6-fluorophenyl)-2-((4-((3S,5R)-4-isopropyl-3,5-dimethylpiperazin-1-yl)-3-methylphenyl)amino)-8,9-dihydroimidazo[1,2-a]pyrimido[5,4-e]pyrimidin-5(6H)-one (Example 53);

6-(2-Chloro-6-fluorophenyl)-2-((3-methoxy-4-(4-methylpiperazin-1-yl)phenyl)amino)-8,9-dihydroimidazo[1,2-a]pyrimido[5,4-e]pyrimidin-5(6H)-one (Example 54);

6-(2-Chloro-6-fluorophenyl)-2-((4-(4-methylpiperazin-1-yl)-3-nitrophenyl)amino)-8,9-dihydroimidazo[1,2-a]pyrimido[5,4-e]pyrimidin-5(6H)-one (Example 55);

6-(2-Chloro-6-fluorophenyl)-2-((3,5-dimethyl-4-(4-methylpiperazin-1-yl)phenyl)amino)-8,9-dihydroimidazo[1,2-a]pyrimido[5,4-e]pyrimidin-5(6H)-one (Example 56);

6-(2-Chloro-6-fluorophenyl)-2-((6-(4-methylpiperazin-1-yl)pyridin-3-yl)amino)-8,9-dihydroimidazo[1,2-a]pyrimido[5,4-e]pyrimidin-5(6H)-one (Example 57);

6-(2-Chloro-6-fluorophenyl)-2-((2'-isopropyl-2',3'-dihydro-1'H-spiro[cyclopropane-1,4'-isoquinolin]-7'-yl)amino)-8,9-dihydroimidazo[1,2-a]pyrimido[5,4-e]pyrimidin-5(6H)-one (Example 58);

6-(2-Chloro-6-fluorophenyl)-2-((5-methyl-4,5,6,7-tetrahydropyrazolo[1,5-a]pyrazin-2-yl)amino)-8,9-dihydroimidazo[1,2-a]pyrimido[5,4-e]pyrimidin-5(6H)-one (Example 59);

6-(2,6-Difluorophenyl)-2-((3-methyl-4-(4-methylpiperazin-1-yl)phenyl)amino)-8,9-dihydroimidazo[1,2-a]pyrimido[5,4-e]pyrimidin-5(6H)-one (Example 60);

6-(2-Fluoro-6-(trifluoromethyl)phenyl)-2-((3-methyl-4-(4-methylpiperazin-1-yl)phenyl)amino)-8,9-dihydroimidazo[1,2-a]pyrimido[5,4-e]pyrimidin-5(6H)-one (Example 61);

6-(2-Fluoro-6-methylphenyl)-2-((3-methyl-4-(4-methylpiperazin-1-yl)phenyl)amino)-8,9-dihydroimidazo[1,2-a]pyrimido[5,4-e]pyrimidin-5(6H)-one (Example 62);

6-(2,6-Dichlorophenyl)-2-((4-(4-isopropylpiperazin-1-yl)phenyl)amino)-8,9-dihydroimidazo[1,2-a]pyrimido[5,4-e]pyrimidin-5(6H)-one (Example 63);

6-(2,6-Dichlorophenyl)-2-((4-((3S,5R)-3,4,5-trimethylpiperazin-1-yl)phenyl)amino)-8,9-dihydroimidazo[1,2-a]pyrimido[5,4-e]pyrimidin-5(6H)-one (Example 64);

6-(2,6-Dichlorophenyl)-2-((4-((3S,5R)-4-isopropyl-3,5-dimethylpiperazin-1-yl)phenyl)amino)-8,9-dihydroimidazo[1,2-a]pyrimido[5,4-e]pyrimidin-5(6H)-one (Example 65);

6-(2,6-Dichlorophenyl)-2-((2-fluoro-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 66);

6-(2,6-Dichlorophenyl)-2-((2-chloro-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 67);

6-(2,6-Dichlorophenyl)-2-((2-trifluoromethyl-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 68);

6-(2,6-Dichlorophenyl)-2-((3-fluoro-4-(4-methylpiperazin-1-yl)phenyl)amino)-8,9-dihydroimidazo[1,2-a]pyrimido[5,4-e]pyrimidin-5(6H)-one (Example 69);

6-(2,6-Dichlorophenyl)-2-((3-fluoro-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 70);

6-(2,6-Dichlorophenyl)-2-((3-chloro-4-(4-methylpiperazin-1-yl)phenyl)amino)-8,9-dihydroimidazo[1,2-a]pyrimido[5,4-e]pyrimidin-5(6H)-one (Example 71);

6-(2,6-Dichlorophenyl)-2-((3-chloro-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 72);

6-(2,6-Dichlorophenyl)-2-((4-(4-methylpiperazin-1-yl)-3-(trifluoromethyl)phenyl)amino)-8,9-dihydroimidazo[1,2-a]pyrimido[5,4-e]pyrimidin-5(6H)-one (Example 73);

6-(2,6-Dichlorophenyl)-2-((3-trifluoromethyl-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 74);

6-(2,6-Dichlorophenyl)-2-((3-methyl-4-(4-methylpiperazin-1-yl)phenyl)amino)-8,9-dihydroimidazo[1,2-a]pyrimido[5,4-e]pyrimidin-5(6H)-one (Example 75);

6-(2,6-Dichlorophenyl)-2-((4-(4-isopropylpiperazin-1-yl)-3-methylphenyl)amino)-8,9-dihydroimidazo[1,2-a]pyrimido[5,4-e]pyrimidin-5(6H)-one (Example 76);

6-(2,6-Dichlorophenyl)-2-((3-methyl-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 77);

6-(2,6-Dichlorophenyl)-2-((4-((3S,5R)-4-isopropyl-3,5-dimethylpiperazin-1-yl)-3-methylphenyl)amino)-8,9-dihydroimidazo[1,2-a]pyrimido[5,4-e]pyrimidin-5(6H)-one (Example 78);

6-(2,6-Dichlorophenyl)-2-((5-methyl-4,5,6,7-tetrahydropyrazolo[1,5-a]pyrazin-2-yl)amino)-8,9-dihydroimidazo[1,2-a]pyrimido[5,4-e]pyrimidin-5(6H)-one (Example 79);

6-(2-Chloro-6-(trifluoromethyl)phenyl)-2-((3-methyl-4-(4-methylpiperazin-1-yl)phenyl)amino)-8,9-dihydroimidazo[1,2-a]pyrimido[5,4-e]pyrimidin-5(6H)-one (Example 80);

6-(2-Chloro-6-methylphenyl)-2-((3-methyl-4-(4-methylpiperazin-1-yl)phenyl)amino)-8,9-dihydroimidazo[1,2-a]pyrimido[5,4-e]pyrimidin-5(6H)-one (Example 81);

6-(2-Chloro-6-methoxyphenyl)-2-((3-methyl-4-(4-methylpiperazin-1-yl)phenyl)amino)-8,9-dihydroimidazo[1,2-a]pyrimido[5,4-e]pyrimidin-5(6H)-one (Example 82);

6-(2,6-Dimethylphenyl)-2-((4-(4-methylpiperazin-1-yl)phenyl)amino)-8,9-dihydroimidazo[1,2-a]pyrimido[5,4-e]pyrimidin-5(6H)-one (Example 83);

6-(2,6-Dimethylphenyl)-2-((4-((3S,5R)-3,4,5-trimethylpiperazin-1-yl)phenyl)amino)-8,9-dihydroimidazo[1,2-a]pyrimido[5,4-e]pyrimidin-5(6H)-one (Example 84);

6-(4-Chlorophenyl)-2-((4-(4-methylpiperazin-1-yl)phenyl)amino)-8,9-dihydroimidazo[1,2-a]pyrimido[5,4-e]pyrimidin-5(6H)-one (Example 85);

6-(3-Chlorophenyl)-2-((4-(4-methylpiperazin-1-yl)phenyl)amino)-8,9-dihydroimidazo[1,2-a]pyrimido[5,4-e]pyrimidin-5(6H)-one (Example 86);

6-(2,4-Dichlorophenyl)-2-((4-(4-methylpiperazin-1-yl)phenyl)amino)-8,9-dihydroimidazo[1,2-a]pyrimido[5,4-e]pyrimidin-5(6H)-one (Example 87);

6-(2-Chloro-4-fluorophenyl)-2-((4-(4-methylpiperazin-1-yl)phenyl)amino)-8,9-dihydroimidazo[1,2-a]pyrimido[5,4-e]pyrimidin-5(6H)-one (Example 88);

6-(2-Chloro-3-fluorophenyl)-2-((4-(4-methylpiperazin-1-yl)phenyl)amino)-8,9-dihydroimidazo[1,2-a]pyrimido[5,4-e]pyrimidin-5(6H)-one (Example 89);

6-(2,5-Dichlorophenyl)-2-((4-(4-methylpiperazin-1-yl)phenyl)amino)-8,9-dihydroimidazo[1,2-a]pyrimido[5,4-e]pyrimidin-5(6H)-one (Example 90);

6-(2,3-Dichlorophenyl)-2-((4-(4-methylpiperazin-1-yl)phenyl)amino)-8,9-dihydroimidazo[1,2-a]pyrimido[5,4-e]pyrimidin-5(6H)-one (Example 91);

6-(Pyrimidin-2-yl)-2-((4-(4-methylpiperazin-1-yl)phenyl)amino)-8,9-dihydroimidazo[1,2-a]pyrimido[5,4-e]pyrimidin-5(6H)-one (Example 92);

2-((4-(4-Methylpiperazin-1-yl)phenyl)amino)-8,9-dihydroimidazo[1,2-a]pyrimido[5,4-e]pyrimidin-5(6H)-one (Example 93);

6-Cyclobutyl-2-((4-(4-methylpiperazin-1-yl)phenyl)amino)-8,9-dihydroimidazo[1,2-a]pyrimido[5,4-e]pyrimidin-5(6H)-one (Example 94);

6-Cyclopentyl-2-((4-(4-methylpiperazin-1-yl)phenyl)amino)-8,9-dihydroimidazo[1,2-a]pyrimido[5,4-e]pyrimidin-5(6H)-one (Example 95);

6-Phenyl-2-((4-(4-methylpiperazin-1-yl)phenyl)amino)-8,9-dihydroimidazo[1,2-a]pyrimido[5,4-e]pyrimidin-5(6H)-one (Example 96);

6-(Pyridin-2-yl)-2-((4-(4-methylpiperazin-1-yl)phenyl)amino)-8,9-dihydroimidazo[1,2-a]pyrimido[5,4-e]pyrimidin-5(6H)-one (Example 97);

6-(Pyridin-3-yl)-2-((4-(4-methylpiperazin-1-yl)phenyl)amino)-8,9-dihydroimidazo[1,2-a]pyrimido[5,4-e]pyrimidin-5(6H)-one (Example 98);

6-(Pyridin-4-yl)-2-((4-(4-methylpiperazin-1-yl)phenyl)amino)-8,9-dihydroimidazo[1,2-a]pyrimido[5,4-e]pyrimidin-5(6H)-one (Example 99);

6-(2,6-Difluorophenyl)-2-((3-chloro-4-(4-methylpiperazin-1-yl)phenyl)amino)-8,9-dihydroimidazo[1,2-a]pyrimido[5,4-e]pyrimidin-5(6H)-one (Example 100);

6-(2,6-Difluorophenyl)-2-((3,5-dimethyl-4-(4-methylpiperazin-1-yl)phenyl)amino)-8,9-dihydroimidazo[1,2-a]pyrimido[5,4-e]pyrimidin-5(6H)-one (Example 101);

6-(2-Chloro-6-fluorophenyl)-2-((4-(1H-imidazol-1-yl)phenyl)amino)-8,9-dihydroimidazo[1,2-a]pyrimido[5,4-e]pyrimidin-5(6H)-one (Example 102);

6-(2-Chloro-6-fluorophenyl)-2-((4-(4-methyl-1,4-diazepan-1-yl)phenyl)amino)-8,9-dihydroimidazo[1,2-a]pyrimido[5,4-e]pyrimidin-5(6H)-one (Example 103);

6-(2-Chloro-6-fluorophenyl)-2-((4-((4-methylpiperazin-1-yl)methyl)phenyl)amino)-8,9-dihydroimidazo[1,2-a]pyrimido[5,4-e]pyrimidin-5(6H)-one (Example 104);

6-(2-Chloro-6-fluorophenyl)-2-((4-(2-(dimethylamino)ethoxy)phenyl)amino)-8,9-dihydroimidazo[1,2-a]pyrimido[5,4-e]pyrimidin-5(6H)-one (Example 105);

6-(2-Chloro-6-fluorophenyl)-2-((4-(3-(dimethylamino)propoxy)phenyl)amino)-8,9-dihydroimidazo[1,2-a]pyrimido[5,4-e]pyrimidin-5(6H)-one (Example 106);

6-(2-Chloro-6-fluorophenyl)-2-((4-((1-methylpiperidin-4-yl)oxy)phenyl)amino)-8,9-dihydroimidazo[1,2-a]pyrimido[5,4-e]pyrimidin-5(6H)-one (Example 107);

6-(2-Chloro-6-fluorophenyl)-2-((4-((2-(dimethylamino)ethyl)amino)phenyl)amino)-8,9-dihydroimidazo[1,2-a]pyrimido[5,4-e]pyrimidin-5(6H)-one (Example 108);

6-(2-Chloro-6-fluorophenyl)-2-((4-((2-(dimethylamino)ethyl)(methyl)amino)phenyl)amino)-8,9-dihydroimidazo[1,2-a]pyrimido[5,4-e]pyrimidin-5(6H)-one (Example 109);

6-(2-Chloro-6-fluorophenyl)-2-((4-((3-(dimethylamino)propyl)amino)phenyl)amino)-8,9-dihydroimidazo[1,2-a]pyrimido[5,4-e]pyrimidin-5(6H)-one (Example 110);

6-(2-Chloro-6-fluorophenyl)-2-((4-((3-(dimethylamino)propyl)(methyl)amino)phenyl)amino)-8,9-dihydroimidazo[1,2-a]pyrimido[5,4-e]pyrimidin-5(6H)-one (Example 111);

6-(2-Chloro-6-fluorophenyl)-2-((4-((1-methylpiperidin-4-yl)amino)phenyl)amino)-8,9-dihydroimidazo[1,2-a]pyrimido[5,4-e]pyrimidin-5(6H)-one (Example 112);

6-(2-Chloro-6-fluorophenyl)-2-((4-(methyl(1-methylpiperidin-4-yl)amino)phenyl)amino)-8,9-dihydroimidazo[1,2-a]pyrimido[5,4-e]pyrimidin-5(6H)-one (Example 113);

6-(2-Chloro-6-fluorophenyl)-2-((4-(1-methylpiperidin-4-yl)phenyl)amino)-8,9-dihydroimidazo[1,2-a]pyrimido[5,4-e]pyrimidin-5(6H)-one (Example 114);

6-(2-Chloro-6-fluorophenyl)-2-((4-(4-(dimethylamino)piperidin-1-yl)phenyl)amino)-8,9-dihydroimidazo[1,2-a]pyrimido[5,4-e]pyrimidin-5(6H)-one (Example 115);

6-(2-Chloro-6-fluorophenyl)-2-((4-(4-(dimethylamino)piperidin-1-yl)-3-fluorophenyl)amino)-8,9-dihydroimidazo[1,2-a]pyrimido[5,4-e]pyrimidin-5(6H)-one (Example 116);

6-(2-Chloro-6-fluorophenyl)-2-((3-chloro-4-(4-(dimethylamino)piperidin-1-yl)phenyl)amino)-8,9-dihydroimidazo[1,2-a]pyrimido[5,4-e]pyrimidin-5(6H)-one (Example 117);

6-(2-Chloro-6-fluorophenyl)-2-((3-bromo-4-(4-(dimethylamino)piperidin-1-yl)phenyl)amino)-8,9-dihydroimidazo[1,2-a]pyrimido[5,4-e]pyrimidin-5(6H)-one (Example 118);

6-(2-Chloro-6-fluorophenyl)-2-((4-(4-(dimethylamino)piperidin-1-yl)-3-methylphenyl)amino)-8,9-dihydroimidazo[1,2-a]pyrimido[5,4-e]pyrimidin-5(6H)-one (Example 119);

6-(2-Chloro-6-fluorophenyl)-2-((3-fluoro-5-methyl-4-(4-(dimethylamino)piperidin-1-yl)phenyl)amino)-8,9-dihydroimidazo[1,2-a]pyrimido[5,4-e]pyrimidin-5(6H)-one (Example 120);

6-(2-Chloro-6-fluorophenyl)-2-((5-(4-methylpiperazin-1-yl)pyrazin-2-yl)amino)-8,9-dihydroimidazo[1,2-a]pyrimido[5,4-e]pyrimidin-5(6H)-one (Example 121);

6-(2-Chloro-6-fluorophenyl)-2-((3,5-dichloro-4-(4-methylpiperazin-1-yl)phenyl)amino)-8,9-dihydroimidazo[1,2-a]pyrimido[5,4-e]pyrimidin-5(6H)-one (Example 122);

6-(2-Chloro-6-fluorophenyl)-2-((3-fluoro-5-methyl-4-(4-methylpiperazin-1-yl)phenyl)amino)-8,9-dihydroimidazo[1,2-a]pyrimido[5,4-e]pyrimidin-5(6H)-one (Example 123);

6-(2-Chloro-6-fluorophenyl)-2-((3-fluoro-5-methoxy-4-(4-methylpiperazin-1-yl)phenyl)amino)-8,9-dihydroimidazo[1,2-a]pyrimido[5,4-e]pyrimidin-5(6H)-one (Example 124);

6-(2-Chloro-6-fluorophenyl)-2-((3-chloro-5-methyl-4-(4-methylpiperazin-1-yl)phenyl)amino)-8,9-dihydroimidazo[1,2-a]pyrimido[5,4-e]pyrimidin-5(6H)-one (Example 125);

6-(2-Chloro-6-fluorophenyl)-2-((3-chloro-5-methoxy-4-(4-methylpiperazin-1-yl)phenyl)amino)-8,9-dihydroimidazo[1,2-a]pyrimido[5,4-e]pyrimidin-5(6H)-one (Example 126);

6-(2-Chloro-6-fluorophenyl)-2-((3-bromo-5-methoxy-4-(4-methylpiperazin-1-yl)phenyl)amino)-8,9-dihydroimidazo[1,2-a]pyrimido[5,4-e]pyrimidin-5(6H)-one (Example 127);

6-(2-Chloro-6-fluorophenyl)-2-((3-methyl-4-(4-methylpiperazin-1-yl)-5-(trifluoromethyl)phenyl)amino)-8,9-dihydroimidazo[1,2-a]pyrimido[5,4-e]pyrimidin-5(6H)-one (Example 128);

6-(2-Chloro-6-fluorophenyl)-2-((3-methoxy-5-methyl-4-(4-methylpiperazin-1-yl)phenyl)amino)-8,9-dihydroimidazo[1,2-a]pyrimido[5,4-e]pyrimidin-5(6H)-one (Example 129);

6-(2,6-Dichlorophenyl)-2-((5-chloro-2-methyl-1,2,3,4-tetrahydroisoquinolin-7-yl)amino)-8,9-dihydroimidazo[1,2-a]pyrimido[5,4-e]pyrimidin-5(6H)-one (Example 130);

6-(2,6-Dichlorophenyl)-2-((2,5-dimethyl-1,2,3,4-tetrahydroisoquinolin-7-yl)amino)-8,9-dihydroimidazo[1,2-a]pyrimido[5,4-e]pyrimidin-5(6H)-one (Example 131);

6-(2,6-Dichlorophenyl)-2-((5-chloro-2,4,4-trimethyl-1,2,3,4-tetrahydroisoquinolin-7-yl)amino)-8,9-dihydroimidazo[1,2-a]pyrimido[5,4-e]pyrimidin-5(6H)-one (Example 132);

6-(2,6-Dichlorophenyl)-2-((2,4,4,5-tetramethyl-1,2,3,4-tetrahydroisoquinolin-7-yl)amino)-8,9-dihydroimidazo[1,2-a]pyrimido[5,4-e]pyrimidin-5(6H)-one (Example 133);

6-(2,6-Dichlorophenyl)-2-((5'-chloro-2'-methyl-2',3'-dihydro-1'H-spiro[cyclopropane-1,4'-isoquinolin]-7'-yl)amino)-8,9-dihydroimidazo[1,2-a]pyrimido[5,4-e]pyrimidin-5(6H)-one (Example 134);

6-(2,6-Dichlorophenyl)-2-((2',5'-dimethyl-2',3'-dihydro-1'H-spiro[cyclopropane-1,4'-isoquinolin]-7'-yl)amino)-8,9-dihydroimidazo[1,2-a]pyrimido[5,4-e]pyrimidin-5(6H)-one (Example 135);

6-(2,6-Dichlorophenyl)-2-((3,5-dichloro-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 136);

6-(2,6-Dichlorophenyl)-2-((3-chloro-5-methyl-4-((3S,5R)-3,4,5-trimethylpiperazin-1-yl)phenyl)amino)-8,9-dihydroimidazo[1,2-a]pyrimido[5,4-e]pyrimidin-5(6H)-one (Example 137);

6-(2,6-Dichlorophenyl)-2-((4-(4-(dimethylamino)piperidin-1-yl)phenyl)amino)-8,9-dihydroimidazo[1,2-a]pyrimido[5,4-e]pyrimidin-5(6H)-one (Example 138);

6-(2,6-Dichlorophenyl)-2-((3-chloro-4-(4-(dimethylamino)piperidin-1-yl)phenyl)amino)-8,9-dihydroimidazo[1,2-a]pyrimido[5,4-e]pyrimidin-5(6H)-one (Example 139);

6-(2,6-Dichlorophenyl)-2-((3-bromo-4-(4-(dimethylamino)piperidin-1-yl)phenyl)amino)-8,9-dihydroimidazo[1,2-a]pyrimido[5,4-e]pyrimidin-5(6H)-one (Example 140);

6-(2,6-Dichlorophenyl)-2-((4-(4-(dimethylamino)piperidin-1-yl)-3-methylphenyl)amino)-8,9-dihydroimidazo[1,2-a]pyrimido[5,4-e]pyrimidin-5(6H)-one (Example 141);

6-(2,6-Dichlorophenyl)-2-((3,5-dichloro-4-(4-(dimethylamino)piperidin-1-yl)phenyl)amino)-8,9-dihydroimidazo[1,2-a]pyrimido[5,4-e]pyrimidin-5(6H)-one (Example 142);

6-(2,6-Dichlorophenyl)-2-((4-(4-(dimethylamino)piperidin-1-yl)-3-fluoro-5-methylphenyl)amino)-8,9-dihydroimidazo[1,2-a]pyrimido[5,4-e]pyrimidin-5(6H)-one (Example 143);

6-(2,6-Dichlorophenyl)-2-((3-chloro-4-(4-(dimethylamino)piperidin-1-yl)-5-methoxyphenyl)amino)-8,9-dihydroimidazo[1,2-a]pyrimido[5,4-e]pyrimidin-5(6H)-one (Example 144);

6-(2,6-Dichlorophenyl)-2-((3-bromo-4-(4-methylpiperazin-1-yl)phenyl)amino)-8,9-dihydroimidazo[1,2-a]pyrimido[5,4-e]pyrimidin-5(6H)-one (Example 145);

6-(2,6-Dichlorophenyl)-2-((3-methoxy-4-(4-methylpiperazin-1-yl)phenyl)amino)-8,9-dihydroimidazo[1,2-a]pyrimido[5,4-e]pyrimidin-5(6H)-one (Example 146);

6-(2,6-Dichlorophenyl)-2-((3-chloro-5-fluoro-4-(4-methylpiperazin-1-yl)phenyl)amino)-8,9-dihydroimidazo[1,2-a]pyrimido[5,4-e]pyrimidin-5(6H)-one (Example 147);

6-(2,6-Dichlorophenyl)-2-((3-fluoro-5-methyl-4-(4-methylpiperazin-1-yl)phenyl)amino)-8,9-dihydroimidazo[1,2-a]pyrimido[5,4-e]pyrimidin-5(6H)-one (Example 148);

6-(2,6-Dichlorophenyl)-2-((3-fluoro-5-methoxy-4-(4-methylpiperazin-1-yl)phenyl)amino)-8,9-dihydroimidazo[1,2-a]pyrimido[5,4-e]pyrimidin-5(6H)-one (Example 149);

6-(2,6-Dichlorophenyl)-2-((3,5-dichloro-4-(4-methylpiperazin-1-yl)phenyl)amino)-8,9-dihydroimidazo[1,2-a]pyrimido[5,4-e]pyrimidin-5(6H)-one (Example 150);

6-(2,6-Dichlorophenyl)-2-((3-chloro-5-methyl-4-(4-methylpiperazin-1-yl)phenyl)amino)-8,9-dihydroimidazo[1,2-a]pyrimido[5,4-e]pyrimidin-5(6H)-one (Example 151);

6-(2,6-Dichlorophenyl)-2-((3-chloro-4-(4-methylpiperazin-1-yl)-5-(trifluoromethyl)phenyl)amino)-8,9-dihydroimidazo[1,2-a]pyrimido[5,4-e]pyrimidin-5(6H)-one (Example 152);

6-(2,6-Dichlorophenyl)-2-((3-chloro-5-methoxy-4-(4-methylpiperazin-1-yl)phenyl)amino)-8,9-dihydroimidazo[1,2-a]pyrimido[5,4-e]pyrimidin-5(6H)-one (Example 153);

6-(2,6-Dichlorophenyl)-2-((3-bromo-5-fluoro-4-(4-methylpiperazin-1-yl)phenyl)amino)-8,9-dihydroimidazo[1,2-a]pyrimido[5,4-e]pyrimidin-5(6H)-one (Example 154);

6-(2,6-Dichlorophenyl)-2-((3-bromo-5-chloro-4-(4-methylpiperazin-1-yl)phenyl)amino)-8,9-dihydroimidazo[1,2-a]pyrimido[5,4-e]pyrimidin-5(6H)-one (Example 155);

6-(2,6-Dichlorophenyl)-2-((3-bromo-5-methyl-4-(4-methylpiperazin-1-yl)phenyl)amino)-8,9-dihydroimidazo[1,2-a]pyrimido[5,4-e]pyrimidin-5(6H)-one (Example 156);

6-(2,6-Dichlorophenyl)-2-((3-bromo-5-methoxy-4-(4-methylpiperazin-1-yl)phenyl)amino)-8,9-dihydroimidazo[1,2-a]pyrimido[5,4-e]pyrimidin-5(6H)-one (Example 157);

6-(2,6-Dichlorophenyl)-2-((3,5-dimethyl-4-(4-methylpiperazin-1-yl)phenyl)amino)-8,9-dihydroimidazo[1,2-a]pyrimido[5,4-e]pyrimidin-5(6H)-one (Example 158);

6-(2,6-Dichlorophenyl)-2-((3-methoxy-5-methyl-4-(4-methylpiperazin-1-yl)phenyl)amino)-8,9-dihydroimidazo[1,2-a]pyrimido[5,4-e]pyrimidin-5(6H)-one (Example 159);

6-(2-Bromo-6-chlorophenyl)-2-((4-(4-(dimethylamino)piperidin-1-yl)-3-fluoro-5-methylphenyl)amino)-8,9-dihydroimidazo[1,2-a]pyrimido[5,4-e]pyrimidin-5(6H)-one (Example 160);

6-(2-Bromo-6-chlorophenyl)-2-((3-chloro-4-(4-methylpiperazin-1-yl)phenyl)amino)-8,9-dihydroimidazo[1,2-a]pyrimido[5,4-e]pyrimidin-5(6H)-one (Example 161);

6-(2-Bromo-6-chlorophenyl)-2-((3-bromo-4-(4-methylpiperazin-1-yl)phenyl)amino)-8,9-dihydroimidazo[1,2-a]pyrimido[5,4-e]pyrimidin-5(6H)-one (Example 162);

6-(2-Bromo-6-chlorophenyl)-2-((3-methyl-4-(4-methylpiperazin-1-yl)phenyl)amino)-8,9-dihydroimidazo[1,2-a]pyrimido[5,4-e]pyrimidin-5(6H)-one (Example 163);

6-(2-Bromo-6-chlorophenyl)-2-((3,5-dichloro-4-(4-methylpiperazin-1-yl)phenyl)amino)-8,9-dihydroimidazo[1,2-a]pyrimido[5,4-e]pyrimidin-5(6H)-one (Example 164);

6-(2-Bromo-6-chlorophenyl)-2-((3-fluoro-5-methyl-4-(4-methylpiperazin-1-yl)phenyl)amino)-8,9-dihydroimidazo[1,2-a]pyrimido[5,4-e]pyrimidin-5(6H)-one (Example 165);

6-(2-Bromo-6-chlorophenyl)-2-((3-chloro-5-methyl-4-(4-methylpiperazin-1-yl)phenyl)amino)-8,9-dihydroimidazo[1,2-a]pyrimido[5,4-e]pyrimidin-5(6H)-one (Example 166);

6-(2-Bromo-6-chlorophenyl)-2-((3-bromo-5-methyl-4-(4-methylpiperazin-1-yl)phenyl)amino)-8,9-dihydroimidazo[1,2-a]pyrimido[5,4-e]pyrimidin-5(6H)-one (Example 167);

6-(2-Fluoro-6-methylphenyl)-2-((3-chloro-4-(4-methylpiperazin-1-yl)phenyl)amino)-8,9-dihydroimidazo[1,2-a]pyrimido[5,4-e]pyrimidin-5(6H)-one (Example 168);

6-(2-Fluoro-6-methylphenyl)-2-((3,5-dimethyl-4-(4-methylpiperazin-1-yl)phenyl)amino)-8,9-dihydroimidazo[1,2-a]pyrimido[5,4-e]pyrimidin-5(6H)-one (Example 169);

6-(2-Chloro-6-methylphenyl)-2-((4-(4-(dimethylamino)piperidin-1-yl)-3-fluoro-5-methylphenyl)amino)-8,9-dihydroimidazo[1,2-a]pyrimido[5,4-e]pyrimidin-5(6H)-one (Example 170);

6-(2-Chloro-6-methylphenyl)-2-((3-chloro-4-(4-methylpiperazin-1-yl)phenyl)amino)-8,9-dihydroimidazo[1,2-a]pyrimido[5,4-e]pyrimidin-5(6H)-one (Example 171);

6-(2-Chloro-6-methylphenyl)-2-((3,5-dichloro-4-(4-methylpiperazin-1-yl)phenyl)amino)-8,9-dihydroimidazo[1,2-a]pyrimido[5,4-e]pyrimidin-5(6H)-one (Example 172);

6-(2-Chloro-6-methylphenyl)-2-((3-chloro-5-methyl-4-(4-methylpiperazin-1-yl)phenyl)amino)-8,9-dihydroimidazo[1,2-a]pyrimido[5,4-e]pyrimidin-5(6H)-one (Example 173);

6-(2-Chloro-6-methylphenyl)-2-((3,5-dimethyl-4-(4-methylpiperazin-1-yl)phenyl)amino)-8,9-dihydroimidazo[1,2-a]pyrimido[5,4-e]pyrimidin-5(6H)-one (Example 174);

6-(2,6-Dichlorophenyl)-2-((4-(piperazin-1-yl)phenyl)amino)-8,9-dihydroimidazo[1,2-a]pyrimido[5,4-e]pyrimidin-5(6H)-one (Example 175);

6-(2,6-Dichlorophenyl)-2-((3-chloro-4-(piperazin-1-yl)phenyl)amino)-8,9-dihydroimidazo[1,2-a]pyrimido[5,4-e]pyrimidin-5(6H)-one (Example 176);

6-(2,6-Dichlorophenyl)-2-((3-methyl-4-(piperazin-1-yl)phenyl)amino)-8,9-dihydroimidazo[1,2-a]pyrimido[5,4-e]pyrimidin-5(6H)-one (Example 177);

6-(2,6-Dichlorophenyl)-2-((3-methoxy-4-(piperazin-1-yl)phenyl)amino)-8,9-dihydroimidazo[1,2-a]pyrimido[5,4-e]pyrimidin-5(6H)-one (Example 178);

6-(2-Chloro-6-fluorophenyl)-2-((3-(hydroxymethyl)-4-(piperazin-1-yl)phenyl)amino)-8,9-dihydroimidazo[1,2-a]pyrimido[5,4-e]pyrimidin-5(6H)-one (Example 179);

6-(2,6-Dichlorophenyl)-2-((3-(hydroxymethyl)-4-(piperazin-1-yl)phenyl)amino)-8,9-dihydroimidazo[1,2-a]pyrimido[5,4-e]pyrimidin-5(6H)-one (Example 180);

6-(2,6-Dichlorophenyl)-2-((3-(hydroxymethyl)-4-(4-methylpiperazin-1-yl)phenyl)amino)-8,9-dihydroimidazo[1,2-a]pyrimido[5,4-e]pyrimidin-5(6H)-one (Example 181);

6-(2,6-Dichlorophenyl)-2-((4-(4-(2-hydroxyethyl)piperazin-1-yl)phenyl)amino)-8,9-dihydroimidazo[1,2-a]pyrimido[5,4-e]pyrimidin-5(6H)-one (Example 182);

6-(2,6-Dichlorophenyl)-2-((4-morpholinophenyl)amino)-8,9-dihydroimidazo[1,2-a]pyrimido[5,4-e]pyrimidin-5(6H)-one (Example 183);

6-(2,6-Dichlorophenyl)-2-((3-((methylamino)methyl)-4-morpholinophenyl)amino)-8,9-dihydroimidazo[1,2-a]pyrimido[5,4-e]pyrimidin-5(6H)-one (Example 184);

6-(2-Bromo-6-chlorophenyl)-2-((3-chloro-4-(4-(dimethylamino)piperidin-1-yl)phenyl)amino)-8,9-dihydroimidazo[1,2-a]pyrimido[5,4-e]pyrimidin-5(6H)-one (Example 185);

6-(2,6-Dichlorophenyl)-2-((3-chloro-4-(4-methylpiperazin-1-yl)phenyl)amino)-8,9-dihydroimidazo[1,2-a]pyrimido[5,4-e]pyrimidin-5(6H)-one dihydrochloride (Example 186);

and pharmaceutically acceptable salts or prodrugs thereof.

The term "alkyl" as employed herein by itself or as part of another group refers to both straight and branched chain radicals of up to ten carbons. Useful alkyl groups include straight-chained and branched $C_{1-10}$ alkyl groups, more preferably $C_{1-6}$ alkyl groups. In some embodiments, alkyl is $C_{1-4}$ alkyl. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "alkenyl" as employed herein means a straight or branched chain radical of 2-10 carbon atoms, unless the chain length is limited thereto, including at least one double bond between two of the carbon atoms in the chain; preferred $C_2$-$C_6$ alkenyl. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain; preferred $C_2$-$C_6$ alkynyl. Typical alkynyl groups include ethynyl, 1-propynyl, 1-methyl-2-propynyl, 2-propynyl, 1-butynyl and 2-butynyl.

Useful alkoxy groups include oxygen substituted by $C_{1-10}$ alkyl groups, preferred $C_1$-$C_6$ alkyl or $C_1$-$C_4$ alkyl, mentioned above, for example, methoxy, ethoxy, etc. The alkyl in the alkoxy group may be optionally substituted. Alkoxy substituents include, without limitation, halo, morpholino, amino including alkylamino and dialkylamino, and carboxy including esters thereof.

Useful alkylthio groups include sulfur substituted by $C_{1-10}$ alkyl groups, preferred $C_1$-$C_6$ alkyl, mentioned above.

The alkyl in the alkylthio group may be optionally substituted. Also included are the sulfoxides and sulfones of such alkylthio groups.

Useful amino and optionally substituted amino groups include —$NH_2$, —NHR' and —NR'R", wherein R' and R" are optionally substituted $C_{1-10}$ alkyl, cycloalkyl, aryl, heteroaryl, or amino; or R' and R" are combined with the N to form a 5-8 membered heterocyclic ring structure, such as a piperidine; or R' and R" are combined with the N and an additional N or O atom to form a 5-8 membered heterocyclic ring, such as a piperazine. The alkyl and heterocyclic ring are optionally substituted.

Except as otherwise noted, the groups as described herein, such as alkyl, alkoxy, alkylthio, alkenyl, alkynyl, cycloalkyl, carbonyl, carbocyclic and heterocyclic groups, aryl, arylalkyl, arylalkenyl, arylalkynyl and heteroaryl and heteroarylalkyl groups, may be optionally substituted by one or more (such as 1, 2, 3, or 4) substituents selected from the group consisting of halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_1$-$C_6$ alkyl, $C_1$-$C_6$ acyl, $C_6$-$C_{10}$ aryl, $C_3$-$C_5$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic and heteroaryl, methylenedioxy, $C_1$-$C_6$ haloalkyl, $C_6$-$C_{10}$ aryl($C_1$-$C_6$)alkyl, $C_1$-$C_6$ hydroxyalkyl, ureido, thiol, azido, carbonyl, di($C_{1-10}$ alkyl)amino, alkylsulfonyl, aminosulfonyl, dialkylaminosulfonyl, and alkylsulfiniyl, and the like. The substituent itself may also be optionally substituted.

Except as otherwise noted, when substituted, preferably, substituents on the alkyl, alkoxy, alkylthio, alkenyl, alkynyl, cycloalkyl, carbonyl, carbocyclic and heterocyclic groups may be one or more (such as 1, 2, 3, or 4) groups selected from the group consisting of halo, hydroxy, carboxyl, amino, nitro, cyano, $C_1$-$C_6$ acylamino, $C_1$-$C_6$ acyl, $C_1$-$C_6$ acyloxy, $C_1$-$C_6$ alkoxy, aryloxy, alkylthio, $C_6$-$C_{10}$ aryl, $C_3$-$C_8$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic and heteroaryl.

Except as otherwise noted, when substituted, substituents on the aryl, arylalkyl, arylalkenyl, arylalkynyl, heteroaryl and heteroarylalkyl groups may be one or more (such as 1, 2, 3, or 4) groups selected from the group consisting of halo, methylenedioxy, $C_1$-$C_6$ haloalkyl, $C_6$-$C_{10}$ aryl, $C_3$-$C_8$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, ureido, cyano, $C_1$-$C_6$ acylamino, hydroxy, thiol, $C_1$-$C_6$ acyloxy, azido, $C_1$-$C_6$ alkoxy, carbonyl, carboxy, di($C_1$-$C_{10}$ alkyl)amino, alkylsulfonyl, aminosulfonyl, dialkylaminosulfonyl, and alkylsulfiniyl.

It should be understood that in each embodiment, when the substituent is heterocyclic, aryl or heteraryl, the number of heterocyclic, aryl or heteraryl substituents is usually 1.

The term "aryl" as employed herein by itself or as part of another group refers to monocyclic, bicyclic or tricyclic aromatic groups containing from 6 to 14 carbons in the ring portion.

Useful aryl groups include $C_6$-$C_{14}$ aryl, preferably $C_6$-$C_{10}$ aryl. Typical $C_6$-$C_{14}$ aryl groups include phenyl, naphthyl, phenanthrenyl, anthracenyl, indenyl, azulenyl, biphenyl, biphenylenyl and fluorenyl groups.

The term "carbocycle" as employed herein include cycloalkyl and partially saturated carbocyclic groups. Useful cycloalkyl groups are $C_3$-$C_8$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluoro, chloro, bromo and iodo.

The term "arylalkyl" is used herein to mean any of the above-mentioned $C_1$-$C_{10}$ alkyl groups substituted by any of the above-mentioned $C_6$-$C_{14}$ aryl groups. Preferably the arylalkyl group is benzyl, phenethyl or naphthylmethyl.

The term "arylalkenyl" is used herein to mean any of the above-mentioned $C_2$-$C_{10}$ alkenyl groups substituted by any of the above-mentioned $C_6$-$C_{14}$ aryl groups.

The term "arylalkynyl" is used herein to mean any of the above-mentioned $C_2$-$C_{10}$ alkynyl groups substituted by any of the above-mentioned $C_6$-$C_{14}$ aryl groups.

The term "aryloxy" is used herein to mean oxygen substituted by one of the above-mentioned $C_6$-$C_{14}$ aryl groups, which may be optionally substituted. Useful aryloxy groups include phenoxy and 4-methylphenoxy.

The term "arylalkoxy" is used herein to mean any of the above mentioned $C_1$-$C_{10}$ alkoxy groups substituted by any of the above-mentioned aryl groups, which may be optionally substituted. Useful arylalkoxy groups include benzyloxy and phenethyloxy.

Useful haloalkyl groups include $C_1$-$C_{10}$ alkyl, or preferably $C_1$-$C_6$ alkyl substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_1$-$C_6$ acyl (alkanoyl) attached to an amino nitrogen, e.g., acetamido, chloroacetamido, propionamido, butanoylamido, pentanoylamido and hexanoylamido, as well as aryl-substituted $C_1$-$C_6$ acylamino groups, e.g., benzoylamido, and pentafluorobenzoylamido. Usefule acyl includes $C_1$-$C_6$ acyl, such as acetyl.

Useful acyloxy groups are any $C_1$-$C_6$ acyl (alkanoyl) attached to an oxy (—O—) group, e.g., formyloxy, acetoxy, propionoyloxy, butanoyloxy, pentanoyloxy and hexanoyloxy.

The term heterocycle (heterocyclic group) is used herein to mean a saturated or partially saturated 3-7 membered monocyclic, or 7-10 membered bicyclic ring system, which consists of carbon atoms and one to four heteroatoms independently selected from the group consisting of O, N, and S, wherein the nitrogen and sulfur heteroatoms can be optionally oxidized, the nitrogen can be optionally quaternized. The term also includes any bicyclic group in which any of the above-defined heterocyclic rings is fused to a benzene ring. The heterocyclic ring of heterocycle can be substituted on carbon or on a nitrogen atom if the resulting compound is stable.

Useful saturated or partially saturated heterocyclic groups include tetrahydrofuranyl, pyranyl, piperidinyl, piperazinyl, 1,4-diazepan-1-yl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetrahydroisoquinolinyl, 2',3'-dihydro-1'H-spiro[cyclopropane-1,4'-isoquinolin]-7'-yl and 4,5,6,7-tetrahydropyrazolo[1,5-a]pyrazin-2-yl, tetronoyl and tetramoyl groups, which are optionally substituted.

The term "heteroaryl" as employed herein refers to groups having 5 to 14 ring atoms; 6, 10 or 14 π electrons shared in a cyclic array; and containing, as ring atom, carbon atoms and 1-3 heteroatoms selected from oxygen, nitrogen and sulfur.

Useful heteroaryl groups include thienyl (thiophenyl), benzo[d]isothiazol-3-yl, benzo[b]thienyl, naphtho[2,3-b] thienyl, thianthrenyl, furyl (furanyl), pyranyl, isobenzofuranyl, chromenyl, xanthenyl, phenoxanthiinyl, pyrrolyl, imidazolyl, pyrazolyl, pyridyl (pyridinyl, including without limitation 2-pyridyl, 3-pyridyl, and 4-pyridyl), pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-amino-isocoumarin, pyrido[1,2-a]pyrimidin-4-one, tetrahydrocyclopenta[c]pyrazol-3-yl, pyrazolo[1,5-a]pyrimidinyl, benzoisoxazolyl such as 1,2-benzoisoxazol-3-yl, benzimidazolyl, 2-oxindolyl, thiadiazolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above-mentioned $C_1$-$C_{10}$ alkoxy groups substituted by any of the above-mentioned heteroaryl groups, which may be optionally substituted.

Some of the compounds of the present disclosure may exist as stereoisomers including optical isomers. The disclosure includes all stereoisomers and both the racemic mixtures of such stereoisomers as well as the individual enantiomers that may be separated according to methods that are well known to those of ordinary skill in the art.

Examples of pharmaceutically acceptable salts include inorganic and organic acid salts, such as hydrochloride, hydrobromide, phosphate, sulphate, citrate, lactate, tartrate, maleate, fumarate, mandelate and oxalate; and inorganic and organic base salts with bases, such as sodium hydroxy, tris(hydroxymethyl)aminomethane (TRIS, tromethane) and N-methyl-glucamine.

Examples of prodrugs of the compounds of the disclosure include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (J. Med. Chem. 42:3623-3628 (1999)) and Greenwald, et al., (J. Med. Chem. 42:3657-3667 (1999)); and acetals and ketals of alcohol containing compounds (e.g., those obtained by condensation with chloromethyl methyl ether or chloromethyl ethyl ether according to methods known in the art).

The compounds of this disclosure may be prepared using methods known to those skilled in the art, or the novel methods of this disclosure. Specifically, the compounds of this disclosure with Formula I can be prepared as illustrated by the exemplary reaction in Scheme 1. Reaction of N-tert-butoxycarbonyl-1,2-ethylenediamine and substituted isocyanatobenzene, such as 1-chloro-2-isocyanatobenzene in diethyl ether at r.t. produced tert-butyl (2-(3-(2-chlorophenyl)ureido)ethyl)carbamate. Reaction of tert-butyl (2-(3-(2-chlorophenyl)ureido)ethyl)carbamate and dixoane solution of hydrochloric acid in dichloromethane (DCM) at r.t. produced 1-(2-aminoethyl)-3-(2-chlorophenyl)urea hydrochloride. Heating treatment of the urea hydrochloride, ethyl 4-chloro-2-(methylthio)pyrimidine-5-carboxylate, and diisopropylethylamine (DIPEA) in acetonitrile (MeCN) produced ethyl 4-((2-(3-(2-chlorophenyl)ureido)ethyl)amino)-2-(methylthio)pyrimidine-5-carboxylate. Heating reaction of ethyl 4-((2-(3-(2-chlorophenyl)ureido)ethyl)amino)-2-(methylthio)pyrimidine-5-carboxylate in POCl3 produced 6-(2-chlorophenyl)-2-(methylthio)-8,9-dihydroimidazo[1,2-a]pyrimido[5,4-e]pyrimidin-5(6H)-one. Reaction of 6-(2-chlorophenyl)-2-(methylthio)-8,9-dihydroimidazo[1,2-a] pyrimido[5,4-e]pyrimidin-5(6H)-one and metachloroperbenzoic acid in chloroform at r.t. produced 6-(2-chlorophenyl)-2-(methylsulfonyl)-8,9-dihydroimidazo [1,2-a]pyrimido[5,4-e]pyrimidin-5(6H)-one. Heating treatment of the ketone and 4-(4-methylpiperazin-1-yl)aniline in i-PrOH produced the targeted compound 6-(2-chlorophenyl)-2-((4-(4-methylpiperazin-1-yl)phenyl)amino)-8,9-dihydroimidazo[1,2-a]pyrimido[5,4-e]pyrimidin-5(6H)-one.

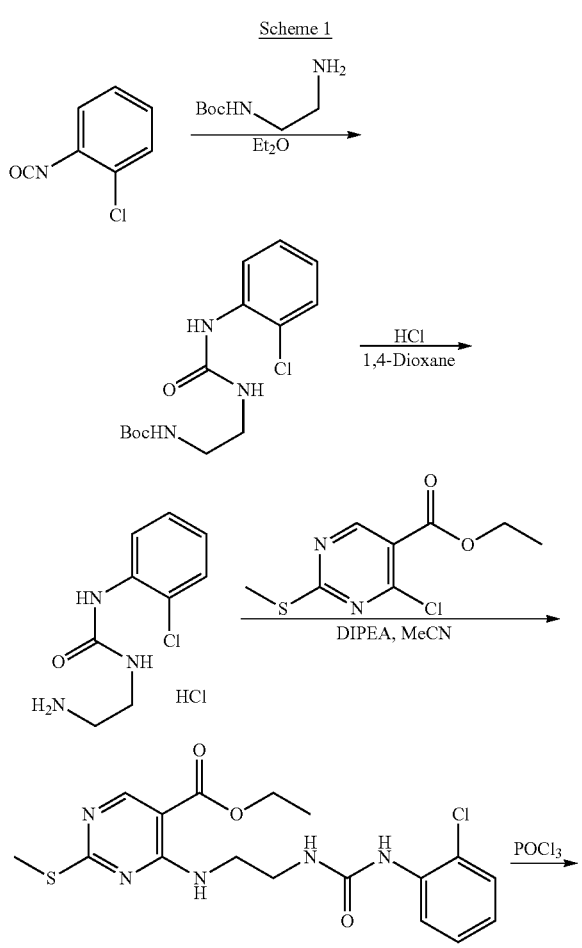

Scheme 1

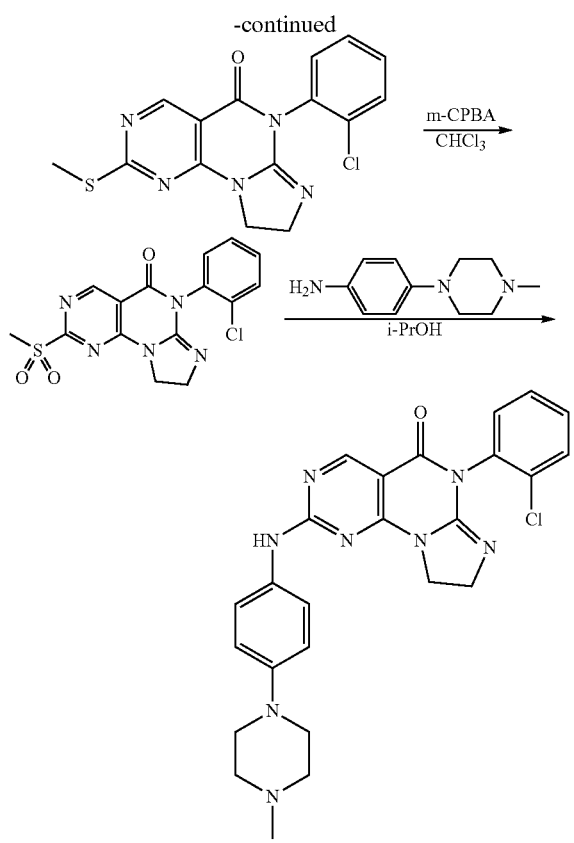

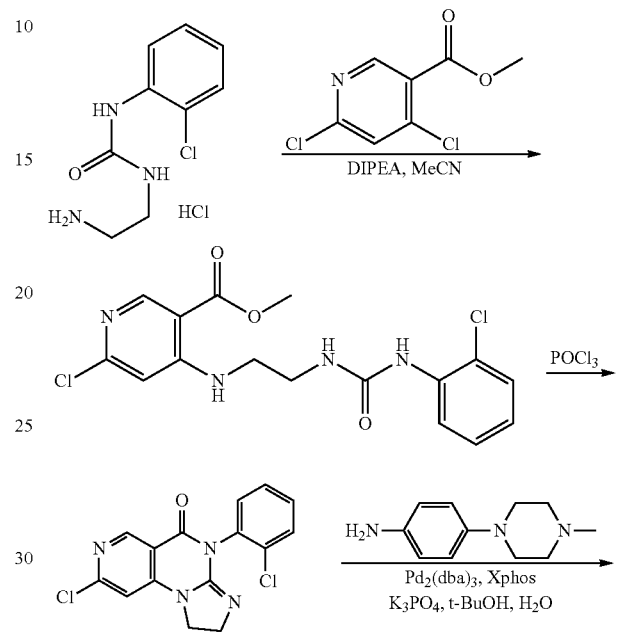

2-dicyclohexylphosphino-2,4,6-triisopropylbiphenyl and K₃PO₄ in the mixture of t-BuOH and H₂O under heating produced the targeted compound 4-(2-chlorophenyl)-8-((4-(4-methylpiperazin-1-yl)phenyl)amino)-1,2-dihydroimidazo[1,2-a]pyrido[3,4-e]pyrimidin-5(4H)-one.

Other related compounds can be prepared similarly. For example, replacement of 1-chloro-2-isocyanatobenzene with 1-chloro-3-fluoro-2-isocyanatobenzene produced the targeted compound 6-(2-chloro-6-fluorophenyl)-2-((4-(4-methylpiperazin-1-yl)phenyl)amino)-8,9-dihydroimidazo[1,2-a]pyrimido[5,4-e]pyrimidin-5(6H)-one. Replacement of 4-(4-methylpiperazin-1-yl)aniline with 4-(4-isopropylpiperazin-1-yl)aniline produced the targeted compound 6-(2-chloro-6-fluorophenyl)-2-((4-(4-isopropylpiperazin-1-yl)phenyl)amino)-8,9-dihydroimidazo[1,2-a]pyrimido[5,4-e]pyrimidin-5(6H)-one. Replacement of 4-(4-methylpiperazin-1-yl)aniline with 2-methyl-1,2,3,4-tetrahydroisoquinolin-7-amine produced the targeted compound 6-(2-chloro-6-fluorophenyl)-2-((2-methyl-1,2,3,4-tetrahydroisoquinolin-7-yl)amino)-8,9-dihydroimidazo[1,2-a]pyrimido[5,4-e]pyrimidin-5(6H)-one. Replacement of 4-(4-methylpiperazin-1-yl)aniline with 1-(4-aminophenyl)-N,N-dimethylpiperidin-4-amine produced the targeted compound 6-(2-chloro-6-fluorophenyl)-2-((4-(4-(dimethylamino)piperidin-1-yl)phenyl)amino)-8,9-dihydroimidazo[1,2-a]pyrimido[5,4-e]pyrimidin-5(6H)-one.

Compounds of this disclosure can be prepared as illustrated by the exemplary reaction in Scheme 2. Heating reaction of 1-(2-aminoethyl)-3-(2-chlorophenyl)urea, methyl 4,6-dichloronicotinate and DIPEA in MeCN produced methyl 6-chloro-4-((2-(3-(2-chlorophenyl)ureido)ethyl)amino)nicotinate. Treatment of methyl 6-chloro-4-((2-(3-(2-chlorophenyl)ureido)ethyl)amino)nicotinate in POCl₃ under heating produced 8-chloro-4-(2-chlorophenyl)-1,2-dihydroimidazo[1,2-a]pyrido[3,4-e]pyrimidin-5(4H)-one. Coupling of 8-chloro-4-(2-chlorophenyl)-1,2-dihydroimidazo[1,2-a]pyrido[3,4-e]pyrimidin-5(4H)-one with 4-(4-methylpiperazin-1-yl)aniline in the presence of tris(dibenzylideneacetone)dipalladium (Pd₂(dba)₃), Compounds of this disclosure can be prepared as illustrated by the exemplary reaction in Scheme 3. Use the method similar to that shown in Scheme 1 can produced 2-(methylsulfonyl)-6-(2,6-dichlorophenyl)-8,9-dihydroimidazo[1,2-a]pyrimido[5,4-e]pyrimidin-5(6H)-one. Coupling of 2-(methylsulfonyl)-6-(2,6-dichlorophenyl)-8,9-dihydroimidazo[1,2-a]pyrimido[5,4-e]pyrimidin-5(6H)-one with 4-(4-methylpiperazin-1-yl)aniline in the presence of trifluoroacetic acid in MeCN at r.t. produced the targeted compound 6-(2,6-dichlorophenyl)-2-((4-(4-methylpiperazin-1-yl)phenyl)amino)-8,9-dihydroimidazo[1,2-a]pyrimido[5,4-e]pyrimidin-5(6H)-one.

Scheme 3

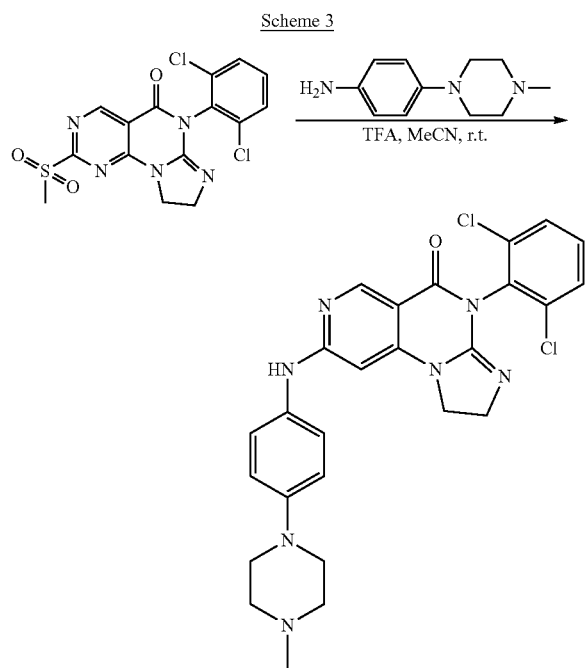

Other related compounds can be prepared similarly. For example, replacement of 4-(4-methylpiperazin-1-yl)aniline with 2,4,4-trimethyl-1,2,3,4-tetrahydroisoquinolin-7-amine produced the targeted compound 2-((2,4,4-trimethyl-1,2,3,4-tetrahydroisoquinolin-7-yl)amino)-6-(2,6-dichlorophenyl)-8,9-dihydroimidazo[1,2-a]pyrimido[5,4-e]pyrimidin-5(6H)-one. Replacement of 4-(4-methylpiperazin-1-yl)aniline with 4-((3R,5S)-3,4,5-trimethylpiperazin-1-yl)aniline produced the targeted compound 2-((4-((3R,5S)-3,4,5-trimethylpiperazin-1-yl)phenyl)amino)-6-(2,6-dichlorophenyl)-8,9-dihydroimidazo[1,2-a]pyrimido[5,4-e]pyrimidin-5(6H)-one. Replacement of 2-(methylsulfonyl)-6-(2,6-dichlorophenyl)-8,9-dihydroimidazo[1,2-a]pyrimido[5,4-e]pyrimidin-5(6H)-one with 2-methylsulfonyl-6-(2-chloro-4-fluorophenyl)-8,9-dihydroimidazo[1,2-a]pyrimido[5,4-e]pyrimidin-5(6H)-one produced the targeted compound 2-((4-(4-methylpiperazin-1-yl)phenyl)amino)-6-(2-chloro-4-fluorophenyl)-8,9-dihydroimidazo[1,2-a]pyrimido[5,4-e]pyrimidin-5(6H)-one. Replacement of 2-(methylsulfonyl)-6-(2,6-dichlorophenyl)-8,9-dihydroimidazo[1,2-a]pyrimido[5,4-e]pyrimidin-5(6H)-one with 2-methylsulfonyl-6-isopropyl-8,9-dihydroimidazo[1,2-a]pyrimido[5,4-e]pyrimidin-5(6H)-one produced the targeted compound 6-isopropyl-2-((4-(4-methylpiperazin-1-yl)phenyl)amino)-8,9-dihydroimidazo[1,2-a]pyrimido[5,4-e]pyrimidin-5(6H)-one. Replacement of 2-(methylsulfonyl)-6-(2,6-dichlorophenyl)-8,9-dihydroimidazo[1,2-a]pyrimido[5,4-e]pyrimidin-5(6H)-one with 2-methylsulfonyl-6-(pyrimidin-2-yl)-8,9-dihydroimidazo[1,2-a]pyrimido[5,4-e]pyrimidin-5(6H)-one produced the targeted compound 2-((4-(4-methylpiperazin-1-yl)phenyl)amino)-6-(pyrimidin-2-yl)-8,9-dihydroimidazo[1,2-a]pyrimido[5,4-e]pyrimidin-5(6H)-one. Replacement of 2-(methylsulfonyl)-6-(2,6-dichlorophenyl)-8,9-dihydroimidazo[1,2-a]pyrimido[5,4-e]pyrimidin-5(6H)-one with 2-methylsulfinyl-6-(2-chloro-6-fluorophenyl)-8,8-dimethyl-8,9-dihydroimidazo[1,2-a]pyrimido[5,4-e]pyrimidin-5(6H)-one produced the targeted compound 6-(2-chloro-6-fluorophenyl)-2-((4-(4-methylpiperazin-1-yl)phenyl)amino)-8,8-dimethyl-8,9-dihydroimidazo[1,2-a]pyrimido[5,4-e]pyrimidin-5(6H)-one. Replacement of 4-(4-methylpiperazin-1-yl)aniline with 1-(4-aminophenyl)-N,N-dimethylpiperidin-4-amine produced the targeted compound 6-(2,6-dichlorophenyl)-2-((4-(4-(dimethylamino)piperidin-1-yl)phenyl)amino)-8,9-dihydroimidazo[1,2-a]pyrimido[5,4-e]pyrimidin-5(6H)-one.

An important aspect of the present disclosure is the discovery that compounds having Formula I (including the compounds of Formula II or III) are kinase inhibitors, especially Wee1 kinase inhibitors. Therefore, these compounds are useful for the treatment of Wee1-related diseases, such as cancer.

The present disclosure includes a therapeutic method comprising administering to a mammal an effective amount of a compound of Formula I, II or III, or a pharmaceutically acceptable salt or prodrug thereof, wherein said therapeutic method is useful for the treatment of diseases related with kinase, especially Wee1 kinase, such as cancer. Such diseases that can be treated or prevented by the method or pharmaceutical composition of the present disclosure include, but are not limited to, liver cancer, melanoma, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head and neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

Compounds of the present disclosure also are useful for the treatment or prevention of other diseases due to abnormal kinase activity, especially Wee1, such as neurology or neuropsychiatric diseases or conditions, such as depression.

In practicing the therapeutic methods, effective amounts of compositions containing therapeutically effective concentrations of the compounds of Formula I, II or III formulated for oral, intravenous, local or topical application, for the treatment of cancer and other diseases, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to an effective regimen. The amount may cure the disease but, typically, is administered in order to ameliorate the symptoms of the disease. Typically, repeated administration is required to achieve the desired amelioration of symptom.

In another embodiment, a pharmaceutical composition comprising a compound of Formula I, II or III or a pharmaceutically acceptable salt thereof, which functions as kinase inhibitor, in combination with a pharmaceutically acceptable vehicle, is provided.

Another embodiment of the present disclosure is directed to a composition effective to treat cancer comprising a compound of Formula I, II or III, or a pharmaceutically acceptable salt or prodrug thereof, which functions as a kinase inhibitor, in combination with at least one known anticancer agent or a pharmaceutically acceptable salt thereof. In particular, the compound herein can be combined with other anticancer drugs related to the mechanism of DNA damage and repair, including PARP inhibitors Olaparib, Niraprib, Rucaparib and Talazoparib; HDAC inhibitors Volinota, Romididesin, Papiseta and Bailesta; and so on. And the compound herein can be combined with other anticancer drugs related to cell division detection sites, including Chk1/2 inhibitors, CDK4/6 inhibitors such as Paposinib, ATM/ATR inhibitors, and so on. Other examples of known anticancer agents which may be used for combination therapy include, but not are limited to alkylating agents, such as busulfan, melphalan, chlorambucil, cyclophosphamide, ifosfamide, temozolomide, bendamustine, cis-platin, mitomycin C, bleomycin, and carboplatin; topoisomerase I inhibitors, such as camptothecin, irinotecan, and topotecan; topoisomerase II inhibitors, such as doxorubicin, epirubicin, aclarubicin, mitoxantrone, elliptinium and etoposide; RNA/DNA antimetabolites, such as 5-azacytidine, gemcitabine, 5-fluorouracil and methotrexate; DNA antimetabolites, such as 5-fluoro-2'-deoxy-uridine, fludarabine, nelarabine, ara-C, pralatrexate, pemetrexed, hydroxyurea and thioguanine; antimitotic agents, such as colchicine, vinblastine, vincristine, vinorelbine, paclitaxel, ixabepilone, cabazitaxel and docetaxel; antibodies such as campath, panitumumab, metazotuzumab, navuzumab, pymzumab, remoluzumab, bevacizumab, partuzumab, trastuzumab, cetuximab, obinutuzumab, olfactuzumab, rituximab, alemtuzumab, tiemuzumab, toximab, bentuximab, daremuzumab, errotuzumab, T-DM1, ofatumumab, dinutuximab, blinatumomab, ipilimma, avastin, trastuzumab and rituximab; kinase inhibitors such as imatinib, gefitinib, erlotinib, osimertinib, afatinib, ceritinib, aletinib, crizotinib, erlotinib, lapatinib, sorafenib, regorafenib, vemurafenib, dabrafenib, aflibercept, sunitinib, nilotinib, dasatinib, bosutinib, pratinib, ibrutinib, cabozatinib, lenvatinib, vandetanib, trametinib, cobimetinib, axitinib, temsirolimus, idelalisib, pazopanib, temsirolimus and everolimus. Other known anticancer agents which may be used for combination therapy include tamoxifen, letrozole, fulvestrant, mitoguazone, octreotide, retinoic acid, arsenic trioxide, zoledronic acid, bortezomib, carfazomide, ixazomib, erivedge, sonidegib, denosumab, thalidomide, lenalidomide, venetoclax, aldesleukin (recombinant human interleukin-2) and sipueucel-T (prostate cancer therapeutic vaccine).

In practicing the methods of the present disclosure, the compound of the disclosure may be administered together with at least one known anticancer agent as part of a unitary pharmaceutical composition. Alternatively, the compound of the disclosure may be administered apart from at least one known anticancer agent. In one embodiment, the compound of the disclosure and at least one known anticancer agent are administered substantially simultaneously, i.e. the compounds are administered at the same time or one after the other, so long as the compounds reach therapeutic levels in the blood at the same time. In another embodiment, the compound of the disclosure and at least one known anticancer agent are administered according to their individual dose schedule, so long as the compounds reach therapeutic levels in the blood.

Another embodiment of the present disclosure is directed to a composition effective to inhibit neoplasia comprising a bioconjugate of a compound described herein, which functions as a kinase inhibitor, in bioconjugation with at least one known therapeutically useful antibody, such as trastuzumab or rituximab, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of the therapeutically useful antibodies, such as trastuzumab or rituximab.

Similarly, another embodiment of the present disclosure is directed to a composition effective to inhibit neoplasia comprising a compound of Formula I, II or III, or its pharmaceutically acceptable salt or prodrug, which functions as a kinase inhibitor, in combination with radiation therapy. In this embodiment, the compound of the disclosure may be administered at the same time as the radiation therapy is administered or at a different time.

Yet another embodiment of the present disclosure is directed to a composition effective for post-surgical treatment of cancer, comprising a compound of Formula I, II or III, or its pharmaceutically acceptable salt or prodrug, which functions as a kinase inhibitor. The disclosure also relates to a method of treating cancer by surgically removing the tumor and then treating the mammal with one of the pharmaceutical compositions described herein.

Pharmaceutical compositions within the scope of this disclosure include all compositions wherein the compounds of the present disclosure are contained in an amount that is effective to achieve its intended purpose. While individual needs vary, determination of optimal ranges of effective amounts of each component is within the skill of the art. Typically, the compounds may be administered to mammals, orally at a dose of from about 0.0025 to 50 mg/kg of body weight, per day, or an equivalent amount of the pharmaceutically acceptable salt thereof, to a mammal being treated. Preferably, from approximately 0.01 to approximately 10 mg/kg of body weight is orally administered. If a known anticancer agent is also administered, it is administered in an amount that is effective to achieve its intended purpose. The optimal amounts of such known anticancer agents effective for cancer are well known to those skilled in the art.

The unit oral dose may comprise from approximately 0.01 to approximately 50 mg, preferably approximately 0.1 to approximately 10 mg of the compound of the disclosure. The unit dose may be administered one or more times daily, as one or more tablets, each containing from approximately 0.1 to approximately 50 mg, conveniently approximately 0.25 to 10 mg of the compound or its solvates.

In a topical formulation, the compound may be present at a concentration of approximately 0.01 to 100 mg per gram of carrier.

In addition to administering the compound as a raw chemical, the compounds of the disclosure may be administered as part of a pharmaceutical preparation containing suitable pharmaceutically acceptable carriers comprising excipients and auxiliaries, which facilitate processing of the compounds into preparations that may be used pharmaceutically. Preferably, the preparations, particularly those preparations which may be administered orally and that may be used for the preferred type of administration, such as tablets, dragees, and capsules, as well as suitable solutions for administration by injection or orally, contain from approximately 0.01 to 99 percent, preferably from approximately 0.25 to 75 percent of active compound(s), together with the excipient.

Also included within the scope of the present disclosure are the non-toxic pharmaceutically acceptable salts of the compounds of the present disclosure. Acid addition salts are formed by mixing a solution of the compounds of the present disclosure with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Base addition salts are formed by mixing a solution of the compounds of the present disclosure with a solution of a pharmaceutically acceptable non-toxic base, such as sodium hydroxide, potassium hydroxide, choline hydroxide, sodium carbonate, tris(hydroxymethyl)aminomethane (TRIS), N-methyl-glucamine and the like.

The pharmaceutical compositions of the disclosure may be administered to any mammal, so long as they may experience the therapeutic effects of the compounds of the disclosure. Foremost among such mammals are humans and veterinary animals, although the disclosure is not intended to be so limited.

The pharmaceutical compositions of the present disclosure may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present disclosure are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethyl-cellulose phthalate, are used. Dye stuffs or pigments may be added to the tablets or dragee coatings, e.g., for identification or in order to characterize combinations of active compound doses.

Other pharmaceutical preparations, which may be used orally, include push-fit capsules made of gelatin, as well as soft, sealed capsules made of gelatin and a plasticizer, such as glycerol or sorbitol. The push-fit capsules may contain the active compounds in the form of: granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Suitable formulations for parenteral administration include aqueous solutions of the active compounds, e.g., aqueous solutions and alkaline solutions of water-soluble salts. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400, or cremophor, or cyclodextrins. Aqueous injection suspensions may contain substances which increase the viscosity of the suspension, e.g., sodium carboxymethyl cellulose, sorbitol, and/or dextran. Optionally, the suspension may also contain stabilizers.

In accordance with one aspect of the present disclosure, compounds of the disclosure are employed in topical and parenteral formulations and are used for the treatment of skin cancer.

The topical compositions of this disclosure are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than Cu). The preferred carriers are those in which the active ingredient is soluble. Emulsifiers, stabilizers, humectants and antioxidants may also be included, as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The present disclosure also includes the use of the compounds of the subject disclosure in the manufacture of a medicament for treating a clinical condition responsive to the inhibition of kinase (especially Wee1) activity. The medicament may include the pharmaceutical compositions as described above.

The following examples are illustrative, but not limiting, of the method and compositions of the present disclosure. Other suitable modifications and adaptations of the variety of conditions and parameters normally encountered in clinical therapy and which are obvious to those skilled in the art are within the spirit and scope of the disclosure.

EXAMPLES

General Remarks

All reagents were of commercial quality. Solvents were dried and purified by standard methods. Mass spectrum analyses were recorded on a Platform II (Agilent 6110) quadrupole mass spectrometer fitted with an electrospray rinterface. $^1$H NMR spectra was recorded at 400 MHz, on a Brücker Ascend 400 apparatus. Chemical shifts were recorded as parts per million (ppm) downfield from TMS (0.00 ppm), and J coupling constants were reported in hertz (Hz).

Example 1

6-(2-Chlorophenyl)-2-((4-(4-methylpiperazin-1-yl) phenyl)amino)-8,9-dihydroimidazo[1,2-a]pyrimido [5,4-e]pyrimidin-5(6H)-one a) Tert-butyl (2-(3-(2-chlorophenyl)ureido)ethyl)carbamate: to the solution of N-tert-butoxycarbonyl-1,2-ethylenediamine (1.56 g, 9.76 mmol) in diethyl ether (20 mL) was added 1-chloro-2-isocyanatobenzene (500 mg, 3.26 mmol) slowly at 0° C. The mixture was stirred for 3 hrs at r.t., and then filtered. The filter cake was washed with a few diethyl ether, and produced the targeted compound tert-butyl (2-(3-(2-chlorophenyl)ureido)ethyl)carbamate (622 mg, 62% yield, white solid). LC-MS (ESI): m/z (M+1) 314.37.

b) 1-(2-Aminoethyl)-3-(2-chlorophenyl)urea hydrochloride: to the solution of tert-butyl (2-(3-(2-chlorophenyl) ureido)ethyl)carbamate (622 mg, 1.98 mmol) in DCM (20 mL) was added dioxane solution of hydrochloric acid (4N, 20 mL). The mixture was stirred for 4 hrs at r.t., and the solvent was removed via evaporation under reduced pressure to produce the targeted compound 1-(2-aminoethyl)-3-(2-chlorophenyl)urea hydrochloride (470 mg, 95% yield, white solid). LC-MS (ESI): m/z (M+1) 214.42.

c) Ethyl 4-((2-(3-(2-chlorophenyl)ureido)ethyl)amino)-2-(methylthio)pyrimidine-5-carboxylate: the mixture of 1-(2-aminoethyl)-3-(2-chlorophenyl)urea hydrochloride (200 mg, 0.8 mmol), ethyl 4-chloro-2-(methylthio)pyrimidine-5-carboxylate (284 mg, 1.22 mmol) and DIPEA (485 mg, 3.75 mmol) in MeCN (8 mL) was stirred for 3 hrs at 80° C. under the protection of nitrogen. After cooled down to r.t., the mixture was filtered, and the filter cake was washed with a few MeOH to produce the targeted compound ethyl 4-((2-(3-(2-chlorophenyl)ureido)ethyl)amino)-2-(methylthio)pyrimidine-5-carboxylate (270 mg, 82% yield, white solid) after dry. LC-MS (ESI): m/z (M+1) 410.33.

d) 6-(2-Chlorophenyl)-2-(methylthio)-8,9-dihydroimidazo[1,2-a]pyrimido[5,4-e]pyrimidin-5(6H)-one: the solution of ethyl 4-((2-(3-(2-chlorophenyl)ureido)ethyl)amino)-2-(methylthio)pyrimidine-5-carboxylate (200 mg, 0.49 mmol) in POCl$_3$ (8 mL) was heated to 110° C. and stirred overnight. The solvent was removed via evaporation under reduced pressure, and the residue was diluted with EtOAc and washed with saturated NaHCO$_3$ aqueous solution. The organic layer was washed with saturated saline solution and dried with anhydrous sodium sulfate. The mixture was filtered, and the filtrate was concentrated under reduced pressure to give the crude product, which was purified by column chromatography (silica gel, petroleum eterh (PE): EtOAc=1:1) to give the target compound 6-(2-chlorophenyl)-2-(methylthio)-8,9-dihydroimidazo[1,2-a]pyrimido[5, 4-e]pyrimidin-5(6H)-one (92 mg, 54% yield, yellow solid). LC-MS (ESI): m/z (M+1) 346.37.

e) 6-(2-Chlorophenyl)-2-(methylsulfonyl)-8,9-dihydroimidazo[1,2-a]pyrimido[5,4-e]pyrimidin-5(6H)-one: to the solution of 6-(2-chlorophenyl)-2-(methylthio)-8,9-dihydroimidazo[1,2-a]pyrimido[5,4-e]pyrimidin-5(6H)-one (92 mg, 0.27 mmol) in chloroform (10 mL) was added m-chloroperoxybenzoic acid (m-CPBA) (80%, 122 mg, 0.56 mmol). The reaction liquor was stirred for 4 hrs at r.t., then saturated sodium thiosulfate aqueous solution was added to quench the reaction. The mixture was extracted with EtOAc, and the organic layer was washed with saturated saline solution and dried with anhydrous sodium sulfate. The mixture was filtered, and the filtrate was concentrated under reduced pressure to give the crude product, which was purified by column chromatography (silica gel, DCM:MeOH=20:1, as eluent) to give the target compound (54 mg, 53% yield, light-yellow solid). LC-MS (ESI): m/z (M+1) 378.31.

f) 6-(2-Chlorophenyl)-2-((4-(4-methylpiperazin-1-yl) phenyl)amino)-8,9-dihydroimidazo[1,2-a]pyrimido[5,4-e] pyrimidin-5(6H)-one: the mixture of 6-(2-chlorophenyl)-2-(methylsulfonyl)-8,9-dihydroimidazo[1,2-a]pyrimido[5,4-e]pyrimidin-5(6H)-one (54 mg, 0.14 mmol) and 4-(4-methylpiperazin-1-yl)aniline (27 mg, 0.14 mmol) in isopropanol (2 mL) was stirred for 1 h at 80° C. The solvent was removed under reduced pressure to give the crude product, which was purified by preparative liquid chromatography (C18 column, 0-100% MeCN/H$_2$O as mobile phase) to give the targeted compound (12 mg, 18% yield, white solid). LC-MS (ESI): m/z (M+1) 489.39. $^1$H NMR (400 MHz, DMSO-d$_6$): δ 8.61 (s, 1H), 8.24-8.13 (m, 2H), 7.69-7.62 (m, 2H), 7.53-7.45 (m, 3H), 6.96-6.88 (m, 2H), 4.17-4.07 (m, 2H), 3.78 (t, J=8.8 Hz, 2H), 3.13-3.07 (m, 4H), 2.48-2.42 (m, 4H), 2.23 (s, 3H).

Example 2

6-(2-Chloro-6-fluorophenyl)-2-((4-(4-methylpiperazin-1-yl)phenyl)amino)-8,9-dihydroimidazo[1,2-a] pyrimido[5,4-e]pyrimidin-5(6H)-one The target compound 6-(2-chloro-6-fluorophenyl)-2-((4-(4-methylpiperazin-1-yl)phenyl)amino)-8,9-dihydroimidazo[1,2-a]pyrimido[5,4-e]pyrimidin-5(6H)-one (58 mg, 38% yield, white solid) was prepared from 1-chloro-3-fluoro-2-isocyanatobenzene, N-tert-butoxycarbonyl-1,2-ethylenediamine, ethyl 4-chloro-2-(methylthio)pyrimidine-5-carboxylate and 4-(4-methylpiperazin-1-yl)aniline using a procedure similar to those described for the synthesis of compound of Example 1. LC-MS (ESI): m/z (M+1) 507.36. $^1$H NMR (400 MHz, DMSO-d$_6$): δ 8.64 (s, 1H), 8.17-8.16 (m, 1H), 7.74-7.51 (m, 4H), 7.48-7.43 (m, 1H), 6.92 (d, J=8.9 Hz, 2H), 4.19-4.11 (m, 2H), 3.84-3.77 (m, 2H), 3.15-3.05 (m, 4H), 2.49-2.45 (m, 4H), 2.24 (d, J=5.7 Hz, 3H).

Example 3

4-(2-Chlorophenyl)-8-((4-(4-methylpiperazin-1-yl) phenyl)amino)-2,4-dihydroimidazo[1,2-a]pyrido[3, 4-e]pyrimidin-5(1H)-one a) 8-Chloro-4-(2-chlorophenyl)-1,2-dihydroimidazo[1,2-a]pyrido[3,4-e]pyrimidin-5(4H)-one: the target compound 8-chloro-4-(2-chlorophenyl)-1,2-dihydroimidazo[1,2-a] pyrido[3,4-e]pyrimidin-5(4H)-one (173 mg, 66% yield, light-yellow solid) was prepared from 1-(2-aminoethyl)-3-(2-chlorophenyl)urea hydrochloride and methyl 4,6-dichloronicotinate using procedures similar to those described for the syntheses of compounds of Examples 1c and 1d successively. LC-MS (ESI): m/z (M+1) 333.26.

b) 4-(2-Chlorophenyl)-8-((4-(4-methylpiperazin-1-yl) phenyl)amino)-2,4-dihydroimidazo[1,2-a]pyrido[3,4-e]pyrimidin-5(1H)-one: the mixture of 8-chloro-4-(2-chlorophenyl)-1,2-dihydroimidazo[1,2-a]pyrido[3,4-e]pyrimidin-5

(4H)-one (120 mg, 0.36 mmol, 4-(4-methylpiperazin-1-yl) aniline (83 mg, 0.43 mmol), Pd$_2$(dba)$_3$ (33 mg, 0.036 mmol), 2-dicyclohexylphosphino-2,4,6-triisopropylbiphenyl (34 mg, 0.072 mmol), and K$_3$PO$_4$ (229 mg, 1.08 mmol) in tert-Butanol (4 mL) and H$_2$O (1 mL) was stirred overnight under the protection of nitrogen at 80° C. The solvent was removed under reduced pressure to give the crude product, which was purified by preparative liquid chromatography (C18 column, 0-100% MeCN/H$_2$O as mobile phase) to give the targeted compound 4-(2-chlorophenyl)-8-((4-(4-methylpiperazin-1-yl)phenyl)amino)-2,4-dihydroimidazo[1,2-a] pyrido[3,4-e]pyrimidin-5(1H)-one (55 mg, 31% yield, white solid). LC-MS (ESI): m/z (M+1) 488.40. $^1$H NMR (400 MHz, DMSO-d$_6$): δ 9.37 (s, 1H), 8.49 (s, 1H), 7.64-7.59 (m, 1H), 7.51-7.37 (m, 5H), 6.96-6.88 (m, 2H), 5.95 (s, 1H), 4.01-3.89 (m, 2H), 3.80-3.72 (m, 2H), 3.12-3.06 (m, 4H), 2.48-2.43 (m, 4H), 2.23 (s, 3H).

Example 4

6-(2,6-Dichlorophenyl)-2-((4-(4-methylpiperazin-1-yl)phenyl)amino)-8,9-dihydroimidazo[1,2-a]pyrimido[5,4-e]pyrimidin-5(6H)-one a) 2-(Methylsulfonyl)-6-(2,6-dichlorophenyl)-8,9-dihydroimidazo[1,2-a]pyrimido[5,4-e]pyrimidin-5(6H)-one: the compound was prepared from N-tert-butoxycarbonyl-1,2-ethylenediamine, ethyl 4-chloro-2-(methylthio)pyrimidine-5-carboxylate and 1,3-dichloroisocyanatobenzene using procedures similar to those described for the syntheses of compounds of Examples 1a-1e.

b) 6-(2,6-Dichlorophenyl)-2-((4-(4-methylpiperazin-1-yl)phenyl)amino)-8,9-dihydroimidazo[1,2-a]pyrimido[5,4-e]pyrimidin-5(6H)-one: to the mixture of 2-(methylsulfonyl)-6-(2,6-dichlorophenyl)-8,9-dihydroimidazo[1,2-a]pyrimido[5,4-e]pyrimidin-5(6H)-one (40 mg, 0.1 mmol) and 4-(4-methylpiperazin-1-yl)aniline (30 mg, 0.15 mmol) in MeCN (1 mL) was added trifluoroacetic acid (0.2 mL) at r.t. The reaction liquor was stirred overnight at r.t., and concentrated under reduced pressure to give the crude product, which was purified by preparative liquid chromatography (C18 column, 0-100% MeCN/H$_2$O as mobile phase) to give the targeted compound (18 mg, 36% yield, yellow solid). LC-MS (ESI): m/z (M/2+1) 263.16. $^1$H NMR (400 MHz, DMSO-d$_6$): δ 10.27 (s, 1H), 8.65 (s, 1H), 7.75-7.59 (m, 3H), 7.61-7.41 (m, 2H), 6.93 (d, J=8.9 Hz, 2H), 4.23-4.08 (m, 2H), 3.87-3.75 (m, 2H), 3.19-2.99 (m, 4H), 2.49-2.45 (m, 4H), 2.24 (s, 3H).

The compounds of Examples 6-8 were prepared from 2-(methylsulfonyl)-6-(2-chloro-6-fluorophenyl)-8,9-dihydroimidazo[1,2-a]pyrimido[5,4-e]pyrimidin-5(6H)-one (the compound was prepared from N-tert-butoxycarbonyl-1,2-ethylenediamine, ethyl 4-chloro-2-(methylthio)pyrimidine-5-carboxylate and 1-chloro-3-fluoro-2-isocyanatobenzene using procedures similar to those described for the syntheses of compounds of Examples 1a-1e.) and the corresponding substituted aniline or substituted tetrahydroisoquinoline amine using procedure similar to those described for the synthesis of compound of Example 1.

The compounds of Examples 5 and 9-26 were prepared from 2-(methylsulfonyl/methylsulfinyl)-6-substituent-8,9-dihydroimidazo[1,2-a]pyrimido[5,4-e]pyrimidin-5(6H)-one (the compounds were prepared from N-tert-butoxycarbonyl-1,2-ethylenediamine, ethyl 4-chloro-2-(methylthio)pyrimidine-5-carboxylate and the corresponding substituted isocyanatobenzene) and the corresponding substituted amine using procedure similar to those described for the synthesis of compound of Example 4b.

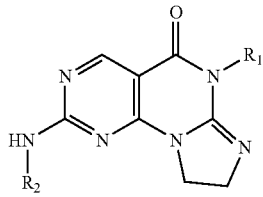

| Example | R$_1$ | R$_2$ | LC-MS (ESI) | $^1$H NMR |
|---|---|---|---|---|
| 5 | 2-methyl-3-chlorophenyl | —N(piperazine)N—phenyl—* | (M + 1) 503.35 | 400 MHz, DMSO-d$_6$: 10.20 (brs, 1H), 8.62 (s, 1H), 7.73-7.52 (m, 2H), 7.48-7.42 (m, 1H), 7.41-7.31 (m, 2H), 6.92 (d, J = 8.8 Hz, 2H), 4.19-4.08 (m, 2H), 3.79 (t, J = 9.2 Hz, 2H), 3.14-3.05 (m, 4H), 2.46 (t, J = 4.6 Hz, 4H), 2.23 (s, 3H), 2.17 (s, 3H) |
| 6 | 2-fluoro-6-chlorophenyl | iPr-N(piperazine)N—phenyl—* | (M/2 + 1) 268.19 | 400 MHz, DMSO-d$_6$: 10.2.0 (brs, 1H), 8.64 (s, 1H), 7.77-7.40 (m, 5H), 6.93 (d, J = 8.9 Hz, 2H), 4.20-4.13 (m, 2H), 3.81 (t, J = 8.9 Hz, 2H), 3.19-3.05 (m, 4H), 2.83-2.74 (m, 1H), 2.72-2.59 (m, 4H), 1.04 (d, J = 6.5 Hz, 6H) |
| 7 | 2-fluoro-6-chlorophenyl | Ac-N(piperazine)N—phenyl—* | (M + 1) 535.19 | 400 MHz, DMSO-d$_6$: 10.2.9 (brs, 1H), 8.65 (s, 1H), 7.77-7.42 (m, 5H), 6.96 (d, J = 8.9 Hz, 2H), 4.25-4.09 (m, 2H), 3.86-3.76 (m, 2H), 3.66-3.52 (m, 4H), 3.17-3.03 (m, 4H), 2.04 (s, 3H) |

-continued

| Example | R₁ | R₂ | LC-MS (ESI) | ¹H NMR |
|---|---|---|---|---|
| 8 | 2-fluoro-6-chlorophenyl | 2-methyl-1,2,3,4-tetrahydroisoquinolin-7-yl | (M + 1) 478.25 | 400 MHz, DMSO-d₆: 10.33 (s, 1H), 8.68 (s, 1H), 7.64-7.42 (m, 5H), 7.08 (d, J = 8.4 Hz, 1H), 4.21-4.13 (m, 2H), 3.87-3.78 (m, 2H), 3.56 (s, 2H), 2.85-2.78 (m, 2H), 2.72-2.64 (m, 2H), 2.40 (s, 3H) |
| 9 | 2-fluoro-6-chlorophenyl | 2,4,4-trimethyl-1,2,3,4-tetrahydroisoquinolin-7-yl | (M + 1) 506.21 | 400 MHz, DMSO-d₆: 10.31 (brs, 1H), 8.67 (s, 1H), 7.62-7.51 (m, 3H). 7.49-7.35 (m, 2H), 7.32-7.28 (m, 1H), 4.18 (t, J = 10.0 Hz, 2H), 3.82 (t, J = 8.8 Hz, 2H), 3.45 (s, 2H), 2.38-2.28 (m, 5H), 1.23 (s, 6H) |
| 10 | 2-fluoro-6-chlorophenyl | 2-methyl-spirocyclopropyl-tetrahydroisoquinolin-yl | (M + 1) 504.50 | 400 MHz, DMSO-d₆: 10.32 (s, 1H), 8.67 (s, 1H), 7.69-7.36 (m, 5H), 6.69 (d, J = 8.6 Hz, 1H), 4.23-4.11 (m, 2H), 3.87-3.78 (m, 2H), 3.59 (s, 2H), 2.45 (s, 2H), 2.32 (s, 3H), 0.87 (d, J = 25.2 Hz, 4H) |
| 11 | 2-fluoro-6-chlorophenyl | 2-acetyl-spirocyclopropyl-tetrahydroisoquinolin-yl | (M + 1) 532.39 | 400 MHz, DMSO-d₆: 10.18 (brs, 1H), 8.69 (s, 1H), 7.65-7.50 (m, 4H), 7.46-7.40 (m, 1H), 6.83 (d, J = 8.5 Hz, 1H), 4.73 (s, 2H), 4.23-4.15 (m, 2H), 3.89-3.81 (m, 2H), 3.54 (s, 2H), 2.10 (s, 3H), 1.04-0.89 (m, 4H) |
| 12 | 2,6-dichlorophenyl | 2-methyl-1,2,3,4-tetrahydroisoquinolin-7-yl | (M + 1) 494.35 | 400 MHz, DMSO-d₆: 10.33 (brs, 1H), 8.68 (s, 1H), 7.67 (d, J = 7.9 Hz, 2H), 7.61-7.44 (m, 3H), 7.07 (d, J = 8.4 Hz, 1H), 4.18 (t, J = 8.3 Hz, 2H), 3.82 (t, J = 8.6 Hz, 2H), 3.48 (s, 2H), 2.78 (t, J = 5.5 Hz, 2H), 2.59 (t, J = 5.9 Hz, 2H), 2.34 (s, 3H) |
| 13 | 2,6-dichlorophenyl | 2,4,4-trimethyl-1,2,3,4-tetrahydroisoquinolin-7-yl | (M + 1) 522.19 | 400 MHz, DMSO-d₆: 10.33 (brs, 1H), 8.68 (s, 1H), 7.74-7.62 (m, 2H), 7.62-7.39 (m, 3H), 7.30 (d, J = 8.5 Hz, 1H), 4.18 (t, J = 8.7 Hz, 2H), 3.83 (t, J = 8.7 Hz, 2H), 3.45 (s, 2H), 2.41-2.25 (m, 5H), 1.24 (s, 6H) |
| 14 | 2,6-dichlorophenyl | 2-methyl-spirocyclopropyl-tetrahydroisoquinolin-yl | (M + 1) 520.17 | 400 MHz, CDCl₃: 8.81 (s, 1H), 7.53-7.40 (m, 4H), 7.38-7.33 (m, 1H), 6.71 (d, J = 8.9 Hz, 1H), 4.21 (t, J = 8.8 Hz, 2H), 4.09-3.94 (m, 2H), 2.85 (s, 2H), 2.65 (s, 3H), 1.34-1.06 (m, 2H), 1.05-0.95 (m, 2H) |
| 15 | 2,6-dimethylphenyl | 2-methyl-1,2,3,4-tetrahydroisoquinolin-7-yl | (M + 1) 454.32 | 400 MHz, CDCl₃: 8.81 (s, 1H), 7.45-7.37 (m, 2H), 7.25-7.21 (m, 1H), 7.21-7.09 (m, 3H), 4.20 (t, J = 8.7 Hz, 2H), 3.99 (t, J = 8.8 Hz, 2H), 3.76 (s, 2H), 2.99 (t, J = 5.8 Hz, 2H), 2.88 (t, J = 5.9 Hz, 2H), 2.58 (s, 3H), 2.18 (s, 6H) |

-continued

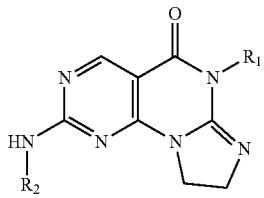

| Example | R₁ | R₂ | LC-MS (ESI) | ¹H NMR |
|---|---|---|---|---|
| 16 | 2,6-dimethylphenyl | 2,4,4-trimethyl-1,2,3,4-tetrahydroisoquinolin-7-yl | (M + 1) 482.29 | 400 MHz, DMSO-d₆: 10.19 (brs, 1H), 8.63 (s, 1H), 7.61-7.49 (m, 2H), 7.32-7.28 (m, 1H), 7.25-7.20 (m, 1H), 7.18-7.13 (m, 2H), 4.14 (t 2H), 3.80 (t, J = 8.8 Hz, 2H), 3.44 (s, 2H), 2.37-2.29 (m, 5H), 2.08 (s, 6H), 1.24 (s, 6H) |
| 17 | 2,6-dimethylphenyl | 2'-methyl-2',3'-dihydro-1'H-spiro[cyclopropane-1,4'-isoquinolin]-7'-yl | (M + 1) 480.31 | 400 MHz, CDCl₃: 8.80 (s, 1H), 7.46-7.39 (m, 2H), 7.25-7.22 (m, 1H), 7.20-7.14 (m, 2H), 6.70 (d, J = 9.2 Hz, 1H), 4.19 (t, J = 8.8 Hz, 2H), 3.99 (t, J = 8.8 Hz, 2H), 3.90 (s, 2H), 2.74 (s, 2H), 2.58 (s, 3H), 2.18 (s, 6H), 1.11-1.03 (m, 2H), 1.01-0.94 (m, 2H) |
| 18 | isopropyl | 4-(4-methylpiperazin-1-yl)phenyl | (M + 1) 421.30 | 400 MHz, CDCl₃: 8.71 (s, 1H), 7.54 (d, J = 8.1 Hz, 2H), 6.94 (d, J = 8.9 Hz, 2H), 5.16-5.10 (m, 1H), 4.12-3.99 (m, 4H), 3.64-3.53 (m, 4H), 3.39-3.16 (m, 4H), 2.84 (s, 3H), 1.54 (d, J = 6.9 Hz, 6H) |
| 19 | tert-butyl | 4-(4-methylpiperazin-1-yl)phenyl | (M + 1) 435.5 | 400 MHz, CDCl₃: 8.66 (s, 1H), 7.49 (d, J = 8.9 Hz, 2H), 6.93 (d, J = 8.0 Hz, 2H), 4.03-3.94 (m, 4H), 3.26-3.19 (m, 4H), 2.66 (s, 4H), 2.41 (s, 3H), 1.76 (s, 9H) |
| 20 | cyclopropyl | 4-(4-methylpiperazin-1-yl)phenyl | (M + 1) 419.45 | 400 MHz, CDCl₃: 8.72 (s, 1H), 7.50 (d, J = 8.0 Hz, 2H), 6.93 (d, J = 9.0 Hz, 2H), 4.19-3.96 (m, 4H), 3.29-3.07 (m, 4H), 2.82-2.75 (m, 1H), 2.70-2.51 (m, 4H), 2.37 (s, 3H), 1.22-1.08 (m, 2H), 0.98-0.85 (m, 2H) |
| 21 | cyclohexyl | 4-(4-methylpiperazin-1-yl)phenyl | (M + 1) 461.60 | 400 MHz, CDCl₃: 8.70 (s, 1H), 7.50 (d, J = 8.8 Hz, 2H), 6.93 (d, J = 9.0 Hz, 2H), 4.73-4.67 (m, 1H), 4.10-3.97 (m, 4H), 3.26-3.14 (m, 4H), 2.66-2.55 (m, 4H), 2.54-2.44 (m, 2H), 2.37 (s, 3H), 1.87-1.81 (m, 2H), 1.73-3.68 (m, 2H), 1.42-1.25 (m, 4H) |
| 22 | allyl | 4-(4-methylpiperazin-1-yl)phenyl | (M + 1) 419.15 | 400 MHz, CDCl₃: 8.75 (s, 1H), 7.51 (d, J = 8.9 Hz, 2H), 6.94 (d, J = 8.0 Hz, 2H), 5.94 (ddd, J = 15.9, 10.7, 5.2 Hz, 1H), 5.30 (dd, J = 17.2, 1,4 Hz, 1H), 5.22 (dd, J = 10.3, 1.2 Hz, 1H), 4.60 (d, J = 5.6 Hz, 2H), 4.21-4.08 (m, 2H), 4.07-3.98 (m, 2H), 3.43-3.25 (m, 4H), 2.99-2.78 (m, 4H), 2.56 (s, 3H) |

-continued

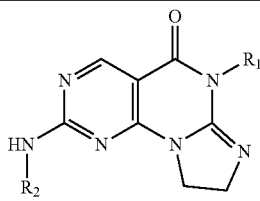

| Example | R$_1$ | R$_2$ | LC-MS (ESI) | $^1$H NMR |
|---|---|---|---|---|
| 23 | 2-thienyl | 4-(4-methylpiperazin-1-yl)phenyl | (M + 1) 461.28 | 400 MHz, DMSO-d$_6$: 10.15 (brs, 1H), 8.58 (s, 1H), 7.76-7.57 (m, 2H), 7.56 (dd, J = 5.6 Hz, J = 1.6 Hz, 1H), 7.09 (dd, J = 13.6 Hz, J = 3.6 Hz, 1H), 7.05 (dd, J = 17.6 Hz, J = 3.6 Hz, 1H), 6.92 (d, J = 9.0 Hz, 2H), 4.09 (t, J = 8.3 Hz, 2H), 3.81 (t, J = 8.9 Hz, 2H), 3.09 (t, J = 5.0 Hz, 4H), 2.45 (t, J = 5.0 Hz, 4H), 2.22 (s, 3H) |
| 24 | 2-furyl | 4-(4-methylpiperazin-1-yl)phenyl | — | — |
| 25 | 2-pyrrolyl | 4-(4-methylpiperazin-1-yl)phenyl | — | — |
| 26 | imidazolyl | 4-(4-methylpiperazin-1-yl)phenyl | — | — |

The compounds of Examples 27 and 28 were prepared from 1-chloro-3-fluoro-2-isocyanatobenzene, tert-butyl (1-amino-2-methylpropan-2-yl)carbamate or tert-butyl (2-amino-2-methylpropyl)carbamate, ethyl 4-chloro-2-(methylthio)pyrimidine-5-carboxylate and 4-(4-methylpiperazin-1-yl)aniline using procedures similar to those described for the syntheses of compounds of Example 1a-e and 4b.

Example 27

6-(2-Chloro-6-fluorophenyl)-8,8-dimethyl-2-((4-(4-methylpiperazin-1-yl)phenyl)amino)-8,9-dihydro-imidazo[1,2-a]pyrimido[5,4-e]pyrimidin-5(6H)-one White solid (60 mg, 63% yield). LC-MS (ESI): m/z (M+1) 535.28. $^1$H NMR (400 MHz, DMSO-d$_6$) δ 10.25 (br s, 1H), 8.64 (s, 1H), 7.76-7.59 (m, 2H), 7.58-7.49 (m, 2H), 7.49-7.42 (m, 1H), 6.94 (d, J=8.5 Hz, 2H), 3.93-3.81 (m, 2H), 3.10 (t, J=4.6 Hz, 4H), 2.45 (t, J=4.8 Hz, 4H), 2.22 (s, 3H), 1.23 (d, J=4.4 Hz, 6H).

Example 28

6-(2-Chloro-6-fluorophenyl)-9,9-dimethyl-2-((4-(4-methylpiperazin-1-yl)phenyl)amino)-8,9-dihydro-imidazo[1,2-a]pyrimido[5,4-e]pyrimidin-5(6H)-one Yellow solid (10 mg, 19% yield). LC-MS (ESI): (M+1) 535.24. $^1$H NMR (400 MHz, DMSO-d$_6$) δ 10.17 (br s, 1H), 8.66 (s, 1H), 7.60-7.42 (m, 5H), 6.94 (d, J=8.9 Hz, 2H), 3.55 (s, 2H), 3.11 (t, J=4.8 Hz, 4H), 2.47 (t, J=4.8 Hz, 4H), 2.23 (s, 3H), 1.76-1.57 (m, 6H).

Example 29

2-Methylsulfonyl-6-(pyrimidin-2-yl)-8,9-dihydro-imidazo[1,2-a]pyrimido[5,4-e]pyrimidin-5(6H)-one a) (4-Nitrophenyl-pyrimidin-2-yl)carbamate: to the solution of 2-aminopyrimidine (1 g, 10.5 mmol) in anhydrous DCM (30 mL) was added pyridine (1.66 mL, 21 mmol). At 0° C., anhydrous DCM (15 mL) solution of nitrophenyl chloroformate (2.1 g, 10.5 mmol) was added dropwise, and then the reaction liquor was stirred for 10 min at 0° C. The mixture was filtered, and the filter cake was washed with DCM and dried to give the targeted compound (1.6 g, 60% yield, white solid). LC-MS (ESI): m/z [M+H]$^+$ 261.08.

b) Tert-butyl (2-(3-(pyrimidin-2-yl)ureido)ethyl)carbamate: the reaction mixture of (4-nitrophenyl-pyrimidin-2-yl)carbamate (1 g, 3.8 mmol) and tert-butyl (2-aminoethyl)carbamate (1.85 g, 11.5 mmol) in anhydrous THF (30 mL) was reacted for 1 h in a microwave reactor at 80° C. After cooled to r.t., the mixture was concentrated under reduced pressure to give the crude product, which was purified by column chromatography (silica gel, DCM:MeOH=10:1, as eluent) to give the targeted compound (760 mg, 70% yield, yellow solid). LC-MS (ESI): m/z [M+H]$^+$ 282.21.

c) 2-Methylsulfonyl-6-(pyrimidin-2-yl)-8,9-dihydroimidazo[1,2-a]pyrimido[5,4-e]pyrimidin-5(6H)-one: the compound (light-yellow solid) was prepared from tert-butyl (2-(3-(pyrimidin-2-yl)ureido)ethyl)carbamate and ethyl 4-chloro-2-(methylthio)pyrimidine-5-carboxylate using procedures similar to those described for the syntheses of compounds of Examples 1b-1e. LC-MS (ESI): m/z [M+H]$^+$ 346.11.

Example 30

2-Fluoro-4-((3R,5S)-3,4,5-trimethylpiperazin-1-yl) aniline a) (2S,6R)-1,2,6-Trimethyl-4-(3-fluoro-4-nitrophenyl) piperazine: to the solution of (2S,6R)-1,2,6-trimethylpiperazine (403 mg, 3.14 mmol) in MeCH (10 mL) was added DIPEA (0.82 mL, 4.71 mmol) and 2,4-difluoronitrobenzene (500 mg, 3.14 mmol) at r.t. The reaction liquor was stirred for 3 hrs at 80° C., and then cooled down to r.t., and the mixture was extracted with EtOAc (20 mL) and H$_2$O (20 mL). The organic layer was washed with saturated saline, and dried with anhydrous sodium sulfate. The mixture was filtered, and the filtrate was concentrated under reduced pressure to give the crude product, which was purified by column chromatography (silica gel, DCM:MeOH=20:1, as eluent) to give the targeted compound (268 mg, 32% yield, yellow solid). LC-MS (ESI): m/z [M+H]$^+$ 268.21.

b) 2-Fluoro-4-((3R,5S)-3,4,5-trimethylpiperazin-1-yl) aniline: to the solution of (2S,6R)-1,2,6-trimethyl-4-(3-fluoro-4-nitrophenyl)piperazine (268 mg, 1.0 mmol) in EtOAc (15 mL) was added 10% Pd/C (30 mg) at r.t. The gas in reaction liquor was replaced by hydrogen for three times. After hydrogenation overnight at r.t., Pd/C was removed by filtration, and the filtrate was concentrated under reduced pressure to give the targeted compound (230 mg, 96% yield, yellow solid). LC-MS (ESI): m/z [M+H]$^+$ 238.32.

Example 31

2-Chloro-4-((3R,5S)-3,4,5-trimethylpiperazin-1-yl) aniline

At r.t., to the solution of (2S,6R)-1,2,6-trimethyl-4-(3-chloro-4-nitrophenyl)piperazine (the compound was prepared from (2S,6R)-1,2,6-trimethylpiperazine and 2-chloro-4-fluoro-1-nitrobenzene using a procedure similar to those described for the synthesis of compound of Example 30a. 200 mg, 0.71 mmol) in EtOH/H$_2$O (10/2.5 mL) was added Fe powder (185 mg, 3.31 mmol) and ammonium chloride (188 mg, 3.52 mmol). The gas in the reaction liquor was replaced with nitrogen for three times, and the mixture was stirred for 4 hrs at 50° C. and then cooled down to r.t. Fe powder was removed by filtration, and the filtrate was concentrated under reduced pressure. The crude product was dissolved in EtOAc (20 mL) and H$_2$O (10 mL), and separated. The organic layer was washed with saturated saline and dried with anhydrous sodium sulfate, filtered, and concentrated under reduced pressure to give the crude product, which was purified by column chromatography (silica gel, DCM:MeOH=15:1 as eluent) to give the targeted compound (160 mg, 89% yield, yellow oil). LC-MS (ESI): m/z [M+H]$^+$ 254.24.

Other substituted amines can be prepared using a procedure similar to those described for the synthesis of compound of Example 30 or 31, or using a known method from those of ordinary skill in the art.

The compounds of Examples 32-33, 36, 54-56 and 85-87 were prepared from 2-(methylsulfonyl)-6-substituent-8,9-dihydroimidazo[1,2-a]pyrimido[5,4-e]pyrimidin-5(6H)-one (the compound was prepared from N-tert-butoxycarbonyl-1,2-ethylenediamine, ethyl 4-chloro-2-(methylthio)pyrimidine-5-carboxylate and the corresponding substituted isocyanatobenzene using procedures similar to those described for the syntheses of compounds of Examples 1a-1e) and the corresponding substituted aniline using a procedure similar to those described for the synthesis of compound of Example 1.

The compounds of Examples 34-35, 37-53, 57-84 and 88-92 were prepared from 2-(methylsulfonyl/methylsulfinyl)-6-substituent-8,9-dihydroimidazo[1,2-e]pyrimido[5,4-e]pyrimidin-5(6H)-one (the compound was prepared from N-tert-butoxycarbonyl-1,2-ethylenediamine, ethyl 4-chloro-2-(methylthio)pyrimidine-5-carboxylate and the corresponding substituted isocyanatobenzene using procedures similar to those described for the syntheses of compounds of Examples 1a-1e; Example 29) and the corresponding substituted amine using a procedure similar to those described for the synthesis of compound of Example 4b.

| Example | R$_1$ | R$_2$ | LC-MS (ESI) | $^1$H NMR (400 MHz) |
|---|---|---|---|---|
| 32 | ![F, Cl phenyl] | 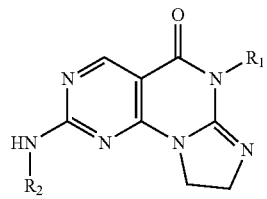 | (M + 1) 522.24 | 400 MHz, DMSO-d$_6$: 10.26 (brs, 1H), 8.64 (s, 1H), 7.75-7.40 (m, 5H), 6.93 (d. J = 8.8 Hz, 2H), 4.23-4.06 (m, 2H), 3.87-3.77 (m, 2H), 3.75-3.64 (m, 2H), 3.59-3.48 (m, 2H), 2.27-2.14 (m, 2H), 1.15 (d, J = 6.2 Hz, 6H) |

-continued

| Example | R₁ | R₂ | LC-MS (ESI) | ¹H NMR (400 MHz) |
|---|---|---|---|---|
| 33 | 2-F, 6-Cl phenyl | 4-(morpholinomethyl)phenyl | (M − 1) 506.2 | 500 MHz, CD₃OD: 8.77 (s, 1H), 7.77 (d, J = 7.4 Hz, 2H), 7.62-7.54 (m, 1H), 7.49 (d, J = 8.2 Hz, 1H), 7.38-7.32 (m, 3H), 4.33-4.28 (m, 2H), 3.97 (t, J = 9.1 Hz, 2H), 3.73 (t, J = 4.4 Hz, 4H), 3.55 (s, 2H), 2.51 (t, J = 3.9 Hz, 4H) |
| 34 | 2-F, 6-Cl phenyl | 4-((2S,5R)-2,5-dimethyl-4-methylpiperazin-1-yl)phenyl | (M/2 + 1) 268.22 | 400 MHz, DMSO-d₆: 10.26 (brs, 1H), 8.64 (s, 1H), 7.75-7.40 (m, 5H), 6.93 (d, J = 8.8 Hz, 2H), 4.22-4.06 (m, 2H), 3.88-3.75 (m, 2H), 3.61-3.46 (m, 2H), 2.46-2.30 (m, 4H), 2.25 (s, 3H), 1.09 (d, J = 5.6 Hz, 6H) |
| 35 | 2-F, 6-Cl phenyl | 4-((2S,5R)-2,5-dimethyl-4-isopropylpiperazin-1-yl)phenyl | (M/2 + 1) 283.48 | 400 MHz, DMSO-d₆: 10.22 (brs, 1H), 8.62 (s, 3H), 7.70-7.40 (m, 5H), 6.78 (d, J = 8.0 Hz, 2H), 4.23-4.08 (m, 2H), 3.87-3.76 (m, 2H), 3.31-3.24 (m, 3H), 3.08-3.00 (m, 2H), 2.95-2.84 (m, 2H), 1.18-0.86 (m, 12H) |
| 36 | 2-F, 6-Cl phenyl | 3-F, 4-(4-methylpiperazin-1-yl)phenyl | (M + 1) 525.17 | 400 MHz, DMSO-d₆: 9.01 (brs, 1H), 8.66 (s, 1H), 794 (s, 1H), 7.65-7.42 (m, 3H), 7.04 (d, J = 9.6 Hz, 1H), 6.98-6.89 (m, 1H), 4.17-4.05 (m, 2H), 3.87-3.77 (m, 2H), 2.99-2.78 (m, 4H), 2.50-2.48 (m, 4H), 2.27 (s, 3H) |
| 37 | 2-F, 6-Cl phenyl | 3-F, 4-((2S,5R)-2,5-dimethyl-4-methylpiperazin-1-yl)phenyl | (M/2 + 1) 278.29 | 400 MHz, DMSO-d₆: 9.01 (s, 1H), 8.67 (s, 1H), 8.07-7.83 (m, 1H), 7.62-7.42 (m, 3H), 7.06-6.90 (m, 2H), 4.16-4.04 (m, 2H), 3.86-3.75 (m, 2H), 2.99-2.88 (m, 2H), 2.49-2.45 (m, 2H), 2.30-2.10 (m, 5H), 1.00 (d, J = 5.9 Hz, 6H) |
| 38 | 2-F, 6-Cl phenyl | 3-Cl, 4-(4-methylpiperazin-1-yl)phenyl | (M/2 + 1) 272.25 | 400 MHz, DMSO-d₆: 9.72 (br s, 1H), 8.58 (s, 1H), 7.60-7.19 (m, 4H), 7.02 (d, J = 2.7 Hz, 1H), 6.93 (dd, J = 8.9, 2.7 Hz, 1H), 4.18-3.92 (m, 2H), 3.87-3.71 (m, 2H), 3.24-3.10 (m, 4H), 2.49-2.38 (m, 4H), 2.23 (s, 3H) |
| 39 | 2-F, 6-Cl phenyl | 3-Cl, 4-((2S,5R)-2,5-dimethyl-4-methylpiperazin-1-yl)phenyl | (M/2 + 1) 286.43 | 400 MHz, DMSO-d₆: 9.71 (s, 1H), 8.58 (br s, 1H), 7.61-7.15 (m, 4H), 7.03 (d, J = 2.6 Hz, 1H), 6.93 (dd, J = 8.9, 2.5 Hz, 1H), 4.24-3.92 (m, 2H), 3.88-3.69 (m, 2H), 3.67-3.55 (m, 2H), 2.48-2.38 (m, 2H), 2.35-2.07 (m, 5H), 1.08 (d, J = 6.1 Hz, 6H) |

-continued

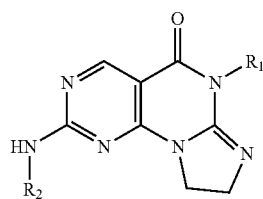

| Example | R₁ | R₂ | LC-MS (ESI) | ¹H NMR (400 MHz) |
|---|---|---|---|---|
| 40 | F, Cl phenyl | piperazine-phenyl-CF₃ | (M/2 + 1) 289.39 | 400 MHz, DMSO-d$_6$: 9.75 (brs, 1H), 8.55 (s, 1H), 7.63-7.49 (m, 2H), 7.48-7.40 (m, 1H), 7.37-7.34 (m, 3H), 4.28-3.88 (m, 2H), 3.87-3.66 (m, 2H), 3.42-3.31 (m, 4H), 2.84-2.56 (m, 4H), 2.40 (s, 3H) |
| 41 | F, Cl phenyl | (2,6-dimethyl)piperazine-phenyl-CF₃ | (M + 1) 603.21 | 400 MHz, DMSO-d$_6$: 9.72 (s, 1H), 8.54 (br s, 1H), 7.66-7.40 (m, 3H), 7.39-7.07 (m, 3H), 4.28-3.94 (m, 2H), 3.87-3.64 (m, 4H), 2.48-2.42 (m, 2H), 2.34-2.07 (m, 5H), 1.09 (d, J = 6.1 Hz, 6H) |
| 42 | F, Cl phenyl | piperazine-phenyl-CH₃ | (M/2 + 1) 261.25 | 400 MHz, DMSO-d$_6$: 9.62 (s, 1H), 8.62-8.51(m, 1H), 7.61-7.48 (m, 2H), 7.47-7.41 (m, 1H), 7.32-7.07 (m, 1H), 6.88-6.75 (m, 2H), 4.16-3.89 (m, 2H), 3.84-3.69 (m, 2H), 3.26-3.07 (m, 4H), 2.75-2.56 (m, 4H), 2.37 (s, 3H), 2.15 (s, 3H) |
| 43 | F, Cl phenyl | (2,6-dimethyl)piperazine-phenyl-CH₃ | (M/2 + 1) 276.48 | 400 MHz, DMSO-d$_6$: 9.60 (s, 1H), 8.62-8.51 (m, 1H), 7.60-7.51 (m, 2H), 7.46-7.42 (m, 1H), 7.32-7.03 (m, 1H), 6.82-6.75 (m, 2H), 4.14-3.90 (m, 2H), 3.79-3.72 (m, 2H), 3.60-3.53 (m, 2H), 2.43-2.33 (m, 4H), 2.24-2.14 (m, 6H), 1.10 (d, J = 5.9 Hz, 6H) |
| 44 | F, Cl phenyl | piperazine-phenyl-F | (M + 1) 525.23 | 400 MHz, DMSO-d$_6$: 10.44 (brs, 1H), 8.69 (s, 1H), 7.95-7.19 (m, 5H), 7.02 (t, J = 9.4 Hz, 1H), 4.30-4.07 (m, 2H), 3.92-3.72 (m, 2H), 3.10-2.86 (m, 4H), 2.49-2.42 (m, 4H), 2.23 (s, 3H) |
| 45 | F, Cl phenyl | (2,6-dimethyl)piperazine-phenyl-F | (M + 1) 553.49 | 400 MHz, DMSO-d$_6$: 10.43 (brs, 1H), 8.69 (s, 1H), 7.70 (d, J = 15.4 Hz, 1H), 7.64-7.50 (m, 3H), 7.48-7.44 (m, 1H), 6.99 (m, 1H), 4.22-4.14 (m, 2H), 3.84 (t, 2H), 3.17 (d, J = 10.7 Hz, 2H), 2.43 (t, 2H), 2.35-2.29 (m, 2H), 2.20 (s, 3H), 1.04 (d, J = 6.1 Hz, 6H) |
| 46 | F, Cl phenyl | piperazine-phenyl-Cl | (M/2 + 1) 272.27 | 400 MHz, DMSO-d$_6$: 10.45 (brs, 1H), 8.70 (s, 1H), 7.95 (s, 1H), 7.85-7.36 (m, 4H), 7.17 (d, J = 8.8 Hz, 1H), 4.30-4.07 (m, 2H), 3.84 (t, J = 8.7 Hz, 2H), 3.10-2.88 (m, 4H), 2.75-2.56 (m, 4H), 2.34 (s, 3H) |

-continued

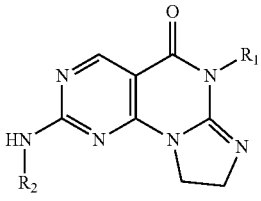

| Example | R₁ | R₂ | LC-MS (ESI) | ¹H NMR (400 MHz) |
|---|---|---|---|---|
| 47 | 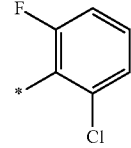 | 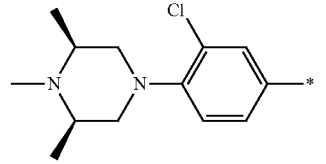 [SMILES: *c1ccc(N2C[C@@H](C)N(C)[C@@H](C)C2)c(Cl)c1] | (M + 1) 569.19 | 400 MHz, DMSO-d₆: 10.44 (brs, 1H), 8.70 (s, 1H), 7.94 (s, 1H), 7.72 (s, 1H), 7.62-7.53 (m, 2H), 7.49-7.43 (m, 1H), 7.12 (d, J = 8.9 Hz, 1H), 4.18 (t, J = 8.8 Hz, 2H), 3.84 (t, 2H), 3.10 (d, J = 10.7 Hz, 2H), 2.47-2.42 (m, 2H), 2.37-2.30 (m, 2H), 2.21 (s, 3H), 1.04 (d, J = 6.1 Hz, 6H) |
| 48 | 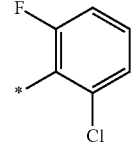 | 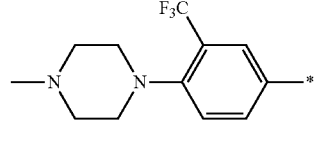 | (M + 1) 575.18 | 400 MHz, DMSO-d₆: 10.62 (brs, 1H), 8.72 (s, 1H), 8.38 (s, 1H), 7.99 (d, J = 8.7 Hz, 1H), 7.70-7.36 (m, 4H), 4.24-4.11 (m, 2H), 3.92-3.79 (m, 2H), 2.95-2.77 (m, 4H), 2.49-2.40 (m, 4H), 2.25 (s, 3H) |
| 49 | 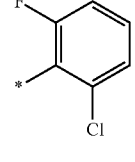 | 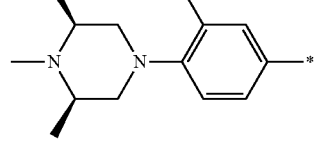 | (M + 1) 603.29 | 400 MHz, DMSO-d₆: 10.61 (brs, 1H), 8.72 (s, 1H), 8.45-8.29 (m, 1H), 7.97 (d, J = 7.1 Hz, 1H), 7.69-7.35 (m, 4H), 4.23-4.11 (m, 2H), 3.90-3.77 (m, 2H), 2.83-2.70 (m, 2H), 2.64-2.54 (m, 2H), 2.35-2.25 (m, 2H), 2.21 (s, 3H), 1.01 (d, J = 6.1 Hz, 6H) |
| 50 | 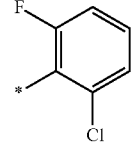 | 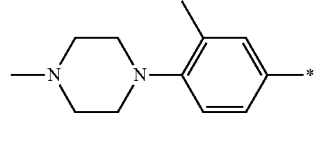 [SMILES: *c1ccc(N2CCN(C)CC2)c(C)c1] | (M + 1) 521.22 | 400 MHz, DMSO-d₆: 10.28 (brs, 1H), 8.66 (s, 1H), 7.70-7.49 (m, 4H), 7.48-7.43 (m, 1H), 7.01 (d, J = 8.6 Hz, 1H), 4.22-4.13 (m, 2H), 3.86-3.79 (m, 2H), 2.88-2.79 (m, 4H), 2.59-2.51 (m, 4H), 2.28 (s, 3H), 2.24 (s, 3H) |
| 51 | 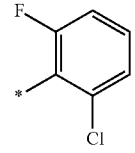 | 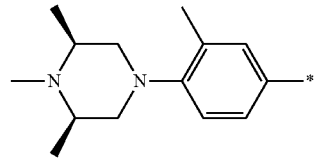 [SMILES: *c1ccc(N2C[C@@H](C)N(C)[C@@H](C)C2)c(C)c1] | (M/2 + 1) 276.32 | 400 MHz, DMSO-d₆: 10.27 (brs, 1H), 8.66 (s, 1H), 7.69-7.40 (m, 5H), 6.97 (d, J = 8.6 Hz, 1H), 4.24-4.12 (m, 2H), 3.88-3.78 (m, 2H), 2.94-2.85 (m, 2H), 2.48-2.33 (m, 5H), 2.30-2.15 (m, 5H), 1.05 (d, J = 5.8 Hz, 6H) |
| 52 | 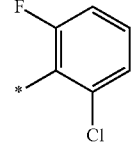 | 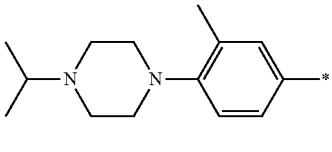 [SMILES: *c1ccc(N2CCN(C(C)C)CC2)c(C)c1] | (M + 1) 549.38 | 400 MHz, CDCl₃: 8.80 (s, 1H), 7.53-7.46 (m, 1H), 7.45-7.28 (m, 3H), 7.21-7.15 (m, 1H), 7.06 (d, J = 8.6 Hz, 1H), 4.29-4.16 (m, 2H), 4.01 (t, J = 8.8 Hz, 2H), 3.06-2.97 (m, 4H), 2.93-2.87 (m, 1H), 2.85-2.74 (m, 4H), 2.32 (s, 3H), 1.16 (d, J = 6.6 Hz, 6H) |
| 53 | 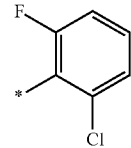 | 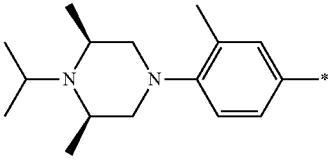 [SMILES: *c1ccc(N2C[C@@H](C)N(C(C)C)[C@@H](C)C2)c(C)c1] | (M + 1) 577.40 | 400 MHz, CDCl₃: 8.80 (s, 1H), 7.52-7.44 (m, 1H), 7.42-7.34 (m, 3H), 7.21-7.15 (m, 1H), 7.04 (d, J = 8.5 Hz, 1H), 4.28-4.15 (m, 2H), 4.01 (t, J = 8.8 Hz, 2H), 3.31-3.23 (m, 1H), 3.17-3.04 (m, 2H), 3.01-2.89 (m, 2H), 2.81-2.70 (m, 2H), 2.35 (s, 3H), 1.36-0.99 (m, 12H) |

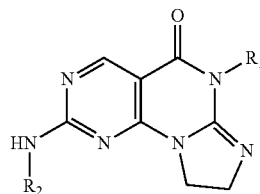

| Example | R₁ | R₂ | LC-MS (ESI) | ¹H NMR (400 MHz) |
|---|---|---|---|---|
| 54 | 2-F, 6-Cl phenyl | 4-methylpiperazinyl-2-methoxyphenyl | (M + 1) 537.19 | 500 MHz, CD₃OD: 8.72 (s, 1H), 7.62-7.51 (m, 3H), 7.45 (d, J = 13.5 Hz, 1H), 7.31 (t, J = 14.3 Hz, 1H), 7.21 (d, J = 12.0 Hz, 1H), 6.96 (d, J = 14.0 Hz, 1H), 4.28 (t, J = 14.3 Hz, 2H), 3.96-3.91 (m, 5H), 3.16-2.98 (m, 4H), 2.75-2.54 (m, 4H), 2.35 (s, 3H) |
| 55 | 2-F, 6-Cl phenyl | 4-methylpiperazinyl-2-nitrophenyl | — | 500 MHz, CD₃OD: 8.73 (d, J = 1.0 Hz, 1H), 8.03 (d, J = 2.5 Hz, 1H), 7.68 (dd, J = 9, 2.5 Hz, 1H), 7.56 (dd, J = 14, 8.5 Hz, 1H), 7.47 (d, J = 8.8 Hz, 1H), 7.43 (d, J = 9.0 Hz, 1H), 7.32 (t, J = 9.0 Hz, 1H), 4.26 (t, J = 8.8 Hz, 2H), 3.98 (t, J = 8.8 Hz, 2H), 3.22 (t, J = 4.5 Hz, 4H), 2.72 (t, J = 3.8 Hz, 4H), 2.44 (s, 3H) |
| 56 | 2-F, 6-Cl phenyl | 4-methylpiperazinyl-2,6-dimethylphenyl | (M + 1) 535.21 | 500 MHz, CD₃OD: 8.74 (s, 1H), 7.60-7.55 (m, 1H), 7.53-7.36 (m, 3H), 7.34 (t, J = 8.3 Hz, 1H), 4.30 (t, J = 9.1 Hz, 2H), 3.97 (t, J = 8.8 Hz, 2H), 3.21 (t, J = 4.3 Hz, 4H), 2.72 (t, J = 4.4 Hz, 4H), 2.48 (s, 3H), 2.38 (s, 6H) |
| 57 | 2-F, 6-Cl phenyl | 4-methylpiperazinyl-pyridinyl | (M + 1) 508.19 | 400 MHz, DMSO-d₆: 10.27 (brs, 1H), 8.64 (s, 1H), 8.55 (s, 1H), 7.96-7.80 (m, 1H), 7.65-7.43 (m, 3H), 6.85 (d, J = 9.1 Hz, 1H), 4.19-4.10 (m, 2H), 3.84-3.76 (m, 2H), 3.47-3.42 (m, 4H), 2.47-2.35 (m, 4H), 2.22 (s, 3H) |
| 58 | 2-F, 6-Cl phenyl | 2-isopropyl-spirocyclopropyl-tetrahydroisoquinolinyl | (M + 1) 532.29 | 400 MHz, DMSO-d₆: 10.31 (brs, 1H), 8.67 (s, 1H), 7.63-7.42 (m, 5H), 6.69 (d, J = 8.6 Hz, 1H), 4.17 (t, J = 10.2 Hz, 2H), 3.82 (t, J = 9.2 Hz, 2H), 3.78 (s, 2H), 2.92-2.86 (m, 1H), 2.57 (s, 2H), 1.07 (d, J = 6.4 Hz, 6H), 0.94-0.88 (m, 2H), 0.87-0.81 (m, 2H) |
| 59 | 2-F, 6-Cl phenyl | 5-methyl-4,5,6,7-tetrahydropyrazolo[1,5-a]pyrazinyl | (M + 1) 468.15 | 400 MHz, DMSO-d₆: 10.77 (brs, 1H), 8.65 (s, 1H), 7.64-7.51 (m, 2H), 7.50-7.42 (m, 1H), 6.59 (s, 1H), 4.23-4.12 (m, 2H), 4.10-3.99 (m, 2H), 3.82 (t, J = 8.8 Hz, 2H), 3.79-3.61 (m, 2H), 3.08-2.90 (m, 2H), 2.53 (s, 3H) |
| 60 | 2,6-diF phenyl | 4-methylpiperazinyl-2-methylphenyl | (M + 1) 505.89 | 400 MHz, CDCl₃: 8.79 (s, 1H), 7.51-7.39 (m, 3H), 7.13-7.02 (m, 3H), 4.22 (t, J = 8.6 Hz, 2H), 4.01 (t, J = 8.9 Hz, 2H), 3.02 (t, J = 4.7 Hz, 4H), 2.89-2.68 (m, 4H), 2.48 (s, 3H), 2.33 (s, 3H) |

-continued

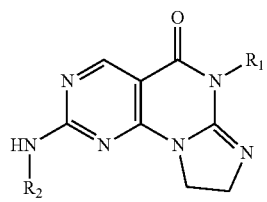

| Example | R₁ | R₂ | LC-MS (ESI) | ¹H NMR (400 MHz) |
|---|---|---|---|---|
| 61 | 2-F, 6-CF₃ phenyl | 4-methyl-piperazinyl-(2-methylphenyl) | (M + 1) 555.31 | 400 MHz, CDCl₃: 8.77 (s, 1H), 7.65-7.58 (m, 2H), 7.58-7.45 (m, 2H), 7.45-7.40 (m, 1H), 7.08 (d, J = 8.6 Hz, 1H), 4.26-4.17 (m, 2H), 4.04-3.96 (m, 2H), 3.27-2.97 (m, 8H), 2.69 (s, 3H), 2.32 (s, 3H) |
| 62 | 2-F, 6-methyl phenyl | 4-methyl-piperazinyl-(2-methylphenyl) | (M + 1) 501.55 | 400 MHz, CDCl₃: 8.79 (s, 1H), 7.53-7.47 (m, 1H), 7.41 (d, J = 2.3 Hz, 1H), 7.35-7.30 (m, 1H), 7.13 (d, J = 7.8 Hz, 1H), 7.10-7.03 (m, 2H), 4.25-4.16 (m, 2H), 4.04-3.95 (m, 2H), 3.00 (t, J = 4.7 Hz, 4H), 2.78-2.66 (m, 4H), 2.45 (s, 3H), 2.33 (s, 3H), 2.25 (s, 3H) |
| 63 | 2,6-dichlorophenyl | 4-isopropyl-piperazinyl-phenyl | (M + 1) 551.52 | 400 MHz, DMSO-d₆: 10.27 (brs, 1H), 8.65 (s, 1H), 7.74-7.61 (m, 3H), 7.54 (dd, J = 8.7, 7.6 Hz, 2H), 6.91 (d, J = 9.0 Hz, 2H), 4.17 (t, J = 8-2 Hz, 2H), 3.81 (t, J = 8.8 Hz, 2H), 3.15-3.03 (m, 4H), 2.70-2.64 (m, 1H), 2.63-2.52 (m, 4H), 1.01 (d, J = 6.5 Hz, 6H) |
| 64 | 2,6-dichlorophenyl | (2S,5R)-2,5-dimethyl-4-methyl-piperazinyl-phenyl | (M/2 + 1) 277.34 | 400 MHz, DMSO-d₆: 10.26 (brs, 1H), 8.65 (s, 1H), 7.75-7.60 (m, 3H), 7.61-7.46 (m, 2H), 6.92 (d, J = 8.9 Hz, 2H), 4.22-4.10 (m, 2H), 3.87-3.76 (m, 2H), 3.56-3.48 (m, 2H), 2.41-2.24 (m, 4H), 2.21 (s, 3H), 1.08 (d, J = 6.0 Hz, 6H) |
| 65 | 2,6-dichlorophenyl | (2S,5R)-2,5-dimethyl-4-isopropyl-piperazinyl-phenyl | (M + 1) 579.50 | 400 MHz, DMSO-d₆: 10.22 (brs, 1H), 8.63 (s, 1H), 7.73-7.59 (m, 3H), 7.57-7.42 (m, 2H), 6.77 (d, J = 8.0 Hz, 2H), 4.16 (t, J = 8 Hz, 2H), 3.81 (t, J = 8.8 Hz, 2H), 3.36-3.25 (m, 8H), 3.22-3.17 (m, 1H), 3.05-2.97 (m, 2H), 2.94-2.85 (m, 2H), 1.06-1.03 (m, 6H) |
| 66 | 2,6-dichlorophenyl | (2S,5R)-2,5-dimethyl-4-methyl-piperazinyl-(3-fluorophenyl) | (M/2 + 1) 286.41 | 400 MHz, DMSO-d₆: 9.04 (s, 1H), 8.67 (s, 1H), 8.03-7.85 (m, 1H), 7.73-7.64 (m, 2H), 7.60-7.50 (m, 1H), 7.05-6.88 (m, 2H), 4.15-4.05 (m, 2H), 3.88-3.73 (m, 2H), 2.98-2.87 (m, 2H), 2.48-2.43 (m, 2H), 2.26-2.04 (m, 5H), 0.99 (d, J = 6.1 Hz, 6H) |
| 67 | 2,6-dichlorophenyl | (2S,5R)-2,5-dimethyl-4-methyl-piperazinyl-(3-chlorophenyl) | (M/2 + 1) 293.20 | 400 MHz, DMSO-d₆: 9.73 (s, 1H), 8.59 (s, 1H), 7.71-7.62 (m, 2H), 7.57-7.51 (m, 1H), 7.46-7.08 (m, 1H), 7.04 (d, J = 2.4 Hz, 1H), 6.94 (dd, J = 8.8, 2.4 Hz, 1H), 4.19-3.89 (m, 2H), 3.89-3.71 (m, 2H), 3.69-3.58 (m, 2H), 2.45-2.20 (m, 7H), 1.10 (d, J = 5.9 Hz, 6H) |

-continued

| Example | R₁ | R₂ | LC-MS (ESI) | ¹H NMR (400 MHz) |
|---|---|---|---|---|
| 68 | 2,6-dichlorophenyl | (2S,5R)-4-methyl-2,5-dimethylpiperazinyl-[3-(trifluoromethyl)phenyl] | (M/2 + 1) 311.49 | 400 MHz, DMSO-d₆: 9.73 (s, 1H), 8.55 (s, 1H), 7.72-7.61 (m, 2H), 7.58-7.46 (m, 1H), 7.42-7.10 (m, 3H), 4.27-3.94 (m, 2H), 3.87-3.72 (m, 2H), 3.71-3.61 (m, 2H), 2.49-2.42 (m, 2H), 2.32-2.10 (m, 5H), 1.09 (d, J = 6.1 Hz, 6H) |
| 69 | 2,6-dichlorophenyl | 4-methylpiperazinyl-(2-fluorophenyl) | (M + 1) 541.40 | 400 MHz, DMSO-d₆: 10.45 (brs, 1H), 8.70 (s, 1H), 7.79-7.62 (m, 3H), 7.59-7.42 (m, 2H), 7.06-6.98 (m, 1H), 4.19 (t, J = 8 Hz, 2H), 3.83 (t, J = 8.7 Hz, 2H), 3.05-2.89 (m, 4H), 2.49-2.41 (m, 4H), 2.22 (s, 3H) |
| 70 | 2,6-dichlorophenyl | (2S,5R)-dimethyl-4-methylpiperazinyl-(2-fluorophenyl) | (M + 1) 569.38 | 400 MHz, DMSO-d₆: 10.45 (brs, 1H), 8.70 (s, 1H), 7.75-7.64 (m, 3H), 7.55 (dd, J = 8.8, 7.5 Hz, 2H), 6.99 (t, J = 9.4 Hz, 1H), 4.19 (t, J = 8.0 Hz, 2H), 3.83 (t, J = 8.8 Hz, 2H), 3.17 (d, J = 11.0 Hz, 2H), 2.47-2.42 (m, 2H), 2.34-2.28 (m, 2H), 2.20 (s, 3H), 1.04 (d, J = 6.1 Hz, 6H) |
| 71 | 2,6-dichlorophenyl | 4-methylpiperazinyl-(2-chlorophenyl) | (M + 1) 557.40 | 400 MHz, DMSO-d₆: 10.46 (brs, 1H), 8.71 (s, 1H), 7.98-7.89 (m, 1H), 7.79-7.61 (m, 3H), 7.55 (dd, J = 8.8, 7.5 Hz, 1H), 7.16 (d, J = 8.8 Hz, 1H), 4.19 (t, J = 8.0 Hz, 2H), 3.83 (t, J = 8.7 Hz, 2H), 3.02-2.87 (m, 4H), 2.49-2.43 (m, 4H), 2.23 (s, 3H) |
| 72 | 2,6-dichlorophenyl | (2S,5R)-dimethyl-4-methylpiperazinyl-(2-chlorophenyl) | (M + 1) 585.44 | 400 MHz, DMSO-d₆: 10.45 (brs, 1H), 8.71 (s, 1H), 7.93 (s, 1H), 7.80-7.70 (m, 1H), 7.68 (d, J = 7.9 Hz, 2H), 7.55 (dd, J = 8.8, 7.5 Hz, 1H), 7.12 (d, J = 8.8 Hz, 1H), 4.19 (t, J = 8.0 Hz, 2H), 3.85 (t, J = 8.8 Hz, 2H), 3.10 (d, J = 10.7 Hz, 2H), 2.47-2.41 (m, 2H), 2.36-2.30 (m, 2H), 2.21 (s, 3H), 1.04 (d, J = 6.1 Hz, 6H) |
| 73 | 2,6-dichlorophenyl | 4-methylpiperazinyl-[2-(trifluoromethyl)phenyl] | (M + 1) 591.20 | 400 MHz, CDCl₃: 8.83 (s, 1H), 7.67-7.55 (m, 2H), 7.49 (d, J = 0.8 Hz, 1H), 7.48-7.46 (m, 1H), 7.42 (d, J = 8.6 Hz, 1H), 7.36 (dd, J = 8.8, 7.5 Hz, 1H), 4.24 (t, J = 8.7 Hz, 2H), 4.04 (t, J = 8.9 Hz, 2H), 3.10-3.01 (m, 4H), 2.88-2.72 (m, 4H), 2.50 (s, 3H) |
| 74 | 2,6-dichlorophenyl | (2S,5R)-dimethyl-4-methylpiperazinyl-[2-(trifluoromethyl)phenyl] | (M + 1) 619.56 | 400 MHz, DMSO-d₆: 8.84 (s, 1H), 8.31 (br s, 1H), 7.70-7.53 (m, 2H), 7.48 (d, J = 7.8 Hz, 2H), 7.42 (d, J = 7.5 Hz, 1H), 7.39-7.34 (m, 1H), 4.24 (t, J = 8.0 Hz, 2H), 4.05 (t, J = 9.0 Hz, 2H), 2.93 (d, J = 9.7 Hz, 2H), 2.51 (s, 3H), 2.12-1.78 (m, 4H), 1.35-1.17 (m, 6H) |

-continued

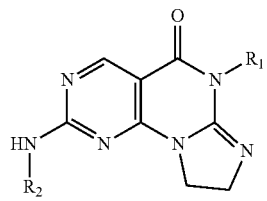

| Example | R₁ | R₂ | LC-MS (ESI) | ¹H NMR (400 MHz) |
|---|---|---|---|---|
| 75 | 2,6-dichlorophenyl | 4-(4-methylpiperazin-1-yl)-3-methylphenyl | (M + 1) 537.36 | 400 MHz, DMSO-d₆: 10.29 (brs, 1H), 8.67 (s, 1H), 7.71-7.60 (m, 3H), 7.59-7.45 (m, 2H), 7.01 (d, J = 8.5 Hz, 1H), 4.18 (t, J = 8.4 Hz, 2H), 3.82 (t, J = 8.6 Hz, 2H), 2.88-2.78 (m, 4H), 2.49-2.46 (m, 4H), 2.32-2.18 (m, 6H) |
| 76 | 2,6-dichlorophenyl | 4-(4-isopropylpiperazin-1-yl)-3-methylphenyl | (M + 1) 565.43 | 400 MHz, DMSO-d₆: 8.81 (s, 1H), 7.48 (d, J = 7.9 Hz, 2H), 7.45-7.29 (m, 3H), 7.11 (d, J = 8.6 Hz, 1H), 4.23 (t, J = 8.0 Hz, 2H), 4.02 (t, J = 8.9 Hz, 2H), 3.48-3.42 (m, 1H), 3.37-3.04 (m, 8H), 2.32 (s, 3H), 1.39 (d, J = 6.7 Hz, 6H) |
| 77 | 2,6-dichlorophenyl | (2S,5R)-2,5-dimethyl-4-methylpiperazin-1-yl-methylphenyl | (M + 1) 565.60 | 400 MHz, CDCl₃: 8.81 (s, 1H), 7.59-7.51 (m, 1H), 7.48 (d, J = 7.9 Hz, 2H), 7.44-7.39 (m, 1H), 7.35 (dd, J = 8.7, 7.5 Hz, 1H), 7.10 (d, J = 8.5 Hz, 1H), 4.23 (t, J = 8.5 Hz, 2H), 4.02 (t, J = 8.8 Hz, 2H), 3.04-2.99 (m, 2H), 2.88-2.56 (m, 4H), 2.32 (s, 3H), 1.91 (s, 3H), 1.51-1.35 (m, 6H) |
| 78 | 2,6-dichlorophenyl | (2S,5R)-2,5-dimethyl-4-isopropylpiperazin-1-yl-methylphenyl | (M + 1) 593.43 | 400 MHz, DMSO-d₆: 10.29 (brs, 1H), 8.67 (s, 1H), 7.67 (d, J = 7.9 Hz, 2H), 7.61 (s, 1H), 7.57-7.43 (m, 2H), 6.97 (d, J = 8.6 Hz, 1H), 4.18 (t, J = 9.2 Hz, 2H), 3.83 (t, J = 9.0 Hz, 2H), 3.18-3.14 (m, 1H), 3.01-2.94 (m, 2H), 2.85-2.78 (m, 2H), 2.61-2.54 (m, 2H), 2.28 (s, 3H), 1.21-0.97 (m, 12H) |
| 79 | 2,6-dichlorophenyl | 5-methyl-4,5,6,7-tetrahydropyrazolo[1,5-a]pyrazin-3-yl | (M + 1) 484.12 | 400 MHz. DMSO-d₆: 10.86 (brs, 1H), 8.67 (s, 1H), 7.67 (d, J = 8.0 Hz, 2H), 7.59-7.51 (m, 1H), 6.69 (s, 1H), 4.40-3.97 (m, 6H), 3.83 (t, J = 8.6 Hz, 2H), 2.83-2.71 (m, 2H), 2.51 (s, 3H) |
| 80 | 2-chloro-6-trifluoromethylphenyl | 4-(4-methylpiperazin-1-yl)-3-methylphenyl | (M + 1) 571.80 | 400 MHz, CDCl₃: 8.79 (s, 1H), 7.81-7.71 (m, 2H), 7.58-7.48 (m, 2H), 7.43-7.40 (m, 1H), 7.06 (d, J = 8.6 Hz, 1H), 4.21 (t, J = 8.3 Hz, 2H), 4.03-3.93 (m, 2H), 2.99 (t, J = 4.7 Hz, 4H), 2.84-2.56 (m, 4H), 2.44 (s, 3H), 2.33 (s, 3H) |
| 81 | 2-chloro-6-methylphenyl | 4-(4-methylpiperazin-1-yl)-3-methylphenyl | (M + 1) 517.40 | 400 MHz, CDCl₃: 8.80 (s, 1H), 7.55-7.48 (m, 1H), 7.42-7.37 (m, 2H), 7.32-7.26 (m, 2H), 7.06 (d, J = 8.6 Hz, 1H), 4.26-4.16 (m, 2H), 4.05-3.96 (m, 2H), 3.01 (t, J = 4.7 Hz, 4H), 2.84-2.67 (m, 4H), 2.47 (s, 3H), 2.33 (s, 3H), 2.26 (s, 3H) |

-continued

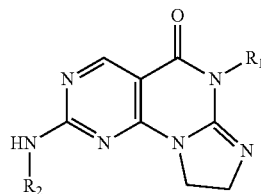

| Example | R₁ | R₂ | LC-MS (ESI) | ¹H NMR (400 MHz) |
|---|---|---|---|---|
| 82 | 2-methoxy-6-chlorophenyl | 4-(2-methylphenyl)piperazin-1-yl (attached at 4-position) | (M + 1) 533.38 | 400 MHz, CDCl₃: 8.79 (s, 1H), 7.43-7.39 (m, 1H), 7.39-7.30 (m, 2H), 7.14 (dd, J = 8.2, 1.0 Hz, 1H), 7.05 (d, J = 8.6 Hz, 1H), 6.95 (d, J = 7.7 Hz, 1H), 4.20 (t, J = 9.5 Hz, 2H), 4.03-3.96 (m, 2H), 3.83 (s, 3H), 2.98 (t, J = 4.4 Hz, 4H), 2.76-2.56 (m, 4H), 2.42 (s, 3H), 2.33 (s, 3H) |
| 83 | 2,6-dimethylphenyl | 4-phenylpiperazin-1-yl | (M + 1) 468.15 | 400 MHz, DMSO-d₆: 10.14 (s, 1H), 8.60 (s, 1H), 7.76-7.48 (m, 2H), 7.27-7.13 (m, 3H), 6.92 (d, J = 9.0 Hz, 2H), 4.18-4.06 (m, 2H), 3.82-3.74 (m, 2H), 3.16-3.03 (m, 4H), 2.50-2.46 (m, 4H), 2,24 (s, 3H), 2.07 (s, 6H) |
| 84 | 2,6-dimethylphenyl | (2R,5S)-2,5-dimethyl-4-phenylpiperazin-1-yl | (M + 1) 511.31 | 400 MHz, DMSO-d₆: 10.13 (brs, 1H), 8.60 (s, 1H), 7.68 (s, 2H), 7.28-7.09 (m, 3H), 6.92 (d, J = 8.9 Hz, 2H), 4.19-4.03 (m, 2H), 3.83-3.70 (m, 2H), 3.57-3.46 (m, 2H), 2.41-2.24 (m, 4H), 2.21 (s, 3H), 2.07 (s, 6H), 1.08 (d, J = 6.0 Hz, 6H) |
| 85 | 4-chlorophenyl | 4-phenylpiperazin-1-yl | (M + 1) 489.16 | 400 MHz, CDCl₃: 8.77 (s, 1H), 7.52 (d, J = 8.1 Hz, 2H), 7.47 (d, J = 8.8 Hz 2H), 7.28 (d, J = 8.8 Hz, 2H), 6.95 (d, J = 9.0 Hz, 2H), 4.17 (t, J = 8.4 Hz, 2H), 3.97 (t, J = 8.9 Hz, 2H), 3.31-3.18 (m, 4H), 2.77-2.65 (m, 4H), 2.43 (s, 3H) |
| 86 | 3-chlorophenyl | 4-phenylpiperazin-1-yl | (M + 1) 489.18 | 400 MHz, CDCl₃: 8.77 (brs, 1H), 7.52 (d, J = 8.0 Hz, 2H), 7.48-7.39 (m, 2H), 7.38-7.32 (m, 1H), 7.25-7.22 (m, 1H), 6.95 (d, J = 9.0 Hz, 2H), 4.17 (t, J = 8.8 Hz, 2H), 3.98 (t, J = 9.0 Hz, 2H), 3.39-3.15 (m, 4H), 2.88-2.66 (m, 4H), 2.46 (s, 3H) |
| 87 | 2,4-dichlorophenyl | 4-phenylpiperazin-1-yl | (M + 1) 523.16 | 400 MHz, DMSO-d₆: 10.22 (brs, 1H), 8.62 (s, 1H), 7.84 (d, J = 1.7 Hz, 1H), 7.68 (s, 1H), 7.66-7.42 (m, 3H), 6.95 (d, J = 9.0 Hz, 2H), 4.20-4.04 (m, 2H), 3.79 (t, J = 8.8 Hz, 2H), 3.25-3.08 (m, 4H), 2.87-2.61 (m, 4H), 2.43 (s, 3H) |
| 88 | 2-chloro-4-fluorophenyl | 4-phenylpiperazin-1-yl | (M + 1) 507.19 | 400 MHz, DMSO-d₆: 10.22 (br s, 1H), 8.62 (s, 1H), 7.76-7.65 (m, 2H), 7.59 (dd, J = 8.8, 5.7 Hz, 2H), 7.41-7.34 (m, 1H), 6.97 (d, J = 8.9 Hz, 2H), 4.20-4.05 (m, 2H), 3.79 (t, J = 8.7 Hz, 2H), 3.29-3.17 (m, 4H), 3.09-2.86 (m, 4H), 2.58 (s, 3H) |

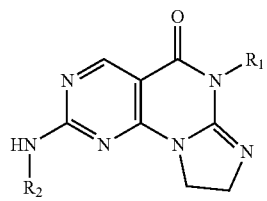

| Example | R₁ | R₂ | LC-MS (ESI) | ¹H NMR (400 MHz) |
|---|---|---|---|---|
| 89 | 3-fluoro-2-chlorophenyl (attached via *) | -N(piperazinyl)-C₆H₄-* (4-position) | (M + 1) 507.14 | 400 MHz, DMSO-$d_6$: 10.21 (br s, 1H), 8.62 (s, 1H), 7.66 (s, 1H), 7.62-7.45 (m, 3H), 7.44-7.39 (m, 1H), 6.92 (d, J = 9.0 Hz, 2H), 4.19-4.06 (m, 2H), 3.79 (t, J = 8.8 Hz, 2H), 3.13-3.06 (m, 4H), 2.48-2.44 (m, 4H), 2.23 (s, 3H) |
| 90 | 2,5-dichlorophenyl | -N(piperazinyl)-C₆H₄-* | (M + 1) 523.12 | 400 MHz, DMSO-$d_6$: 10.25 (br s, 1H), 8.63 (s, 1H), 7.81-7.65 (m, 3H), 7.59 (dd, J = 8.7, 2.5 Hz, 2H), 6.97 (d, J = 9.0 Hz, 2H), 4.20-4.05 (m, 2H), 3.87-3.75 (m, 2H), 3.28-3.16 (m, 4H), 3.10-2.85 (m, 4H), 2.59 (s, 3H) |
| 91 | 2,3-dichlorophenyl | -N(piperazinyl)-C₆H₄-* | (M + 1) 523.18 | 400 MHz, DMSO-$d_6$: 10.21 (br s, 1H), 8.62 (s, 1H), 7.81-7.73 (m, 1H), 7.67 (s, 1H), 7.63-7.39 (m, 3H), 6.92 (d, J = 8.7 Hz, 2H), 4.20-4.06 (m, 2H), 3.79 (t, J = 8.7 Hz, 2H), 3.15-3.04 (m, 4H), 2.49-2.44 (m, 4H), 2.23 (s, 3H) |
| 92 | pyrimidin-2-yl | -N(piperazinyl)-C₆H₄-* | (M + 1) 457.25 | 400 MHz, DMSO-$d_6$: 10.21 (br s, 1H), 9.01 (d, J = 4.9 Hz, 2H), 8.60 (s, 1H), 8.16 (s, 1H), 7.69-7.67 (m, 2H), 6.93 (d, J = 8.9 Hz, 2H), 4.09 (t, J = 8.1 Hz, 2H), 3.79 (t, J = 8.8 Hz, 2H), 3.15-3.10 (m, 4H), 2.57-2.53 (m, 4H), 2.28 (s, 3H) |

The compounds of Examples 102, 103 and 105-115 were prepared from 2-(methylsulfonyl/methylsulfinyl)-6-substituent-8,9-dihydroimidazo[1,2-a]pyrimido[5,4-e]pyrimidin-5(6H)-one (the compound was prepared from N-tert-butoxycarbonyl-1,2-ethylenediamine, ethyl 4-chloro-2-(methylthio)pyrimidine-5-carboxylate and the corresponding substituted isocyanatobenzene using procedures similar to those described for the syntheses of compounds of Examples 1a-1e) and the corresponding substituted aniline using a procedure similar to those described for the synthesis of compound of Example 1.

The compounds of Examples 93-101, 104 and 116-184 were prepared from 2-(methylsulfonyl/methylsulfinyl)-6-substituent-8,9-dihydroimidazo[1,2-a]pyrimido[5,4-e]pyrimidin-5(6H)-one (the compound was prepared from N-tert-butoxycarbonyl-1,2-ethylenediamine, ethyl 4-chloro-2-(methylthio)pyrimidine-5-carboxylate and the corresponding substituted isocyanatobenzene using procedures similar to those described for the syntheses of compounds of Examples 1a-1e) and the corresponding substituted amine using a procedure similar to those described for the synthesis of compound of Example 4b.

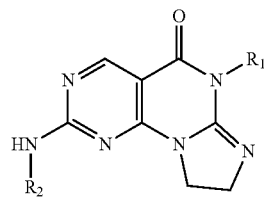

| Example | R₁ | R₂ | LC-MS (ESI) | ¹H NMR |
|---|---|---|---|---|
| 93* | H | —N(piperazine)N-C₆H₄-* | (M + 1) 379.13 | 400 MHz, DMSO-d₆: 9.91 (brs, 1H), 8.62 (s, 1H), 7.56-7.69 (m, 2H), 6.90 (d, J = 9.1 Hz, 2H), 4.17 (t, J = 8.0 Hz, 2H), 3.71 (t, J = 8.0 Hz, 2H), 3.14-2.99 (m, 4H), 2.48-2.36 (m, 4H), 2.23 (s, 3H) |
| 94 | cyclobutyl-* | —N(piperazine)N-C₆H₄-* | (M + 1) 433.24 | 400 MHz, CDCl₃: 8.71 (s, 1H), 7.50 (d, J = 8.8 Hz, 2H), 6.93 (d, J = 8.8 Hz, 2H), 5.33-5.25 (m, 1H), 4.15-3.96 (m, 4H), 3.36-3.20 (m, 4H), 3.16-3.06 (m, 2H), 2.83-2.65 (m, 4H), 2.47 (s, 3H), 2.26-2.19 (m, 2H), 1.92-1.89 (m, 1H), 1.76-1.70 (m, 1H) |
| 95 | cyclopentyl-* | —N(piperazine)N-C₆H₄-* | (M + 1) 447.52 | 400 MHz, CDCl₃ 8.70 (s, 1H), 7.50 (d, J = 8.4 Hz, 2H), 6.93 (d, J = 9.0 Hz, 2H), 5.24-5.18 (m, 1H), 4.12-3.97 (m, 4H), 3.26-3.14 (m, 4H), 2.66-2.52 (m, 4H), 2.37 (s, 3H), 2.30-2.21 (m, 2H), 2.00-1.83 (m, 4H), 1.64-1.59 (m, 2H) |
| 96 | phenyl-* | —N(piperazine)N-C₆H₄-* | (M + 1) 455.38 | 400 MHz, CDCl₃: 8.78 (s, 1H), 7.56-7.48 (m, 4H), 7.46-7.41 (m, 1H), 7.35-7.29 (m, 2H), 6.97-6.91 (m, 2H), 4.17 (t, J = 8.8 Hz, 2H), 3.98 (t, J = 9.0 Hz, 2H), 3.26 (t, J = 5.0 Hz, 4H), 2.71 (t, J = 5.0 Hz, 4H), 2.43 (s, 3H) |
| 97 | 2-pyridyl-* | —N(piperazine)N-C₆H₄-* | (M + 1) 456.34 | 400 MHz, CDCl₃: δ 8.77 (s, 1H), 8.70 (dd, J = 4.8, 1.1 Hz, 1H), 7.94-7.89 (m, 1H), 7.54 (d, J = 8.4 Hz, 2H), 7.45-7.38 (m, 2H), 6.95 (d, J = 9.0 Hz, 2H), 4.15 (t, J = 8.8 Hz, 2H), 4.00 (t, J = 8.5 Hz, 2H), 3.41 (t, J = 4.8 Hz, 4H), 3.03-2.90 (m, 4H), 2.61 (s, 3H) |
| 98 | 3-pyridyl-* | —N(piperazine)N-C₆H₄-* | (M + 1) 456.23 | 400 MHz, DMSO-d₆: 10.17 (brs, 1H), 8.63-8.57 (m, 2H), 8.55 (d, J = 2.2 Hz, 1H), 7.85-7.80 (m, 1H), 7.74-7.57 (m, 2H), 7.56-7.53 (m, 1H), 6.92 (d, J = 8.9 Hz, 2H), 4.10 (t, J = 8.2 Hz, 2H), 3.79 (t, J = 8.8 Hz, 2H), 3.12-3.06 (m, 4H), 2.49-2.44 (m, 4H), 2.23 (s, 3H) |
| 99 | 4-pyridyl-* | —N(piperazine)N-C₆H₄-* | (M + 1) 456.28 | 400 MHz, DMSO-d₆: 10.15 (brs, 1H), 8.71 (dd, J = 4.5, 1.6 Hz, 2H), 8.59 (s, 1H), 7.71-7.56 (m, 2H), 7.44 (dd, J = 4.5, 1.6 Hz, 2H), 6.92 (d, J = 9.0 Hz, 2H), 4.09 (t, J = 8.5 Hz, 2H), 3.79 (t, J = 8.8 Hz, 2H), 3.11-3.06 (m, 4H), 2.47-2.43 (m, 4H), 2.22 (s, 3H) |

-continued

[Structure: pyrimido-imidazole scaffold with R1 on amide N and HN-R2 substituent]

| Example | R1 | R2 | LC-MS (ESI) | 1H NMR |
|---|---|---|---|---|
| 100 | 2,6-difluorophenyl | 4-(4-methylpiperazin-1-yl)-3-chlorophenyl | (M + 1) 525.30 | 400 MHz, CDCl$_3$: 8.81 (s, 1H), 7.91 (br s, 1H), 7.51-7.34 (m, 3H), 7.12-7.03 (m, 3H), 4.23 (t, J = 8.6 Hz, 2H), 4.03 (t, J = 8.8 Hz, 2H), 3.24-3.09 (m, 4H), 2.88-2.69 (m, 4H), 2.47 (s, 3H) |
| 101 | 2,6-difluorophenyl | 4-(4-methylpiperazin-1-yl)-3,5-dimethylphenyl | (M + 1) 519.30 | 400 MHz, DMSO-d$_6$: 10.19 (brs, 1H), 8.65 (s, 1H), 7.63-7.59 (m, 1H), 7.48-7.38 (m, 2H), 7.34-7.29 (m, 2H), 4.17 (t, J = 8.6 Hz, 2H), 3.83 (t, J = 8.6 Hz, 2H), 3.03-2.96 (m, 4H), 2.43-2.38 (m, 4H), 2.27 (s, 6H), 2.23 (s, 3H) |
| 102 | 2-fluoro-6-chlorophenyl | 4-(1H-imidazol-1-yl)phenyl | (M + 1) 476.2 | 500 MHz, CDCl$_3$: 8.46 (s, 1H), 7.89 (s, 1H), 7.59-7.52 (m, 4H), 7.47-7.41 (m, 1H), 7.38 (d, J = 8.2 Hz, 1H), 7.30 (s, 1H), 7.24 (s, 1H), 7.20 (td, J = 8.7, 1.0 Hz, 1H), 4.33-4.24 (m, 2H), 4.09-4.00 (m, 2H) |
| 103 | 2-fluoro-6-chlorophenyl | 4-(4-methyl-1,4-diazepan-1-yl)phenyl | (M + 1) 521.2 | 300 MHz, CD$_3$OD: 8.65 (s, 1H), 7.67-7.39 (m, 4H), 7.35-7.26 (m, 1H), 6.79 (d, J = 9.1 Hz, 2H), 4.22 (t, J = 9.1 Hz, 2H), 3.90 (t, J = 9.0 Hz, 2H), 3.72 (t, J = 4.8 Hz, 2H), 3.53 (t, J = 6.3 Hz, 2H), 3.22 (t, J = 4.9 Hz, 2H), 3.13 (t, J = 5.0 Hz, 2H), 2.75 (s, 3H), 2.27-2.12 (m, 2H) |
| 104 | 2-fluoro-6-chlorophenyl | 4-((4-methylpiperazin-1-yl)methyl)phenyl | (M + 1) 521.2 | 300 MHz, CDCl$_3$: 8.81 (s, 1H), 7.63 (d, J = 8.4 Hz, 2H), 7.48-7.29 (m, 4H), 7.23-7.13 (m, 1H), 4.23 (t, J = 7.9 Hz, 2H), 4.01 (t, J = 8.9 Hz, 2H), 3.58 (s, 2H), 2.87-2.65 (m, 8H), 2.51 (s, 3H) |
| 105 | 2-fluoro-6-chlorophenyl | 4-(2-(dimethylamino)ethoxy)phenyl | (M + 1) 496.4 | 300 MHz, CDCl$_3$: 8.78 (s, 1H), 8.31 (brs, 1H), 7.50 (d, J = 8.5 Hz, 2H), 7.43-7.31 (m, 2H), 7.21-7.11 (m, 1H), 6.92 (d, J = 7.0 Hz, 2H), 4.17 (t, J = 8.1 Hz, 2H), 4.07 (t, J = 5.7 Hz, 2H), 3.97 (t, J = 8.3 Hz, 2H), 2.74 (t, J = 5.7 Hz, 2H), 2.34 (s, 6H) |
| 106 | 2-fluoro-6-chlorophenyl | 4-(3-(dimethylamino)propoxy)phenyl | (M + 1) 510.4 | 300 MHz, CDCl$_3$: 8.79 (s, 1H), 7.52 (d, J = 8.5 Hz, 2H), 7.45-7.32 (m, 2H), 7.22-7.12 (m, 1H), 6.90 (d, J = 8.9 Hz, 2H), 4.22-4.15 (m, 2H), 4.08-3.96 (m, 4H), 2.83 (t, J = 7.5 Hz, 2H), 2.54 (s, 6H), 2.23-2.07 (m, 2H) |

-continued

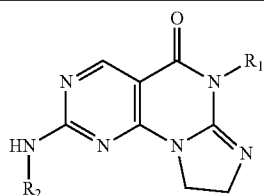

| Example | R₁ | R₂ | LC-MS (ESI) | ¹H NMR |
|---|---|---|---|---|
| 107 | 2-F, 6-Cl phenyl | 1-methylpiperidin-4-yloxy-phenyl | (M + 1) 522.2 | 300 MHz, CDCl₃: 8.79 (s, 1H), 7.57 (d, J = 8.4 Hz, 2H), 7.46-7.32 (m, 2H), 7.21-7.15 (m, 1H), 6.91 (d, J = 8.9 Hz, 2H), 4.66-4.56 (m, 1H), 4.19 (t, J = 9.4 Hz, 2H), 3.99 (t, J = 8.9 Hz, 2H), 3.26-2.96 (m, 4H), 2.73 (s, 3H), 2.52-2.41 (m, 2H), 2.20-2.09 (m, 2H) |
| 108 | 2-F, 6-Cl phenyl | (dimethylamino)ethyl-NH-phenyl | (M + 1) 495.3 | 500 MHz, CDCl₃: 8.77 (s, 1H), 7.44-7.33 (m, 4H), 7.17 (t, J = 8.5 Hz, 1H), 6.64 (d, J = 8.7 Hz, 2H), 4.24-4.12 (m, 2H), 3.97 (t, J = 8.9 Hz, 2H), 3.16 (t, J = 5.8 Hz, 2H), 2.58 (t, J = 5.8 Hz, 2H), 2.27 (s, 6H) |
| 109 | 2-F, 6-Cl phenyl | (dimethylamino)ethyl-N(Me)-phenyl | (M + 1) 509.2 | 300 MHz, CDCl₃: 8.77 (s, 1H), 7.50-7.33 (m, 4H), 7.17 (t, J = 8.3 Hz, 1H), 6.72 (d, J = 8.7 Hz, 2H), 4.18 (t, J = 8.4 Hz, 2H), 3.97 (t, J = 8.7 Hz, 2H), 3.49 (t, J = 7.4 Hz, 2H), 2.96 (s, 3H), 2.56 (t, J = 7.4 Hz, 2H), 2.35 (s, 6H) |
| 110 | 2-F, 6-Cl phenyl | (dimethylamino)propyl-NH-phenyl | (M + 1) 509.2 | 500 MHz, MeOD: 8.66 (s, 1H), 7.58-7.50 (m, 2H), 7.45 (d, J = 8.2 Hz, 2H), 7.30 (t, J = 8.7 Hz, 1H), 6.69 (d, J = 8.8 Hz, 2H), 4.24-4.18 (m, 2H), 3.90 (t, J = 8.6 Hz, 2H), 3.27-3.21 (m, 4H), 2.86 (s, 6H), 2.08-1.98 (m, 2H) |
| 111 | 2-F, 6-Cl phenyl | (dimethylamino)propyl-N(Me)-phenyl | (M + 1) 523.2 | 500 MHz, CDCl₃: 8.76 (s, 1H), 7.53-7.43 (m, 2H), 7.41-7.32 (m, 2H), 7.18 (d, J = 8.1 Hz, 1H), 6.80-6.70 (m, 2H), 4.22-4.13 (m, 2H), 3.98 (t, J = 8.3 Hz, 2H), 3.50-3.40 (m, 2H), 3.09-3.01 (m, 2H), 2.94 (s, 3H), 2.78 (s, 6H), 2.24-2.14 (m, 2H) |
| 112 | 2-F, 6-Cl phenyl | 1-methylpiperidin-4-yl-NH-phenyl | (M + 1) 521.2 | 300 MHz, CDCl₃: 8.76 (s, 1H), 7.42-7.33 (m, 4H), 7.19-7.14 (m, 1H), 6.60 (d, J = 8.5 Hz, 2H), 4.15 (t, J = 8.3 Hz, 2H), 3.97 (t, J = 8.7 Hz, 2H), 3.28 (t, J = 9.6 Hz, 1H), 2.82 (d, J = 11.4 Hz, 2H), 2.30 (s, 3H), 2.17-2.04 (m, 4H), 1.55-1.44 (m, 2H) |
| 113 | 2-F, 6-Cl phenyl | 1-methylpiperidin-4-yl-N(Me)-phenyl | (M + 1) 535.2 | 300 MHz, CDCl₃: 8.77 (s, 1H), 7.54-7.32 (m, 4H), 7.17 (t, J = 8.1 Hz, 1H), 6.80 (d, J = 8.6 Hz, 2H), 4.17 (t, J = 7.4 Hz, 2H), 3.97 (t, J = 8.7 Hz, 2H), 3.62-3.53 (m, 1H), 3.04 (d, J = 11.3 Hz, 2H), 2.79 (s, 3H), 2.35 (s, 3H), 2.14 (t, J = 11.6 Hz, 2H), 2.01-1.82 (m, 2H), 1.79-170 (m, 2H) |

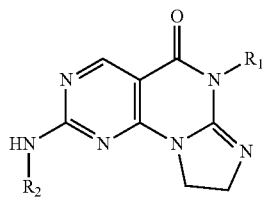

| Example | R₁ | R₂ | LC-MS (ESI) | ¹H NMR |
|---|---|---|---|---|
| 114 | 2-Cl, 6-F-phenyl | 1-methyl-piperidin-4-yl-phenyl | (M + 1) 506.2 | 300 MHz, CD₃OD: 8.71 (s, 1H), 7.75 (d, J = 7.8 Hz, 2H), 7.60-7.52 (m, 1H), 7.47 (d, J = 8.1 Hz, 1H), 7.35-7.28 (m, 3H), 4.25 (t, J = 8.9 Hz, 2H), 3.92 (t, J = 8.8 Hz, 2H), 3.62-3.58 (m, 2H), 3.21-3.13 (m, 2H), 2.92-2.86 (m, 4H), 2.23-3.91 (m, 4H) |
| 115 | 2-Cl, 6-F-phenyl | 4-(dimethylamino)piperidin-1-yl-phenyl | (M + 1) 535.40 | 300 MHz, CDCl₃: 8.78 (s, 1H), 7.49 (d, J = 7.6 Hz, 2H), 7.43-7.32 (m, 2H), 7.22-7.11 (m, 1H), 6.94 (d, J = 9.0 Hz, 2H), 4.17 (t, J = 8.2 Hz, 2H), 3.98 (t, J = 8.8 Hz, 2H), 3.71 (d, J = 12.3 Hz, 2H), 2.72 (t, J = 11.3 Hz, 2H), 2.43-2.28 (s, 7H), 1.98 (d, J = 12.4 Hz, 2H), 1.68 (qd, J = 12.2, 3.8 Hz, 2H) |
| 116 | 2-Cl, 6-F-phenyl | 4-(dimethylamino)piperidin-1-yl-2-F-phenyl | (M + 1) 553.34 | 400 MHz, CDCl₃: 8.81 (s, 1H), 7.70-7.60 (m, 1H), 7.52 (br s, 1H), 7.43-7.35 (m, 2H), 7.22-7.11 (m, 2H), 6.97-6.91 (m, 1H), 4.29-4.17 (m, 2H), 4.03 (t, J = 9.2 Hz, 2H), 3.55-3.47 (m, 2H), 2.76-2.67 (m, 2H), 2.60-2.53 (m, 1H), 2.46 (s, 6H), 2.04-2.00 (m, 2H), 1.85-1.76 (m, 2H) |
| 117 | 2-Cl, 6-F-phenyl | 4-(dimethylamino)piperidin-1-yl-2-Cl-phenyl | (M + 1) 569.26 | 400 MHz, CDCl₃: 8.81 (s, 1H), 8.00-7.86 (m, 1H), 7.52 (br s, 1H), 7.44-7.32 (m, 3H), 7.21-7.16 (m, 1H), 7.03 (d, J = 8.7 Hz, 1H), 4.29-4.18 (m, 2H), 4.02 (t, J = 8.9 Hz, 2H), 3.52-3.44 (m, 2H), 2.92-2.85 (m, 1H), 2.71 (t, J = 11.2 Hz, 2H), 2.59 (s, 6H), 2.11-2.07 (m, 2H), 1.92-1.84 (m, 2H) |
| 118 | 2-Cl, 6-F-phenyl | 4-(dimethylamino)piperidin-1-yl-2-Br-phenyl | (M + 1) 613.10 | 400 MHz, CDCl₃: 8.81 (s, 1H), 8.14 (s, 1H), 7.52 (brs, 1H), 7.43-7.35 (m, 3H), 7.21-7.16 (m, 1H), 7.03 (d, J = 8.7 Hz, 1H), 4.27-4.19 (m, 2H), 4.03 (t, J = 8.8 Hz, 2H), 3.47-3.42 (m, 2H), 2.87-2.82 (m, 1H), 2.72-2.68 (m, 2H), 2.57 (s, 6H), 2.09-2.04 (m, 2H), 1.91-1.83 (m, 2H) |
| 119 | 2-Cl, 6-F-phenyl | 4-(dimethylamino)piperidin-1-yl-2-Me-phenyl | (M + 1) 549.45 | 400 MHz, CDCl₃ 8.80 (s, 1H), 7.52-7.31 (m, 5H), 7.20-7.16 (m, 1H), 7.01 (d, J = 8.6 Hz, 1H), 4.25-4.16 (m, 2H), 4.01 (t, J = 8.9 Hz, 2H), 3.22-3.15 (m, 2H), 2.67 (t, J = 11.1 Hz, 2H), 2.56-2.42 (m, 7H), 2.32 (s, 3H), 2.04-1.99 (m, 2H), 1.78-1.73 (m, 2H) |

-continued

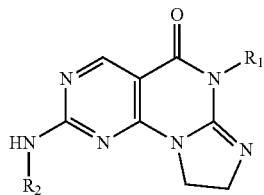

| Example | R₁ | R₂ | LC-MS (ESI) | ¹H NMR |
|---|---|---|---|---|
| 120 | 2-F, 6-Cl phenyl | 1-(4-(dimethylamino)piperidin-1-yl)-2-methyl-6-fluorophenyl | (M + 1) 567.29 | 400 MHz, CDCl₃: 8.81 (s, 1H), 7.60-7.53 (m, 1H), 7.52-7.43 (m, 1H), 7.43-7.35 (m, 2H), 7.21-7.15 (m, 1H), 7.00 (d, J = 1.6 Hz, 1H), 4.28-4.19 (m, 2H), 4.04 (t, J = 9.2 Hz, 2H), 3.18 (t, J = 11.9 Hz, 2H), 3.09-3.03 (m, 2H), 2.84-2.78 (m, 1H), 2.58 (s, 6H), 2.32 (s, 3H), 2.07-2.01 (m, 2H), 1.80-1.71 (m, 2H) |
| 121 | 2-F, 6-Cl phenyl | 4-methylpiperazinyl-pyrazinyl | (M/2 + 1) 255.12 | 400 MHz, DMSO-d₆: 10.57 (brs, 1H), 8.89 (s, 1H), 8.68 (s, 1H), 8.13 (d, J = 1.4 Hz, 1H), 7.62-7.53 (m, 2H), 7.49-7.44 (m, 1H), 4.22-4.13 (m, 2H), 3.85-3.77 (m, 2H), 3.56-3.48 (m, 4H), 2.46-2.39 (m, 4H), 2.23 (s, 3H) |
| 122 | 2-F, 6-Cl phenyl | 4-methylpiperazinyl-2,6-dichlorophenyl | (M + 1) 575.26 | 400 MHz, CDCl₃: 8.83 (s, 1H), 7.71 (s, 2H), 7.61 (brs, 1H), 7.44-7.35 (m, 2H), 7.21-7.16 (m, 1H), 4.28-4.20 (m, 2H), 4.04 (t, J = 8.8 Hz, 2H), 3.48-3.37 (m, 4H), 3.06-2.98 (m, 4H), 2.67 (s, 3H) |
| 123 | 2-F, 6-Cl phenyl | 4-methylpiperazinyl-2-methyl-6-fluorophenyl | (M + 1) 539.29 | 00 MHz, CDCl₃: 8.81 (s, 1H), 7.64-7.55 (m, 1H), 7.43-7.36 (m, 2H), 7.21-7.16 (m, 1H), 7.01-6.97 (m, 1H), 4.28-4.19 (m, 2H), 4.03 (t, J = 8.8 Hz, 2H), 3.34-3.07 (m, 4H), 2.87-2.63 (m, 4H), 2.50 (s, 3H), 2.33 (s, 3H) |
| 124 | 2-F, 6-Cl phenyl | 4-methylpiperazinyl-2-methoxy-6-fluorophenyl | (M + 1) 555.18 | 400 MHz, CDCl₃: 8.82 (s, 1H), 7.52 (brs, 1H), 7.43-7.35 (m, 2H), 7.21-7.13 (m, 2H), 6.98-6.95 (m, 1H), 4.26-4.19 (m, 2H), 4.03 (t, 8.8 Hz, 2H), 3.87 (s, 3H), 3.33-3.24 (m, 4H), 2.83-2.73 (m, 4H), 2.50 (s, 3H) |
| 125 | 2-F, 6-Cl phenyl | 4-methylpiperazinyl-2-methyl-6-chlorophenyl | (M + 1) 555.22 | 400 MHz, CDCl₃: 8.81 (s, 1H), 7.81 (brs, 1H), 7.49-7.34 (m, 3H), 7.22-7.15 (m, 2H), 4.28-4.19 (m, 2H), 4.03 (t, J = 8.9 Hz, 2H), 3.57 (t, J = 8.5 Hz, 2H), 3.09-2.99 (m, 2H), 2.94-2.86 (m, 2H), 2.69-2.59 (m, 2H), 2.51 (s, 3H), 2.36 (s, 3H) |

-continued
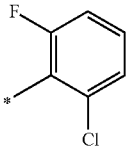
| Example | R₁ | R₂ | LC-MS (ESI) | ¹H NMR |
|---|---|---|---|---|
| 126 | 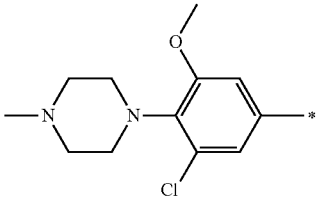 | 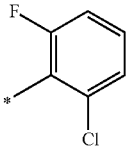 | (M + 1) 571.14 | 400 MHz, CDCl₃: 8.82 (s, 1H), 7.52 (brs, 1H), 7.44-7.34 (m, 3H), 7.21-7.15 (m, 2H), 4.27-4.18 (m, 2H), 4.04 (t, J = 9.0 Hz, 2H), 3.85 (s, 3H), 3.67-3.46 (m, 2H), 3.12-2.85 (m, 4H), 2.73-2.59 (m, 2H), 2.53 (s, 3H) |
| 127 | 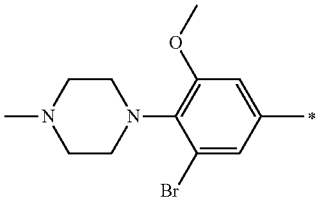 | 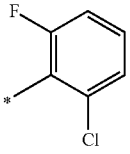 | (M + 1) 615.09 | 400 MHz, CDCl₃: 8.82 (s, 1H), 7.63-7.48 (m, 2H), 7.43-7.35 (m, 2H), 7.25-7.22 (m, 1H), 7.21-7.16 (m, 1H), 4.27-4.19 (m, 2H), 4.06-4.01 (m, 2H), 3.84 (s, 3H), 3.65-3.53 (m, 2H), 2.98-2.81 (m, 4H), 2.58-2.45 (m, 5H) |
| 128 | 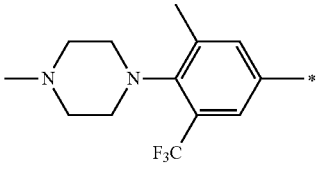 | 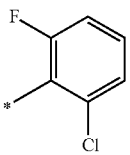 | (M + 1) 589.39 | 400 MHz, CDCl₃: 8.82 (s, 1H), 8.21 (brs, 1H), 7.59-7.48 (m, 1H), 7.44-7.31 (m, 3H), 7.21-7.36 (m, 1H), 4.27-4.19 (m, 2H), 4.05 (t, J = 9.2 Hz, 2H), 3.54 (t, J = 12.0 Hz, 2H), 2.95-2.78 (m, 4H), 2.56-2.36 (m, 8H) |
| 129 | 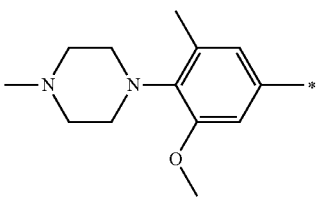 | 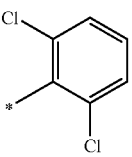 | (M + 1) 551.40 | 400 MHz, CDCl₃: 8.81 (s, 1H), 7.44-7.35 (m, 3H), 7.20-7.16 (m, 1H), 6.89 (d, J = 2.0 Hz, 1H), 4.26-4.18 (m, 2H), 4.02 (t, J = 8.9 Hz, 2H), 3.84 (s, 3H), 3.76-3.64 (m, 2H), 3.06-2.93 (m, 2H), 2.81-2.72 (m, 2H), 2.61-2.46 (m, 5H), 2.31 (s, 3H) |
| 130 | 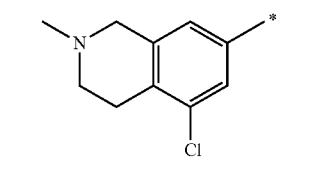 | 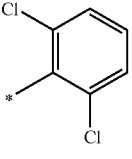 | (M + 1) 528.17 | 400 MHz, CDCl₃: 8.83 (s, 1H), 7.80 (s, 1H), 7.49-7.47 (m, 2H), 7.36 (dd, J = 8.8, 7.5 Hz, 1H), 7.18 (s, 1H), 4.24 (t, J = 8.5 Hz, 2H), 4.04 (t, J = 8.9 Hz, 2H), 3.72 (s, 2H), 3.06-2.82 (m, 4H), 2.58 (s, 3H) |
| 131 | 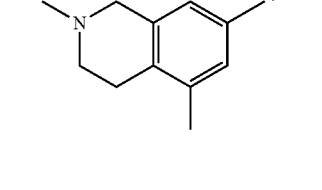 | 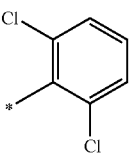 | (M + 1) 508.28 | 400 MHz, DMSO-d₆: 10.26 (brs, 1H), 8.68 (s, 1H), 7.68 (s, 1H), 7.66 (s, 1H), 7.57-7.52 (m, 1H), 7.43-7.40 (m, 2H), 4.18 (t, J = 8.3 Hz, 2H), 3.83 (t, J = 8.7 Hz, 2H), 3.45 (s, 2H), 2.65-2.60 (m, 4H), 2.33 (s, 3H), 2.17 (s, 3H). |
| 132 | 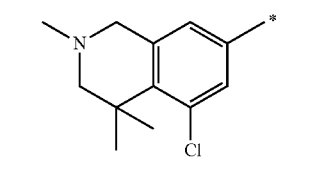 | 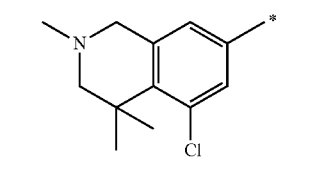 | — | — |

-continued

| Example | R₁ | R₂ | LC-MS (ESI) | ¹H NMR |
|---|---|---|---|---|
| 133 | 2,6-dichlorophenyl | 2,5,7-trimethyl-4,4-dimethyl-1,2,3,4-tetrahydroisoquinolin-7-yl (N-methyl) | (M + 1) 536.02 | 400 MHz, DMSO-d₆: 10.25 (brs, 1H), 8.68 (s, 1H), 7.69-7.65 (m, 2H), 7.55 (dd, J = 8.8, 7.5 Hz, 1H), 7.43-7.31 (m, 2H), 4.19 (t, J = 8.4 Hz, 2H), 3.83 (t, J = 8.7 Hz, 2H), 3.44 (s, 2H), 2.42 (s, 3H), 2.30 (s, 3H), 2.28 (s, 2H), 1.32 (s, 6H) |
| 134 | 2,6-dichlorophenyl | 5-chloro-spiro-cyclopropane-tetrahydroisoquinoline | — | — |
| 135 | 2,6-dichlorophenyl | 5-methyl-spiro-cyclopropane-tetrahydroisoquinoline | — | — |
| 136 | 2,6-dichlorophenyl | (2S,6R)-4-(2,6-dichloro-4-yl-phenyl)-2,6-dimethylpiperazine (N-methyl) | (M + 1) 619.21 | 400 MHz, CDCl₃: 8.83 (s, 1H), 7.74-7.69 (m, 1H), 7.67-7.62 (m, 1H), 7.53-7.42 (m, 2H), 7.36 (dd, J = 8.8, 7.5 Hz, 1H), 4.25 (t, J = 8.7 Hz, 2H), 4.05 (t, J = 8.8 Hz, 2H), 3.54-3.35 (m, 2H), 2.86 (d, J = 11.7 Hz, 2H), 2.78-2.55 (m, 2H), 2.44 (s, 3H), 1.20 (s, 6H) |
| 137 | 2,6-dichlorophenyl | (2S,6R)-4-(2-chloro-6-methyl-4-yl-phenyl)-2,6-dimethylpiperazine (N-methyl) | (M + 1) 599.39 | 400 MHz, DMSO-d₆: 10.23 (brs, 1H), 8.71 (s, 1H), 7.79-7.75 (m, 1H), 7.67 (d, J = 0.9 Hz, 1H), 7.65-7.64 (m, 1H), 7.59-7.52 (m, 2H), 4.19 (t, J = 8.8 Hz, 2H), 3.86 (t, J = 8.7 Hz, 2H), 2.73-2.65 (m, 2H), 2.50-2.49 (m, 2H), 2.35-2.30 (m, 5H), 2.23 (s, 3H), 1.02 (d, J = 6.1 Hz, 6H) |
| 138 | 2,6-dichlorophenyl | 4-(dimethylamino)-1-(phenyl-4-yl)piperidine | (M + 1) 551.47 | 400 MHz, CDCl₃: 8.80 (s, 1H), 7.53-7.46 (m, 4H), 7.37-7.33 (m, 1H), 6.95 (d, J = 9.0 Hz, 2H), 4.19 (t, J = 8.3 Hz, 2H), 4.03-3.97 (m, 2H), 3.76-3.70 (m, 2H), 2.78-2.71 (m, 2H), 2.55-2.49 (m, 1H), 2.43 (s, 6H), 2.03-2.00 (m, 2H), 1.76-1.69 (m, 2H) |
| 139 | 2,6-dichlorophenyl | 4-(dimethylamino)-1-(2-chloro-phenyl-4-yl)piperidine | (M + 1) 585.42 | 400 MHz, CDCl₃: 8.82. (s, 1H), 7.97-7.88 (m, 1H), 7.49-7.46 (m, 2H), 7.38-7.33 (m, 2H), 7.03 (d, J = 8.7 Hz, 1H), 4.24 (t, J = 8.4 Hz, 2H), 4.06-4.00 (m, 2H), 3.49-3.44 (m, 2H), 2.73-2.66 (m, 3H), 2.52 (s, 6H), 2.07-2.04 (m, 2H), 1.87-1.82 (m, 2H) |

-continued

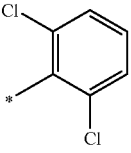

| Example | R₁ | R₂ | LC-MS (ESI) | ¹H NMR |
|---|---|---|---|---|
| 140 | 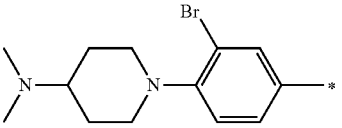 | 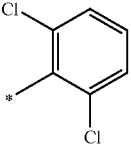 | (M + 1) 629.05 | 400 MHz, CDCl₃: 8.81 (s, 1H), 8.16 (s, 1H), 7.72 (brs, 1H), 7.50-7.46 (m, 2H), 7.45-7.38 (m, 1H), 7.35 (dd, J = 8.8, 7.5 Hz, 1H), 7.03 (d, J = 8.7 Hz, 1H), 4.23 (t, J = 8.4 Hz, 2H), 4.03 (t, J = 8.8 Hz, 2H), 3.46-3.40 (m, 2H), 2.74-2.65 (m, 3H), 2.52 (s, 6H), 2.05-1.99 (m, 2H), 1.89-1.80 (m, 2H) |
| 141 | 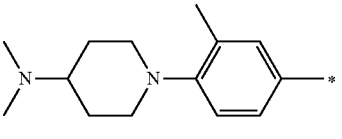 | 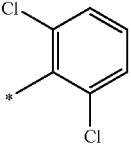 | (M + 1) 565.06 | 400 MHz, CDCl₃: 8.81 (s, 1H), 7.51-7.40 (m, 4H), 7.35 (dd, J = 8.8, 7.5 Hz, 3H), 7.01 (d, J = 8.6 Hz, 1H), 4.22 (t, J = 8.3 Hz, 2H), 4.01 (t, J = 9.0 Hz, 2H), 3.22-3.15 (m, 2H), 2.70-2.63 (m, 2H), 2.52-2.44 (m, 7H), 2.32 (s, 3H), 2.03-1.97 (m, 2H), 1.80-1.70 (m, 2H) |
| 142 | 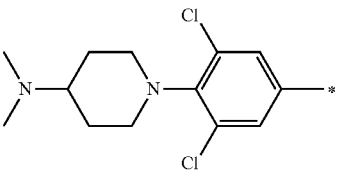 | 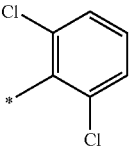 | (M + 1) 619.05 | 400 MHz, CDCl₃: 8.84 (s, 1H), 7.72 (d, J = 2.5 Hz, 1H), 7.65 (d, J = 2.4 Hz, 1H), 7.51-7.45 (m, 2H), 7.39 (brs, 1H), 7.38-7.33 (m, 1H), 4.25 (t, J = 8.7 Hz, 2H), 4.05 (t, J = 8.9 Hz, 2H), 3.41 (t, J = 11.1 Hz, 2H), 3.15-3.09 (m, 2H), 2.85-2.78 (m, 1H), 2.58 (s, 6H), 2.05-2.01 (m, 2H), 1.85-1.80 (m, 2H) |
| 143 | 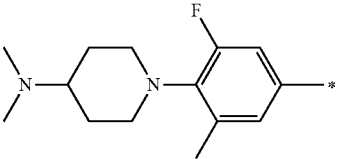 | 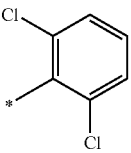 | (M + 1) 583.18 | 400 MHz, CDCl₃: 8.82 (s, 1H), 7.60-7.53 (m, 1H), 7.53-7.38 (m, 3H), 7.38-7.33 (m, 1H), 6.94 (d, J = 1.6 Hz, 1H), 4.24 (t, J = 8.6 Hz, 2H), 4.03 (t, J = 9.0 Hz, 2H), 3.17 (t, J = 11.8 Hz, 2H), 3.08-3.02 (m, 2H), 2.72-2.66 (m, 1H), 2.53 (s, 6H), 2.32 (s, 3H), 2.03-1.98 (m, 2H), 1.77-1.68 (m, 2H) |
| 144 | 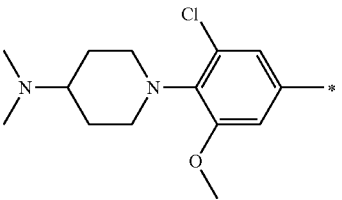 | 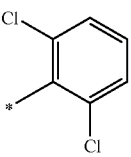 | (M + 1) 615.36 | 400 MHz, CDCl₃: 8.83 (s, 1H), 7.52-7.41 (m, 3H), 7.40-7.32 (m, 2H), 7.20-7.15 (m, 1H), 4.24 (t, J = 8.7 Hz, 2H), 4.03 (t, J = 8.9 Hz, 2H), 3.84 (s, 3H), 3.26 (t, J = 10.9 Hz, 2H), 3.10-3.02 (m, 2H), 2.72-2.64 (m, 1H), 2.51 (s, 6H), 1.97-1.92 (m, 2H), 1.79-1.71 (m, 2H) |
| 145 | 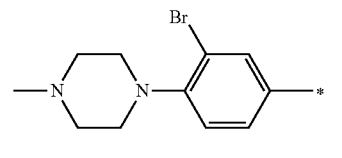 | 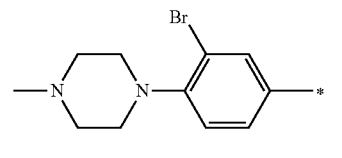 | (M + 1) 601.21 | 400 MHz, CDCl₃: 8.82 (s, 1H), 8.14 (brs, 1H), 7.52-7.39 (m, 4H), 7.36 (dd, J = 8.8, 7.5 Hz, 1H), 7.09 (d, J = 8.7 Hz, 1H), 4.25 (t, J = 8.6 Hz, 2H), 4.04 (t, J = 9.0 Hz, 2H), 3.24-3.13 (m, 4H), 2.95-2.78 (m, 4H), 2.53 (s, 3H) |

-continued

| Example | R₁ | R₂ | LC-MS (ESI) | ¹H NMR |
|---|---|---|---|---|
| 146 | 2,6-dichlorophenyl | 4-methylpiperazinyl-2-methoxyphenyl | (M + 1) 553.70 | 400 MHz, CDCl₃: 8.81 (s, 1H), 7.49-7.45 (m, 2H), 7.44-7.39 (m, 1H), 7.37 (dd, J = 7.6, 1.2 Hz, 1H), 7.07 (d, J = 7.9 Hz, 1H), 6.95 (d, J = 8.4 Hz, 1H), 4.22 (t, J = 8.4 Hz, 2H), 4.01 (t, J = 8.8 Hz, 2H), 3.91 (s, 3H), 3.28-3.09 (m, 4H), 2.93-2.75 (m, 4H), 2.50 (s, 3H) |
| 147 | 2,6-dichlorophenyl | 4-methylpiperazinyl-2-chloro-6-fluorophenyl | (M + 1) 575.20 | 400 MHz, DMSO-d₃: 10.60 (br s, 1H), 8.75 (s, 1H), 7.81-7.64 (m, 4H), 7.55 (dd, J = 8.8, 7.5 Hz, 1H), 4.19 (t, J = 8.3 Hz, 2H), 3.85 (t, J = 8.8 Hz, 2H), 3.11-2.99 (m, 4H), 2.47-2.37 (m, 4H), 2.22 (s, 3H) |
| 148 | 2,6-dichlorophenyl | 4-methylpiperazinyl-2-methyl-6-fluorophenyl | (M + 1) 555.34 | 400 MHz, CDCl₃: 8.82 (s, 1H), 7.64-7.58 (m, 1H), 7.50-7.46 (m, 2H), 7.38-7.34 (m, 1H), 7.01-6.98 (m, 1H), 4.25 (t, J = 8.6 Hz, 2H), 4.03 (t, J = 8.8 Hz, 2H), 3.32-3.14 (m, 4H), 2.90-2.72 (m, 4H), 2.54 (s, 3H), 2.33 (s, 3H) |
| 149 | 2,6-dichlorophenyl | 4-methylpiperazinyl-2-methoxy-6-fluorophenyl | (M + 1) 571.16 | 400 MHz, CDCl₃: 8.83 (s, 1H), 7.62 (brs, 1H), 7.50-7.46 (m, 2H), 7.36 (dd, J = 8.8, 7.5 Hz, 1H), 7.16 (d, J = 12.6 Hz, 1H), 6.98-6.94 (m, 1H), 4.23 (t, J = 8.6 Hz, 2H), 4.03 (t, J = 8.8 Hz, 2H), 3.86 (s, 3H), 3.29-3.22 (m, 4H), 2.72-2.65 (m, 4H), 2.44 (s, 3H) |
| 150 | 2,6-dichlorophenyl | 4-methylpiperazinyl-2,6-dichlorophenyl | (M + 1) 591.77 | 400 MHz, DMSO-d₆: 10.59 (brs, 1H), 8.75 (s, 1H), 7.96-7.88 (m, 2H), 7.71-7.65 (m, 2H), 7.55 (dd, J = 8.8, 7.5 Hz, 1H), 4.19 (t, J = 8.7 Hz, 2H), 3.85 (t, J = 8.8 Hz, 2H), 3.15-3.07 (m, 4H), 2.46-2.39 (m, 4H), 2.23 (s, 3H) |
| 151 | 2,6-dichlorophenyl | 4-methylpiperazinyl-2-chloro-6-methylphenyl | (M + 1) 571.29 | 400 MHz, CDCl₃: 8.82 (s, 1H), 7.81 (brs, 3H), 7.59-7.40 (m, 3H), 7.38-7.33 (m, 1H), 7.21-7.15 (m, 1H), 4.24 (t, J = 8.7 Hz, 2H), 4.03 (t, J = 9.0 Hz, 2H), 3.57 (t, J = 9.4 Hz, 2H), 3.07-2.97 (m, 2H), 2.92-2.83 (m, 2H), 2.64-2.55 (m, 2H), 2.49 (s, 3H), 2.36 (s, 3H) |
| 152 | 2,6-dichlorophenyl | 4-methylpiperazinyl-2-chloro-6-trifluoromethylphenyl | (M + 1) 625.26 | 400 MHz, CDCl₃: 8.85 (s, 1H), 8.06 (brs, 1H), 7.93-7.86 (m, 1H), 7.67-7.57 (m, 1H), 7.53-7.45 (m, 2H), 7.39-7.34 (m, 1H), 4.24 (t, J = 8.9 Hz, 2H), 4.07 (t, J = 8.9 Hz, 2H), 3.87 (t, J = 10.9 Hz, 2H), 3.02-2.93 (m, 2H), 2.88-2.80 (m, 2H), 2.58-2.44 (m, 5H) |

-continued

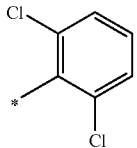

| Example | R₁ | R₂ | LC-MS (ESI) | ¹H NMR |
|---|---|---|---|---|
| 153 | 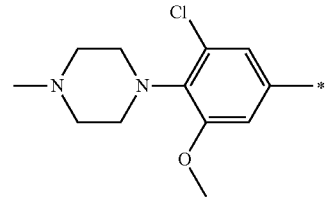 | 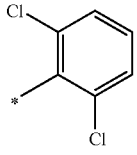 | (M + 1) 587.27 | 00 MHz, CDCl₃: 8.83 (s, 1H), 7.50-7.46 (m, 2H), 7.39-7.33 (m, 2H), 7.21 (d, J = 2.3 Hz, 1H), 4.24 (t, J = 8.8 Hz, 2H), 4.03 (t, J = 8.9 Hz, 2H), 3.85 (s, 3H), 3.76-3.39 (m, 4H), 3.07-2.84 (m, 4H), 2.53 (s, 3H) |
| 154 | 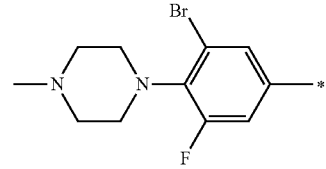 | 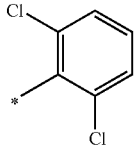 | (M + 1) 619.26 | 400 MHz, CDCl₃: 8.83 (s, 1H), 7.71-7.67 (m, 1H), 7.62-7.52 (m, 2H), 7.50-7.46 (m, 2H), 7.36 (dd, J = 8.8, 7.4 Hz, 1H), 4.25 (t, J = 8.7 Hz, 2H), 4.05 (t, J = 8.8 Hz, 2H), 3.44-3.21 (m, 4H), 2.99-2.75 (m, 4H), 2.56 (s, 3H) |
| 155 | 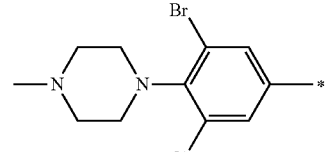 | 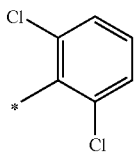 | (M + 1) 635.24 | 400 MHz, CDCl₃: 8.83 (s, 1H), 7.91 (d, J = 2.4 Hz, 1H), 7.72 (d, J = 2.6 Hz, 1H), 7.55-7.44 (m, 3H), 7.36 (dd, J = 8.8, 7.4 Hz, 1H), 4.24 (t, J = 8.9 Hz, 2H), 4.05 (t, J = 8.8 Hz, 2H), 3.51-3.43 (m, 2H), 3.20-3.13 (m, 2H), 2.84-2.77 (m, 2H), 2.68-2.60 (m, 2H), 2.46 (s, 3H) |
| 156 | 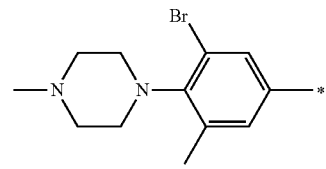 | 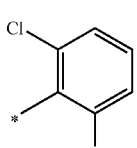 | (M + 1) 615.45 | 400 MHz, CDCl₃: 8.82 (s, 1H), 8.10-7.98 (m, 1H), 7.54-7.43 (m, 3H), 7.36 (dd, J = 8.8, 7.5 Hz, 1H), 7.23-7.19 (m, 1H), 4.25 (t, J = 8.7 Hz, 2H), 4.04 (t, J = 8.8 Hz, 2H), 3.49-3.41 (m, 2H), 3.23-3.15 (m, 2H), 2.89-2.83 (m, 2H), 2.79-2.72 (m, 2H), 2.53 (s, 3H), 2.38 (s, 3H) |
| 157 | 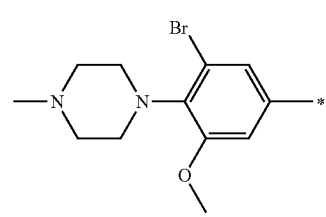 | 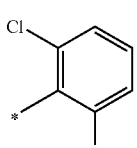 | (M + 1) 631.11 | 400 MHz, CDCl₃: 8.83 (s, 1H), 7.59-7.54 (m, 1H), 7.50-7.47 (m, 2H), 7.43 (br s, 1H), 7.36 (dd, J = 8.8, 7.5 Hz, 1H), 7.26-7.23 (m, 1H), 4.24 (t, J = 8.6 Hz, 2H), 4.05 (t, J = 9.0 Hz, 2H), 3.85 (s, 3H), 3.70-3.60 (m, 2H), 3.07-2.96 (m, 2H), 2.94-2.86 (m, 2H), 2.65-2.48 (m, 5H) |
| 158 | 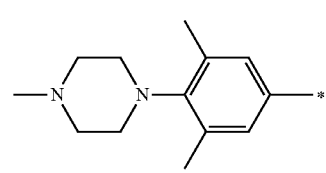 |  | (M + 1) 551.23 | 400 MHz, DMSO-d₆: 10.23 (brs, 1H), 8.67 (s, 1H), 7.71-7.63 (m, 2H), 7.54 (dd, J = 8.8, 7.5 Hz, 1H), 7.51-7.35 (m, 2H), 4.18 (t, J = 8,9 Hz, 2H), 3.82 (t, J = 8.7 Hz, 2H), 3.04-2.95 (m, 4H), 2.44-2.37 (m, 4H), 2.27 (s, 6H), 2.23 (s, 3H) |

-continued

[Structure: pyrimidine-fused imidazoline core with R1 on amide N, R2-NH on pyrimidine]

| Example | R₁ | R₂ | LC-MS (ESI) | ¹H NMR |
|---|---|---|---|---|
| 159 | 2,6-dichlorophenyl | 4-methyl-2-methoxy-6-methylphenyl-piperazinyl (N-methylpiperazine linked to 2-methoxy-6-methylphenyl) | (M + 1) 567.00 | 400 MHz, CDCl₃: 8.82. (s, 1H), 7.50-7.47 (m, 2H), 7.40-7.32 (m, 2H), 6.89 (d, J = 1.9 Hz, 1H), 4.22 (t, J = 8.7 Hz, 2H), 4.03 (t, J = 8.7 Hz, 2H), 3.85 (s, 3H), 3.82-3.67 (m, 2H), 3.10-2.95 (m, 2H), 2.78 (s, 3H), 2.61-2.49 (m, 4H), 2.31 (s, 3H) |
| 160 | 2-bromo-6-chlorophenyl | 4-(dimethylamino)piperidinyl linked to 2-fluoro-6-methylphenyl | (M + 1) 627.18 | 400 MHz, CDCl₃: 8.83 (s, 1H), 7.64 (dd, J = 8.1, 1.3 Hz, 1H), 7.60-7.54 (m, 1H), 7.54-7.45 (m, 2H), 7.31-7.27 (m, 1H), 7.00 (d, J = 2.0 Hz, 1H), 4.24 (t, J = 8.5 Hz, 2H), 4.03 (t, J = 8.9 Hz, 2H), 3.17 (t, J = 13.9 Hz, 2H), 3.08-3.03 (m, 2H), 2.76-2.71 (m, 1H), 2.54 (s, 6H), 2.32 (s, 3H), 2.03-1.99 (m, 2H), 1.77-1.69 (m, 2H) |
| 161 | 2-bromo-6-chlorophenyl | 4-methylpiperazinyl linked to 2-chlorophenyl | (M + 1) 601.47 | 400 MHz, CDCl₃ 8.82 (s, 1H), 7.92 (brs, 1H), 7.64 (dd, J = 8.1, 1.3 Hz, 1H), 7.56-7.42 (m, 2H), 7.38 (dd, J = 8.7, 2.4 Hz, 1H), 7.31-7.27 (m, 1H), 7.07 (d, J = 8.7 Hz, 1H), 4.24 (t, J = 8.3 Hz, 2H), 4.03 (t, J = 8.8 Hz, 2H), 3.21-3.08 (m, 4H), 2.83-2.65 (m, 4H), 2.46 (s, 3H) |
| 162 | 2-bromo-6-chlorophenyl | 4-methylpiperazinyl linked to 2-bromophenyl | (M + 1) 645.07 | 400 MHz, CDCl₃: 8.82 (s, 1H), 8.21-8.08 (m, 1H), 7.64 (dd, J = 8.1, 1.3 Hz, 1H), 7.56-7.46 (m, 2H), 7.45-7.41 (m, 1H), 7.31-7.27 (m, 1H), 7.08 (d, J = 8.7 Hz, 1H), 4.25 (t, J = 8.4 Hz, 2H), 4.04 (t, J = 9.2 Hz, 2H), 3.17-3.09 (m, 4H), 2.81-2.67 (m, 4H), 2.46 (s, 3H) |
| 163 | 2-bromo-6-chlorophenyl | 4-methylpiperazinyl linked to 2-methylphenyl | (M + 1) 581.32 | 400 MHz, CDCl₃: 8.81 (s, 1H), 7.64 (dd, J = 8.1. 1.3 Hz, 1H), 7.59-7.43 (m, 3H), 7.41 (d, J = 2.3 Hz, 1H), 7.30-7.26 (m, 1H), 7.07 (d, J = 8.6 Hz, 1H), 4.21 (t, J = 8.2 Hz, 2H), 4.03 (t, J = 9.2 Hz, 2H), 3.03 (t, J = 4.6 Hz, 4H), 2.84-2.68 (m, 4H), 2.48 (s, 3H), 2.33 (s, 3H), |
| 164 | 2-bromo-6-chlorophenyl | 4-methylpiperazinyl linked to 2,6-dichlorophenyl | (M + 1) 634.99 | 400 MHz, CDCl₃: 8.84 (s, 1H), 7.72-7.68 (m, 2H), 7.64 (dd, J = 8.1, 1.3 Hz, 1H), 7.58-7.48 (m, 2H), 7.31-7.27 (m, 1H), 4.25 (t, J = 9.0 Hz, 2H), 4.06 (t, J = 9.2 Hz, 2H), 3.40-3.32 (m, 4H), 2.82-2.75 (m, 4H), 2.52 (s, 3H) |

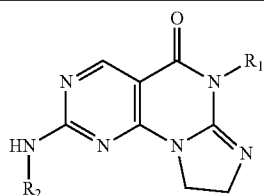

| Example | R₁ | R₂ | LC-MS (ESI) | ¹H NMR |
|---|---|---|---|---|
| 165 | 2-Br-6-Cl-phenyl | 4-methylpiperazinyl-(2-methyl-6-fluoro)phenyl | (M + 1) 599.28 | 400 MHz, CDCl₃ 8.83 (s, 1H), 7.66-7.57 (m, 2H), 7.53-7.51 (m, 1H), 7.46 (brs, 1H), 7.32-7.27 (m, 1H), 7.01-6.97 (m, 1H), 4.24 (t, J = 8.5 Hz, 2H), 4.03 (t, J = 8.9 Hz, 2H), 3.33-3.07 (m, 4H), 2.83-2.60 (m, 4H), 2.48 (s, 3H), 2.33 (s, 3H) |
| 166 | 2-Br-6-Cl-phenyl | 4-methylpiperazinyl-(2-methyl-6-chloro)phenyl | (M + 1) 615.19 | 400 MHz, CDCl₃,: 8.83 (s, 1H), 7.86-7.75 (m, 1H), 7.64 (dd, J = 8.1, 1.3 Hz, 1H), 7.52 (dd, J = 8.2, 1.3 Hz, 1H), 7.46 (brs, 1H), 731-7.26 (m, 1H), 7.18 (s, 1H), 4.25 (t, J = 8.6 Hz, 2H), 4.05 (t, J = 9.2 Hz, 2H), 3.60-3.52 (m, 2H), 3.07-2.97 (m, 2H), 2.88-2.81 (m, 2H), 2.60-2.52 (m, 2H), 2.47 (s, 3H), 2.36 (s, 3H) |
| 167 | 2-Br-6-Cl-phenyl | 4-methylpiperazinyl-(2-methyl-6-bromo)phenyl | (M + 1) 659.05 | 400 MHz, CDCl₃: 8.82 (s, 1H), 8.10-7.97 (m, 1H), 7.64 (dd, J = 8.1, 1.3 Hz, 1H), 7.60-7.47 (m, 2H), 7.31-7.26 (m, 1H), 7.22 (s, 1H), 4.24 (t, J = 8.5 Hz, 2H), 4.04 (t, J = 8.9 Hz, 2H), 3.49-3.41 (m, 2H), 3.24-3.15 (m, 2H), 2.89-2.83 (m, 2H), 2.80-2.73 (m, 2H), 2.53 (s, 3H), 2.37 (s, 3H) |
| 168 | 2-methyl-6-fluoro-phenyl | 4-methylpiperazinyl-(2-chloro)phenyl | (M + 1) 521.40 | 400 MHz, CDCl₃: 8.81 (s, 1H), 7.92 (brs, 1H), 7.52-7.41 (m, 1H), 7.39 (dd, J = 8.7, 2.5 Hz, 1H), 7.36-7.30 (m, 1H), 7.13 (d, J = 7.7 Hz, 1H), 7.10-7.03 (m, 2H), 4.21 (t, J = 8.7 Hz, 2H), 4.05-3.96 (m, 2H), 3.25-3.09 (m, 4H), 2.90-2.70 (m, 4H), 2.50 (s, 3H), 2.25 (s, 3H) |
| 169 | 2-F-6-methyl-phenyl | 4-methylpiperazinyl-(2,6-dimethyl)phenyl | (M + 1) 515.33 | 400 MHz, DMSO-d₆,: 10.14 (brs, 1H), 8.64 (s, 1H), 7.49-7.35 (m, 3H), 7.23-7.16 (m, 2H), 4.19-4.11 (m, 2H), 3.81 (t, J = 8.8 Hz, 2H), 3.05-2.95 (m, 4H), 2.43-2.37 (m, 4H), 2.27 (s, 6H), 2.23 (s, 3H), 2.16 (s, 3H) |
| 170 | 2-methyl-6-chloro-phenyl | 4-(dimethylamino)piperidinyl-(2-methyl-6-fluoro)phenyl | (M + 1) 563.05 | 400 MHz, CDCl₃: 8.82 (s, 1H), 7.66-7.46 (m, 2H), 7.39 (dd, J = 7.8, 1.3 Hz, 1H), 7.32-7.28 (m, 1H), 7.26-7.23 (m, 1H), 7.00 (d, J = 2.0 Hz, 1H), 4.28-4.18 (m, 2H), 4.06-3.96 (m, 2H), 3.19-3.11 (m, 2H), 3.07-3.01 (m, 2H), 2.56-2.50 (m, 1H), 2.46 (s, 6H), 2.32 (s, 3H), 2.26 (s, 3H), 2.00-1.94 (m, 2H), 1.73-1.63 (m, 2H) |

-continued

[Core structure: pyrimido-imidazole scaffold with R1 and HN-R2 substituents]

| Example | R₁ | R₂ | LC-MS (ESI) | ¹H NMR |
|---|---|---|---|---|
| 171 | 2,6-dimethylphenyl (with Cl) — 2-chloro-6-methylphenyl | 4-(2-chlorophenyl)-piperazin-1-yl-methyl | (M + 1) 537.35 | 400 MHz, CDCl₃: 8.81 (s, 1H), 7.92 (brs, 1H), 7.51-7.34 (m, 3H), 7.32-7.27 (m, 1H), 7.26-7.22 (m, 1H), 7.07 (d, J = 8.7 Hz, 1H), 4.28-4.17 (m, 2H), 4.07-3.96 (m, 2H), 3.24-3.07 (m, 4H), 2.89-2.67 (m, 4H), 2.47 (s, 3H), 2.26 (s, 3H) |
| 172 | 2-chloro-6-methylphenyl | 4-(2,6-dichlorophenyl)-piperazin-1-yl-methyl | (M + 1) 571.26 | 400 MHz, CDCl₃: 8.83 (s, 1H), 7.74 (s, 2H), 7.39 (dd, J = 7.8, 1.2 Hz, 1H), 7.30 (t, J = 7.7 Hz, 1H), 7.26-7.23 (m, 1H), 4.28-4.20 (m, 2H), 4.08-4.00 (m, 2H), 3.59-3.41 (m, 4H), 3.28-3.18 (m, 4H), 2.82 (s, 3H), 2.26 (s, 3H) |
| 173 | 2-chloro-6-methylphenyl | 4-(2-chloro-6-methylphenyl)-piperazin-1-yl-methyl | (M + 1) 551.34 | 400 MHz, CDCl₃: 8.81 (s, 1H), 7.84 (brs, 1H), 7.61-7.50 (m, 1H), 7.39 (dd, J = 7.9, 1.2 Hz, 1H), 7.32-7.28 (m, 1H), 7.26-7.23 (m, 1H), 7.22-7.18 (m, 1H), 4.27-4.20 (m, 2H), 4.07-3.99 (m, 2H), 3.66-3.57 (m, 2H), 3.19-3.10 (m, 2H), 3.08-3.02 (m, 2H), 2.87-2.79 (m, 2H), 2.62 (s, 3H), 2.36 (s, 3H), 2.26 (s, 3H) |
| 174 | 2-chloro-6-methylphenyl | 4-(2,6-dimethylphenyl)-piperazin-1-yl-methyl | (M + 1) 531.29 | 400 MHz, DMSO-d₆: 10.15 (brs, 1H), 8.64 (s, 1H), 7.48-7.32 (m, 5H), 4.20-4.11 (m, 2H), 3.84-3.77 (m, 2H), 3.03-2.96 (m, 4H), 2.44-2.38 (m, 4H), 2.27 (s, 6H), 2.23 (s, 3H), 2.17 (s, 3H) |
| 175 | 2,6-dichlorophenyl | 4-phenyl-piperazin-1-yl | (M + 1) 508.97 | 400 MHz, DMSO-d₆: 10.29 (brs, 1H), 8.65 (s, 1H), 7.76-7.59 (m, 4H), 7.54 (dd, J = 8.8, 1.3 Hz, 1H), 6.93 (d, J = 9.0 Hz, 2H), 4.16 (t, J = 8.1 Hz, 2H), 3.81 (t, J = 8.8 Hz, 2H), 3.11-3.06 (m, 4H), 2.97-2.91 (m, 4H) |
| 176 | 2,6-dichlorophenyl | 4-(2-chlorophenyl)-piperazin-1-yl | (M + 1) 543.05 | 400 MHz, DMSO-d₆: 10.47 (brs, 1H), 8.71 (s, 3H), 8.00-7.91 (m, 1H), 7.80-7.70 (m, 1H), 7.69-7.65 (m, 2H), 7.55 (dd, J = 8.8, 7.5 Hz, 1H), 7.15 (d, J = 8.8 Hz, 1H), 4.19 (t, J = 8.3 Hz, 2H), 3.84 (t, J = 8.8 Hz, 2H), 2.97-2.85 (m, 8H) |
| 177 | 2,6-dichlorophenyl | 4-(2-methylphenyl)-piperazin-1-yl | (M + 1) 523.02 | 400 MHz, CDCl₃: 8.81 (s, 1H), 7.54-7.45 (m, 4H), 7.43-7.40 (m, 1H), 7.35 (dd, J = 8.7, 7.6 Hz, 1H), 7.04 (d, J = 8.6 Hz, 1H), 4.21 (t, J = 8.4 Hz, 2H), 4.01 (t, J = 8.8 Hz, 2H), 3.08-3.01 (m, 4H), 2.92-2.85 (m, 4H), 2.35 (s, 3H) |

-continued

| Example | R₁ | R₂ | LC-MS (ESI) | ¹H NMR |
|---|---|---|---|---|
| 178 | 2,6-dichlorophenyl | 4-(2-methoxyphenyl)piperazin-1-yl (HN-piperazine, phenyl with OMe) | (M + 1) 539.21 | 400 MHz, DMSO-d₆: 10.35 (brs, 1H), 8.68 (s, 1H), 7.83-7.69 (m, 1H), 7.69-7.64 (m, 2H), 7.55 (dd, J = 8.8, 7.5 Hz, 1H), 7.21 (d, J = 6.1 Hz, 1H), 6.86 (d, J = 8.6 Hz, 1H), 4.25-4.16 (m, 2H), 3.86-3.77 (m, 5H), 2.98-2.88 (m, 8H) |
| 179 | 2-fluoro-6-chlorophenyl | 4-(2-(hydroxymethyl)phenyl)piperazin-1-yl | (M + 1) 523.25 | 400 MHz, DMSO: 10.36 (brs, 1H), 8.66 (s, 1H), 8.06-7.94 (m, 1H), 7.69-7.62 (m, 1H), 7.60-7.52 (m, 2H), 7.48-7.43 (m, 1H), 7.03 (d, J = 8.7, Hz, 1H), 5.10 (br s, 1H), 4.56 (s, 2H), 4.22-4.14 (m, 2H), 3.85-3.78 (m, 2H), 2.99-2.89 (m, 4H), 2.86-2.77 (m, 4H) |
| 180 | 2,6-dichlorophenyl | 4-(2-(hydroxymethyl)phenyl)piperazin-1-yl | (M + 1) 539.03 | 400 MHz, DMSO-d₆: 10.36 (brs, 1H), 8.67 (s, 1H), 8.07-7.93 (m, 1H), 7.69-7.62 (m, 3H), 7.54 (dd, J = 8.8, 7.5 Hz, 1H), 7.02 (d, J = 8.7, Hz, 1H), 4.56 (s, 2H), 4.21-4.15 (m, 2H), 3.82 (t, J = 8.8 Hz, 2H), 2.91-2.86 (m, 4H), 2.80-2.75 (m, 4H) |
| 181 | 2,6-dichlorophenyl | 4-methyl-4'-(2-(hydroxymethyl)phenyl)piperazine | (M + 1) 553.17 | 400 MHz, CDCl₃: 8.82 (s, 1H), 7.60-7.55 (m, 2H), 7.50-7.46 (m, 2H), 7.36 (dd, J = 8.8, 7.5 Hz, 1H), 7.26-7.22 (m, 1H), 4.80 (s, 2H), 4.22 (t, J = 8.6 Hz, 2H), 4.02 (t, J = 8.9 Hz, 2H), 3.17-3.07 (m, 4H), 2.91-2.69 (m, 4H), 2.50 (s, 3H) |
| 182 | 2,6-dichlorophenyl | 4-(2-hydroxyethyl)-4'-phenylpiperazine | (M + 1) 553.25 | 400 MHz, CDCl₃: 8.81 (s, 1H), 7.58-7.50 (m, 2H), 7.50-7.45 (m, 2H), 7.36 (dd, J = 7.6, 1.2 Hz, 1H), 6.95 (d, J = 9.0 Hz, 2H), 4.20 (t, J = 8.7 Hz, 2H), 4.01 (t, J = 9.0 Hz, 2H), 3.80 (t, J = 5.0 Hz, 2H), 3.41-3.29 (m, 4H), 3.00-2.85 (m, 4H), 2.84-2.78 (m, 2H) |
| 183 | 2,6-dichlorophenyl | 4-morpholinophenyl | (M + 1) 510.08 | 400 MHz, CDCl₃: 8.80 (s, 1H), 7.60-7.52 (m, 2H), 7.50-7.46 (m, 2H), 7.36 (dd, J = 8.8, 7.5 Hz, 3H), 7.04-6.95 (m, 2H), 4.21 (t, J = 8.0 Hz, 2H), 4.01 (t, J = 8.8 Hz, 2H), 3.91 (t, J = 4.4 Hz, 4H), 3.18 (t, J = 4.6 Hz, 4H) |

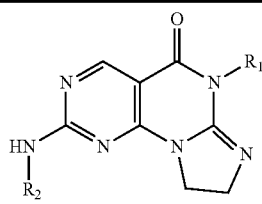

| Example | R₁ | R₂ | LC-MS (ESI) | ¹H NMR |
|---|---|---|---|---|
| 184 | 2,6-dichlorophenyl (*) | 4-morpholino-3-((methylamino)methyl)phenyl (*) | (M + 1) 552.99 | 400 MHz, DMSO-d₆: 10.36 (brs, 1H), 8.68 (s, 1H), 8.00-7.87 (m, 1H), 7.70-7.61 (m, 3H), 7.55 (dd, J = 8.7, 7.6 Hz, 1H), 7.14 (d, J = 8.7 Hz, 1H), 4.24-4.16 (m, 2H), 3.85-3.79 (m, 4H), 3.76-3.71 (m, 4H), 2.89-2.82 (m, 4H), 2.39 (s, 3H) |
| 185 | 3-bromo-2-chlorophenyl (*) | 2-chloro-4-(4-(dimethylamino)piperidin-1-yl)phenyl (*) | — | — |

Note: *The compound of Example 93 is the by-product of the targeted compound of Example 19.

Example 186

6-(2,6-Dichlorophenyl)-2-((3-chloro-4-(4-methylpiperazin-1-yl)phenyl)amino)-8,9-dihydroimidazo[1,2-a]pyrimido[5,4-e]pyrimidin-5(6H)-one dihydrochloride To a mixture of 2-((3-chloro-4-(4-methylpiperazin-1-yl)phenyl)amino)-6-(2,6-dichlorophenyl)-8,9-dihydroimidazo[1,2-a]pyrimido[5,4-e]pyrimidin-5(6H)-one (Example 71, 1.0 g, 1.8 mmol) in MeCN (5 mL) and pure $H_2O$ (5 mL) was added hydrochloric acid (1N, 3.6 mL). The mixture was freeze-dried for 48 hrs to give the targeted compound (1.09 g, 96% yield, yellow solid). LC-MS (ESI): m/z (M+1) 557.16. ¹H NMR (400 MHz, DMSO-d₆): δ 10.64 (brs, 2.5H), 8.82 (s, 1H), 8.01-7.94 (m, 1H), 7.82-7.68 (m, 3H), 7.64-7.58 (m, 1H), 7.24 (d, J=8.8 Hz, 1H), 4.32-4.25 (m, 2H), 3.91 (t, J=8.6 Hz, 2H), 3.54-3.47 (m, 2H), 3.41-3.35 (m, 2H), 3.23-3.15 (m, 2H), 3.13-3.06 (m, 2H), 2.84 (d, J=4.7 Hz, 3H).

Intermediate: Synthesis of Substituted Amine 1) 4-(4-Methyl-1,4-diazepan-1-yl)aniline N-Methyl diazepane (414 mg, 3.63 mmol), 4-fluoronitrobenzene (454 mg, 3.22 mmol), potassium carbonate (529 mg, 3.83 mmol) and DMSO (4 mL) were added into a stand-up bottle with 50 mL volume. The mixture was heated to 100° C. and reacted for 4 hrs, and then the reaction was stopped. 50 mL of Water was added and the mixture was stirred, then stewing, and filtered to give 1-methyl-4-(4-nitrophenyl)-1,4-diazepane (yellow solid, 500 mg, 66% yield). To a reaction bottle with 50 mL volume was added 1-methyl-4-(4-nitrophenyl)-1,4-diazepane (500 mg, 2.12 mmol), Fe powder (473 mg, 8.48 mmol), ammonia chloride (226 mg, 4.24 mmol), EtOH (10 mL) and $H_2O$ (10 mL), and the mixture was heated to reflux for 1 h, and then the reaction was stopped. After cooled down, the mixture was filtered, removed the solvent, and extracted with EtOAc (20 mL×3). The organic layer was dried with anhydrous sodium sulfate, filtered, removed the solvent to give the crude product, which was purified by column chromatography (MeOH:DCM=1:20) to give the targeted compound (243 mg, 56% yield).

2) 4-(2-(Dimethylamino)ethyoxyl)aniline

Dimethylaminochloroethane hydrochloride (1.44 g, 10 mmol) and 4-nitrophenol (1.39 g, 10 mmol) were dissolved in 20 mL of DMF. Then cesium carbonate (5.29 g, 15 mmol) was added, and the mixture was reacted at 100° C. for 3 hrs. The mixture was cooled down, filtered, and removed solvent, and then 100 mL $H_2O$ was added and stirred. The mixture was extracted with EtOAc, and the organic layer was washed with saturated sodium carbonate, dried, filtered, and removed the solvent to give the crude product of N,N-dimethyl-2-(4-nitrophenoxy)ethamine (1.37 g). The crude product (1.37 g, 6.5 mmol) was dissolved in EtOH (10 mL) and $H_2O$ (10 mL), then Fe powder (1.46 g, 26 mmol) and ammonia chloride (696 mg, 13 mmol) were added, and the reaction liquor was heated to reflux for 2 hrs. The reaction liquor was filtered, removed the solvent, extracted with EtOAc, dried with anhydrous sodium sulfate, filtered, and removed the solvent to give the crude product, which was purified by column chromatography (MeOH:DCM=1: 20) to give the targeted compound (630 mg, 35% yield for two-step).

3) 3,5-Dimethyl-4-(4-methylpiperazin-1-yl)aniline a) N-Acetyl-3,5-dimethylaniline: at r.t., to the solution of 3,5-dimethylaniline (8 g, 66 mmol) in anhydrous DCM (120 mL) was added triethylamine (18 mL, 132 mmol). At 0° C., to the reaction mixture was added acetic anhydride (8.09 g, 79 mmol), and the mixture was stirred for 2 hrs at r.t., then to which was added saturated aqueous sodium bicarbonate (50 mL). The mixture was extracted with DCM (50 mL), and the organic layer was collected, washed with saturated saline, dried with anhydrous sodium sulfate, filtered, and removed the organic solvent under reduced pressure to give the crude product, which was purified by column chromatography (silica gel, PE:EtOAc=5:1) to give the targeted compound (10 g, 94% yield, white solid). LC-MS (ESI): m/z $(M+H)^+$ 164.09.

b) N-Acetyl-3,5-dimethyl-4-bromoaniline: at r.t., N-acetyl-3,5-dimethylaniline (10 g, 61.3 mmol) was dissolved in the mixed solvent of DCM (400 mL) and methanol (160 mL), and the mixture was stirred for 1 h at r.t., then to which was added tetrabutylammonium tribromide (32.5 g, 67.4 mmol). The reaction mixture was stirred overnight at r.t. And the organic solvent was removed under reduced pressure. Then $H_2O$ (100 mL) and EtOAc (200 mL) were added to extract, and the aqueous layer was extracted with EtOAc (100 mL). The organic layers were collected, washed with saturated saline, dried with anhydrous sodium sulfate, filtered, and removed the organic solvent under reduced pressure to give the crude product, which was purified by column chromatography (silica gel, PE:EtOAc=5:1 as eluent) to give the targeted compound (4.2 g, 28% yield, white solid). LC-MS (ESI): m/z $(M+H)^+$ 242.09.

c) N-Acetyl-3,5-dimethyl-4-(4-methylpiperazin-1-yl)aniline: at r.t., N-acetyl-3,5-dimethyl-4-bromoaniline (400 mg, 1.65 mmol), N-methylpiperazine (199 mg, 1.98 mmol), tris(dibenzylideneacetone)dipalladium (76 mg, 0.08 mmol) and 2-(ditert-butylphosphine) biphenyl (49 mg, 0.16 mmol) were added to anhydrous THE (10 mL). After vacuumized, the gas in the reaction system was replaced with nitrogen for three times, and then lithium bis(trimethylsilyl)amide (1 M, 4.13 mL) was added. The reaction mixture was microwave reacted at 100° C. for 1 h, and then cooled down to r.t., filtered, and removed the organic solvent under reduced pressure to give the crude product, which was purified by column chromatography (silica gel, DCM:MeOH=15:1 as eluent) to give the targeted compound (288 mg, 66% yield, yellow solid). LC-MS (ESI): m/z $(M+H)^+$262.41.

d) 3,5-Dimethyl-4-(4-methylpiperazin-1-yl)aniline: at r.t., to the solution of N-acetyl-3,5-dimethyl-4-(4-methylpiperazin-1-yl)aniline (280 mg, 1.07 mmol) in MeOH (10 mL) was added concentrated hydrochloric acid (2.5 mL). The reaction mixture was stirred for 1 h at 90° C., cooled down to r.t., and pH was adjusted to 8-9 with saturated aqueous sodium bicarbonate. EtOAc (15 mL) was added to extract, and the aqueous layer was extracted with EtOAc (15 mL×2). The organic layers were collected, washed with saturated saline, dried with anhydrous sodium sulfate, filtered, and removed the organic solvent under reduced pressure to give the targeted compound (200 mg, 85% yield, yellow solid). LC-MS (ESI): m/z $(M+H)^+$220.21.

4) 3-Fluoro-4-(4-methylpiperazin-1-yl)-5-methylaniline a) 1-(2-Bromo-4-nitro-6-fluorophenyl)-4-methylpiperazine: at r.t., to trifluoroacetic acid (10 mL) was added 3-fluoro-4-(4-methylpiperazin-1-yl)nitrobenzene (400 mg, 1.67 mmol), and then added N-bromobutanimide (NBS, 595 mg, 3.34 mmol) and concentrate sulfuric acid (0.5 mL) separately. The reaction mixture was stirred at 50° C. overnight, then cooled down to r.t., and concentrated to remove trifluoroacetic acid under reduced pressure. The pH of the mixture was adjusted to 8-9 with saturated aqueous sodium bicarbonate. To the mixture was added EtOAc (30 mL) for extraction, and the aqueous layer was extracted with EtOAc (15 mL×2). The organic layers were collected, washed with saturated saline, dried with anhydrous sodium sulfate, and filtered. The filtrate was concentrated to remove the organic solvent under reduced pressure to give the crude product, which was purified by column chromatography (silica gel, DCM:MeOH=15:1 as eluent) to give the targeted compound (480 mg, 90% yield, yellow solid). LC-MS (ESI): m/z $(M+H)^+$ 318.11.

b) 1-(2-Methyl-4-nitro-6-fluorophenyl)-4-methylpiperazine: at r.t., to dioxane (10 mL) and $H_2O$ (2 mL) were added 1-(2-bromo-4-nitro-6-fluorophenyl)-4-methylpiperazine (480 mg, 1.5 mmol, methyl boric acid (906 mg, 15 mmol), 1,1'-bis(diphenylphosphino)ferrocene-palladium(II)dichloride dichloromethane complex (62 mg, 0.08 mmol) and potassium phosphate (964 mg, 4.5 mmol). The gas in the reaction system was replaced with nitrogen for three times, and then the mixture was stirred at 100° C. overnight. After cooled down to r.t., the mixture was filtered, concentrated to remove the organic solvent under reduced pressure to give the crude product, which was purified by column chromatography (silica gel, DCM:MeOH=15:1 as eluent) to give the targeted compound (180 mg, 47% yield, yellow solid). LC-MS (ESI): m/z $(M+H)^+$ 254.21.

c) 3-Fluoro-4-(4-methylpiperazin-1-yl)-5-methylaniline: at r.t., to the solution of 1-(2-methyl-4-nitro-6-fluorophenyl)-4-methylpiperazine (180 mg, 0.71 mmol) in EtOAc (30 mL) was added Pd/C (20 mg). The gas in the reaction system was replaced with nitrogen for three times, and then the mixture was stirred for 3 hrs at r.t., filtered to remove Pd/C, and concentrated to remove the organic solvent to give the targeted compound (149 mg, 94% yield, yellow solid). LC-MS (ESI): m/z $(M+H)^+$224.19.

5) 3-Chloro-4-(4-methylpiperazin-1-yl)-5-methylaniline a) 1-(2-Chloro-4-nitro-6-methylphenyl)-4-methylpiperazine: to MeOH (5 mL) was added 3-methyl-4-(4-methylpiperazin-1-yl)nitrobenzene (382 mg, 1.62 mmol). After the reaction system was cooled down to 0° C., to which concentrated hydrochloric acid (2.5 mL) was added, and hydrogen peroxide (2.5 mL) was added dropwise slowly. After the addition, the reaction mixture was stirred under refluxing overnight. When the reaction liquor was cooled down to r.t., to which saturated aqueous sodium sulfite (5 mL) was added, and then the mixture was stirred for 10 min at r.t., and pH was adjusted to 8-9 with saturated aqueous sodium bicarbonate. To the mixture was added EtOAc (30 mL) for extraction, and the aqueous layer was extracted with EtOAc (15 mL×2). The organic layers were collected, washed with saturated saline, dried with anhydrous sodium sulfate, and filtered. The filtrate was concentrated to remove the organic solvent under reduced pressure to give the crude product, which was purified by column chromatography (silica gel, DCM:MeOH=15:1 as eluent) to give the targeted compound (406 mg, 93% yield, yellow solid). LC-MS (ESI): m/z $(M+H)^+$270.11.

b) 3-Chloro-4-(4-methylpiperazin-1-yl)-5-methylaniline: 1-(2-chloro-4-nitro-6-methylphenyl)-4-methylpiperazine (120 mg, 0.44 mmol) was dissolved in the mixed solvent of EtOH (8 mL) and $H_2O$ (2 mL). Then to the mixture was added Fe powder (125 mg, 2.22 mmol) and ammonium chloride (238 mg, 4.4 mmol) separately. The reaction mixture was stirred for 4 hrs at 80° C., then cooled down to r.t., filtered, concentrated to remove the organic solvent under the reduced pressure to give the crude product, which was purified by column chromatography (silica gel, DCM:MeOH=15:1 as eluent) to give the targeted compound (100 mg, 94% yield, yellow solid). LC-MS (ESI): m/z (M+H)$^+$ 240.11.

Other substituted amines can be prepared using methods similar to those described for the syntheses of Intermediate 1)-5), or methods known by those of ordinary skill in the art.

Example 187

Determination of the inhibitory effect of 6-(2-chlorophenyl)-2-((4-(4-methylpiperazin-1-yl)phenyl)amino)-8,9-dihydroimidazo[1,2-a]pyrimido[5,4-e]pyrimidin-5(6H)-one and Analogs on the Enzyme Activity of Wee1 Kinase by Using the Wee1 Kinase (h) Detection Method Wee1 (h) is incubated with 20 mM Tris/HCl pH 8.5, 0.2 mM EDTA, 500 µM LSNLYHQGKFLQTFCGSPLYRRR, 10 mM MgAcetate and 10 µM [γ-$^{33}$P]-ATP. Then the stock solution of all compounds under test with 50× concentration in 100% DMSO was added to make the final concentration of 10/1/0.1/0.01 µM, and then mixed the mixture well. The reaction is initiated by the addition of the Mg/ATP mix. After incubation for 40 minutes at room temperature, the reaction is stopped by the addition of phosphoric acid to a concentration of 0.5%. 10 µL of the reaction liquor is then spotted onto a P30 filtermat and washed four times in 0.425% phosphoric acid and once in methanol prior to drying and scintillation counting. Each compound sample is duplicated in duplicate. The negative control was lack of all the components of Wee1 enzyme, and the positive was addition of 30% phosphoric acid to terminate the reaction. The Wee1 inhibitor AZD1775 was detected at 10 µM at the same experiment condition. Table 1 summarizes the inhibition data of compounds on Wee1 kinase (count and activity).

TABLE 1

The inhibitory effect of 6-(2-chlorophenyl)-2-((4-(4-methylpiperazin-1-yl)phenyl)amino)-8,9-dihydroimidazo[1,2-a]pyrimido[5,4-e]pyrimidin-5(6H)-one and analogs on the enzyme activity of Wee1 kinase

| Example | | | | | | | | | |
|---|---|---|---|---|---|---|---|---|---|
| Example | 1 | | | 2 | | | 3 | | |
| C (µm) | 10 | | | 10 | | | 10 | | |
| Inh. (%) | 96 | | | 95 | | | 56 | | |
| Example | 4 | | | 5 | | | 6 | | |
| C (µm) | 1 | 0.1 | 0.01 | 1 | | | 1 | 0.1 | 0.01 |
| Inh. (%) | 97 | 93 | 55 | 88 | | | 98 | 89 | 33 |
| Example | 7 | | | 8 | | | 9 | | |
| C (µm) | 1 | 0.1 | 0.01 | 1 | 0.1 | 0.01 | 1 | 0.1 | 0.01 |
| Inh. (%) | 96 | 84 | 31 | 99 | 93 | 60 | 100 | 79 | 28 |
| Example | 10 | | | 11 | | | 12 | | |
| C (µm) | 1 | 0.1 | 0.01 | 1 | 0.1 | 0.01 | 1 | 0.1 | 0.01 |
| Inh. (%) | 98 | 93 | 46 | 97 | 85 | 23 | 98 | 83 | 32 |
| Example | 13 | | | 14 | | | 15 | | |
| C (µm) | 1 | 0.1 | 0.01 | 1 | 0.1 | 0.01 | 1 | | |
| Inh. (%) | 100 | 87 | 29 | 92 | 86 | 12 | 89 | | |
| Example | 16 | | | 17 | | | 18 | | |
| C (µm) | 1 | 0.1 | 0.01 | 1 | | | 1 | | |
| Inh. (%) | 98 | 59 | 15 | 87 | | | 14 | | |
| Example | 19 | | | 20 | | | 21 | | |
| C (µm) | 1 | | | 1 | | | 1 | | |
| Inh. (%) | 7 | | | 9 | | | 9 | | |
| Example | 22 | | | 23 | | | 27 | | |
| C | 1 | | | 1 | | | 1 | | |
| Inh. (%) | 8 | | | 22 | | | 17 | | |
| Example | 28 | | | 32 | | | 33 | | |
| C (µm) | 1 | | 1 | 0.1 | 0.01 | | 1 | | |
| Inh. (%) | 67 | | 94 | 69 | 19 | | 87 | | |
| Example | 34 | | | 35 | | | 36 | | |
| C (µm) | 1 | 0.1 | 0.01 | 1 | 0.1 | 0.01 | 1 | | |
| Inh. (%) | 97 | 93 | 38 | 100 | 82 | 27 | 0 | | |
| Example | 37 | | | 38 | | | 39 | | |
| C (µm) | 1 | | | 1 | | | 1 | | |
| Inh. (%) | 1 | | | 34 | | | 28 | | |
| Example | 40 | | | 41 | | | 42 | | |
| C (µm) | 1 | | | 1 | | | 1 | | |
| Inh. (%) | 4 | | | 2 | | | 19 | | |
| Example | 43 | | | 44 | | | 45 | | |
| C (µm) | 1 | | 1 | 0.1 | 0.01 | | 1 | 0.1 | 0.01 |
| Inh. (%) | 27 | | 93 | 75 | 23 | | 95 | 80 | 28 |
| Example | 46 | | | 47 | | | 48 | | |
| C (µm) | 1 | 0.1 | 001 | 1 | 0.1 | 0.01 | 1 | 0.1 | 0.01 |
| Inh. (%) | 97 | 85 | 36 | 98 | 89 | 45 | 91 | 75 | 29 |
| Example | 49 | | | 50 | | | 51 | | |
| C (µm) | 1 | 0 | 0.01 | 1 | 0.1 | 0.01 | 1 | 0 | 0.01 |
| Inh. (%) | 95 | 86 | 43 | 100 | 95 | 62 | 96 | 86 | 66 |
| Example | 52 | | | 53 | | | 54 | | |
| C (µm) | 1 | 0.1 | 0.01 | 1 | 0.1 | 0.01 | 1 | | |
| Inh. (%) | 93 | 80 | 111 | 91 | 82 | 13 | 81 | | |
| Example | 55 | | | 56 | | | 57 | | |
| C (µm) | 1 | | 1 | 0.1 | 0.01 | | 1 | 0.1 | 0.01 |
| Inh. (%) | 12 | | 90 | 80 | 14 | | 89 | 80 | 36 |

TABLE 1-continued

The inhibitory effect of 6-(2-chlorophenyl)-2-((4-(4-methylpiperazin-1-yl)phenyl)amino)-8,9-dihydroimidazo[1,2-a]pyrimido[5,4-e]pyrimidin-5(6H)-one and analogs on the enzyme activity of Wee1 kinase

| Example | 58 | | | 59 | | | 60 | | |
|---|---|---|---|---|---|---|---|---|---|
| C (μm) | 1 | 0.1 | 0.01 | 1 | | | 1 | 0.1 | 0.01 |
| Inh. (%) | 100 | 92 | 46 | 49 | | | 91 | 71 | 15 |
| Example | 61 | | | 62 | | | 63 | | |
| C (μm) | 1 | | | 1 | | | 1 | 0.1 | 0.0 |
| Inh. (%) | 82 | | | 83 | | | 99 | 76 | 17 |
| Example | 64 | | | 65 | | | 66 | | |
| C (μm) | 1 | 0.1 | 0.01 | 1 | 0.1 | 0.01 | 1 | | |
| Inh. (%) | 100 | 88 | 52 | 98 | 68 | 18 | 0 | | |
| Example | 67 | | | 68 | | | 69 | | |
| C (μm) | 1 | | | 1 | | | 1 | 0.1 | 0.01 |
| Inh. (%) | 24 | | | 6 | | | 97 | 73 | 24 |
| Example | 70 | | | 71 | | | 72 | | |
| C (μm) | 1 | 0.1 | 0.01 | 1 | 0.1 | 0.01 | 1 | 0.1 | 0.01 |
| Inh. (%) | 99 | 69 | 17 | 98 | 74 | 36 | 97 | 75 | 22 |
| Example | 73 | | | 74 | | | 75 | | |
| C (μm) | 1 | | | 1 | 0.1 | 0.01 | 1 | 0.1 | 0.01 |
| Inh. (%) | 83 | | | 98 | 61 | 15 | 100 | 80 | 24 |
| Example | 76 | | | 77 | | | 78 | | |
| C | 1 | 0.1 | 0.01 | 1 | 0.1 | 0.01 | 1 | 0.1 | 0.01 |
| Inh. (%) | 97 | 74 | 22 | 88 | 86 | 11 | 100 | 77 | 29 |
| Example | 79 | | | 80 | | | 81 | | |
| C (μm) | 1 | | | 1 | | | 1 | 0.1 | 0.0 |
| Inh. (%) | 69 | | | 80 | | | 89 | 72 | 7 |
| Example | 82 | | | 83 | | | 84 | | |
| C (μm) | 1 | | | 1 | 0 | 0.01 | 1 | 0.1 | 0.01 |
| Inh. (%) | 83 | | 94 | 59 | | 15 | 93 | 49 | 18 |
| Example | 85 | | | 86 | | | 87 | | |
| C (μm) | 1 | | | 1 | | | 1 | | |
| Inh. (%) | 17 | | | 13 | | | 75 | | |
| Example | 88 | | | 89 | | | 90 | | |
| C (μm) | 1 | | | 1 | | | 1 | | |
| Inh. (%) | 75 | | | 89 | | | 29 | | |
| Example | 91 | | | 92 | | | 93 | | |
| C (μm) | 1 | | | 1 | | | 1 | | |
| Inh. (%) | 75 | | | 1 | | | 0 | | |
| Example | 94 | | | 95 | | | 96 | | |
| C (μm) | 1 | | | 1 | | | 1 | | |
| Inh. (%) | 19 | | | 8 | | | 29 | | |
| Example | 97 | | | 98 | | | 99 | | |
| C (μm) | 1 | | | 1 | | | 1 | | |
| Inh. (%) | 9 | | | 2 | | | 8 | | |
| Example | 100 | | | 101 | | | 102 | | |
| C (μm) | 1 | | 1 | 0.1 | 0.01 | | 1 | | |
| Inh. (%) | 87 | | 95 | 70 | 22 | | 7 | | |
| Example | 103 | | | 104 | | | 105 | | |
| C (μm) | 1 | 0.1 | 0.01 | 1 | | | 1 | 0.1 | 0.01 |
| Inh. (%) | 92 | 70 | 30 | 93 | | | 97 | 85 | 40 |
| Example | 106 | | | 107 | | | 108 | | |
| C (μm) | 1 | 0.1 | 0.01 | 1 | | | 1 | | |
| Inh. (%) | 94 | 83 | 38 | 95 | | | 96 | | |
| Example | 109 | | | 110 | | | 111 | | |
| C (μm) | 1 | | | 1 | | | 1 | | |
| Inh. (%) | 96 | | | 96 | | | 96 | | |
| Example | 112 | | | 113 | | | 114 | | |
| C (μm) | 1 | | | 1 | | | 1 | | |
| Inh. (%) | 97 | | | 96 | | | 98 | | |
| Example | 115 | | | 116 | | | 117 | | |
| C (μm) | 1 | 0.1 | 0.01 | 1 | 0.1 | 0.01 | 1 | 0.1 | 0.01 |
| Inh. (%) | 96 | 81 | 34 | 98 | 77 | 19 | 98 | 84 | 22 |
| Example | 118 | | | 119 | | | 120 | | |
| C (μm) | 1 | 0.1 | 0.01 | 1 | 0.1 | 0.01 | 1 | 0.1 | 0.01 |
| Inh. (%) | 96 | 82 | 25 | 99 | 86 | 24 | 98 | 80 | 16 |
| Example | 121 | | | 122 | | | 123 | | |
| C (μm) | 1 | | | 1 | 0.1 | 0.01 | 1 | 0.1 | 0.01 |
| Inh. (%) | 15 | | 91 | 58 | 20 | | 97 | 87 | 43 |
| Example | 124 | | | 125 | | | 126 | | |
| C (μm) | 1 | 0.1 | 0.01 | 1 | 0.1 | 0.01 | 1 | | |
| Inh. (%) | 92 | 62 | 18 | 95 | 74 | 18 | 89 | | |
| Example | 127 | | | 128 | | | 129 | | |
| C (μm) | 1 | | 1 | 0.1 | 0.01 | | 1 | 0.1 | 0.01 |
| Inh. (%) | 88 | | 89 | 61 | 8 | | 93 | 73 | 26 |
| Example | 130 | | | 131 | | | 133 | | |
| C (μm) | 1 | | 1 | 0.1 | 0.01 | | 1 | | |
| Inh. (%) | 93 | | 100 | 89 | 27 | | 95 | | |

TABLE 1-continued

The inhibitory effect of 6-(2-chlorophenyl)-2-((4-(4-methylpiperazin-1-yl)phenyl)amino)-8,9-dihydroimidazo[1,2-a]pyrimido[5,4-e]pyrimidin-5(6H)-one and analogs on the enzyme activity of Wee1 kinase

| Example | C (μM) | Inh. (%) | C (μM) | Inh. (%) | C (μM) | Inh. (%) |
|---|---|---|---|---|---|---|
| 136 | 1 / 0.1 / 0.01 | 94 / 75 / 36 | | | | |
| 137 | 1 / 0.1 / 0.01 | 96 / 78 / 20 | | | | |
| 138 | 1 / 0.1 / 0.01 | 96 / 77 / 22 | | | | |
| 139 | 1 / 0.1 / 0.01 | 95 / 81 / 31 | | | | |
| 140 | 1 / 0.1 / 0.01 | 98 / 82 / 32 | | | | |
| 142 | 1 / 0.1 / 0.01 | 95 / 75 / 22 | | | | |
| 143 | 1 / 0.1 / 0.01 | 99 / 75 / 13 | | | | |
| 144 | 1 / 0.1 / 0.01 | 97 / 76 / 19 | | | | |
| 145 | 1 / 0.1 / 0.01 | 97 / 72 / 21 | | | | |
| 146 | 1 / 0.1 / 0.01 | 95 / 85 / 9 | | | | |
| 147 | 1 / 0.1 / 0.01 | 96 / 86 / 42 | | | | |
| 148 | 1 / 0.1 / 0.01 | 94 / 90 / 40 | | | | |
| 149 | 1 / 0.1 / 0.01 | 94 / 72 / 22 | | | | |
| 150 | 1 / 0.1 / 0.01 | 93 / 81 / 20 | | | | |
| 151 | 1 / 0.1 / 0.01 | 97 / 98 / 42 | | | | |
| 152 | 1 | 88 | | | | |
| 153 | 1 / 0.1 / 0.01 | 94 / 84 / 30 | | | | |
| 154 | 1 / 0.1 / 0.01 | 96 / 72 / 25 | | | | |
| 155 | 1 / 0.1 / 0.01 | 94 / 66 / 16 | | | | |
| 156 | 1 / 0.1 / 0.01 | 96 / 81 / 19 | | | | |
| 157 | 1 | 91 | | | | |
| 158 | 1 / 0.1 / 0.01 | 95 / 84 / 27 | | | | |
| 160 | 1 / 0.1 / 0.01 | 98 / 85 / 31 | | | | |
| 161 | 1 / 0.1 / 0.01 | 97 / 72 / 27 | | | | |
| 162 | 1 / 0.1 / 0.01 | 98 / 86 / 22 | | | | |
| 163 | 1 / 0.1 / 0.01 | 99 / 87 / 25 | | | | |
| 164 | 1 / 0.1 / 0.01 | 97 / 68 / 17 | | | | |
| 165 | 1 | 92 | | | | |
| 166 | 1 / 0.1 / 0.01 | 98 / 86 / 28 | | | | |
| 167 | 1 / 0.1 / 0.01 | 98 / 82 / 21 | | | | |
| 168 | 1 | 89 | | | | |
| 169 | 1 / 0.1 / 0.01 | 93 / 73 / 16 | | | | |
| 171 | 1 / 0.1 / 0.01 | 95 / 59 / 16 | | | | |
| 172 | 1 / 0.1 / 0.01 | 91 / 60 / 12 | | | | |
| 173 | 1 / 0.1 / 0.01 | 94 / 71 / 26 | | | | |
| 174 | 1 / 0.1 / 0.01 | 94 / 83 / 30 | | | | |
| 175 | 1 | 95 | | | | |
| 176 | 1 | 96 | | | | |
| 178 | 1 | 94 | | | | |
| 179 | 1 | 95 | | | | |
| 180 | 1 | 96 | | | | |
| 181 | 1 | 96 | | | | |
| 182 | 1 | 94 | | | | |
| 183 | 1 | 95 | | | | |
| AZD1775 | 10 | 97 | | | | |

In summary, as measure by Wee1 kinase (h) detection, 6-(2-chlorophenyl)-2-((4-(4-methylpiperazin-1-yl)phenyl)amino)-8,9-dihydroimidazo[1,2-a]pyrimido[5,4-e]pyrimidin-5(6H)-one (Example 1) and analogs had good inhibitory effect on the activity of Wee1 kinase. The inhibitory rates on Wee1 enzyme activity of compounds of Examples 1 and 2 were 9600 and 950% at the concentration of 10 iM, similar to that of reference compound AZD1775. The inhibitory rate on Wee1 enzyme activity of compound of Example 4 reached 51% at 0.01 μM, indicating that the compound of Example 4 had a high inhibitory activity on Wee1 kinase.

Example 188

Determination of Wee1 Dissociation Constant ($K_d$)

The Wee1 dissociation constants ($K_d$) which measures the affinity of tested compound to Wee 1 have been determined in the KINOMEscan™ KdELECT Service at DiscoveRx. KINOMEscan™ assay is based on competitive binding test. The affinity index $K_d$ for Wee1 is calculated by qPCR measurement of the compounds that compete with the immobilized ligand and bind to the enzyme activity center.

Wee1 kinase-tagged T7 phage strains were prepared in an *E. coli* BL21 strain. *E. coli* was grown to log-phase and infected with T7 phage and incubated with shaking at 32° C. until lysis. The lysates were centrifuged and filtered to remove cell debris. A partial length construct of human Wee1 (amino acids M291 to K575 based on reference sequence NP_003381.1) was expressed on the T7 phage coat. A short DNA sequence, embedded within the T7 phage genome, was used as amplicon for detection via qPCR.

Streptavidin-coated magnetic beads (Dynal M280) were treated with a biotinylated small molecule ligand for 30 minutes at room temperature to generate affinity resins for the binding assays. The liganded resins were blocked with excess biotin and fully washed with blocking buffer (SeaBlock (Pierce), 1% BSA, 0.05% Tween 20, 1 mM DTT) to remove unbound ligand and to reduce nonspecific binding.

The binding reaction was assembled by combining 16 μl of phage lysate, 3.8 μl liganded affinity resins, and 0.18 μl test compound (PBS/0.05% Tween 20/10 mM DTT/0.1% BSA/2 μg/ml sonicated salmon sperm DNA). Test compounds were prepared as 111× stocks in 100% DMSO. Kas were determined using an 11-point 3-fold compound dilution series with three DMSO control points. The highest concentration of the test compound is 100,000 nM and the final concentration of DMSO was 0.9%. All reactions performed in polypropylene 384-well plates. Each was a final volume of 0.02 mL. Assays were incubated with shaking for 1 hour at room temperature. Then the resins were collected and washed with wash buffer (1x PBS, 0.05% Tween 20) to remove displaced kinase and test compound. The washed resins were resuspended in elution buffer (1x PBS, 0.05% Tween 20, 0.5 µM non-biotinylated affinity ligand) and incubated at room temperature with shaking for 30 minutes. The kinase concentration in the eluates was measured by qPCR. qPCR reactions were assembled by adding 2.5 µL of kinase eluate to 7.5 µL of qPCR master mix containing 0.15 µM amplicon primers and 0.15 µM amplicon probe. The qPCR protocol consisted of a 10 minute hot start at 95° C., followed by 35 cycles of 95° C. for 15 seconds, 60° C. for 1 minute. Each concentration was repeated twice in the experiment.

The constants ($K_{dS}$) were calculated with a standard dose-response curve using the Hill equation:

$$\text{Response} = \text{Background} + \frac{(\text{Signal} - \text{Background})}{\left(1 + \left(\frac{Kd^{HillSlope}}{Dose^{HillSlope}}\right)\right)}$$

The Hill Slope was set to −1. Curves were fitted using a non-linear least square fit with the Levenberg-Marquardt algorithm (Levenberg, K., Q. Appl. Math. 2, 164-168 (1944)).

The values of $K_d$ by calculation show the inhibitory effect of 6-(2-chlorophenyl)-2-((4-(4-methylpiperazin-1-yl)phenyl)amino)-8,9-dihydroimidazo[1,2-a]pyrimido[5,4-e]pyrimidin-5(6H)-one and analogs on the enzyme activity of Wee1 kinase, summarized in Table 2.

TABLE 2

The inhibitory effect of 6-(2-chlorophenyl)-2-((4-(4-methylpiperazin-1-yl)phenyl)-8,9-dihydroimidazo[1,2-a]pyrimido[5,4-e]pyrimidin-5(6H)-one and analogs on the enzyme activity of Wee1 kinase (Kd)

| Example | 1 | 2 |
|---|---|---|
| $K_d$ (nM) | 250 | 34 |

In summary, as measured by the determination of $K_d$, 6-(2-chlorophenyl)-2-((4-(4-methylpiperazin-1-yl)phenyl)amino)-8,9-dihydroimidazo[1,2-a]pyrimido[5,4-e]pyrimidin-5(6H)-one (Example 1) and its analogs have shown good inhibitory effect on the enzyme activity of Wee1 kinase.

Example 189

Determination of the cell growth inhibiting activity of 6-(2-chlorophenyl)-2-((4-(4-methylpiperazin-1-yl)phenyl)amino)-8,9-dihydroimidazo[1,2-a]pyrimido[5,4-e]pyrimidin-5(6H)-one and analogs on LoVo cells using a MTT based cell viability assay The thawed LoVo cells were cultured and passaged to the third generation, and the growth state was good and the confluence was about 90%, which began to be used in the experiment. The LoVo cells were digested with trypsin, centrifuged at 800 rpm for 5 min, the supernatant was discarded, resuspended with fresh culture medium, and counted. 6000 Cells are seeded to each well of a 96-well plate. The cells are incubated at 37° C. in a 5% $CO_2$ cell culture incubator overnight. The tested sample (including the tested compound and the reference compound AZD1775) was diluted continuously to 8 concentrations (the last concentration was negative control of DMSO) with a 1:3 and 1:10 dilution in DMSO respectively: 10 µM, 3.3 µM, 1 µM, 0.33 µM, 0.1 µM, 0.033 µM, 0.01 µM, 0 µM (the final concentration of DMSO was 1%). 5 µL of each concentration was added to 120 µL of culture medium (25 times diluted), and the mixture was shaken well. The overnight cells were taken and the culture medium was removed, 195 µL of fresh culture medium was added to each well, and 5 µL of diluted culture medium containing the corresponding concentration of the tested sample was added respectively, and the culture plate was then placed in the 5% $CO_2$ cell culture incubator at 37° C. for 3 d. After removing the original solution and adding 100 µL of fresh serum-free DMEM culture medium containing MTT (0.5 mg/mL) per well, the culture was continued. The original solution was removed after 4 hrs and 100 µl DMSO was added to each well. The 96-well cell culture plates were shaken away from light for 10 min and readed in a multifunctional reader at 552/630/690 nm to give absorption values (OD values). The data were analyzed using a commercial graphic software (Graph Pad Prism 5.0) and the inhibitory activity of the compound on cell proliferation was plotted in terms of cell survival and compound concentration. The $IC_{50}$ values were fitted by the S-shaped dose-response curve equation as follows: Y=100/(1+10^(Log C-Log $IC_{50}$)), where C was the concentration of testing compounds.

The inhibitory effect of compounds on the LoVo cell growth is expressed as $IC_{50}$ values and listed in Table 3.

TABLE 3

Growth inhibition of LoVo cells by 6-(2-chlorophenyl)-2-((4-(4-methylpiperazin-1-yl)phenyl)amino)-8,9-dihydroimidazo[1,2-a]pyrimido[5,4-e]pyrimidin-5(6H)-one and analogs

| Example | 1 | 2 | 3 | 4 | 5 | 6 |
|---|---|---|---|---|---|---|
| $IC_{50}$ (µm) | 3.575 | 0.4249 | >100 | 0.1691 | 0.4307 | 0.3393 |
| Example | 7 | 8 | 9 | 10 | 11 | 12 |
| $IC_{50}$ (µm) | 1.432 | 0.2018 | 0.1261 | 0.0887 | 0.1006 | 0.2186 |
| Example | 13 | 14 | 15 | 16 | 17 | 18 |
| $IC_{50}$ (µm) | 0.07671 | 0.1491 | 1.728 | 4.755 | 0.2903 | >1 |
| Example | 19 | 20 | 21 | 22 | 23 | 27 |
| $IC_{50}$ (µm) | >100 | >100 | 2.133 | >100 | >3 | >100 |
| Example | 28 | 32 | 33 | 34 | 35 | 36 |
| $IC_{50}$ (µm) | >1 | 0.8361 | >100 | 0.3488 | 0.2615 | >100 |
| Example | 37 | 38 | 39 | 40 | 41 | 42 |
| $IC_{50}$ (µm) | >100 | >100 | >100 | >100 | >100 | >100 |
| Example | 43 | 44 | 45 | 46 | 47 | 48 |
| $IC_{50}$ (µm) | >100 | 0.0371 | 1.175 | 0.0261 | 0.0305 | 0.1174 |
| Example | 49 | 50 | 51 | 52 | 53 | 54 |
| $IC_{50}$ (µm) | 0.0969 | 0.05893 | 0.1048 | 0.0874 | 0.0855 | 0.1547 |

TABLE 3-continued

Growth inhibition of LoVo cells by 6-(2-chlorophenyl)-2-((4-(4-methylpiperazin-1-yl)phenyl)
amino)-8,9-dihydroimidazo[1,2-a]pyrimido[5,4-e]pyrimidin-5(6H)-one and analogs

| Example | 55 | 56 | 57 | 58 | 59 | 60 |
|---|---|---|---|---|---|---|
| $IC_{50}$ (μm) | >100 | 0.0470 | 13.55 | 0.0900 | >100 | 0.1585 |
| Example | 61 | 62 | 63 | 64 | 65 | 66 |
| $IC_{50}$ (μm) | 0.7569 | 0.1935 | 0.0768 | 0.0965 | 0.1025 | >100 |
| Example | 67 | 68 | 69 | 70 | 71 | 72 |
| $IC_{50}$ (μm) | >100 | >100 | 0.1048 | 0.1238 | 0.0443 | 0.0592 |
| Example | 73 | 74 | 75 | 76 | 77 | 78 |
| $IC_{50}$ (μm) | 0.1938 | 0.1816 | 0.0402 | 0.0488 | 0.0524 | 0.0414 |
| Example | 79 | 80 | 81 | 82 | 83 | 84 |
| $IC_{50}$ (μm) | >100 | 0.5393 | 0.1354 | 0.9464 | 2.899 | 3.058 |
| Example | 85 | 86 | 87 | 88 | 89 | 90 |
| $IC_{50}$ (μm) | >100 | >100 | >100 | >100 | 0.2200 | 1.308 |
| Example | 91 | 92 | 93 | 94 | 95 | 96 |
| $IC_{50}$ (μm) | 0.1854 | >100 | >100 | 1.906 | 1.884 | >100 |
| Example | 97 | 98 | 99 | 100 | 101 | 102 |
| $IC_{50}$ (μm) | >100 | >100 | >100 | 0.1725 | 0.0954 | >100 |
| Example | 103 | 104 | 105 | 106 | 107 | 108 |
| $IC_{50}$ (μm) | 0.6776 | 0.4601 | 0.3727 | 0.3301 | 0.3605 | 1.502/ |
| Example | 109 | 110 | 111 | 112 | 113 | 114 |
| $IC_{50}$ (μm) | 1.150 | 0.4715 | 0.8349 | 0.3926 | 0.4827 | 0.1049 |
| Example | 115 | 116 | 117 | 118 | 119 | 120 |
| $IC_{50}$ (μm) | 0.2651 | 0.1232 | 0.0662 | 0.0811 | 0.0543 | 0.0359 |
| Example | 121 | 122 | 123 | 124 | 125 | 126 |
| $IC_{50}$ (μm) | >100 | 0.0518 | 0.0391 | 0.0497 | 0.0264 | 0.0567 |
| Example | 127 | 128 | 129 | 130 | 131 | 133 |
| $IC_{50}$ (μm) | 0.0423 | 0.0688 | 0.0703 | 0.6240 | 0.1873 | 0.1651 |
| Example | 136 | 137 | 138 | 139 | 140 | 141 |
| $IC_{50}$ (μm) | 0.2139 | 0.1136 | 0.1986 | 0.0456 | 0.0582 | 0.03732 |
| Example | 142 | 143 | 144 | 145 | 146 | 147 |
| $IC_{50}$ (μm) | 0.0514 | 0.0206 | 0.0615 | 0.0849 | 0.0833 | 0.0911 |
| Example | 148 | 149 | 150 | 151 | 152 | 153 |
| $IC_{50}$ (μm) | 0.0398 | 0.0594 | 0.1158 | 0.0308 | 0.1387 | 0.0563 |
| Example | 154 | 155 | 156 | 157 | 158 | 159 |
| $IC_{50}$ (μm) | 0.0633 | 0.0741 | 0.0627 | 0.0386 | 0.0585 | 0.05221 |
| Example | 160 | 161 | 162 | 163 | 164 | 165 |
| $IC_{50}$ (μm) | 0.0273 | 0.0933 | 0.0652 | 0.0625 | 0.1010 | 0.0241 |
| Example | 166 | 167 | 168 | 169 | 170 | 171 |
| $IC_{50}$ (μm) | 0.0555 | 0.0627 | 0.2956 | 0.1649 | 0.07690 | 0.2281 |
| Example | 172 | 173 | 174 | 175 | 176 | 177 |
| $IC_{50}$ (μm) | 0.1170 | 0.0992 | 0.1357 | 0.1920 | 0.0736 | 0.05948 |
| Example | 178 | 179 | 180 | 181 | 182 | 183 |
| $IC_{50}$ (μm) | 0.2806 | 2.862 | 2.383 | 0.1418 | 0.2426 | 0.7754 |
| Example | 184 | 186 | AZD1775 | | | |
| $IC_{50}$ (μm) | 1.489 | 0.04235 | 0.3889 | | | |

In summary, as measured by the determination of MTT method, 6-(2-chlorophenyl)-2-((4-(4-methylpiperazin-1-yl)phenyl)amino)-8,9-dihydroimidazo[1,2-a] pyrimido[5,4-e]pyrimidin-5(6H)-one (Example 1) and its analogs have shown inhibitory effect on the growth of LoVo cells. In several of these embodiments, such as embodiment 75, the compound has a stronger inhibitory effect on the growth of LoVo cells than AZD1775.

Example 190

Determination of the cell growth inhibiting activity of 6-(2-chlorophenyl)-2-((4-(4-methylpiperazin-1-yl)phenyl)amino)-8,9-dihydroimidazo[1,2-a]pyrimido[5,4-e]pyrimidin-5(6H)-one and analogs on NCI-H1299 cells using a MTT based cell viability assay The thawed NCI-H1299 cells were cultured and passaged to the third generation, and the growth state was good and the confluence was about 90%, which began to be used in the experiment. The NCI-H1299 cells were digested with trypsin, centrifuged at 800 rpm for 5 min, the supernatant was discarded, resuspended with fresh culture group, and counted. 1000 Cells are seeded to each well of a 96-well plate. The cells are incubated at 37° C. in a 5% $CO_2$ cell culture incubator overnight. The tested sample (including the tested compound and the reference compound AZD1775) was diluted continuously to 8 concentrations (the last concentration was negative control of DMSO) with a 1:3 and 1:10 dilution in DMSO respectively: 10 μM, 3.3 μM, 1 μM, 0.33 μM, 0.1 μM, 0.033 μM, 0.01 μM, 0 μM (the final concentration of DMSO was 1‰). 5 μL of each concentration was added to 120 μL of culture medium (25 times diluted), and the mixture was shaken well. The overnight cells were taken and the culture medium was removed, 195 μL of fresh culture medium was added to each well, and 5 μL of diluted culture medium containing the corresponding concentration of the tested sample was added respectively, and the culture plate was then placed in the 5% $CO_2$ cell culture incubator at 37° C. for 3 d. After removing the original solution and adding 100 μL of fresh serum-free DMEM culture medium containing MTT (0.5 mg/mL) per well, the culture was continued. The original solution was removed after 4 hrs and 100 μl DMSO was added to each well. The 96-well cell culture plates were shaken away from light for 10 min and read in a multifunctional reader at 552/630/690 nm to give absorption values (OD values). The data were analyzed using a commercial graphic software (Graph Pad Prism 5.0) and the inhibitory activity of the compound on cell proliferation was plotted in terms of cell survival and compound concentration. The $IC_{50}$ values were fitted by the S-shaped dose-response curve equation as follows: $Y=100/(1+10^{(Log\ C - Log\ IC_{50})})$, where C was the concentration of testing compounds.

The inhibitory effect of compounds on the NCI-H1299 cell growth is expressed as IC$_{50}$ values and listed in Table 4.

TABLE 4

Growth inhibition of NCI-H1299 cells by 6-(2-chlorophenyl)-2-((4-(4-methylpiperazin-1-yl)phenyl)amino)-8,9-dihydroimidazo[1,2-a]pyrimido[5,4-e]pyrimidin-5(6H)-one and analogs (IC$_{50}$)

| Example | 1 | 2 | 3 | 4 | 5 | 6 |
|---|---|---|---|---|---|---|
| IC$_{50}$ (μm) | 1.59 | 0.7817 | >10 | 0.2036 | 0.9410 | 0.4611 |
| Example | 7 | 8 | 9 | 10 | 11 | 12 |
| IC$_{50}$ (μm) | 1.263 | 0.1593 | 0.1827 | 0.1718 | 0.7049 | 0.2318 |
| Example | 13 | 14 | 15 | 16 | 17 | 18 |
| IC$_{50}$ (μm) | 0.1014 | 0.0987 | 0.9664 | 0.6170 | 0.4468 | >10 |
| Example | 19 | 20 | 21 | 22 | 23 | 27 |
| IC$_{50}$ (μm) | >10 | >10 | 3.302 | >10 | >10 | >10 |
| Example | 28 | 32 | 33 | 34 | 35 | 36 |
| IC$_{50}$ (μm) | >3 | >10 | >10 | 0.4679 | 0.2867 | >10 |
| Example | 37 | 38 | 39 | 40 | 41 | 42 |
| IC$_{50}$ (μm) | >10 | >10 | >10 | >10 | >10 | >10 |
| Example | 43 | 44 | 45 | 46 | 47 | 48 |
| IC$_{50}$ (μm) | >10 | 0.5970 | 0.6158 | 0.5282 | 0.3300 | 1.122 |
| Example | 49 | 50 | 51 | 52 | 53 | 54 |
| IC$_{50}$ (μm) | 0.5434 | 0.2292 | 0.1651 | 0.1273 | 0.1448 | 1.533 |
| Example | 55 | 56 | 57 | 58 | 59 | 60 |
| IC$_{50}$ (μm) | >10 | 0.3177 | >10 | 0.4265 | >10 | 0.9918 |
| Example | 61 | 62 | 63 | 64 | 65 | 66 |
| IC$_{50}$ (μm) | 1.229 | 0.9249 | 0.3596 | 0.1774 | 0.4045 | >10 |
| Example | 67 | 68 | 69 | 70 | 71 | 72 |
| IC$_{50}$ (μm) | >10 | >10 | 0.4261 | 0.4477 | 0.6032 | 0.3282 |
| Example | 73 | 74 | 75 | 76 | 77 | 78 |
| IC$_{50}$ (μm) | 1.433 | 0.7080 | 0.1614 | 0.1976 | 0.2168 | 0.1492 |
| Example | 79 | 80 | 81 | 82 | 83 | 84 |
| IC$_{50}$ (μm) | >10 | 0.9778 | 0.3099 | 1.198 | 1.435 | 0.8364 |
| Example | 85 | 86 | 87 | 88 | 89 | 90 |
| IC$_{50}$ (μm) | >10 | >10 | >10 | >3 | 0.9571 | >10 |
| Example | 91 | 92 | 93 | 94 | 95 | 96 |
| IC$_{50}$ (μm) | 2.359 | >10 | >10 | 2.394 | 2.132 | >10 |
| Example | 97 | 98 | 99 | 100 | 101 | 102 |
| IC$_{50}$ (μm) | >10 | >10 | >10 | 0.5322 | 0.2142 | >10 |
| Example | 103 | 104 | 105 | 106 | 107 | 108 |
| IC$_{50}$ (μm) | 1.049 | 1.050 | 0.9111 | 0.8351 | 0.7944 | 0.8991 |
| Example | 109 | 110 | 111 | 112 | 113 | 114 |
| IC$_{50}$ (μm) | 0.8844 | 0.5993 | 0.9132 | 0.4811 | 0.6715 | 0.2329 |
| Example | 115 | 116 | 117 | 118 | 119 | 120 |
| IC$_{50}$ (μm) | 0.3813 | 0.2650 | 0.1026 | 0.0964 | 0.0923 | 0.0593 |
| Example | 121 | 122 | 123 | 124 | 125 | 126 |
| IC$_{50}$ (μm) | >10 | 0.3345 | 0.2184 | 0.1384 | 0.0929 | 0.0670 |
| Example | 127 | 128 | 129 | 130 | 131 | 133 |
| IC$_{50}$ (μm) | 0.0965 | 0.3060 | 0.0782 | 0.2429 | 0.0588 | 0.0460 |
| Example | 136 | 137 | 138 | 139 | 140 | 141 |
| IC$_{50}$ (μm) | 0.3103 | 0.1221 | 0.1702 | 0.0859 | 0.0929 | 0.04285 |
| Example | 142 | 143 | 144 | 145 | 146 | 147 |
| IC$_{50}$ (μm) | 0.1093 | 0.0583 | 0.1400 | 0.2193 | 0.2505 | 0.2093 |
| Example | 148 | 149 | 150 | 151 | 152 | 153 |
| IC$_{50}$ (μm) | 0.1226 | 0.1127 | 0.3469 | 0.1746 | 1.947 | 0.2352 |
| Example | 154 | 155 | 156 | 157 | 158 | 159 |
| IC$_{50}$ (μm) | 0.1740 | 0.1089 | 0.1500 | 0.2222 | 0.1054 | 0.05677 |
| Example | 160 | 161 | 162 | 163 | 164 | 165 |
| IC$_{50}$ (μm) | 0.0628 | 0.2173 | 0.2068 | 0.0978 | 0.1590 | 0.0973 |
| Example | 166 | 167 | 168 | 169 | 170 | 171 |
| IC$_{50}$ (μm) | 0.0993 | 0.1067 | 0.5994 | 0.2738 | 0.08986 | 0.4424 |
| Example | 172 | 173 | 174 | 175 | 176 | 177 |
| IC$_{50}$ (μm) | 0.3624 | 0.2264 | 0.1518 | 0.2689 | 0.1260 | 0.08313 |
| Example | 178 | 179 | 180 | 181 | 182 | 183 |
| IC$_{50}$ (μm) | 0.3597 | 70.57 | 2.047 | 0.1869 | 0.5029 | 1.042 |
| Example | 184 | 186 | AZD1775 | | | |
| IC$_{50}$ (μm) | 0.8786 | 0.1543 | 0.2873 | | | |

In summary, as measured by the determination of MTT method, 6-(2-chlorophenyl)-2-((4-(4-methylpiperazin-1-yl)phenyl)amino)-8,9-dihydroimidazo[1,2-a]pyrimido[5,4-e]pyrimidin-5(6H)-one (Example 1) and its analogs have shown inhibitory effect on the growth of NCI-H1299 cell. In several of these embodiments, such as embodiment 75, the compound has a stronger inhibitory effect on the growth of NCI-H1299 cells than AZD1775.

Having now fully described this disclosure, it will be understood by those of ordinary skill in the art that the same can be performed within a wide and equivalent range of conditions, formulations and other parameters without affecting the scope of the disclosure or any embodiment thereof. All patents, patent applications and publications cited herein are fully incorporated by reference herein in their entirety.

What is claimed is:

1. A method for treating Wee1-mediated disease in a subject in need thereof comprising administering to the subject an effective amount of a compound of Formula I, or a pharmaceutically acceptable salt thereof, or a pharmaceutical composition comprising the compound of Formula I or a pharmaceutically acceptable salt thereof, combined with an effective amount of at least one known anticancer agent, or a pharmaceutically acceptable salt of the said anticancer agent:

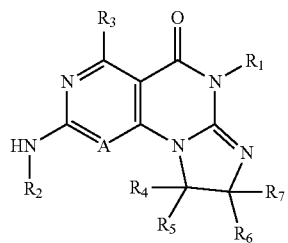

or a pharmaceutically acceptable salt thereof, wherein:
A is N or $CR_{15}$;
$R_1$ is H, optionally substituted $C_{1-8}$ alkyl, optionally substituted $C_{2-8}$ alkenyl, optionally substituted $C_{3-8}$ cycloalkyl, optionally substituted aryl, or optionally substituted heteroaryl;
$R_2$ is an optionally substituted heterocyclic group, optionally substituted aryl, or optionally substituted heteroaryl;
$R_3$, $R_4$, $R_5$, $R_6$, $R_7$, and $R_{15}$ are each independently H, halo, optionally substituted amino, optionally substituted alkoxy, optionally substituted $C_{1-10}$ alkyl, haloalkyl, alkenyl, alkynyl, hydroxyalkyl, aminoalkyl, carboxyalkyl, nitro, cyano, acylamido, hydroxy, thiol, acyloxy, azido, carboxy, ethylenedioxo, hydroxyacylamino or optionally substituted alkylthiol;
wherein the disease is a cancer selected from liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoide, head and neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, or prostatic carcinoma;
wherein said at least one known anticancer agent is selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxyuridine, fludarabine, nelarabine, ara-C, pralatrexate, pemetrexed, hydroxyurea, thioguanine, colchicine, vinblastine, vincristine, vinorelbine, paclitaxel, ixabepilone, cabazitaxel, docetaxel, campath, panitumumab, metazotuzumab, navuzumab, pymzumab, remoluzumab, bevacizumab, partuzumab, trastuzumab, cetuximab, obinutuzumab, olfamzumab, rituximab, alemtuzumab, tiemuzumab, toximab, bentuximab, daremuzumab, errotuzumab, T-DM1, ofatumumab, dinutuximab, blinatumomab, ipilimma, avastin, imatinib, gefitinib, erlotinib, osimertinib, afatinib, ceritinib, aletinib, crizotinib, lapatinib, sorafenib, sunitinib, nilotinib, dasatinib, pazopanib, temsirolimus, everolimus, vorinostat, romidepsin, panobinostat, belinostat, tamoxifen, letrozole, fulvestrant, mitoguazone, octreotide, retinoic acid, arsenic trioxide, zoledronic acid, bortezomib, carfilzomib, ixazomib, vismodegib, sonidegib, denosumab, thalidomide, lenalidomide, venetoclax, aldesleukin (recombinant human interleukin-2), sipueucel-T (prostate cancer therapeutic vaccine), palbociclib, olaparib, niraparib, rucaparib and talazoparib.

2. The method of claim 1, wherein A is N; $R_1$ and $R_2$ are each independently optionally substituted aryl; $R_3$, $R_4$, $R_5$, $R_6$, and $R_7$ are each independently H, halo or $C_{1-6}$ alkyl; and $R_{15}$ is H or $C_{1-6}$ alkyl.

3. The method of claim 1, wherein said compound has Formula II:

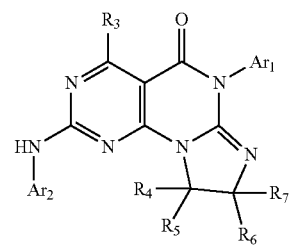

or pharmaceutically acceptable salts thereof, wherein:
$R_3$, $R_4$, $R_5$, $R_6$, and $R_7$ are independently H, halo, optionally substituted amino, optionally substituted alkoxy, optionally substituted $C_{1-10}$ alkyl, haloalkyl, alkenyl, alkynyl, hydroxyalkyl, aminoalkyl, carboxyalkyl, nitro, cyano, acylamido, hydroxy, thiol, acyloxy, azido, carboxy, ethylenedioxo, hydroxyacylamino or optionally substituted alkylthiol;
$Ar_1$ and $Ar_2$ are optionally substituted aryl or optionally substituted heteroaryl.

4. The method of claim 3, wherein $R_3$, $R_4$, $R_5$, $R_6$, and $R_7$ are H, and $Ar_1$ and $Ar_2$ are optionally substituted phenyl.

5. The method of claim 3, wherein $Ar_2$ is phenyl optionally substituted by one, two, three or four groups selected from the group consisting of: optionally substituted piperazinyl, optionally substituted piperazinyl-$C_1$-$C_4$ alkyl, optionally substituted piperidinyl, imidazolyl, optionally substituted 1,4-diazepan-1-yl, $C_1$-$C_6$ alkyl, $C_1$-$C_6$ acyl, optionally substituted morpholinyl, morpholinyl-$C_1$-$C_4$ alkyl, halo, halo $C_1$-$C_6$ alkyl, optionally substituted $C_1$-$C_6$ alkoxy, optionally substituted hydroxy $C_1$-$C_6$ alkyl, optionally substituted amino $C_1$-$C_6$ alkyl, optionally substituted piperidinylamino, optionally substituted $C_1$-$C_6$ alkyl amino, optionally substituted heterocyclic alkyl-O— and nitro; wherein the substituents on the optionally substituted group may be 1-4 groups selected from the following groups:

$C_1$-$C_6$ alkyl, $C_1$-$C_6$ acyl, halo, —$NR_aR_b$ and $C_1$-$C_6$ alkyl substituted by hydroxy, wherein $R_a$ and $R_b$ are each independently H and $C_1$-$C_6$ alkyl.
6. The method of claim 3, wherein
Ar$_1$ is selected from:
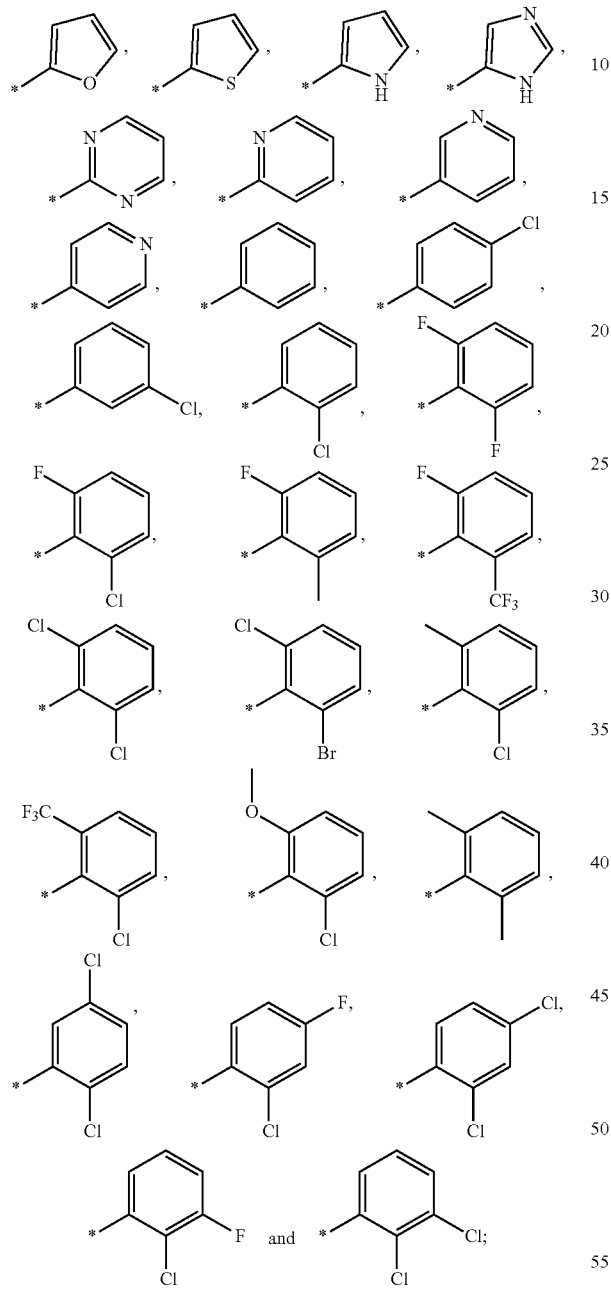
and
Ar$_2$ is selected from:
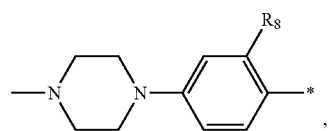
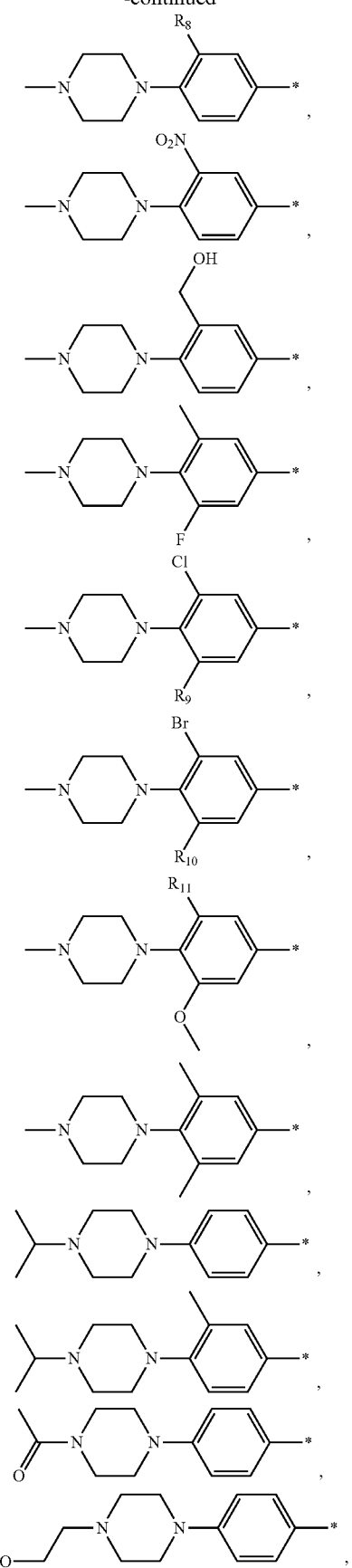

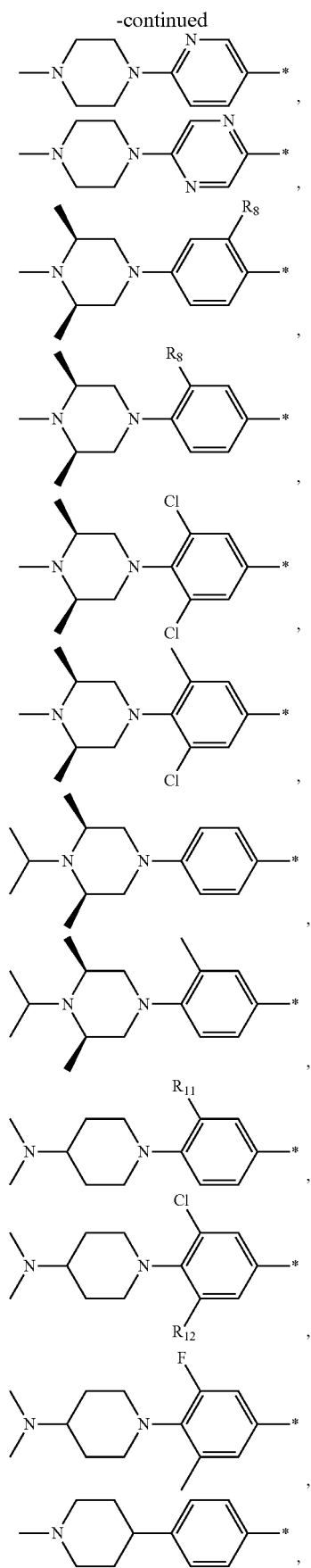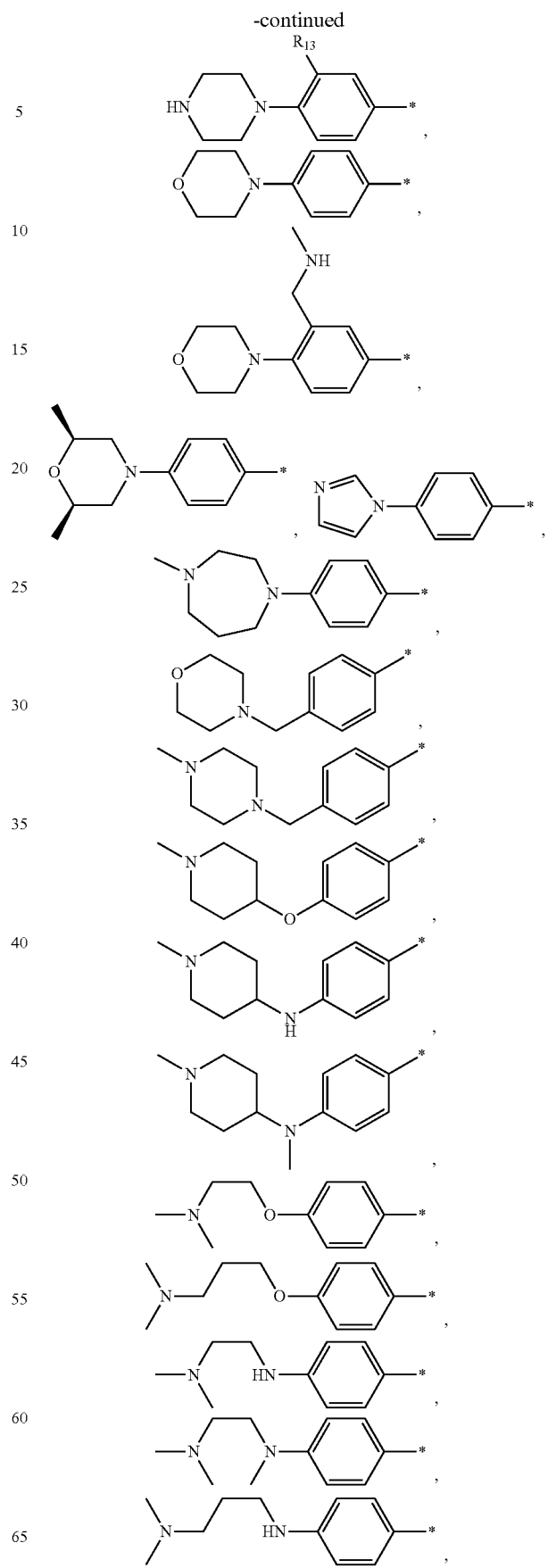

-continued

[chemical structures showing various substituents with $R_{14}$ groups and related moieties]

wherein:
- $R_8$ is independently H, halo, $C_1$-$C_4$ alkyl and halo $C_1$-$C_4$ alkyl;
- $R_9$ is independently halo, $C_1$-$C_4$ alkyl and halo $C_1$-$C_4$ alkyl;
- $R_{10}$ is independently H, halo, $C_1$-$C_4$ alkyl and $C_1$-$C_4$ alkoxy;
- $R_{11}$ is independently H, halo, and $C_1$-$C_4$ alkyl;
- $R_{12}$ is independently halo and $C_1$-$C_4$ alkoxy;
- $R_{13}$ is independently H, halo, $C_1$-$C_4$ alkyl, $C_1$-$C_4$ alkoxy, and $C_1$-$C_4$ alkyl substituted by hydroxy; and
- $R_{14}$ is independently H, halo, and $C_1$-$C_4$ alkyl.

7. The method of claim 1, wherein the compound has a structure represented by Formula III:

(III)

[chemical structure of Formula III showing fused ring system with $Ar_1$ and $Ar_2$ substituents]

wherein,
$Ar_1$ is selected from phenyl substituted by 1 or 2 substituents selected from halo, halo $C_1$-$C_6$ alkyl, $C_1$-$C_6$ alkoxy and $C_1$-$C_6$ alkyl; and $Ar_2$ is selected from:
substituted phenyl, of which the substituents are selected from: halo; nitro; $C_1$-$C_6$ alkyl, which is optionally substituted by one piperazinyl or one morpholinyl, 1-3 hydroxy, 1-5 halo, or —$NR_aR_b$, and the piperazinyl is optionally substituted by 1-3 substituents selected from $C_1$-$C_4$ alkyl; an oxy group, which is optionally substituted by $C_1$-$C_6$ alkyl or piperidinyl, and the piperidinyl is optionally substituted by 1-3 substituents selected from $C_1$-$C_4$ alkyl; amino, of which one hydrogen is replaced by piperidinyl, and the other hydrogen is not replaced or substituted by $C_1$-$C_4$ alkyl, or 1 or 2 hydrogens are substituted by $C_1$-$C_6$ alkyl, and the piperidinyl is optionally substituted by 1-3 substituents selected from $C_1$-$C_4$ alkyl, the $C_1$-$C_6$ alkyl is optionally substituted by —$NR_aR_b$; piperazinyl optionally substituted by 1-3 substituents selected from $C_1$-$C_6$ alkyl, hydroxy $C_1$-$C_6$ alkyl and $C_1$-$C_6$ acyl; piperidinyl optionally substituted by one substituent selected from —$NR_aR_b$; 1,4-diazepan-1-yl optionally substituted by 1-3 substituents selected from $C_1$-$C_6$ alkyl; imidazolyl; and morpholinyl optionally substituted by 1-3 $C_1$-$C_6$ alkyl;

tetrahydroisoquinolinyl optionally substituted by 1-3 substituents selected from $C_1$-$C_6$ alkyl and halo;

2',3'-dihydro-1'H-spiro[cyclopropane-1,4'-isoquinolin]-7'-yl optionally substituted by 1-3 substituents selected from $C_1$-$C_6$ alkyl, $C_1$-$C_6$ acyl and halo;

pyridyl optionally substituted by one piperazinyl which is optionally substituted by 1-3 $C_1$-$C_6$ alkyl;

pyrazinyl optionally substituted by one piperazinyl which is optionally substituted by 1-3 $C_1$-$C_6$ alkyl; and 4,5,6,7-tetrahydropyrazolo[1,5-a]pyrazin-2-yl optionally substituted by 1-3 $C_1$-$C_6$ alkyl;

wherein $R_a$ and $R_b$ are each independently H and $C_1$-$C_6$ alkyl.

8. The method of claim 7, wherein $Ar_1$ is

[six phenyl structures with various F, Cl, Br substituents]

and
$Ar_2$

[piperazinyl-phenyl structures with $R_8$, $R_9$, $R_{10}$ and other substituents]

-continued

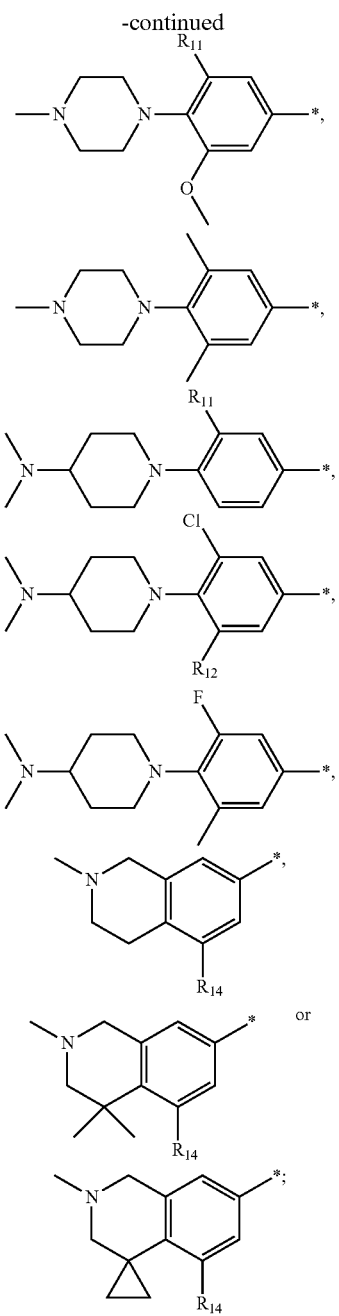

wherein:
$R_8$ is independently H, fluoro, chloro, bromo and methyl;
$R_9$ is independently H, chloro and methyl;
$R_{10}$ is independently H, chloro, methyl and methoxy;
$R_{11}$ is independently H, fluoro, chloro, bromo and methyl;
$R_{12}$ is independently H, chloro, methyl and methoxy;
$R_{14}$ is independently H, chloro and methyl.

9. The method of claim 1, wherein the compound is selected from the group consisting of:
6-(2-Chlorophenyl)-2-((4-(4-methylpiperazin-1-yl)phenyl)amino)-8,9-dihydroimidazo[1,2-a]pyrimido[5,4-e]pyrimidin-5(6H)-one;
6-(2-Chloro-6-fluorophenyl)-2-((4-(4-methylpiperazin-1-yl)phenyl)amino)-8,9-dihydroimidazo[1,2-a]pyrimido[5,4-e]pyrimidin-5(6H)-one;
4-(2-Chlorophenyl)-8-((4-(4-methylpiperazin-1-yl)phenyl)amino)-2,4-dihydroimidazo[1,2-a]pyrido[3,4-e]pyrimidin-5(1H)-one;
6-(2,6-Dichlorophenyl)-2-((4-(4-methylpiperazin-1-yl)phenyl)amino)-8,9-dihydroimidazo[1,2-a]pyrimido[5,4-e]pyrimidin-5(6H)-one;
6-(2-Chloro-6-methylphenyl)-2-((4-(4-methylpiperazin-1-yl)phenyl)amino)-8,9-dihydroimidazo[1,2-a]pyrimido[5,4-e]pyrimidin-5(6H)-one;
6-(2-Chloro-6-fluorophenyl)-2-((4-(4-isopropylpiperazin-1-yl)phenyl)amino)-8,9-dihydroimidazo[1,2-a]pyrimido[5,4-e]pyrimidin-5(6H)-one;
2-((4-(4-Acetylpiperazin-1-yl)phenyl)amino)-6-(2-chloro-6-fluorophenyl)-8,9-dihydroimidazo[1,2-a]pyrimido[5,4-e]pyrimidin-5(6H)-one;
6-(2-Chloro-6-fluorophenyl)-2-((2-methyl-1,2,3,4-tetrahydroisoquinolin-7-yl)amino)-8,9-dihydroimidazo[1,2-a]pyrimido[5,4-e]pyrimidin-5(6H)-one;
6-(2-Chloro-6-fluorophenyl)-2-((2,4,4-trimethyl-1,2,3,4-tetrahydroisoquinolin-7-yl)amino)-8,9-dihydroimidazo[1,2-a]pyrimido[5,4-e]pyrimidin-5(6H)-one;
6-(2-Chloro-6-fluorophenyl)-2-((2'-methyl-2',3'-dihydro-1'H-spiro(cyclopropane-1,4'-isoquinolin)-7'-yl)amino)-8,9-dihydroimidazo[1,2-a]pyrimido[5,4-e]pyrimidin-5(6H)-one;
6-(2-Chloro-6-fluorophenyl)-2-((2'-acetyl-2',3'-dihydro-1'H-spiro(cyclopropane-1,4'-isoquinolin)-7'-yl)amino)-8,9-dihydroimidazo[1,2-a]pyrimido[5,4-e]pyrimidin-5(6H)-one;
6-(2,6-Dichlorophenyl)-2-((2-methyl-1,2,3,4-tetrahydroisoquinolin-7-yl)amino)-8,9-dihydroimidazo[1,2-a]pyrimido[5,4-e]pyrimidin-5(6H)-one 5(6H)-one;
6-(2,6-Dichlorophenyl)-2-((2,4,4-trimethyl-1,2,3,4-tetrahydroisoquinolin-7-yl)amino)-8,9-dihydroimidazo[1,2-a]pyrimido[5,4-e]pyrimidin-5(6H)-one;
6-(2,6-Dichlorophenyl)-2-((2'-methyl-2',3'-dihydro-1'H-spiro(cyclopropane-1,4'-isoquinolin)-7'-yl)amino)-8,9-dihydroimidazo[1,2-a]pyrimido[5,4-e]pyrimidin-5(6H)-one;
6-(2,6-Dimethylphenyl)-2-((2-methyl-1,2,3,4-tetrahydroisoquinolin-7-yl)amino)-8,9-dihydroimidazo[1,2-a]pyrimido[5,4-e]pyrimidin-5(6H)-one;
6-(2,6-Dimethylphenyl)-2-((2,4,4-trimethyl-1,2,3,4-tetrahydroisoquinolin-7-yl)amino)-8,9-dihydroimidazo[1,2-a]pyrimido[5,4-e]pyrimidin-5(6H)-one;
6-(2,6-Dimethylphenyl)-2-((2'-methyl-2',3'-dihydro-1'H-spirocyclopropane-1,4'isoquinolin-7'-yl)amino)-8,9-dihydroimidazo[1,2-a]pyrimido[5,4-e]pyrimidin-5(6H)-one;
6-Isopropyl-2-((4-(4-methylpiperazin-1-yl)phenyl)amino)-8,9-dihydroimidazo[1,2-a]pyrimido[5,4-e]pyrimidin-5(6H)-one;
6-(Tert-butyl)-2-((4-(4-methylpiperazin-1-yl)phenyl)amino)-8,9-dihydroimidazo[1,2-a]pyrimido[5,4-e]pyrimidin-5(6H)-one;
6-Cyclopropyl-2-((4-(4-methylpiperazin-1-yl)phenyl)amino)-8,9-dihydroimidazo[1,2-a]pyrimido[5,4-e]pyrimidin-5(6H)-one;
6-Cyclohexyl-2-((4-(4-methylpiperazin-1-yl)phenyl)amino)-8,9-dihydroimidazo[1,2-a]pyrimido[5,4-e]pyrimidin-5(6H)-one;
6-Allyl-2-((4-(4-methylpiperazin-1-yl)phenyl)amino)-8,9-dihydroimidazo[1,2-a]pyrimido[5,4-e]pyrimidin-5(6H)-one;
2-((4-(4-Methylpiperazin-1-yl)phenyl)amino)-6-(thiophen-2-yl)-8,9-dihydroimidazo[1,2-a]pyrimido[5,4-e]pyrimidin-5(6l)-one;

6-(Furan-2-yl)-2-((4-(4-methylpiperazin-1-yl)phenyl)amino)-8,9-dihydroimidazo[1,2-a]pyrimido[5,4-e]pyrimidin-5(6H)-one;

2-((4-(4-Methylpiperazin-1-yl)phenyl)amino)-6-(1H-pyrrol-2-yl)-8,9-dihydroimidazo[1,2-a]pyrimido[5,4-e]pyrimidin-5(6H)-one;

6-(1H-Imidazol-5-yl)-2-((4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-8,8-dimethyl-2-((4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-9,9-dimethyl-2-((4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((4-((2S,6R)-2,6-dimethylmorpholino)phenyl)amino)-8,9-dihydroimidazo[1,2-a]pyrimido[5,4-e]pyrimidin-5(6H)-one;

6-(2-Chloro-6-fluorophenyl)-2-((4-(morpholinomethyl)phenyl)amino)-8,9-dihydroimidazo[1,2-a]pyrimido[5,4-e]pyrimidin-5(6H)-one;

6-(2-Chloro-6-fluorophenyl)-2-((4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((4-((3S,5R)-4-isopropyl-3,5-dimethylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((2-fluoro-4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((2-fluoro-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((2-chloro-4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((2-chloro-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((4-(4-methylpiperazin-1-yl)-2-(trifluoromethyl)phenyl)amino)-8,9-dihydroimidazo[1,2-a]pyrimido[5,4-e]pyrimidin-5(6H)-one;

6-(2-Chloro-6-fluorophenyl)-2-((2-trifluoromethyl-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((2-methyl-4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((2-methyl-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((3-fluoro-4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((3-fluoro-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((3-chloro-4-(4-methylpiperazin-1-yl)phenyl)amino)-8,9-dihydroimidazo[1,2-a]pyrimido[5,4-e]pyrimidin-5(6H)-one;

2-((3-Chloro-4-((3S,5R)-3,4,5-trimethylpiperazin-1-yl)phenyl)amino)-6-(2-chloro-6-fluorophenyl)-8,9-dihydroimidazo[1,2-a]pyrimido[5,4-e]pyrimidin-5(6H)-one;

6-(2-Chloro-6-fluorophenyl)-2-((4-(4-methylpiperazin-1-yl)-3-(trifluoromethyl)phenyl)amino)-8,9-dihydroimidazo[1,2-a]pyrimido[5,4-e]pyrimidin-5(6H)-one;

6-(2-Chloro-6-fluorophenyl)-2-((3-trifluoromethyl-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((3-methyl-4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((3-methyl-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((4-(4-isopropylpiperazin-1-yl)-3-methylphenyl)amino)-8,9-dihydroimidazo[1,2-a]pyrimido[5,4-e]pyrimidin-5(6H)-one;

6-(2-Chloro-6-fluorophenyl)-2-((4-((3S,5R)-4-isopropyl-3,5-dimethylpiperazin-1-yl)-3-methylphenyl)amino)-8,9-dihydroimidazo[1,2-a]pyrimido[5,4-e]pyrimidin-5(6H)-one;

6-(2-Chloro-6-fluorophenyl)-2-((3-methoxy-4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((4-(4-methylpiperazin-1-yl)-3-nitrophenyl)amino)-8,9-dihydroimidazo[1,2-a]pyrimido[5,4-e]pyrimidin-5(6H)-one;

6-(2-Chloro-6-fluorophenyl)-2-((3,5-dimethyl-4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((6-4-(4-methylpiperazin-1-yl)pyridin-3-yl)amino)-8,9-dihydroimidazo[1,2-a]pyrimido[5,4-e]pyrimidin-5(6H)-one;

6-(2-Chloro-6-fluorophenyl)-2-((2'-isopropyl-2',3'-dihydro-1'H-spiro(cyclopropane-1,4'-isoquinolin)-7'-yl)amino)-8,9-dihydroimidazo[1,2-a]pyrimido[5,4-e]pyrimidin-5(6H)-one;

6-(2-Chloro-6-fluorophenyl)-2-((5-methyl-4,5,6,7-tetrahydropyrazolo[1,5-a]pyrazine-2-ylamino)-8,9-dihydroimidazo[1,2-a]pyrimido[5,4-e]pyrimidin-5(6H)-one;

6-(2,6-Difluorophenyl)-2-((3-methyl-4-(4-methylpiperazin-1-yl)phenyl)amino)-8,9-dihydroimidazo[1,2-a]pyrimido[5,4-e]pyrimidin-5(6H)-one;

6-(2-Fluoro-6-(trifluoromethyl)phenyl)-2-((3-methyl-4-(4-methylpiperazin-1-yl)phenyl)amino)-8,9-dihydroimidazo[1,2-a]pyrimido[5,4-e]pyrimidin-5(6H)-one;

6-(2-Fluoro-6-methylphenyl)-2-((3-methyl-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((4-(4-isopropylpiperazin-1-yl)phenyl)amino)-8,9-dihydroimidazo[1,2-a]pyrimido[5,4-e]pyrimidin-5(6H)-one;

6-(2,6-Dichlorophenyl)-2-((4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2,6-Dichlorophenyl)-2-((4-((3S,5R)-4-isopropyl-3,5-dimethylpiperazin-1-yl)phenyl)amino)-8,9-dihydroimidazo[1,2-a]pyrimido[5,4-e]pyrimidin-5(6H)-one;

6-(2,6-Dichlorophenyl)-2-((2-fluoro-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2,6-Dichlorophenyl)-2-((2-chloro-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2,6-Dichlorophenyl)-2-((2-trifluoromethyl-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-fluoro-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-fluoro-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-chloro-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-chloro-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2,6-Dichlorophenyl)-2-((4-(4-methylpiperazin-1-yl)-3-(trifluoromethyl)phenyl)amino)-8,9-dihydroimidazo[1,2-a]pyrimido[5,4-e]pyrimidin-5(6H)-one;

6-(2,6-Dichlorophenyl)-2-((3-trifluoromethyl-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-methyl-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((4-(4-isopropylpiperazin-1-yl)-3-methylphenyl)amino)-8,9-dihydroimidazo[1,2-a]pyrimido[5,4-e]pyrimidin-5(6H)-one;

6-(2,6-Dichlorophenyl)-2-((3-methyl-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2,6-Dichlorophenyl)-2-((4-((3S,5R)-4-isopropyl-3,5-dimethylpiperazin-1-yl)-3-methylphenyl)amino)-8,9-dihydroimidazo[1,2-a]pyrimido[5,4-e]pyrimidin-5(6H)-one;

6-(2,6-Dichlorophenyl)-2-((5-methyl-4,5,6,7-tetrahydropyrazolo[1,5-a]pyrazine-2-yl)amino)-8,9-dihydroimidazo[1,2-a]pyrimido[5,4-e]pyrimidin-5(6H)-one;

6-(2-Chloro-6-(trifluoromethyl)phenyl)-2-((3-methyl-4-(4-methylpiperazin-1-yl)phenyl)amino)-8,9-dihydroimidazo[1,2-a]pyrimido[5,4-e]pyrimidin-5(6H)-one;

6-(2-Chloro-6-methylphenyl)-2-((3-methyl-4-(4-methylpiperazin-1-yl)phenyl)amino)-8,9-dihydroimidazo[1,2-a]pyrimido[5,4-e]pyrimidin-5(6H)-one;

6-(2-Chloro-6-methoxyphenyl)-2-((3-methyl-4-(4-methylpiperazin-1-yl)phenyl)amino)-8,9-dihydroimidazo[1,2-a]pyrimido[5,4-e]pyrimidin-5(6H)-one;

6-(2,6-Dimethylphenyl)-2-((4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(4-Chlorophenyl)-2-((4-(4-methylpiperazin-1-yl)phenyl)amino)-8,9-dihydroimidazo[1,2-a]pyrimido[5,4-e]pyrimidin-5(6H)-one;

6-(3-Chlorophenyl)-2-((4-(4-methylpiperazin-1-yl)phenyl)amino)-8,9-dihydroimidazo[1,2-a]pyrimido[5,4-e]pyrimidin-5(6H)-one;

6-(2,4-Dichlorophenyl)-2-((4-(4-methylpiperazin-1-yl)phenyl)amino)-8,9-dihydroimidazo[1,2-a]pyrimido[5,4-e]pyrimidin-5(6H)-one;

6-(2-Chloro-4-fluorophenyl)-2-((4-(4-methylpiperazin-1-yl)phenyl)amino)-8,9-dihydroimidazo[1,2-a]pyrimido[5,4-e]pyrimidin-5(6H)-one;

6-(2-Chloro-3-fluorophenyl)-2-((4-(4-methylpiperazin-1-yl)phenyl)amino)-8,9-dihydroimidazo[1,2-a]pyrimido[5,4-e]pyrimidin-5(6H)-one;

6-(2,5-Dichlorophenyl)-2-((4-(4-methylpiperazin-1-yl)phenyl)amino)-8,9-dihydroimidazo[1,2-a]pyrimido[5,4-e]pyrimidin-5(6H)-one;

6-(2,3-Dichlorophenyl)-2-((4-(4-methylpiperazin-1-yl)phenyl)amino)-8,9-dihydroimidazo[1,2-a]pyrimido[5,4-e]pyrimidin-5(6H)-one;

6-(Pyrimidin-2-yl)-2-((4-(4-methylpiperazin-1-yl)phenyl)amino)-8,9-dihydroimidazo[1,2-a]pyrimido[5,4-e]pyrimidin-5(6H)-one;

2-((4-(4-Methylpiperazin-1-yl)phenyl)amino)-8,9-dihydroimidazo[1,2-a]pyrimido[5,4-e]pyrimidin-5(6H)-one;

6-Cyclobutyl-2-((4-(4-methylpiperazin-1-yl)phenyl)amino)-8,9-dihydroimidazo[1,2-a]pyrimido[5,4-e]pyrimidin-5(6H)-one;

6-Cyclopentyl-2-((4-(4-methylpiperazin-1-yl)phenyl)amino)-8,9-dihydroimidazo[1,2-a]pyrimido[5,4-e]pyrimidin-5(6H)-one;

6-Phenyl-2-((4-(4-methylpiperazin-1-yl)phenyl)amino)-8,9-dihydroimidazo[1,2-a]pyrimido[5,4-e]pyrimidin-5(6H)-one;

6-(Pyridin-2-yl)-2-((4-(4-methylpiperazin-1-yl)phenyl)amino)-8,9-dihydroimidazo[1,2-a]pyrimido[5,4-e]pyrimidin-5(6H)-one;

6-(Pyridin-3-yl)-2-((4-(4-methylpiperazin-1-yl)phenyl)amino)-8,9-dihydroimidazo[1,2-a]pyrimido[5,4-e]pyrimidin-5(6H)-one;

6-(Pyridin-4-yl)-2-((4-(4-methylpiperazin-1-yl)phenyl)amino)-8,9-dihydroimidazo[1,2-a]pyrimido[5,4-e]pyrimidin-5(6H)-one;

6-(2,6-Difluorophenyl)-2-((3-chloro-4-(4-methylpiperazin-1-yl)phenyl)amino)-8,9-dihydroimidazo[1,2-a]pyrimido[5,4-e]pyrimidin-5(6H)-one;

6-(2,6-Difluorophenyl)-2-((3,5-dimethyl-4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((4-(1H-imidazol-1-yl)phenyl)amino)-8,9-dihydroimidazo[1,2-a]pyrimido[5,4-e]pyrimidin-5(6H)-one;

6-(2-Chloro-6-fluorophenyl)-2-((4-(4-methyl-1,4-diazepan-1-yl)phenyl)amino)-8,9-dihydroimidazo[1,2-a]pyrimido[5,4-e]pyrimidin-5(6H)-one;

6-(2-Chloro-6-fluorophenyl)-2-((4-((4-methylpiperazin-1-yl)methyl)phenyl)amino)-8,9-dihydroimidazo[1,2-a]pyrimido[5,4-e]pyrimidin-5(6H)-one;

6-(2-Chloro-6-fluorophenyl)-2-((4-(2-(dimethylamino)ethoxy)phenyl)amino)-8,9-dihydroimidazo[1,2-a]pyrimido[5,4-e]pyrimidin-5(6H)-one;

6-(2-Chloro-6-fluorophenyl)-2-((4-(3-(dimethylamino)propoxy)phenyl)amino)-8,9-dihydroimidazo[1,2-a]pyrimido[5,4-e]pyrimidin-5(6H)-one;

6-(2-Chloro-6-fluorophenyl)-2-((4-((1-methylpiperidin-4-yl)oxy)phenyl)amino)-8,9-dihydroimidazo[1,2-a]pyrimido[5,4-e]pyrimidin-5(6H)-one;

6-(2-Chloro-6-fluorophenyl)-2-((4-((2-(dimethylamino)ethyl)amino)phenyl)amino)-8,9-dihydroimidazo[1,2-a]pyrimido[5,4-e]pyrimidin-5(6H)-one;

6-(2-Chloro-6-fluorophenyl)-2-((4-((2-(dimethylamino)ethyl)(methyl)amino)phenyl)amino)-8,9-dihydroimidazo[1,2-a]pyrimido[5,4-e]pyrimidin-5(6H)-one;

6-(2-Chloro-6-fluorophenyl)-2-((4-((3-(dimethylamino)propyl)amino)phenyl)amino)-8,9-dihydroimidazo[1,2-a]pyrimido[5,4-e]pyrimidin-5(6H)-one;

6-(2-Chloro-6-fluorophenyl)-2-((4-((3-(dimethylamino)propyl)(methyl)amino)phenyl)amino)-8,9-dihydroimidazo[1,2-a]pyrimido[5,4-e]pyrimidin-5(6H)-one;

6-(2-Chloro-6-fluorophenyl)-2-((4-((1-methylpiperidin-4-yl)amino)phenyl)amino)-8,9-dihydroimidazo[1,2-a]pyrimido[5,4-e]pyrimidin-5(6H)-one;

6-(2-Chloro-6-fluorophenyl)-2-((4-(methyl(1-methylpiperidin-4-yl)amino)phenyl)amino)-8,9-dihydroimidazo[1,2-a]pyrimido[5,4-e]pyrimidin-5(6H)-one;

6-(2-Chloro-6-fluorophenyl)-2-((4-(1-methylpiperidin-4-yl)phenyl)amino)-8,9-dihydroimidazo[1,2-a]pyrimido[5,4-e]pyrimidin-5(6H)-one;

6-(2-Chloro-6-fluorophenyl)-2-((4-(4-(dimethylamino)piperidin-1-yl)phenyl)amino)-8,9-dihydroimidazo[1,2-a]pyrimido[5,4-e]pyrimidin-5(6H)-one;

6-(2-Chloro-6-fluorophenyl)-2-((4-(4-(dimethylamino)piperidin-1-yl)-3-fluorophenyl)amino)-8,9-dihydroimidazo[1,2-a]pyrimido[5,4-e]pyrimidin-5(6H)-one;

6-(2-Chloro-6-fluorophenyl)-2-((3-chloro-4-(4-(dimethylamino)piperidin-1-yl)phenyl)amino)-8,9-dihydroimidazo[1,2-a]pyrimido[5,4-e]pyrimidin-5(6H)-one;

6-(2-Chloro-6-fluorophenyl)-2-((3-bromo-4-(4-(dimethylamino)piperidin-1-yl)phenyl)amino)-8,9-dihydroimidazo[1,2-a]pyrimido[5,4-e]pyrimidin-5(6H)-one;

6-(2-Chloro-6-fluorophenyl)-2-((4-(4-(dimethylamino)piperidin-1-yl)-3-methylphenyl)amino)-8,9-dihydroimidazo[1,2-a]pyrimido[5,4-e]pyrimidin-5(6H)-one;

6-(2-Chloro-6-fluorophenyl)-2-((3-fluoro-5-methyl-4-(4-(dimethylamino)piperidin-1-yl)phenyl)amino)-8,9-dihydroimidazo[1,2-a]pyrimido[5,4-e]pyrimidin-5(6H)-one;

6-(2-Chloro-6-fluorophenyl)-2-((5-(4-methylpiperazin-1-yl)pyrazin-2-yl)amino)-8,9-dihydroimidazo[1,2-a]pyrimido[5,4-e]pyrimidin-5(6H)-one;

6-(2-Chloro-6-fluorophenyl)-2-((3,5-dichloro-4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((3-fluoro-5-methyl-4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((3-fluoro-5-methoxy-4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((3-chloro-5-methyl-4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((3-chloro-5-methoxy-4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((3-bromo-5-methoxy-4-(4-methylpiperazin-1-yl)phenyl)amino)-8,9-dihydroimidazo[1,2-a]pyrimido[5,4-e]pyrimidin-5(6H)-one;

6-(2-Chloro-6-fluorophenyl)-2-((3-methyl-4-(4-methylpiperazin-1-yl)-5-(trifluoromethyl)phenyl)amino)-8,9-dihydroimidazo[1,2-a]pyrimido[5,4-e]pyrimidin-5(6H)-one;

6-(2-Chloro-6-fluorophenyl)-2-((3-methoxy-5-methyl-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((5-chloro-2-methyl-1,2,3,4-tetrahydroisoquinolin-7-yl)amino)-8,9-dihydroimidazo[1,2-a]pyrimido[5,4-e]pyrimidin-5(6H)-one;

6-(2,6-Dichlorophenyl)-2-((2,5-dimethyl-1,2,3,4-tetrahydroisoquinolin-7-yl)amino)-8,9-dihydroimidazo[1,2-a]pyrimido[5,4-e]pyrimidin-5(6H)-one;

6-(2,6-Dichlorophenyl)-2-((5-chloro-2,4,4-trimethyl-1,2,3,4-tetrahydroisoquinolin-7-yl)amino)-8,9-dihydroimidazo[1,2-a]pyrimido[5,4-e]pyrimidin-5(6H)-one;

6-(2,6-Dichlorophenyl)-2-((2,4,4,5-tetramethyl-1,2,3,4-tetrahydroisoquinolin-7-yl)amino)-8,9-dihydroimidazo[1,2-a]pyrimido[5,4-e]pyrimidin-5(6H)-one;

6-(2,6-Dichlorophenyl)-2-((5'-chloro-2'-methyl-2',3'-dihydro-1'H-spiro(cyclopropane-1,4'-isoquinolin)-7'-yl)amino)-8,9-dihydroimidazo[1,2-a]pyrimido[5,4-e]pyrimidin-5(6H)-one;

6-(2,6-Dichlorophenyl)-2-((2',5'-dimethyl-2',3'-dihydro-1'H-spiro(cyclopropane-1,4'-isoquinolin)-7'-yl)amino)-8,9-dihydroimidazo[1,2-a]pyrimido[5,4-e]pyrimidin-5(6H)-one;

6-(2,6-Dichlorophenyl)-2-((3,5-dichloro-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-chloro-5-methyl-4-((3S,5R)-3,4,5-trimethylpiperazin-1-yl)phenyl)amino)-8,9-dihydroimidazo[1,2-a]pyrimido[5,4-e]pyrimidin-5(6H)-one;

6-(2,6-Dichlorophenyl)-2-((4-(4-(dimethylamino)piperidin-1-yl)phenyl)amino)-8,9-dihydroimidazo[1,2-a]pyrimido[5,4-e]pyrimidin-5(6H)-one;

6-(2,6-Dichlorophenyl)-2-((3-chloro-4-(4-(dimethylamino)piperidin-1-yl)phenyl)amino)-8,9-dihydroimidazo[1,2-a]pyrimido[5,4-e]pyrimidin-5(6H)-one;

6-(2,6-Dichlorophenyl)-2-((3-bromo-4-(4-(dimethylamino)piperidin-1-yl)phenyl)amino)-8,9-dihydroimidazo[1,2-a]pyrimido[5,4-e]pyrimidin-5(6H)-one;

6-(2,6-Dichlorophenyl)-2-((4-(4-(dimethylamino)piperidin-1-yl)-3-methylphenyl)amino)-8,9-dihydroimidazo[1,2-a]pyrimido[5,4-e]pyrimidin-5(6H)-one;

6-(2,6-Dichlorophenyl)-2-((3,5-dichloro-4-(4-(dimethylamino)piperidin-1-yl)phenyl)amino)-8,9-dihydroimidazo[1,2-a]pyrimido[5,4-e]pyrimidin-5(6H)-one;

6-(2,6-Dichlorophenyl)-2-((4-(4-(dimethylamino)piperidin-1-yl)-3-fluoro-5-methylphenyl)amino)-8,9-dihydroimidazo[1,2-a]pyrimido[5,4-e]pyrimidin-5(6H)-one;

6-(2,6-Dichlorophenyl)-2-((3-chloro-4-(4-(dimethylamino)piperidin-1-yl)-5-methoxyphenyl)amino)-8,9-dihydroimidazo[1,2-a]pyrimido[5,4-e]pyrimidin-5(6H)-one;

6-(2,6-Dichlorophenyl)-2-((3-bromo-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-methoxy-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-chloro-5-fluoro-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-fluoro-5-methyl-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-fluoro-5-methoxy-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3,5-dichloro-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-chloro-5-methyl-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-chloro-4-(4-methylpiperazin-1-yl)-5-(trifluoromethyl)phenyl)amino)-8,9-dihydroimidazo[1,2-a]pyrimido[5,4-e]pyrimidin-5(6H)-one;

6-(2,6-Dichlorophenyl)-2-((3-chloro-5-methoxy-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-bromo-5-fluoro-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-bromo-5-chloro-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-bromo-5-methyl-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-bromo-5-methoxy-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3,5-dimethyl-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((3-methoxy-5-methyl-4-(4-methylpiperazin-1-yl)phenyl)amino)-8,9-dihydroimidazo[1,2-a]pyrimido[5,4-e]pyrimidin-5(6H)-one;

6-(2-Bromo-6-chlorophenyl)-2-((4-(4-(dimethylamino)piperidin-1-yl)-3-fluoro-5-methylphenyl)amino)-8,9-dihydroimidazo[1,2-a]pyrimido[5,4-e]pyrimidin-5(6H)-one;

6-(2-Bromo-6-chlorophenyl)-2-((3-chloro-4-(4-methylpiperazin-1-yl)phenyl)amino)-8,9-dihydroimidazo[1,2-a]pyrimido[5,4-e]pyrimidin-5(6H)-one;

6-(2-Bromo-6-chlorophenyl)-2-((3-bromo-4-(4-methylpiperazin-1-yl)phenyl)amino)-8,9-dihydroimidazo[1,2-a]pyrimido[5,4-e]pyrimidin-5(6H)-one;

6-(2-Bromo-6-chlorophenyl)-2-((3-methyl-4-(4-methylpiperazin-1-yl)phenyl)amino)-8,9-dihydroimidazo[1,2-a]pyrimido[5,4-e]pyrimidin-5(6H)-one;

6-(2-Bromo-6-chlorophenyl)-2-((3,5-dichloro-4-(4-methylpiperazin-1-yl)phenyl)amino)-8,9-dihydroimidazo[1,2-a]pyrimido[5,4-e]pyrimidin-5(6H)-one;

6-(2-Bromo-6-chlorophenyl)-2-((3-fluoro-5-methyl-4-(4-methylpiperazin-1-yl)phenyl)amino)-8,9-dihydroimidazo[1,2-a]pyrimido[5,4-e]pyrimidin-5(6H)-one;

6-(2-Bromo-6-chlorophenyl)-2-((3-chloro-5-methyl-4-(4-methylpiperazin-1-yl)phenyl)amino)-8,9-dihydroimidazo[1,2-a]pyrimido[5,4-e]pyrimidin-5(6H)-one;

6-(2-Bromo-6-chlorophenyl)-2-((3-bromo-5-methyl-4-(4-methylpiperazin-1-yl)phenyl)amino)-8,9-dihydroimidazo[1,2-a]pyrimido[5,4-e]pyrimidin-5(6H)-one;

6-(2-Fluoro-6-methylphenyl)-2-((3-chloro-4-(4-methylpiperazin-1-yl)phenyl)amino)-8,9-dihydroimidazo[1,2-a]pyrimido[5,4-e]pyrimidin-5(6H)-one;

6-(2-Fluoro-6-methylphenyl)-2-((3,5-dimethyl-4-(4-methylpiperazin-1-yl)phenyl)amino)-8,9-dihydroimidazo[1,2-a]pyrimido[5,4-e]pyrimidin-5(6H)-one;

6-(2-Chloro-6-methylphenyl)-2-((4-(4-(dimethylamino)piperidin-1-yl)-3-fluoro-5-methylphenyl)amino)-8,9-dihydroimidazo[1,2-a]pyrimido[5,4-e]pyrimidin-5(6H)-one;

6-(2-Chloro-6-methylphenyl)-2-((3-chloro-4-(4-methylpiperazin-1-yl)phenyl)amino)-8,9-dihydroimidazo[1,2-a]pyrimido[5,4-e]pyrimidin-5(6H)-one;

6-(2-Chloro-6-methylphenyl)-2-((3,5-dichloro-4-(4-methylpiperazin-1-yl)phenyl)amino)-8,9-dihydroimidazo[1,2-a]pyrimido[5,4-e]pyrimidin-5(6H)-one;

6-(2-Chloro-6-methylphenyl)-2-((3-chloro-5-methyl-4-(4-methylpiperazin-1-yl)phenyl)amino)-8,9-dihydroimidazo[1,2-a]pyrimido[5,4-e]pyrimidin-5(6H)-one;

6-(2-Chloro-6-methylphenyl)-2-((3,5-dimethyl-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((4-(piperazin-1-yl)phenyl)amino)-8,9-dihydroimidazo[1,2-a]pyrimido[5,4-e]pyrimidin-5(6H)-one;

6-(2,6-Dichlorophenyl)-2-((3-chloro-4-(piperazin-1-yl)phenyl)amino)-8,9-dihydroimidazo[1,2-a]pyrimido[5,4-e]pyrimidin-5(6H)-one;

6-(2,6-Dichlorophenyl)-2-((3-methyl-4-(piperazin-1-yl)phenyl)amino)-8,9-dihydroimidazo[1,2-a]pyrimido[5,4-e]pyrimidin-5(6H)-one;

6-(2,6-Dichlorophenyl)-2-((3-methoxy-4-(piperazin-1-yl)phenyl)amino)-8,9-dihydroimidazo[1,2-a]pyrimido[5,4-e]pyrimidin-5(6H)-one;

6-(2-Chloro-6-fluorophenyl)-2-((3-(hydroxymethyl)-4-(piperazin-1-yl)phenyl)amino)-8,9-dihydroimidazo[1,2-a]pyrimido[5,4-e]pyrimidin-5(6H)-one;

6-(2,6-Dichlorophenyl)-2-((3-(hydroxymethyl)-4-(piperazin-1-yl)phenyl)amino)-8,9-dihydroimidazo[1,2-a]pyrimido[5,4-e]pyrimidin-5(6H)-one;

6-(2,6-Dichlorophenyl)-2-((3-(hydroxymethyl)-4-(4-methylpiperazin-1-yl)phenyl)amino)-8,9-dihydroimidazo[1,2-a]pyrimido[5,4-e]pyrimidin-5(6H)-one;

6-(2,6-Dichlorophenyl)-2-((4-(4-(2-hydroxyethyl)piperazin-1-yl)phenyl)amino)-8,9-dihydroimidazo[1,2-a]pyrimido[5,4-e]pyrimidin-5(6H)-one;

6-(2,6-Dichlorophenyl)-2-((4-morpholinophenyl)amino)-8,9-dihydroimidazo[1,2-a]pyrimido[5,4-e]pyrimidin-5(6H)-one;

6-(2,6-Dichlorophenyl)-2-((3-((methylamino)methyl)-4-morpholinophenyl)amino)-8,9-dihydroimidazo[1,2-a]pyrimido[5,4-e]pyrimidin-5(6H)-one;

6-(2-Bromo-6-chlorophenyl)-2-((3-chloro-4-(4-(dimethylamino)piperidin-1-yl)phenyl)amino)-8,9-dihydroimidazo[1,2-a]pyrimido[5,4-e]pyrimidin-5(6H)-one;

6-(2,6-dimethylphenyl)-2-((4-(4-methylpiperazin-1-yl)phenyl)amino)-8,9-dihydroimidazo[1,2-a]pyrimido[5,4-e]pyrimidin-5(6H)-one;

or a pharmaceutically acceptable salt thereof.

10. The method of claim 1, wherein the cancer is selected from the group consisting of breast carcinoma, ovarian carcinoma, lung carcinoma, colon carcinoma, head and neck carcinoma, and prostatic carcinoma.

11. A method for treating Wee1-mediated disease in a subject in need thereof comprising administering to the subject an effective amount of a compound having the Formula III, or a pharmaceutically acceptable salt thereof, or a pharmaceutical composition comprising the compound of Formula III or a pharmaceutically acceptable salt thereof, combined with an effective amount of at least one known anticancer agent, or a pharmaceutically acceptable salt of the said anticancer agent:

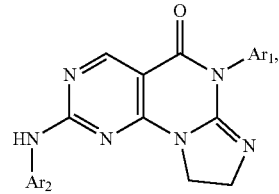

(III)

or a pharmaceutically acceptable salt thereof, wherein:
Ar₁ is selected from phenyl substituted by 2 substituents selected from halo, and C₁-C₆ alkyl; and
Ar₂ is selected from:
substituted phenyl, of which the substituents are selected from: halo; halo C₁-C₆ alkyl; C₁-C₆ alkyl; C₁-C₆ alkoxy; hydroxyl C₁-C₆ alkyl; NR$_a$R$_b$—C₁-C₆ alkyl; C₁-C₄ alkyl substituted by piperazinyl which is optionally substituted by 1-3 C₁-C₄ alkyl; piperidinyl —O— optionally substituted by 1-3 C₁-C₄ alkyl; NR$_a$R$_b$—C₁-C₆ alkoxy; NR$_a$R$_b$—C₁-C₆ alkyl-NR$_a$—; piperazinyl substituted by 1-3 substituents selected from C₁-C₆ alkyl, hydroxy C₁-C₆ alkyl and C₁-C₆ acyl; piperidinyl substituted by 1 substituent selected from C₁-C₆ alkyl and —NR$_a$R$_b$; 1,4-diazepan-1-yl optionally substituted by 1-3 C₁-C₆ alkyl; and morpholinyl optionally substituted by 1-3 C₁-C₆ alkyl; wherein R$_a$ and R$_b$ are independently H and C₁-C₄ alkyl;
tetrahydroisoquinolinyl substituted by 1-3 substituents selected from C₁-C₆ alkyl and halo;
2',3'-dihydro-1'H-spiro[cyclopropane-1,4'-isoquinolin]-7'-yl substituted by 1-3 substituents selected from C₁-C₆ alkyl, C₁-C₄ acyl and halo; and
4,5,6,7-tetrahydropyrazolo[1,5-a]pyrazin-2-yl substituted by 1-3 C₁-C₆ alkyl;
wherein the disease is a cancer selected from liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoide, head and neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, or prostatic carcinoma;
wherein said at least one known anticancer agent is selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxyuridine, fludarabine, nelarabine, ara-C, pralatrexate, pemetrexed, hydroxyurea, thioguanine, colchicine, vinblastine, vincristine, vinorelbine, paclitaxel, ixabepilone, cabazitaxel, docetaxel, campath, panitumumab, metazotuzumab, navuzumab, pymzumab, remoluzumab, bevacizumab, partuzumab, trastuzumab, cetuximab, obinutuzumab, olfamzumab, rituximab, alemtuzumab, tiemuzumab, toximab, bentuximab, daremuzumab, errotuzumab, T-DM1, ofatumumab, dinutuximab, blinatumomab, ipilimma, avastin, imatinib, gefitinib, erlotinib, osimertinib, afatinib, ceritinib, aletinib, crizotinib, lapatinib, sorafenib, sunitinib, nilotinib, dasatinib, pazopanib, temsirolimus, everolimus, vorinostat, romidepsin, panobinostat, belinostat, tamoxifen, letrozole, fulvestrant, mitoguazone, octreotide, retinoic acid, arsenic trioxide, zoledronic acid, bortezomib, carfilzomib, ixazomib, vismodegib, sonidegib, denosumab, thalidomide, lenalidomide, venetoclax, aldesleukin (recombinant human interleukin-2), sipueucel-T (prostate cancer therapeutic vaccine), palbociclib, olaparib, niraparib, rucaparib and talazoparib.

12. A method for treating Wee1-mediated disease in a subject in need thereof comprising administering to the subject an effective amount of a compound of Formula III, or a pharmaceutically acceptable salt thereof, or a pharmaceutical composition comprising the compound of Formula III or a pharmaceutically acceptable salt thereof, combined with an effective amount of at least one known anticancer agent, or a pharmaceutically acceptable salt of the said anticancer agent:

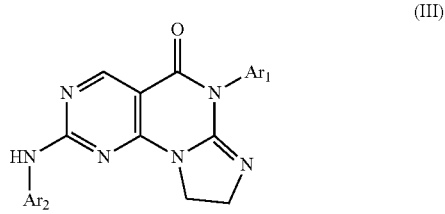
(III)

or a pharmaceutically acceptable salt thereof, wherein:
Ar₁ is disubstituted phenyl substituted by substituents selected from halo, C₁-C₃ alkyl, halo C₁-C₃ alkyl and C₁-C₃ alkoxy, wherein the at least one substituent is at the ortho-position;
Ar₂ is:
phenyl substituted by 1, 2 or 3 substituents, and the substituents are selected from halo; halo C₁-C₆ alkyl; C₁-C₆ alkyl; C₁-C₆ alkoxy; hydroxy C₁-C₆ alkyl; NR$_a$R$_b$—C₁-C₆ alkyl; C₁-C₄ alkyl substituted by piperazinyl optionally substituted by 1-3 C₁-C₄ alkyl; piperidinyl —O— optionally substituted by 1-3 C₁-C₄ alkyl; NR$_a$R$_b$—C₁-C₆ alkoxy; NR$_a$R$_b$—C₁-C₆ alkyl-NR$_a$—; piperazinyl optionally substituted by 1-3 substituents selected from C₁-C₆ alkyl and hydroxy C₁-C₆ alkyl; piperidinyl substituted by 1 substituent selected from C₁-C₆ alkyl and —NR$_a$R$_b$; 1,4-diazepan-1-yl optionally substituted by 1-3 C₁-C₆ alkyl; and morpholinyl optionally substituted by 1-3 C₁-C₆ alkyl; wherein R$_a$ and R$_b$ are independently H and C₁-C₄ alkyl;
tetrahydroisoquinolinyl substituted by 1-3 substituents selected from C₁-C₆ alkyl and halo; or
2',3'-dihydro-1'H-spiro[cyclopropane-1,4'-isoquinolin]-7'-yl substituted by 1-3 substituents selected from C₁-C₆ alkyl, C₁-C₄ acyl and halo;
wherein the disease is a cancer selected from liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoide, head and neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, or prostatic carcinoma; and wherein said at least one known anticancer agent is selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxyuridine, fludarabine, nelarabine, ara-C, pralatrexate, pemetrexed, hydroxyurea, thioguanine, colchicine, vinblastine, vincristine, vinorelbine, paclitaxel, ixabepilone, cabazitaxel, docetaxel, campath, panitumumab, metazotuzumab, navuzumab, pymzumab, remoluzumab, bevacizumab, partuzumab, trastuzumab, cetuximab, obinutuzumab, olfamzumab, rituximab, alemtuzumab, tiemuzumab, toximab, bentuximab, daremuzumab, errotuzumab, T-DM1, ofatumumab, dinutuximab, blinatumomab, ipilimma, avastin, imatinib, gefitinib, erlotinib, osimertinib, afatinib, ceritinib, aletinib, crizotinib, lapatinib, sorafenib, sunitinib, nilotinib, dasatinib, pazopanib, temsirolimus, everolimus, vorinostat, romidepsin, panobinostat, belinostat, tamoxifen, letrozole, fulvestrant, mitoguazone, octreotide, retinoic acid, arsenic trioxide, zoledronic acid, bortezomib, carfilzomib, ixazomib, vismodegib, sonidegib, denosumab, thalidomide, lenalidomide, venetoclax, aldesleukin (recombinant human interleukin-2), sipueucel-T (prostate cancer therapeutic vaccine), palbociclib, olaparib, niraparib, rucaparib and talazoparib.

13. The method of claim 12, wherein $Ar_1$ is

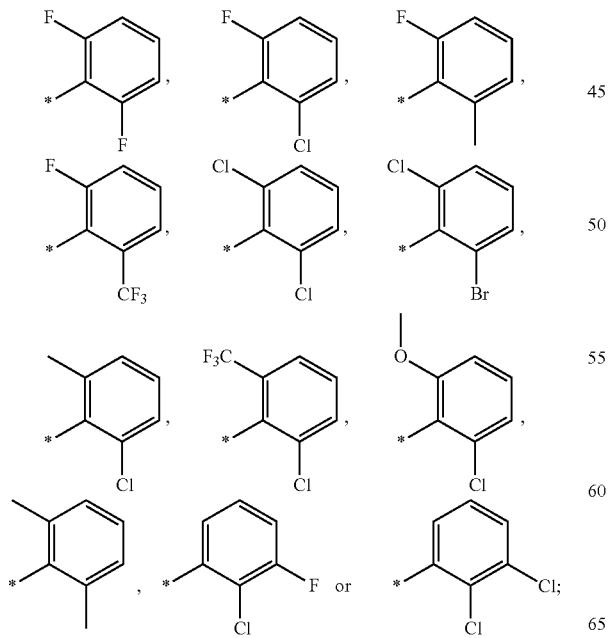

and $Ar_2$ is

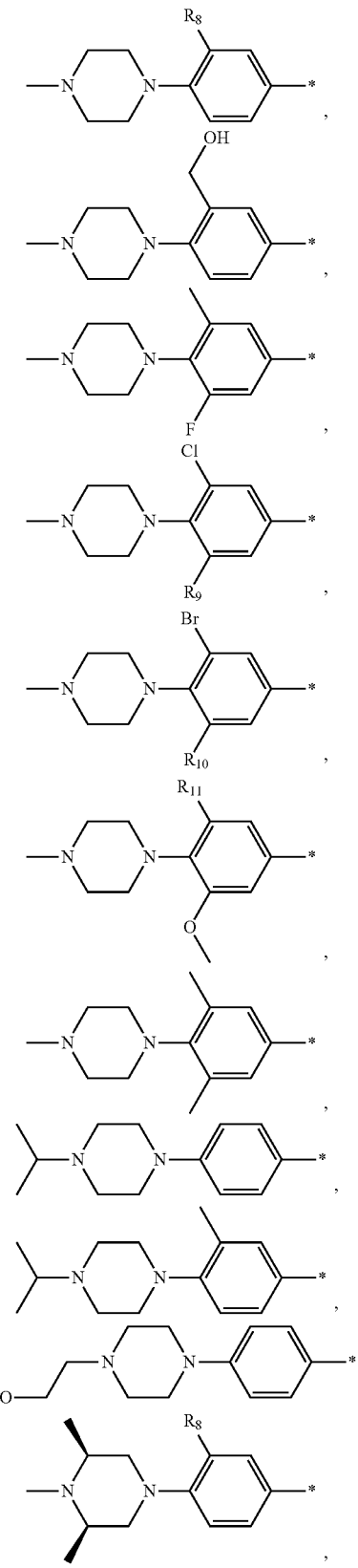

-continued

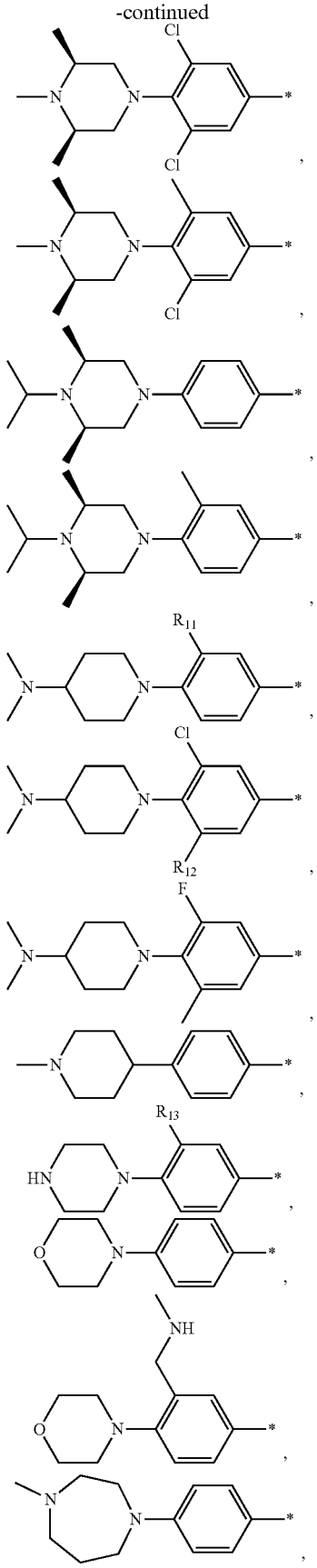

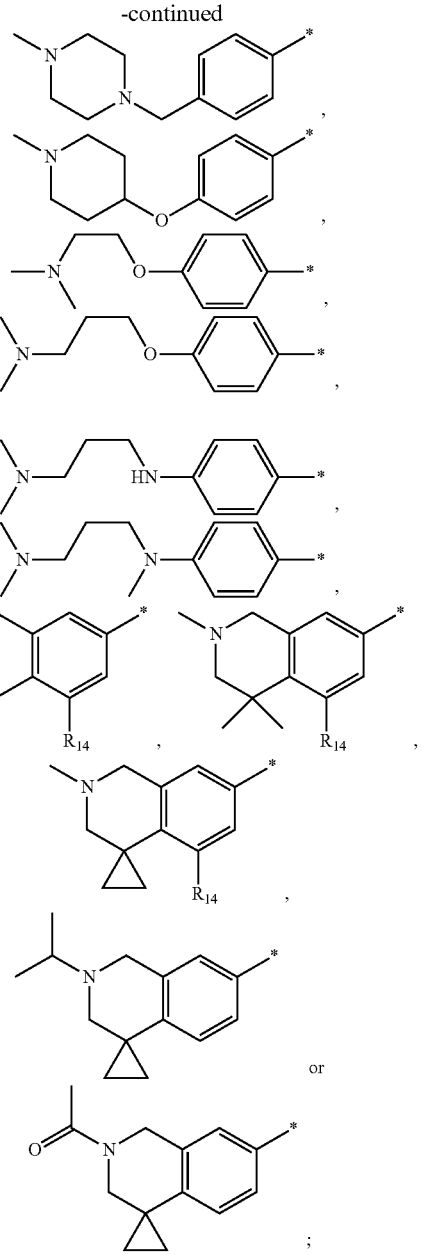

wherein:
R$_8$ is independently H, fluoro, chloro, bromo, methyl and trifluoromethyl;
R$_9$ is independently H, fluoro, chloro, bromo, methyl and trifluoromethyl;
R$_{10}$ is independently H, fluoro, chloro, bromo, methyl and methoxy;
R$_{11}$ is independently H, fluoro, chloro, bromo, methyl and trifluoromethyl;
R$_{12}$ is independently chloro, fluoro, bromo, methyl and methoxy;
R$_{13}$ is independently H, chloro, methyl, methoxy and hydroxymethyl;
R$_{14}$ is independently H, chloro, bromo and methyl.

* * * * *

UNITED STATES PATENT AND TRADEMARK OFFICE
CERTIFICATE OF CORRECTION

| | | |
|---|---|---|
| PATENT NO. | : 11,345,711 B2 | |
| APPLICATION NO. | : 16/883397 | |
| DATED | : May 31, 2022 | |
| INVENTOR(S) | : Cai et al. | |

It is certified that error appears in the above-identified patent and that said Letters Patent is hereby corrected as shown below:

In the Specification

In Column 2, Line 28, replace "Paboxini," with --Palbociclib,--.

In Column 37, Line 13, replace "Paposinib," with --Palbociclib,--.

In Column 50, Line 58, replace "THE" with --THF--.

In Column 51, Line 14, replace "MeCH" with --MeCN--.

In Column 101, Line 33, replace "THE" with --THF--.

In Column 108, Line 54, replace "liganded" with --ligand--.

In Column 108, Line 59, replace "liganded" with --ligand--.

Signed and Sealed this
Twenty-third Day of August, 2022

Katherine Kelly Vidal
*Director of the United States Patent and Trademark Office*